US012247320B2

(12) United States Patent
Krauss et al.

(10) Patent No.: US 12,247,320 B2
(45) Date of Patent: Mar. 11, 2025

(54) MULTIVALENT GLYCOPEPTIDES THAT TIGHTLY BIND TO CARBOHYDRATE-BINDING MONOCLONAL ANTIBODY FAMILY PGT128

(71) Applicant: BRANDEIS UNIVERSITY, Waltham, MA (US)

(72) Inventors: Isaac J. Krauss, Needham Heights, MA (US); Satoru Horiya, Somerville, MA (US); Jennifer Bailey, Waltham, MA (US)

(73) Assignee: Brandeis University, Waltham, MA (US)

( * ) Notice: Subject to any disclaimer, the term of this patent is extended or adjusted under 35 U.S.C. 154(b) by 868 days.

(21) Appl. No.: 17/288,414

(22) PCT Filed: Oct. 24, 2019

(86) PCT No.: PCT/US2019/057921
§ 371 (c)(1),
(2) Date: Apr. 23, 2021

(87) PCT Pub. No.: WO2020/086885
PCT Pub. Date: Apr. 30, 2020

(65) Prior Publication Data

US 2022/0090055 A1 Mar. 24, 2022

Related U.S. Application Data

(60) Provisional application No. 62/879,372, filed on Jul. 26, 2019, provisional application No. 62/750,217, filed on Oct. 24, 2018.

(51) Int. Cl.
*C40B 40/10* (2006.01)
*C07K 19/00* (2006.01)
*C12N 15/10* (2006.01)

(52) U.S. Cl.
CPC .............. *C40B 40/10* (2013.01); *C07K 19/00* (2013.01); *C12N 15/1058* (2013.01); *C12N 15/1062* (2013.01)

(58) Field of Classification Search
None
See application file for complete search history.

(56) References Cited

U.S. PATENT DOCUMENTS 6,906,176 B2 6/2005 Ley et al.
10,125,162 B2 11/2018 Krauss et al.
(Continued)

FOREIGN PATENT DOCUMENTS

WO 2007/107156 A2 9/2007
WO 2013/055745 A2 4/2013
WO 2018/140590 A1 8/2018

OTHER PUBLICATIONS

International Search Report and Written Opinion for corresponding Application No. PCT/US2019/057921 (mailed Apr. 14, 2020).
(Continued)

*Primary Examiner* — Christian C Boesen
(74) *Attorney, Agent, or Firm* — Karen A. LeCuyer; DeWitt LLP

(57) ABSTRACT

The invention relates to a glycopeptide that includes one or more modified amino acid residues having a sidechain comprising a monosaccharide or an oligosaccharide, wherein the glycopeptide binds specifically to a carbohydrate-binding monoclonal antibody from PGT128 family, preferably with an affinity of less than 100 nM. Immunogenic conjugates that include the glycopeptide, and pharmaceutical compositions that include the glycopeptide or the immunogenic conjugate are also disclosed. Various method of using the glycopeptides, immunogenic conjugates, and pharmaceutical compositions are disclosed, including induc-
(Continued)

ing an immune response, inhibiting viral infection, treating a cancerous condition, and detecting a neutralizing antibody.

18 Claims, 24 Drawing Sheets

Specification includes a Sequence Listing.

(56) References Cited

U.S. PATENT DOCUMENTS

| | | | |
|---|---|---|---|
| 10,378,017 | B2 | 8/2019 | Krauss |
| 10,544,412 | B2 | 1/2020 | Krauss et al. |
| 10,563,193 | B2 | 2/2020 | Krauss et al. |
| 10,780,150 | B2 | 9/2020 | Krauss et al. |
| 2016/0051690 | A1 | 2/2016 | Krauss et al. |
| 2016/0304628 | A1 | 10/2016 | Krauss et al. |
| 2016/0304858 | A1 | 10/2016 | Krauss et al. |
| 2016/0304874 | A1 | 10/2016 | Krauss |
| 2019/0117748 | A1 | 4/2019 | Krauss et al. |
| 2019/0367922 | A1 | 12/2019 | Krauss |
| 2020/0002699 | A1 | 1/2020 | MacPherson et al. |
| 2020/0102555 | A1 | 4/2020 | Krauss et al. |
| 2020/0140853 | A1 | 5/2020 | Krauss et al. |

OTHER PUBLICATIONS

Cai et al., "Synthetic Multivalent V3 Glycopeptides Display Enhanced Recognition by Glycan-Dependent HIV-1 Broadly Neutralizing Antibodies," Chem. Commun. 53(39):5453-5456 (2017).
Wiltschi et al., "Fine Tuning the N-Terminal Residue Excision with Methionine Analogues," Chembiochem. 10 (2):217-220 (2009).
Krauss, I., "Directed Evolution-Based Development of Carbohydrate HIV Antigens," Oral Presentation at 14th Annual Midwest Carbohydrate and Glycobiology Symposium, Michigan State University (Sep. 22, 2018) (Abstract and Presentation Slides).
Roberts & Szostak, "RNA-Peptide Fusions for the in vitro Selection of Peptides and Proteins," PNAS 94 (23):12297-12302 (1997).
Shimizu et al., "Cell-Free Translation Reconstituted with Purified Components," Nat. Biotechnol. 19(8):751-755 (2001).
Hartman et al., "An Expanded Set of Amino Acid Analogs for the Ribosomal Translation of Unnatural Peptides," PLoS ONE 2(10):e972 (2007).
Jennifer Bailey, "In Vitro Selections of Glycopeptides that Bind to HIV Broadly Neutralizing Antibodies," Presented to The Faculty of the Graduate School of Arts and Sciences, Department of Chemistry (Aug. 2019) (Thesis).
Bailey, J., "Directed Evolution of Glycopeptides as HIV Vaccine Candidates," Presented at the Boston Symposium on Organic & Bioorganic Chemistry (Oct. 25, 2018) (Presentation Slides).
Ng and Derda, "Phage-Displayed Macrocyclic Glycopeptide Libraries," Org. Biomol. Chem. 14(24):5539-5545 (2016).
Tjhung et al., "Silent Encoding of Chemical Post-Translational Modifications in Phage-Displayed Libraries," J. Am. Chem. Soc. 138(1): 32-35 (2016).
Chou et al., "Genetically-Encoded Fragment-Based Discovery (GE-FBD) of Glycopeptide Ligands with Differential Selectivity for Antibodies Related to Mycobacterial Infections," Org. Biomol. Chem. 16(2):223-227 (2018).
Vinals et al., "Selection of Galectin-3 Ligands Derived from Genetically Encoded Glycopeptide Libraries," Peptide Science 111: e24097 (2018).
Ng et al., "Genetically-Encoded Fragment-Based Discovery of Glycopeptide Ligands for DC-SIGN," Bioorg. Med. Chem. 26(19):5368-5377 (2018).
Ng et al., "Genetically Encoded Fragment-Based Discovery of Glycopeptide Ligands for Carbohydrate-Binding Proteins," J. Am. Chem. Soc. 137(16):5248-5251 (2015).
Kitov et al., "Rapid, Hydrolytically Stable Modification of Aldehyde-Terminated Proteins and Phage Libraries," J. Am. Chem. Soc. 136(23):8149-8152 (2014).
Ng et al., "Quantitative Synthesis of Genetically Encoded Glycopeptide Libraries Displayed on M13 Phage," ACS Chem. Biol. 7(9):1482-1487 (2012).
Arai et al., "A Monosaccharide-Modified Peptide Phage Library for Screening of Ligands to Carbohydrate-Binding Proteins," Bioorg. Med. Chem. Lett. 23(17):4940-4943 (2013).
Orwenyo et al., "Systematic Synthesis and Binding Study of HIV V3 Glycopeptides Reveal the Fine Epitopes of Several Broadly Neutralizing Antibodies," 12(6):1566-1575 (2017).
Schlippe et al., "In Vitro Selection of Highly Modified Cyclic Peptides that Act as Tight Binding Inhibitors," J. Am. Chem. Soc. 134(25):10469-77 (2012).

MULTIVALENT GLYCOPEPTIDES THAT TIGHTLY BIND TO CARBOHYDRATE-BINDING MONOCLONAL ANTIBODY FAMILY PGT128

This application is a national stage application under 35 U.S.C. § 371 of International Application No. PCT/US2019/057921, filed Oct. 24, 2019, which claims the benefit of U.S. Provisional Patent Application Ser. No. 62/879,372 filed Jul. 26, 2019, and U.S. Provisional Application Ser. No. 62/750,217 filed Oct. 24, 2018, which are hereby incorporated by reference in their entirety.

This invention was made with government support under R01 AI90745 awarded by the National Institutes of Health and R01 AI113737 awarded by the National Institutes of Health. The government has certain rights in the invention.

FIELD OF THE INVENTION

The present invention relates to a method for in vitro selection of glycopeptides that mimic native glycosylated epitopes, the glycopeptides obtained following such selection and immunogenic conjugates containing the same, compositions containing these products, and their use to induce immune responses against the glycopeptides.

BACKGROUND OF THE INVENTION

Antibody 2G12, isolated from an HIV positive individual, binds and neutralizes a broad range of HIV strains (Trkola et al., *J. Virol.* 70:1100-1108 (1996) and Binley et al., *J. Virol.* 78:13232-13252 (2004)) and provides sterilizing immunity against SHIV challenge in macaque models of infection (Mascola et al., *Nat. Med.* 6:207-210 (2000); Hessell et al., *Nat. Med.* 15:951-954 (2009); and Hessel et al., *PLoS Pathog.* 5:e1000433 (2009)). 2G12 recognizes an epitope comprised of 2-4 high mannose ($Man_9GlcNAc_2$) glycans on the surface of HIV envelope protein gp120 (Scanlan et al., *J. Virol.* 76:7306-7321 (2002); Calarese et al., *Science* 300:2065-2071 (2003); and Calarese et al. *Proc. Natl. Acad. Sci. U.S.A.* 102:13372-13377 (2005)) and glycopeptides which precisely mimic this glycan clustering and presentation may be useful as vaccines to "re-elicit" 2G12-like antibodies in vivo (Scanlan et al., *Nature* 446:1038-1045 (2007)). Glycans clustered on carbohydrate scaffolds (Ni et al., *Bioconjugate Chem.* 17:493-500 (2006)), peptide scaffolds (Joyce et al., *Proc. Natl. Acad. Sci. U.S.A.* 105:15684-15689 (2008)), and protein scaffolds (Astronomo et al., *J. Virol.* 82:6359-6368 (2008)) as well as phage particles (Astronomo et al., *Chem. Biol.* 17:357-370 (2010)) and yeast (Luallen et al., *J. Virol.* 82:6447-6457 (2008); Luallen et al., *J. Virol.* 83:4861-4870 (2009); Agrawal-Gamse et al., *J. Virol.* 85:470-480 (2011); Ciobanu et al., *Chem. Commun.* 47:9321-9323 (2011); and Marradi et al., *J. Mol. Biol.* 410:798-810 (2011)) have been tested for this purpose, but with little success. In part, this may be due to the difficulty of designing structures in which the clustering of glycans faithfully mimics that of the 2G12 epitope on gp120. Indeed, most of these structures were recognized by 2G12 with orders of magnitude weaker affinity than was gp120, suggesting that they were not optimal mimics of the 2G12 epitope.

The directed evolution of glycopeptides has been of interest, given their relevance in both HIV and cancer vaccine design. Although many powerful methods are available for in vitro selection of peptides, comparatively little has yet been published on in vitro selection of glycopeptides.

Recently phage display with chemically-modified phages enabled selection of peptide 5-mer sequences containing a single central mannose monosaccharide from ~$10^6$ sequences (Arai et al., *Bioorg. Med. Chem. Lett.* 23:4940-4943 (2013)). In an alternative approach, a single mannose was chemically attached to the N-terminal position of a 7-mer phage-displayed library of ~$10^8$ sequences, although selections with this library have not yet been reported (Ng et al., *ACS Chem. Biol.* 7:1482-1487 (2012)). Because carbohydrate epitopes of various pathogen (e.g., HIV) and cancer cells may contain multiple glycans (see Scanlan et al., *J. Virol.* 76:7306-7321 (2002); Calarese et al., *Science* 300:2065-2071 (2003); and Calarese et al. *Proc. Natl. Acad. Sci. U.S.A.* 102:13372-13377 (2005)), it is desirable that a selection method allow access to multivalent glycopeptides containing one or more glycans at variable positions, supported by a peptide framework.

It is desirable for selected glycopeptides to exhibit high affinity binding to known carbohydrate-binding monoclonal antibodies or other targets used during selection. Such carbohydrate-binding monoclonal antibodies include antibodies known to neutralize pathogens and antibodies known to afford protection (i.e., cytotoxicity) against virally infected cells.

mRNA display selection method has been shown to yield glycopeptides that are tightly recognized by an HIV bnAb, 2G12 (Horiya et al., *J. Am. Chem. Soc.* 136(14):5407-5415 (2014)). In recent years, another class of bnAbs, the PGT antibodies, were discovered from the sera of HIV positive individuals (Walker et al., *Nature* 477(7365):466-U117 (2011)). Members of this class (PGT121-123, 125-128, 130-131, 135-137, 141-145) were found to generally have much higher potency and wider neutralization breadth than 2G12. For instance, PGT128 neutralized 72% of viruses tested with an $IC_{50}$<50 μg/mL (median $IC_{50}$ of 0.02 μg/mL), while 2G12 neutralized just 32% of viruses tested with an $IC_{50}$<50 μg/mL (median $IC_{50}$ of 2.38 μg/mL). With such high potency and broad neutralization, the PGT antibodies are attractive subjects for HIV vaccine design.

Members of the PGT128 family (PGT125-128, 130-131) recognize carbohydrates ($Man_8GlcNAc_2$/$Man_9GlcNAc_2$) from the "high-mannose patch," centered around a glycan at $Asn^{332}$ (N332) (Walker et al., *Nature* 477(7365):466-U117 (2011); Doores et al., *Proc. Nat. Acad. Sci. U.S.A.* 107(31):13800-13805 (2010); and Bonomelli et al., *Plos One* 6(8) (2011)). 2G12 binds to the high-mannose patch, interacting most strongly with N332 and N392 glycans, as well as N295 and N339 (Scanlan et al., *J. Virol.* 76(14):7306 (2002); Calarese et al., *Science* 300(5628):2065 (2003); and Murin et al., *J. Virol.* 88(17):10177 (2014)). However, PGT128 was shown to bind peptide components in addition to two high-mannose carbohydrates (Pejchal et al., *Science* 334(6059):1097 (2011) and Kong et al., *Acta Crystallogr. D Biol. Crystallogr.* 71:2099-2108 (2015)). This peptide region (IGDIR, SEQ ID NO:1) is heavily conserved among HIV strains and recognized by many of the PGT antibodies (Garces et al., *Cell* 159(1):69-79 (2014), which is hereby incorporated by reference in its entirety). The ability of PGT128 and other PGT antibodies to penetrate the "glycan shield" to contact gp120 protein contribute to their strong potency and neutralization breadth (Pejchal et al., *Science* 334(6059):1097 (2011)). Thus, it is desirable to select for glycopeptides that exhibit high affinity binding to carbohydrate-binding monoclonal antibodies, such as PGT128.

It is also desirable to select glycopeptides that do not include a sugar at the N-terminal position of the peptide, or at just one position, and/or are not restricted to limited diversity (~$10^9$) and short peptides.

The present invention is directed to overcoming these and other deficiencies in the art.

SUMMARY OF THE INVENTION

A first aspect of the invention relates to a glycopeptide that includes one or more modified amino acid residues having a sidechain comprising an oligosaccharide, wherein the glycopeptide binds specifically to carbohydrate-binding monoclonal antibody of the PGT128 family, preferably with an affinity of less than 100 nM. The PGT128 family includes monoclonal antibodies PGT125, PGT126, PGT127, PGT128, PGT130, PGT131, and germline PGT128. In one embodiment, the glycopeptide binds specifically to carbohydrate-binding monoclonal antibody PGT128. In another embodiment, the glycopeptide binds specifically to carbohydrate-binding monoclonal antibody PGT130. In a further embodiment, the glycopeptide binds specifically to carbohydrate-binding monoclonal antibody germline PGT128 (glPGT128).

A second aspect of the invention relates to an immunogenic conjugate that includes a glycopeptide according to the first aspect of the invention covalently or non-covalently bound to an immunogenic carrier molecule.

A third aspect of the invention relates to a pharmaceutical composition that includes a pharmaceutically acceptable carrier and a glycopeptide according to the first aspect of the invention or an immunogenic conjugate according to the second aspect of the invention.

A fourth aspect of the invention relates to a method of inducing an immune response in an individual. This method includes administering to an individual a glycopeptide according to the first aspect of the invention, an immunogenic conjugate according to the second aspect of the invention, or a pharmaceutical composition according to the third aspect of the invention, wherein the administering is effective to induce an immune response against the glycopeptide.

A fifth aspect of the invention relates to a method of inhibiting viral infection that includes: administering to an individual a glycopeptide according to the first aspect of the invention, an immunogenic conjugate according to the second aspect of the invention, or a pharmaceutical composition according to the third aspect of the invention, wherein the administering is effective to induce a neutralizing immune response against a virus.

A sixth aspect of the invention relates to a method for detecting a neutralizing antibody in serum that includes providing a glycopeptide according to the first aspect of the invention; contacting the glycopeptide with serum from an individual; and detecting whether the glycopeptide binds specifically to an antibody present in the serum, wherein said detecting is carried out using a label.

A seventh aspect relates to a method of preparing glycopeptides that includes the steps of: providing an mRNA-displayed polypeptide having an N-terminal homopropargylglycine or allylglycine residue; treating the mRNA-displayed polypeptide with an enzyme suitable to remove the N-terminal homopropargylglycine or allylglycine residue from the polypeptide; and reacting the mRNA-displayed polypeptide recovered from the treating step with an oligosaccharide linked to a reactive moiety that is capable of reacting with a sidechain of one or more modified amino acids present in the polypeptide to thereby form a glycopeptide comprising one or more oligosaccharides linked to amino acid sidechains.

As demonstrated by the accompanying Examples, the selection method disclosed herein allows for the generation of a pool of multivalent glycopeptides containing up to several glycans at variable positions, supported by a peptide framework. This selection method includes Click chemistry glycosylation of mRNA-displayed peptide libraries of ~$10^{13}$ sequences. The usefulness of this selection method is demonstrated for HIV antigen design, whereby multiple glycopeptides containing 1-5 high-mannose nonasaccharides were generated and these glycopeptides tightly recognize the broadly neutralizing HIV antibody PGT128. These glycopeptides bound to PGT128 with an affinity substantially the same as the affinity between PGT128 and HIV-1 gp120. Multiple glycopeptides exhibited $K_D$'s of about 5 nM or less. As a result, these glycopeptides adequately mimic the native gp120 epitope, and should therefore be useful as a vaccine to induce a neutralizing immune response against HIV-1. Similar results can be obtained for other neutralizing antibodies from the PGT128 family, including PGT130 and germline PFG128.

BRIEF DESCRIPTION OF THE DRAWINGS

FIG. 2A is a schematic illustration of the covalent linkage of nascent peptide to its mRNA, mediated by attachment to mRNA-linked puromycin inside the ribosome. FIG. 2B illustrates the use of PURE system to incorporate alkynes via the AUG codon and CuAAAC "click" chemistry glycosylation with the synthetic $Man_9$-azide. FIG. 2C illustrates the peptide libraries used in this study. The "fixed" library contains 3 constant glycosylation sites, whereas the "variable" library contains only one constant glycosylation site, at position 1. The random regions of both libraries are followed by a flexible linker and a $His_6$ tag. Puromycin attached to mRNA is covalently linked to C-terminal arginine residues in translation (Josephson et al., *J. Am. Chem. Soc.* 127:11727-11735 (2005), which is hereby incorporated by reference in its entirety). FIG. 2D illustrates the scheme for selection of 2G12-binding glycopeptides. The library DNA is comprised of T7 promotor ($P_{T7}$), E-enhancer followed by Shine-Dalgarno sequence (SD), the open reading frame (ORF) of the peptide and the constant region including the sequence for annealing and photo-crosslinking the mRNA to a puromycin-containing oligonucleotide.

FIG. 3A is a generic depiction of bis-alkylation using m-dibromoxylene. FIG. 3B shows MALDI-TOF-MS analysis of a test peptide SEQ ID NO:168 shows complete conversion from the linear product to the cyclized product.

FIG. 5A shows the UV chromatogram and ESI+MS of cyclized peptide H-1 (SEQ ID NO: 291) (calculated 737.26 $[M+9H]^{9+}$, 829.29 $[M+8H]^{8+}$, 947.62 $[M+7H]^{7+}$). FIG. 5B shows the UV chromatogram and ESI+MS of cyclized peptide H-22 (SEQ ID NO:306) (calculated 751.76 $[M+9H]^{9+}$, 845.60 $[M+8H]^{8+}$, 966.26 $[M+7H]^{7+}$). FIG. 4C shows the UV chromatogram and ESI+MS; calculated 962.10 $[M+11H]^{11+}$, 1058.21 $[M+10H]^{10+}$, 1175.68 $[M+9H]^{9+}$.

FIG. 6A is a co-crystal structure of PGT128 Fab (dark grey) with eODmV3-gp120 (dim gray). PDB ID: 3TYG.

FIG. 6B is a co-crystal structure of PGT128 Fab with BG505.SOSIP gp140 (dim gray). PDB ID: 5C7K. PGT128 fits between two $Man_9GlcNAc_2$ carbohydrates (light gray) to make contacts with peptide (IGDIR, SEQ ID NO:1).

FIG. 7A shows the cleavage site for enterokinase follows FLAG-tag (DYKDDDDK, SEQ ID NO:171). FIG. 7B shows SDS-PAGE analysis of peptides MFLAG-10F12, MFLAG-10V1, and MFLAG-10V8 with and without enterokinase (rEK) treatment. FIG. 7C shows SDS-PAGE analysis of peptide MFLAG-10F6 glycosylated following treatment with rEK. A complex mixture of bands is observed following glycosylation.

FIG. 8A shows N-terminal processing of formyl-Met in prokaryotes, where R is a small amino acid. FIG. 8B shows proposed N-terminal processing of formyl-HPG with a small amino acid (Ala) in the second amino acid position.

FIG. 10A shows the glycosylation of peptides 10V1 (MATKTNCKREKTXDNHVTIXRSIPWYTYRWLPNGSGSGCG, SEQ ID NO:339) and (MHPYNTSRTSAXXAALKMXQVTDXYALALFHRILGSGSGCG, SEQ ID NO:288) prepared by translation as free peptides with or without PDF/MAP treatment. Peptides were run on a 4-20% SDS-PAGE gel (Bio-Rad). FIG. 10B shows 10V1 (SEQ ID NO:339) fusions prepared with or without PDF/MAP in translation: mRNA-peptides, cDNA/mRNA-peptides. Fusions were run on a homemade 7.5% SDS-PAGE gel. FIG. 10C shows glycosylated peptides prepared as cDNA/mRNA fusions followed by nuclease digestion. All samples were radiolabeled with 3H-histidine. Glycosylated fusions were digested with Nuclease-P1 for analysis on a 4-20% SDS-PAGE (Bio-Rad). Gels were visualized by fluorography.

FIG. 14A shows library fusions were analyzed by SDS-PAGE (homemade 7.5% gel) at each step for verification.

FIG. 14B shows glycosylated libraries were digested with Nuclease-P1 for analysis on a 4-20% SDS-PAGE (Bio-Rad).

FIG. 15A shows the PGT128 selection conditions and fractions bound for each round. The immobilization carrier used was Protein G (G), Protein A (A), or Streptavidin (SA). FIG. 15B shows glycosylation from round to round for the Heavily Biased library. FIG. 15C shows glycosylation from round to round for the less Biased library. A sample of glycosylated libraries going into each round of selection were digested with Nuclease-P1 and run on 4-20% SDS-PAGE (Bio-Rad).

FIG. 16A show schematic representations of 91-8cy (SEQ ID NO:338) and 91-12cy (SEQ ID NO:76) cyclized glycopeptide sequences, analyzed by SDS-PAGE (FIG. 16B) and showing a mixture of glycosylated species, and tested for binding to PGT128 (FIG. 16C).

FIG. 21A shows PGT130 selection conditions and fractions bound for each round. The immobilization carrier used was Protein G (G) or Protein A (A). FIG. 21B-21C show glycosylation from round to round for the Heavily Biased library (FIG. 21B) and the Less Biased library (FIG. 21C). A sample of glycosylated libraries going into each round of selection were digested with Nuclease-P1 and run on 4-20% SDS-PAGE (Bio-Rad).

DETAILED DESCRIPTION OF THE INVENTION

The present invention provides a method for in vitro selection of glycopeptides, which involves combining mRNA display with the incorporation of unnatural amino acids and "click" chemistry. Using this in vitro selection in combination with directed evolution of glycopeptides, it is possible to develop binding partners with any of a variety of target proteins, including epitope mimics that are bound tightly and specifically by carbohydrate-specific monoclonal antibodies.

Accordingly, the method for selecting a glycopeptide that binds to a target protein includes providing a pool of glycopeptides fused via puromycin linker to an encoding mRNA-cDNA duplex; combining the pool with a target protein to form a mixture; incubating the mixture for a period of time sufficient to allow any target protein to bind to one or more of the glycopeptides, thereby forming glycopeptide-target protein complexes; and isolating from the mixture the glycopeptide-target protein complexes, thereby identifying a plurality of selected glycopeptides. Multiple rounds of selection and regenerating mRNA-linked glycopeptide pools can be performed in the manner illustrated in FIG. 1.

Figure 1:
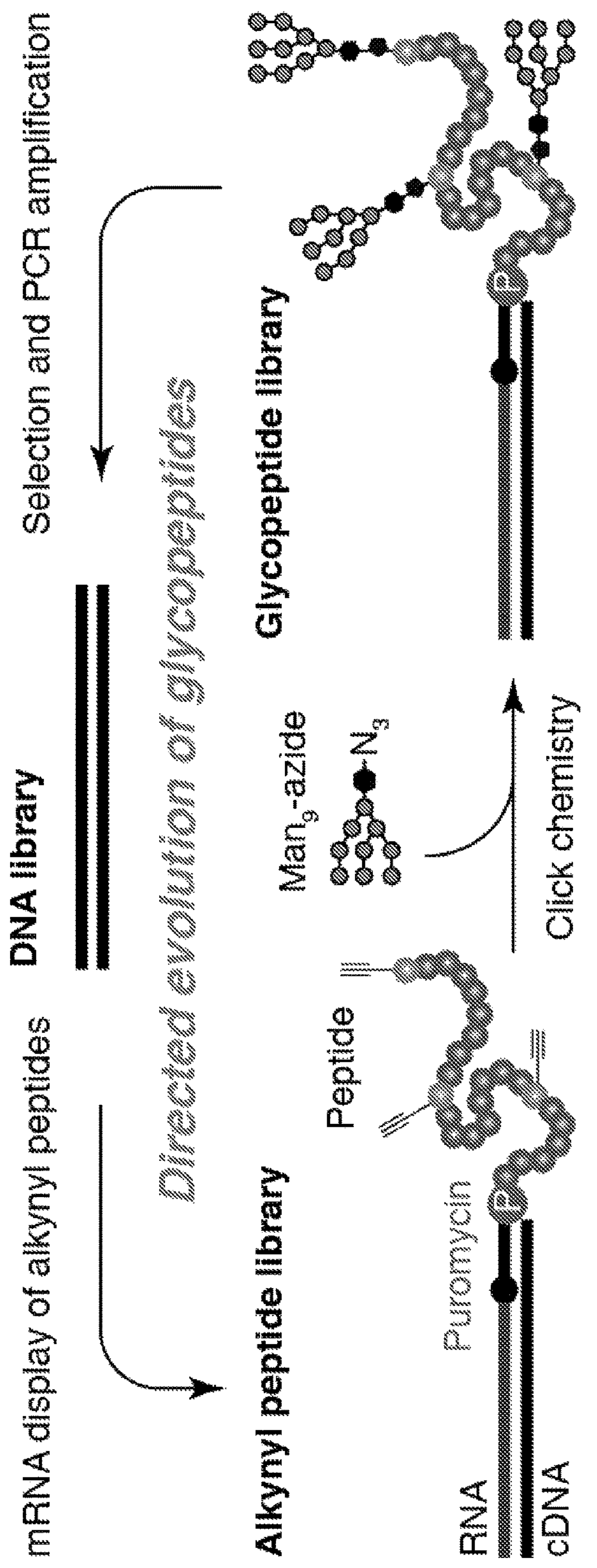
FIG. 1 illustrates how glycopeptide selection can be achieved by the combination of chemical synthesis, "click: chemistry (CuAAAC, or Copper Assisted Azide Alkyne Cycloaddition) (Kolb et al., *Angew. Chem. Int. Ed.* 40:2004-2021 (2001) and Rostovtsev et al., *Angew. Chem. Int. Ed.* 41:2596-2599 (2002), which are hereby incorporated by reference in their entirety), mRNA display selection (Roberts et al., *Proc. Nat. Acad. Sci. U.S.A.* 94:12297-12302 (1997), which is hereby incorporated by reference in its entirety) and codon reassignment (van Hest et al., *J. Am. Chem. Soc.* 122:1282-1288 (2000) and Tan et al., *J. Am. Chem. Soc.* 126:12752-12753 (2004), which are hereby incorporated by reference in their entirety) using PURE system cell-free translation (Shimizu et al., *Nat Biotech* 19:751-755 (2001); Josephson et al., *J. Am. Chem. Soc.* 127:11727-11735 (2005); Shimizu et al., *Methods* 36:299-304 (2005); Hartman et al., *PLoS ONE* 2:e972 (2007); and Guillen et al., *J. Am. Chem. Soc.* 134:10469-10477 (2012), which are hereby incorporated by reference in their entirety).
Figures 2A, 2B:
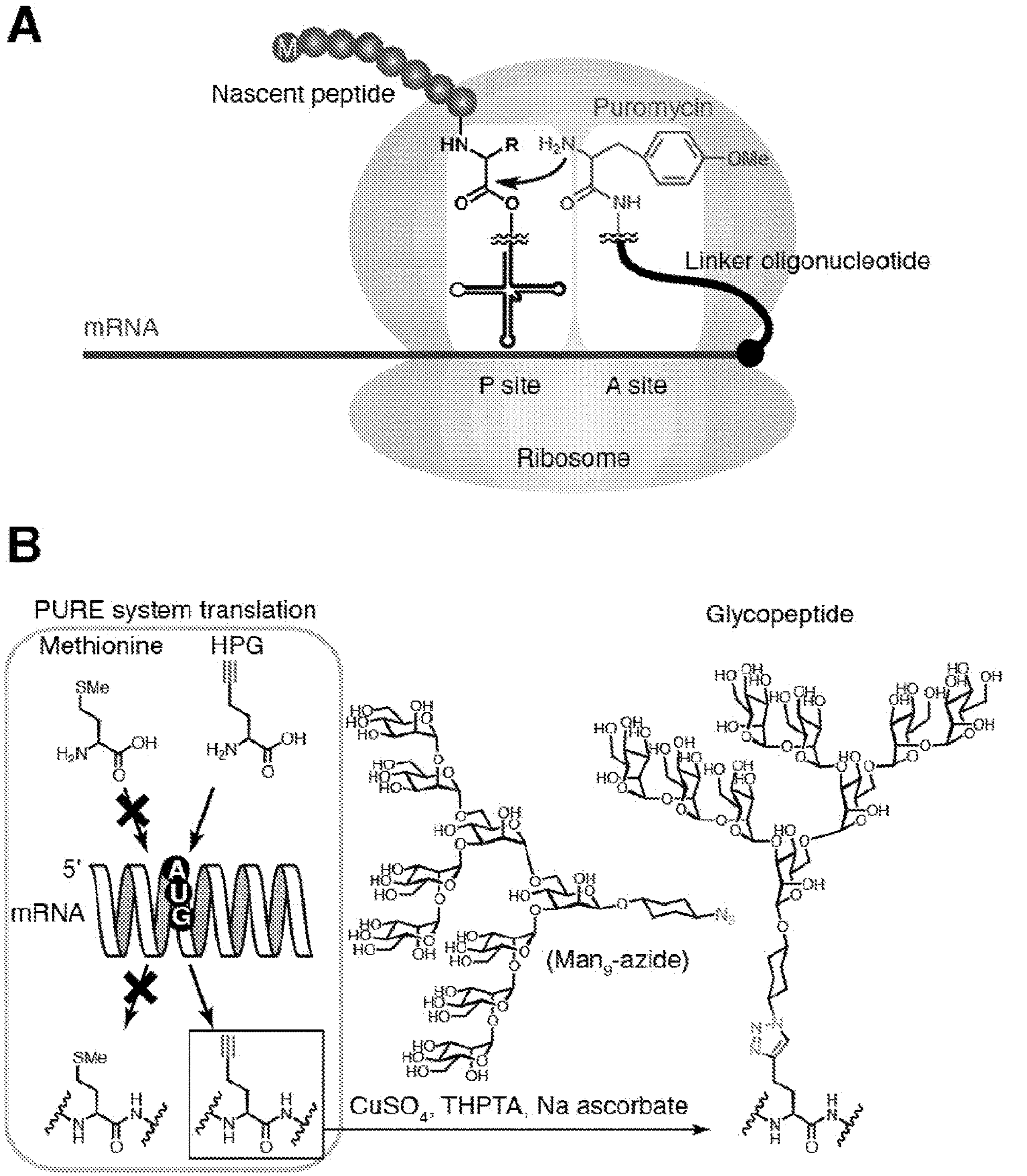
FIGS. 2A-2D illustrate the in vitro selection of glycopeptides.
Figures 2C, 2D:
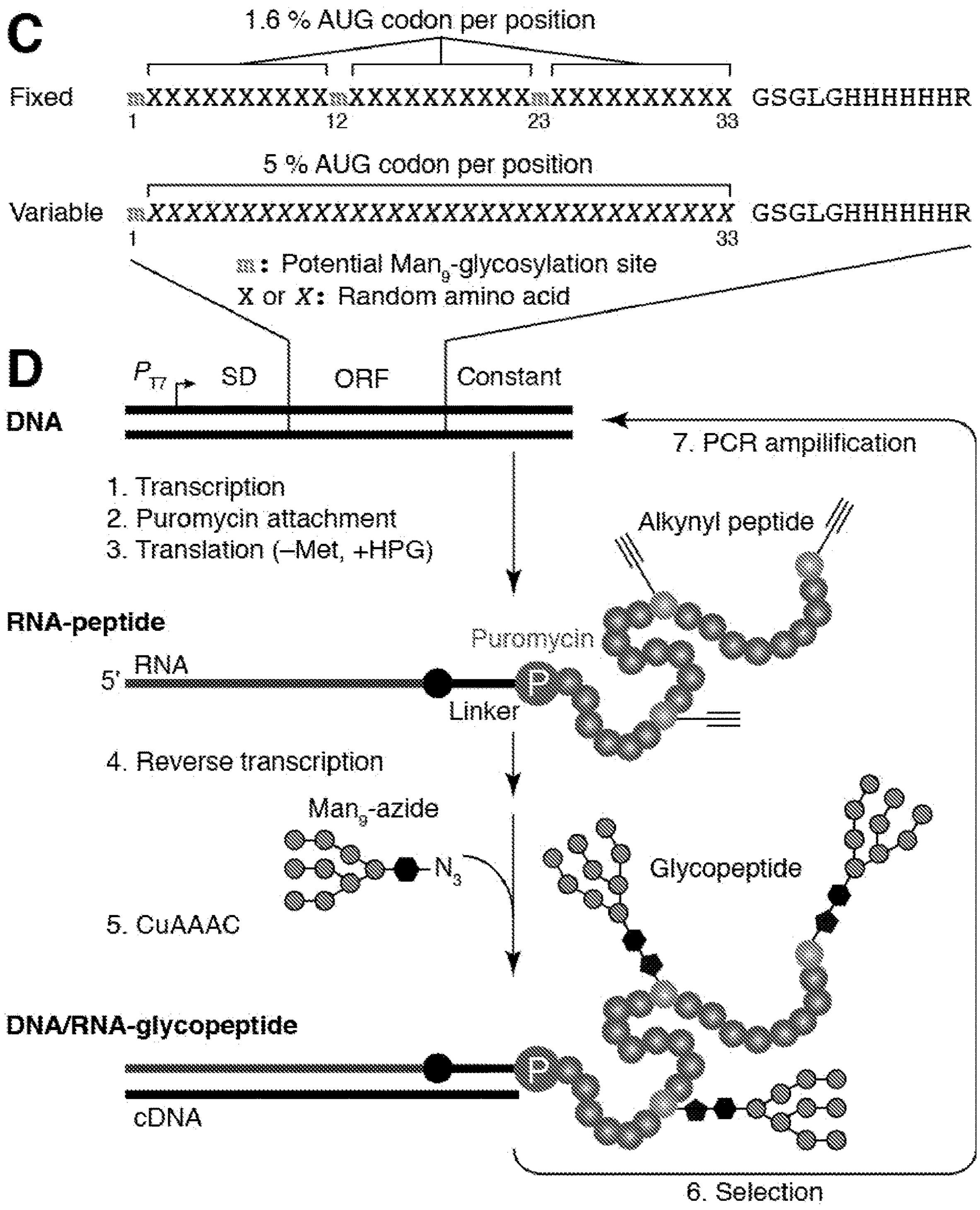

FIG. 1 illustrates how glycopeptide selection can be achieved by the combination of chemical synthesis, "click" chemistry (CuAAAC, or Copper Assisted Azide Alkyne Cycloaddition) (Kolb et al., *Angew. Chem. Int. Ed.* 40:2004-2021 (2001) and Rostovtsev et al., *Angew. Chem. Int. Ed.* 41:2596-2599 (2002), which are hereby incorporated by reference in their entirety), mRNA display selection (Roberts et al., *Proc. Natl. Acad. Sci. U.S.A* 94:12297-12302 (1997), which is hereby incorporated by reference in its entirety), and codon reassignment (van Hest et al., *J. Am. Chem. Soc.* 122:1282-1288 (2000) and Tan et al., *J. Am. Chem. Soc.* 126:12752-12753 (2004), which are hereby incorporated by reference in their entirety) using PURE system cell-free translation (Shimizu et al., *Nat Biotech* 19:751-755 (2001); Josephson et al., *J. Am. Chem. Soc.* 127:11727-11735 (2005); Shimizu et al., *Methods* 36:299-304 (2005); Hartman et al., *PLoS ONE* 2, e972 (2007); and Guillen et al., *J. Am. Chem. Soc.* 134:10469-10477 (2012), which are hereby incorporated by reference in their entirety).

The provided pool of glycopeptides fused via puromycin linker to an encoding mRNA-cDNA duplex is preferably large enough to afford sufficient diversity so as to allow for selection of multiple, diverse glycopeptides that exhibit target protein binding capability. By way of example, the provided pool comprises about $10^{10}$ or greater, about $10^{11}$ or greater, about $10^{12}$ or greater, or about $10^{13}$ or greater glycopeptides fused via puromycin linker to an encoding mRNA-cDNA duplex.

Creation of the first pool is carried out by first generating a library of DNA duplexes of sufficient length to afford a glycopeptide pool of the desired complexity. Each DNA duplex includes a promoter sequence to allow for transcription, optionally an enhancer element sequence, a sequence containing a ribosomal binding site that affords in vitro translation of mRNA transcripts, an open reading frame region that affords sequence variety to generate glycopeptide diversity, and a downstream sequence that encodes, e.g., a His tag followed by a constant region that serves as the linker for puromycin. Any suitable promoter and enhancer sequences suitable for in vitro transcription can be used, and any suitable ribosomal binding sequence can be used. Sequence variation can be introduced using random diversity at each site or semi-random diversity at each site.

As shown in FIG. 1 and FIGS. 2A-2D, the generation of pools of mRNA-supported glycopeptides and selection of individual pool members against target proteins is illustrated. The DNA duplexes are used as templates for generating mRNA templates. This can be achieved using any suitable in vitro transcription protocol. Thereafter, a puromycin linker is attached to the 3' region of the mRNA strand. Briefly, purified transcripts can be photo-crosslinked with puromycin-containing oligonucleotide. Photo-crosslinking is achieved using, e.g., 365 nm UV irradiation as previously described (Kurz et al., *Nucleic Acids Res.* 28:e83 (2000) and Seelig, B. *Nat. Protocols* 6:540-552 (2011), which are hereby incorporated by reference in their entirety).

Use of puromycin at the 3' region of the mRNA transcript allows for mRNA-display of the translated polypeptide based on the physical linkage of the polypeptide to the mRNA that encoded it. Puromycin inhibits translation by mimicking the substrate of the ribosome—the 3' end of an aminoacyl-tRNA. As ribosomes complete the translation of individual mRNAs to the corresponding peptides they encounter the 3' puromycin. Because puromycin is chemically similar to the 3' end of aminoacyl-tRNA, it is recognized by the peptidyl transfer center of the ribosome, which catalyzes the transfer of the nascent polypeptide to the modified tyrosine of puromycin. The mRNA is now covalently attached to the corresponding translated peptide via the puromycin, and the ribosomes are stalled. To promote the covalent attached (or fusion) of the translated polypeptide to the encoding mRNA strand, the reaction mixture is preferably exposed to KCl and $Mg(OAc)_2$ and then maintained at a temperature below 0° C. for sufficient duration to yield the fused product. At this point, the initial pool or library mRNAs have now been translated and linked via puromycin to the peptides that they encode in a stable molecular conjugate referred to as an mRNA-peptide fusion.

To facilitate glycosylation of the translated polypeptide, translation of the mRNA strand is carried out using one or more modified amino acids comprising a reactive side chain. One exemplary amino acid is homopropargylglycine, which is efficiently recognized for incorporation into the polypeptide corresponding to the location of Met codons. Thus, for purposes of translation, homopropargylglycine constitutes a modified methionine. Homopropargylglycine can be prepared using the procedures of Shimizu et al., *Nat Biotech* 19:751-755 (2001); Josephson et al., *J. Am. Chem. Soc.* 127:11727-11735 (2005); Guillen et al., *J. Am. Chem. Soc.* 134:10469-10477 (2012); Shimizu et al., *Methods Mol Biol.* Vol. 607, p 11-21 (2010); and Ma et al., Ribosome Display and Related Technologies; Douthwaite, *J. A., Jackson, R. H., Eds.; Springer* New York: *Methods Mol Biol.* Vol. 805, p 367-390 (2012), which are hereby incorporated by reference in their entirety. Other exemplary amino acids are p-azido-phenylalanine and p-ethynyl-phenylalanine, which are efficiently recognized for incorporation into the polypeptide corresponding to the location of Phe codons when the PheRS A294G substrate is used (see Hartmann et al., *PlosOne DOI* 10.1371/journal.pone.0000972 (2007), which is hereby incorporated by reference in its entirety). Yet another exemplary amino acid is L-allyl glycine which is efficiently recognized for incorporation into the polypeptide corresponding to the location of Leu codons when the editing deficient LeuRS D345A substrate is used. With modified amino acylated-tRNAs introduced into the reaction mixture in the absence of one or more natural amino acylated-tRNAs, the modified amino acids are introduced into the polypeptide chain (Guillen et al., *J. Am. Chem. Soc.* 134:10469-10477 (2012), which is hereby incorporated by reference in its entirety).

After forming the mRNA-polypeptide fusion, the one or more monosaccharides or oligosaccharides are attached using appropriate click chemistry reactions, which include thiol-ene reactions (reaction of a thiol bond across an alkene or alkyne by either a free radical or ionic mechanism) (see, e.g., Hoyle et. al., *Angew. Chem. Int. Ed.* 49:1540-1573 (2010), which is hereby incorporated by reference in its entirety) as well as azide-alkyne cycloaddition reactions (reaction of an azido group with a terminal or internal alkyne) (see, e.g., Temme et al., *Chem. Eur. J.* 19:17291-17295 (2013) and Hong et al., *Angew. Chem. Int. Ed.* 48:9879-9883 (2009), which are hereby incorporated by reference in their entirety).

After recovering the glycopeptide-mRNA fusion, a reverse transcription reaction procedure is performed using the mRNA strand as a template to form a cDNA strand. After synthesis of the cDNA strand, the resulting product includes the glycopeptide linked to the mRNA-cDNA duplex via puromycin. Collectively, these structures constitute the first pool available for selection against a target molecule.

Exemplary target molecules suitable for selection include those that bind to glycosylated naturally occurring proteins, such as monoclonal antibodies that bind to glycosylated epitopes (i.e., carbohydrate-binding monoclonal antibodies). Suitable carbohydrate-binding monoclonal antibodies include those that are neutralizing against a pathogen (e.g., HIV).

Selection of library members that bind to the target protein—in the case of the monoclonal antibodies, mimicking the native glycosyl-epitope to which the antibody binds—is carried out in liquid medium. Briefly, the library is introduced into the selection medium with the target protein. If the target protein is biotinylated, streptavidin-labeled magnetic beads can be used to recover library members that bind to the target protein. Alternatively, where the target protein is a monoclonal antibody, Protein A or Protein G-labeled magnetic beads can be used to recover library members that bind to the target monoclonal antibody. Regardless of the type of beads used, the beads can be magnetically isolated and washed with selection buffer. To elute the selected library members, the beads can be resuspended in selection buffer and then heated to disrupt the affinity binding between library member and target. Recovered supernatant contains the eluted library members.

Following recovery of the selected library members, PCR amplification is used to amplify the cDNA portion of the library member mRNA-cDNA duplexes. PCR using Taq DNA polymerase (Roche) is performed using forward and reverse primers, and the amplified DNAs can be purified and used to regenerate the next selection round. In certain embodiments, error prone PCR can be used to facilitate evolution of the library.

In regenerating the next select round, the transcription, puromycin linkage, translation, and reverse transcription steps described above are used to generate a next generation pool (i.e., the glycopeptides linked mRNA-cDNA duplex via puromycin).

Differences in the selection protocol can performed in subsequent rounds. For instance, the selection stringency can be increased to promote the selection of high affinity binding of pool members. In certain embodiments the temperature can be varied from about 18 to 22° C. in early rounds to temperatures greater than 22° C. or even greater than 27° C. (e.g., about 32° C. to about 42° C.) in later rounds. Any such variation in temperature can be used. In alternative embodiments the target protein concentration can be varied from about 25 to about 200 nM in early rounds, and reduced to about 10 to about 80 nM, or about 5 to about 25 nM in later rounds. Any such variation in target protein concentration can be used. In certain embodiments the duration of the selection step can also be reduced from about 10 to about 30 minutes in early rounds, to about 5 to about 20 minutes in later rounds. Any such variation in duration of the selection step can be used. In another embodiment, the introduction of competitor molecules for negative selection can be introduced in later rounds, including the introduction of free monosaccharides or oligosaccharides, the introduction of unglycosylated peptides (removing polypeptides which bind to target protein without being glycosylated), the introduction of unmodified magnetic beads, e.g., streptavidin, Protein A, or Protein G-conjugated beads (removing polypeptides or glycopeptides that bind directly to a solid support), or combinations thereof. Any number of negative selection steps can be employed. In yet another embodiment, the number and conditions of the wash steps can be made more stringent during later selection rounds.

In between rounds or after the final round, the individual, selected pool members can be sequenced and, thus, the polypeptide sequence identified. Having identified the polypeptide sequence, individual glycopeptides can be synthesized such that the molecule excludes the puromycin linker that links the polypeptide sequence to the mRNA transcript encoding the same. Polypeptide synthesis can be carried out using, e.g., standard peptide synthesis operations. These include both FMOC (9-Fluorenylmethyloxy-carbonyl) and tBoc (tert-Butyl oxy carbonyl) synthesis protocols that can be carried out on automated solid phase peptide synthesis instruments including the Applied Biosystems 431A, 433A synthesizers and Peptide Technologies Symphony or large scale Sonata or CEM Liberty automated solid phase peptide synthesizers. The modified amino acids can be substituted during solid phase synthesis to allow for glycosylation in the same manner as the selected glycopeptides.

The examples of the present application demonstrate a method to prepare libraries $10^{12}$-$10^{13}$ of cyclic peptides, of ~60 amino acids in length, bearing large sugar modifications at multiple internal positions, with the option of not modifying the N-terminus, e.g., formylated homopropargylglycine (fHPG) residue. To avoid having a sugar at the N-terminus of the peptide, the entire peptide library is treated enzymatically. According to one approach, illustrated in FIGS. 8A-8B, the peptide library is digested with peptide deformylase ("PDF") and methionine aminopeptidase ("MAP") prior to sugar attachment. This removes the N-terminal fHPG (alkyne) residue from the peptides so that no sugar can be attached there. This method is used to select glycopeptides with ~5 nM affinity for HIV broadly-neutralizing antibody PGT128. This same approach can be used with formylated allylglycine. In an alternative approach, the peptide includes an enterokinase cleavage site near the N-terminal HPG or allylglycine residue, which allows for its removal.

A first aspect of the invention relates to a glycopeptide that includes one or more modified amino acid residues having a sidechain comprising an oligosaccharide, wherein the glycopeptide binds specifically to carbohydrate-binding monoclonal antibody of the PGT128 family (e.g., PGT128, PGT130, or germline PGT128), preferably with an affinity of less than 100 nM.

The glycopeptide may comprise L-amino acids, D-amino acids, or a mixture of L- and D-amino acids. As noted above, the glycopeptide can be any length. In some embodiments, the glycopeptide comprises about 10 to about 80 amino acids, more preferably between about 15 and about 70 amino acids. In certain embodiments, the glycopeptide can include about 20 amino acids, about 25 amino acids, about 30 amino acids, about 35 amino acids, about 40 amino acids, about 45 amino acids, about 50 amino acids, about 55 amino acids, about 60 amino acids, or about 65 amino acids. The glycopeptide can include one or more of the modified amino acid residues.

In some embodiments, the glycopeptide comprises from 1 to about 10 of said modified amino acid residues. In certain embodiments, the glycopeptide can include from 2 to 5 of said modified amino acid residues, or from 6 to 10 of said modified amino acid residues.

Two or more modified amino acid residues can be located at adjacent positions (i.e., where one modified amino acid is linked via peptide bond to another modified amino acid) or at nonadjacent positions (i.e., where no two modified amino acids are linked via peptide bond to one another). In certain embodiments, the resulting polypeptide includes a plurality of modified amino acids, some of which are adjacent to one another and some of which are not adjacent to another modified amino acid.

The oligosaccharide may be a branched oligosaccharide. Suitable oligosaccharides include branched or unbranched oligosaccharide that include at least 3 saccharide moieties, typically from about 3 saccharide moieties up to about 20 saccharide moieties. The saccharide moieties include, without limitation, glucose, galactose, mannose, arabinose, fucose, rhamnose, sialic acid, and N-acetyl-glucosamine. In some embodiments, the branched oligosaccharide consists of 9 mannose moieties and 2 N-Acetylglucosamine moieties.

Exemplary N-linked glycan structures include high mannose N-glycans present in the human lung:

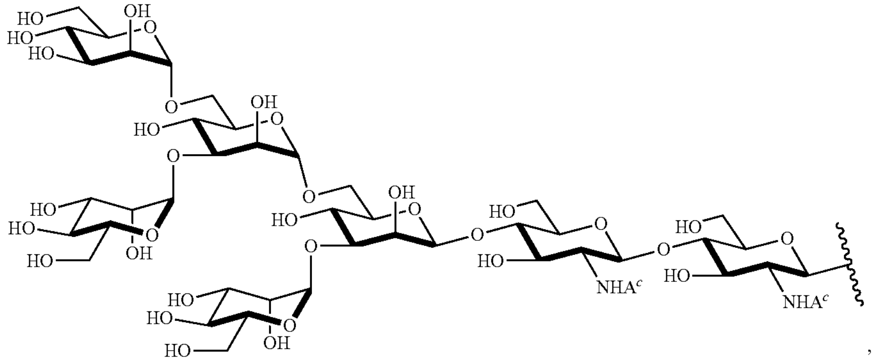

,

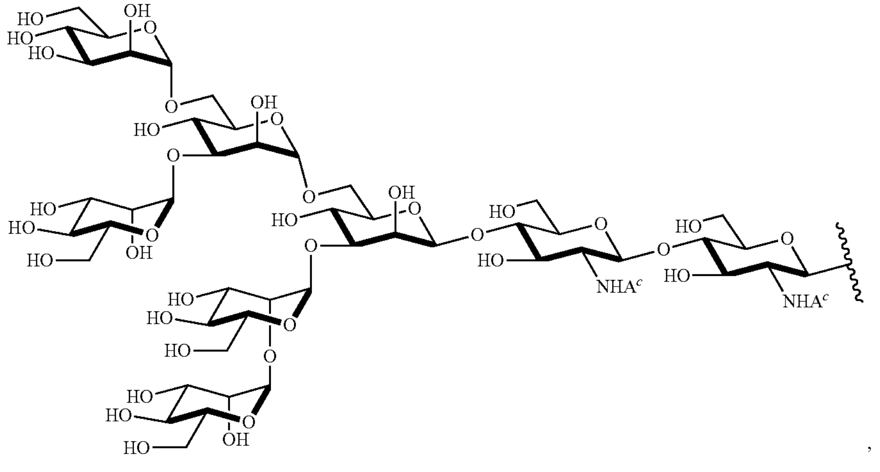

,

-continued

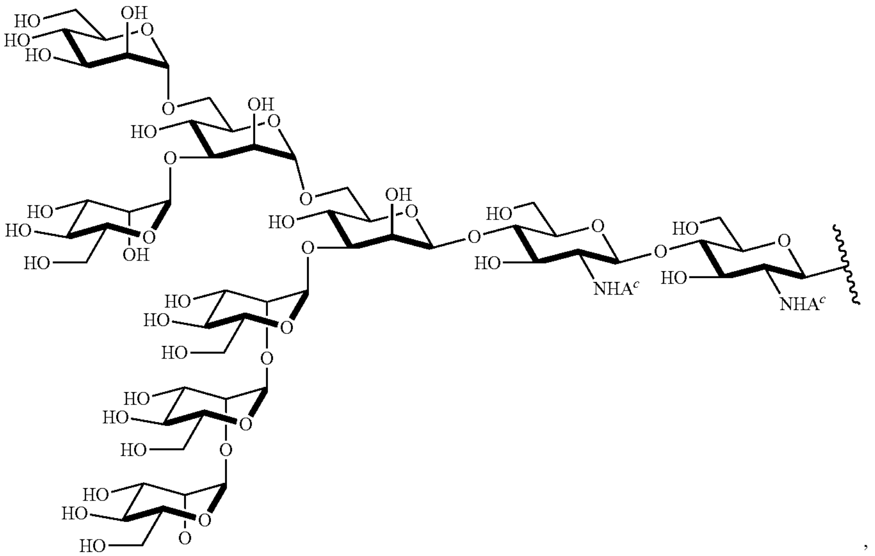

, where saccharide subunits include N-acetylglucosamine and mannose as shown (Walther et al., PLOS Pathogens 9(3): e1003223 (2013), which is hereby incorporated by reference in its entirety).

Exemplary N-linked glycan structures recognized by HIV broadly neutralizing antibodies (PGT151-PGT158) include multi-antennary complex-type N-glycans with terminal galactose with and without sialic acid residues:

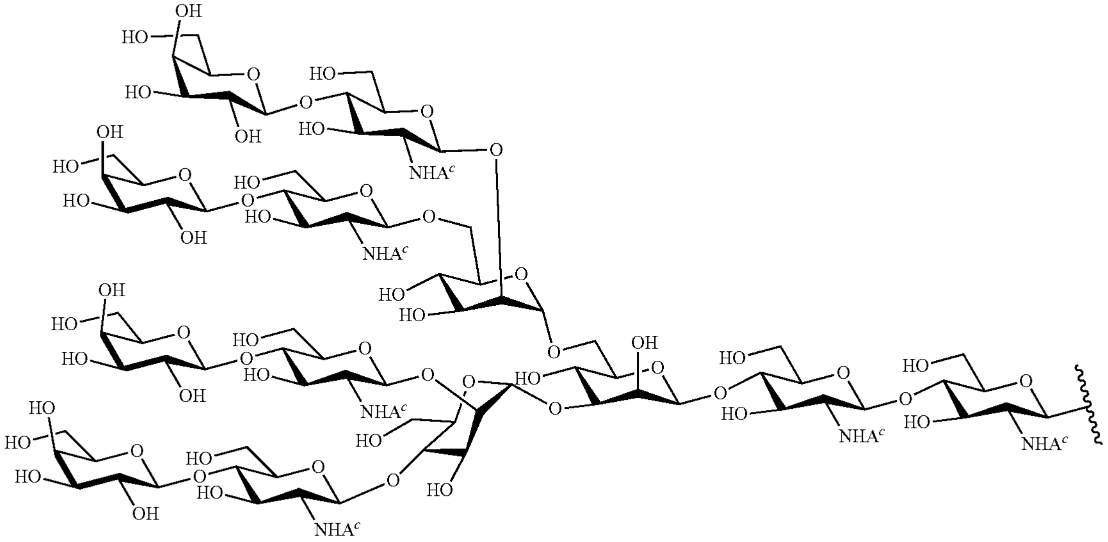

,

-continued
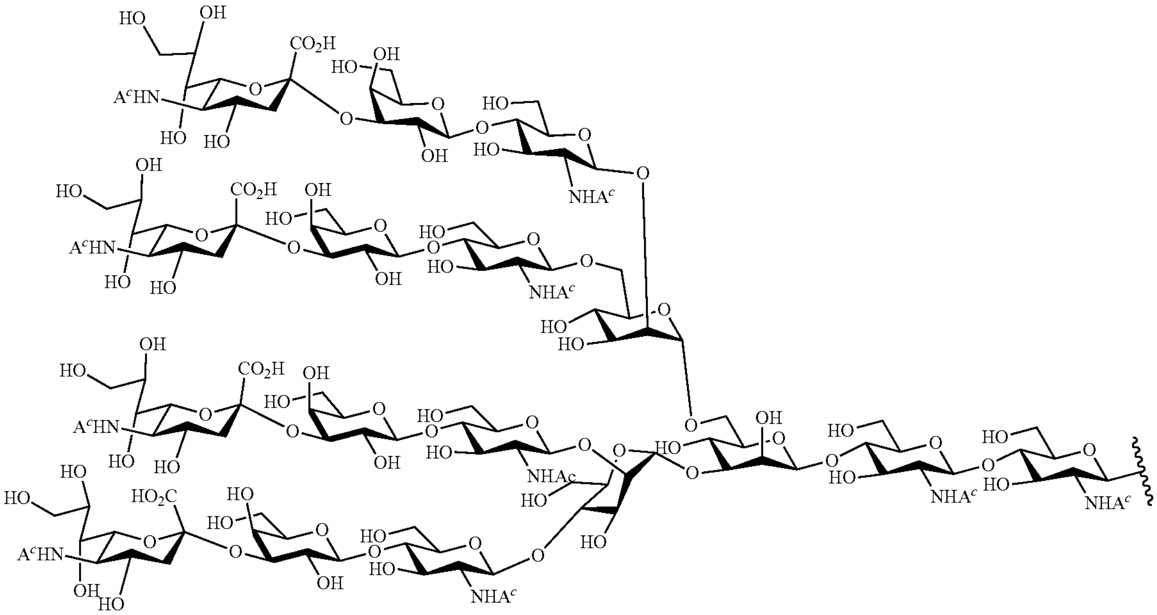
,
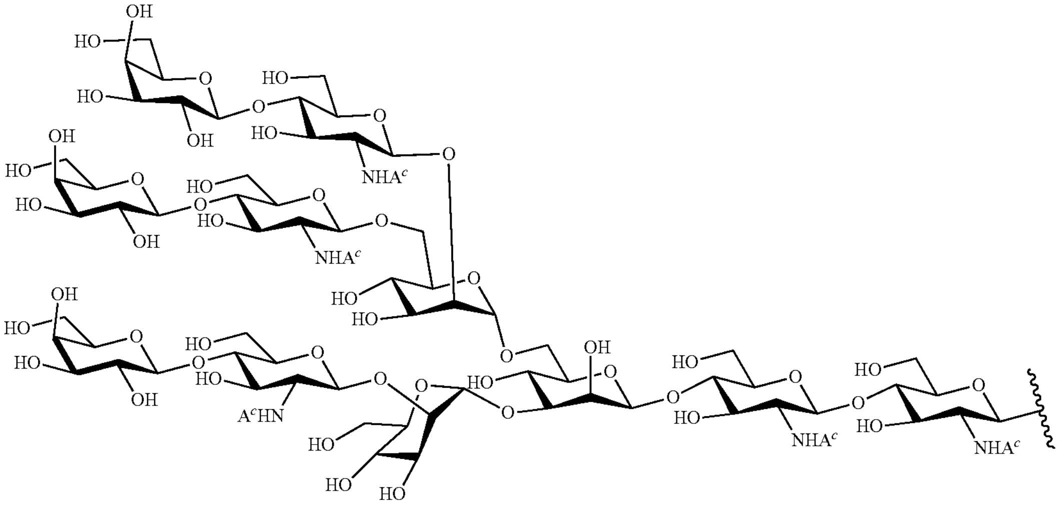
,
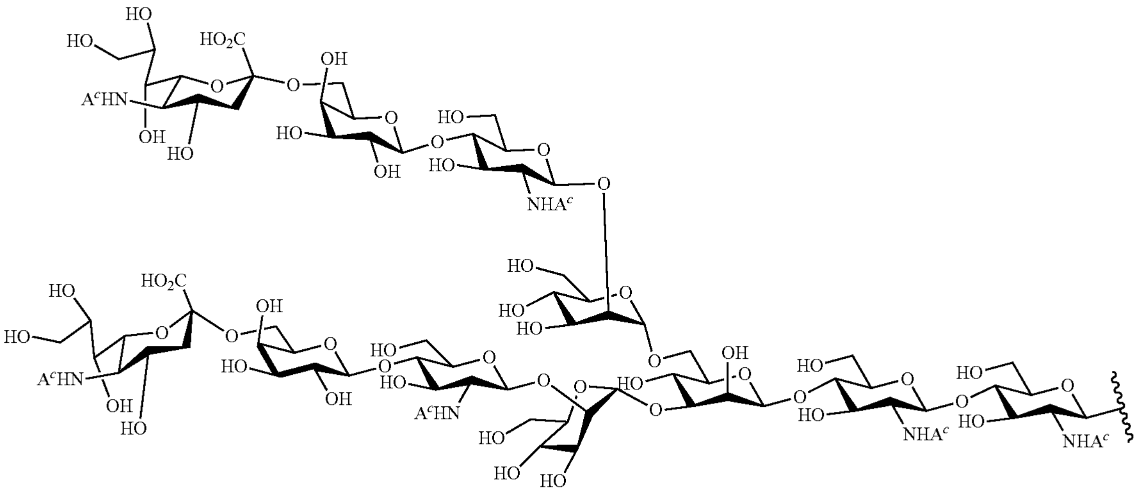
, and

-continued

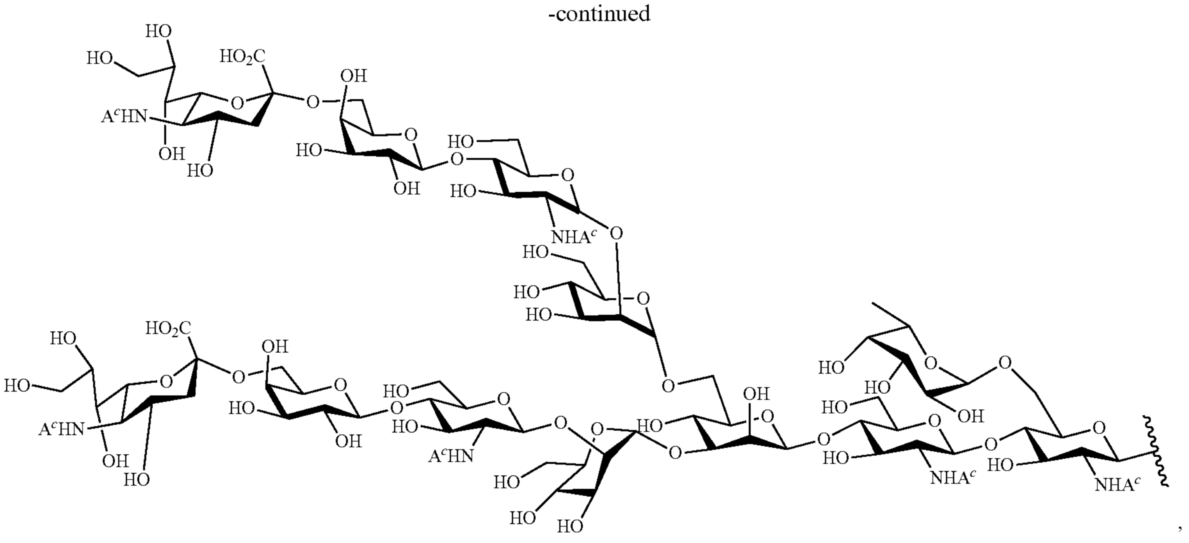

, where saccharide subunits include N-acetylglucosamine, mannose, galactose, sialic acid, and fucose as shown (Walther et al., PLOS Pathogens 9(3):e1003223 (2013) and Falkowska et al., Immunity 40(5): 657-6688 (2014), which are hereby incorporated by reference in their entirety).

Additional exemplary N-linked glycan structures include hybrid-type glycans recognized by HIV antibody PG16:

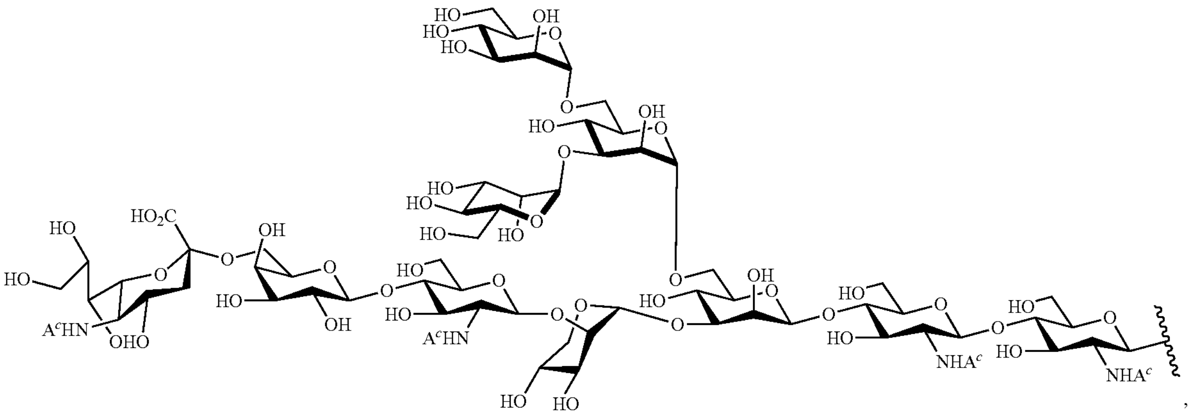

, where saccharide subunits include N-acetylglucosamine, mannose, galactose, and sialic acid (Pancera et al., Nature Struct Mol Biol. 20(7): 804-13 (2013), which is hereby incorporated by reference in its entirety).

Derivatization of the monosaccharides and/or oligosaccharides to introduce the reactive azido, alkynyl, alkenyl, or thiol group can be achieved using known procedures. See, e.g., Hoyle et al., Angew. Chem. Int. Ed. 49:1540-1573 (2010); Temme et al., Chem. Eur. J. 19:17291-17295 (2013); Hong et al., Angew. Chem. Int. Ed. 48:9879-9883 (2009); MacPherson et al., Angew. Chem. Int. Ed. 50:11238-11242 (2011); Kolb et al., Angew. Chem. Int. Ed. 40:2004-2021 (2001); Rostovtsev et al., Angew. Chem. Int. Ed. 41:2596-2599 (2002); Gierlich et al., Org. Lett. 8:3639-3642 (2006); Gierlich et al., Chem. Eur. J. 13:9486-9494 (2007), each of which is hereby incorporated by reference in its entirety.

Additional exemplary modified oligosaccharides (suitable for click reaction) include the following:
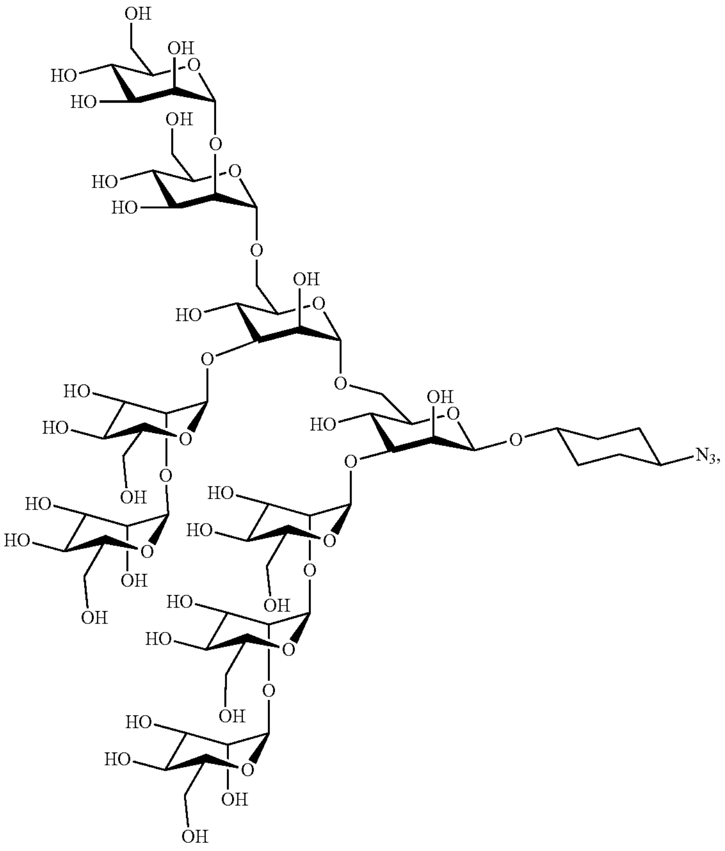
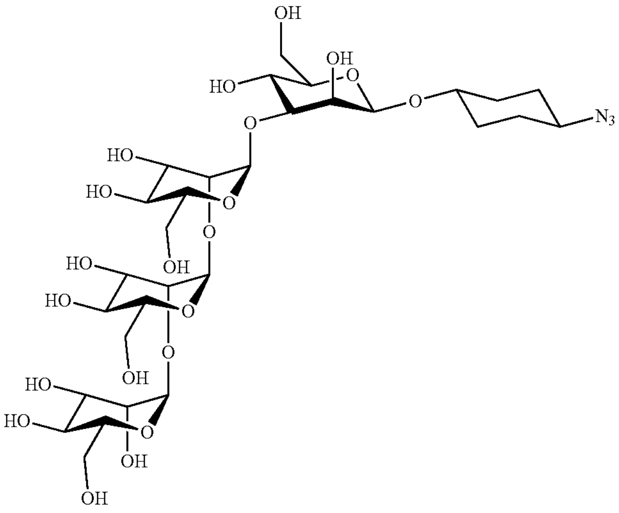
,
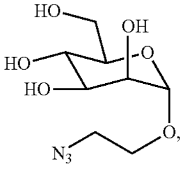

-continued
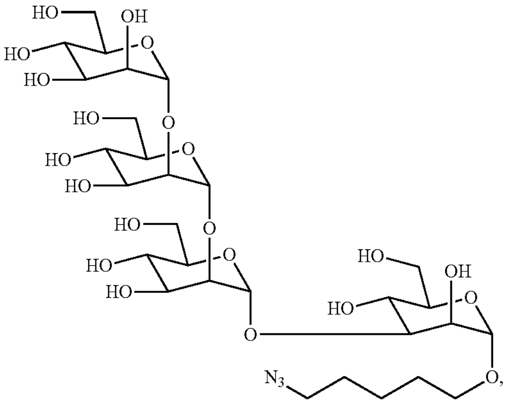
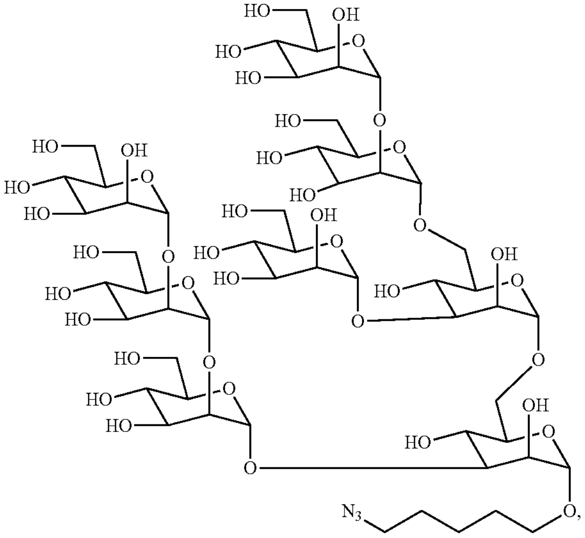
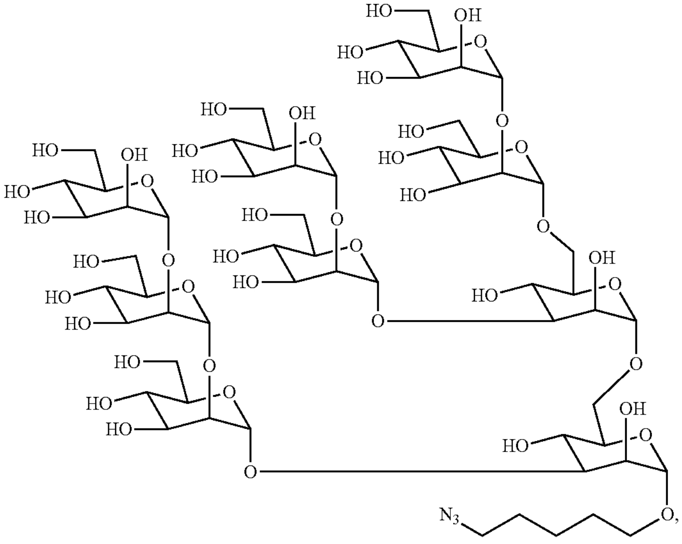

-continued
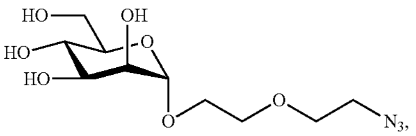
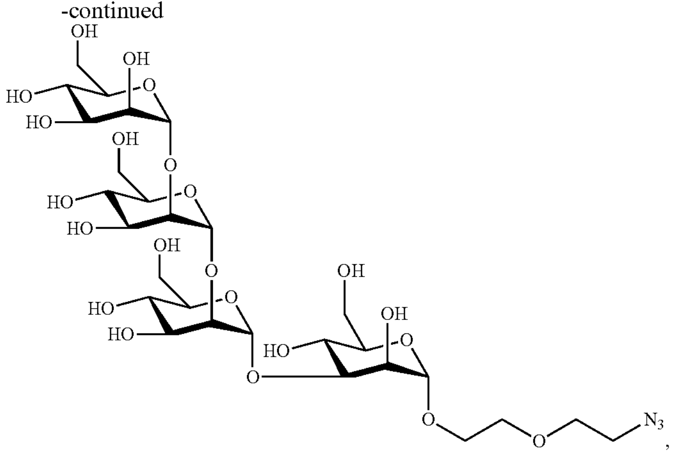
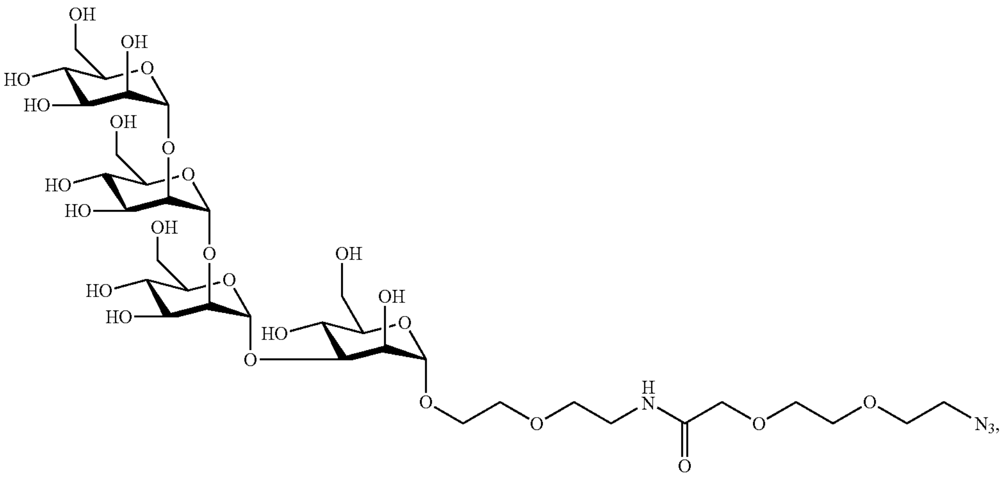
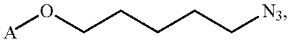

where A is the mono- or oligosaccharide,

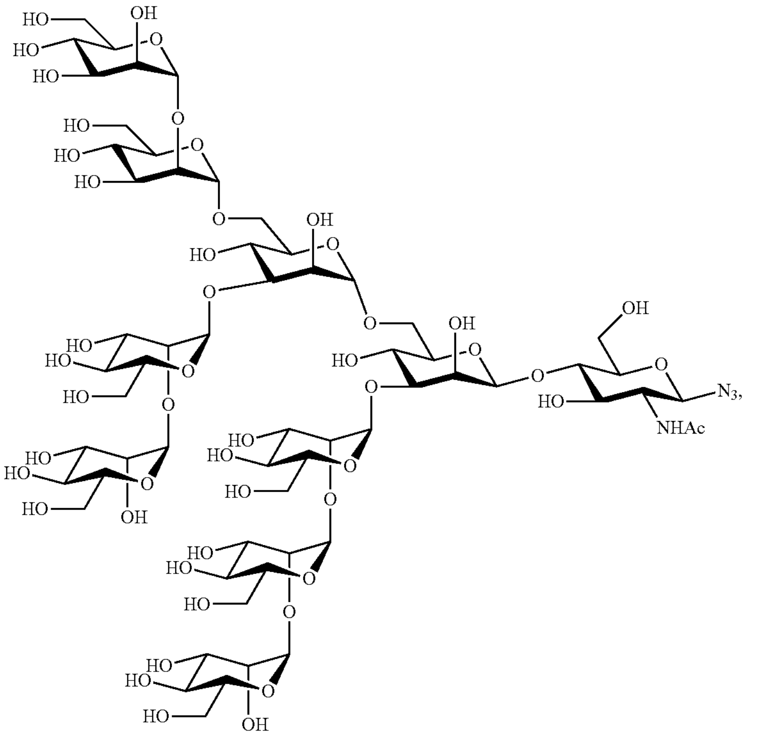

and

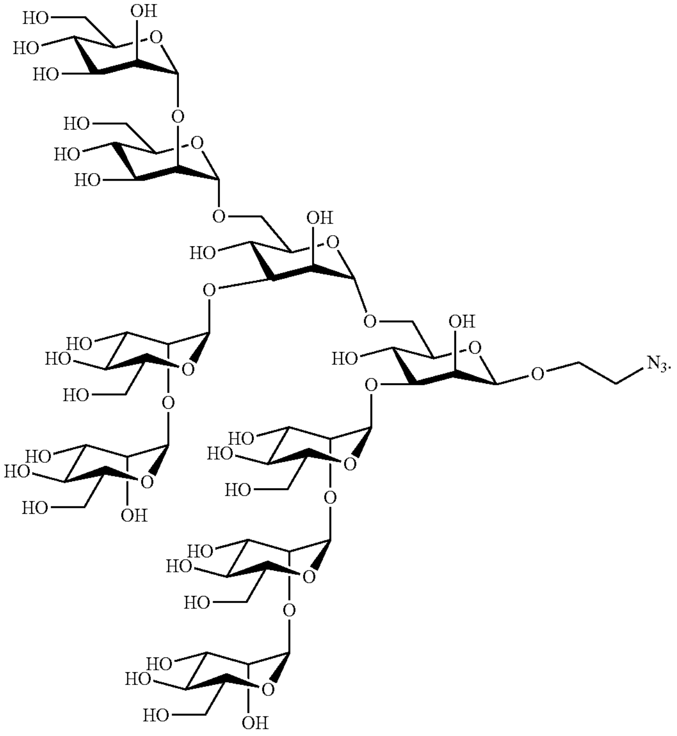

As an alternative to the above structures bearing an azide functional group, equivalent structures can be created with alkynyl, alkenyl, or thiol functional groups.

An exemplary GPI glycan includes the synthetic non-toxic malarial GPI glycan structure $NH_2$—$CH_2$—$CH_2$—$PO_4$-(Manα1-2)$_6$Manα1-2Mana-6Manα1-4GlcN$H_2$α1-6myo-inositol-1,2-cyclic-phosphate (Schofield et al., *Nature* 418(6899):785-9 (2002), which is hereby incorporated by reference in its entirety):

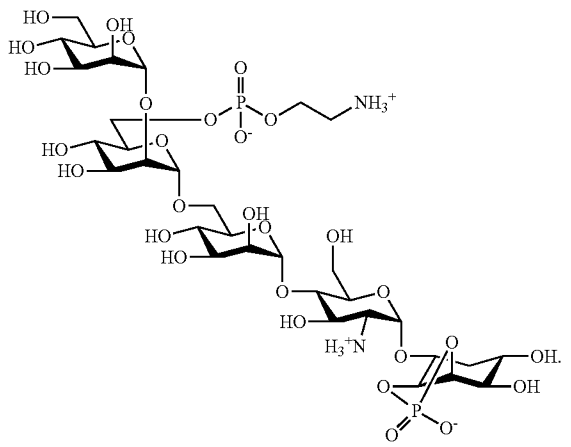

This structure can be derivatized to include an azido, alkynyl, alkenyl, or thiol group using the procedures identified above.

In certain embodiments, the modified amino acid residue comprises a linker molecule between the polypeptide chain and the oligosaccharide. Exemplary linker molecules include, without limitation:

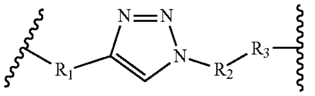

or

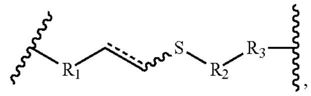

, wherein each of $R_1$ and $R_2$ is optionally a direct link or independently selected from the group consisting of a linear or branched $C_1$ to $C_{18}$ hydrocarbon that is saturated or mono- or poly-unsaturated, optionally interrupted by one or more non-adjacent —O—, —C(═O)—, or —$NR_4$—; a substituted or unsubstituted $C_3$ to $C_{10}$ cycloalkandiyl, a substituted or unsubstituted aryl diradical; a substituted or unsubstituted heteroaryl diradical; a monosaccharide diradical; or a disaccharide diradical; $R_3$ is optional and can be —O—, —S—, or —$NR_4$—; and $R_4$ is H or a $C_1$ to $C_{10}$ alkyl.

Although flexible linkers may be used, the linker between the oligosaccharide and the modified amino acid residue(s) of the glycopeptide preferably includes one or more cyclic moieties which offer some rigidity to the resulting glycosyl group.

In preferred embodiments, the glycopeptide binds specifically to carbohydrate-binding monoclonal antibody PGT128, PGT130, or germline PGT128 with an affinity that is substantially the same as or lower than the affinity of the carbohydrate-binding monoclonal antibody to its naturally occurring binding partner. As used herein, an affinity that is "substantially the same" means that as $K_d$ of glycopeptide for its target is less than 5×, less than 4×, less than 3×, less than 2×, or less than 1.5×$K_d$ of the native binding partner to the monoclonal antibody. In certain embodiments, the glycopeptide binds specifically to the carbohydrate-binding monoclonal antibody with an affinity that is lower than the affinity of the carbohydrate-binding monoclonal antibody to its naturally occurring binding partner.

The glycopeptide of the present invention may include one or more of the modified amino acid residues having a sidechain comprising an oligosaccharide, and the glycopeptide may bind specifically to carbohydrate-binding monoclonal antibody PGT128, PGT130, or germline PGT128 with an affinity of less than 100 nM. In certain embodiments, the glycopeptide binds specifically to monoclonal antibody PGT128 with an affinity ($K_d$) of less than 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM. In certain embodiments, the glycopeptide binds specifically to monoclonal antibody PGT130 with an affinity ($K_d$) of less than 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM. In certain embodiments, the glycopeptide binds specifically to monoclonal antibody glPGT128 with an affinity ($K_d$) of less than 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, or 1 nM.

In some embodiments, the monoclonal antibody PGT128 binds specifically to $Man_9GlcNAc_2$ glycans on HIV gp120 with an affinity comparable to the affinity of PGT128 binding to the glycopeptides of the invention. In other embodiments, the monoclonal antibody PGT128 binds specifically to $Man_8GlcNAc_2$ and/or $Man_9GlcNAc_2$ glycans on HIV gp120 with an affinity comparable to the affinity of PGT128 binding to the glycopeptides of the invention. By "comparable", it is intended that the variation is less than 50%, less than 40%, less than 30%, less than 20%, less than 10%, or less than 5% relative to the affinity of the binding mAb to gp120.

The glycopeptide may bind specifically to the carbohydrate-binding monoclonal antibody PGT128 with an affinity of less than 50 nm. For example, the glycopeptide may bind specifically to the carbohydrate-binding monoclonal antibody PGT128 with an affinity of less than 10 nM. In accordance with such embodiments, the glycopeptide comprises the sequence IGDIR (SEQ ID NO:1); the sequence IGDIRxA (SEQ ID NO:2), where x is any amino acid; the sequence HHHHHHRL (SEQ ID NO:3); the sequence GHHHHHHRL (SEQ ID NO:4); the sequence GxGHHHHHHRL (SEQ ID NO:5), wherein x is any amino acid; the sequence GSGSLGHHHHHHRL (SEQ ID NO:6); and/or the sequence GSGSGLGHHHHHHRL (SEQ ID NO:7.

In certain embodiments, the glycopeptide comprises the sequence IGDIR (SEQ ID NO:1) or IGDIRxA (SEQ ID NO:2), and a modified amino acid residue to which the oligosaccharide is linked. Exemplary glycopeptides containing (SEQ ID NO:1) and a modified amino acid residue to which the oligosaccharide is linked include, without limitation, the following sequences:

| Sequence | SEQ ID NO: |
|---|---|
| MAYFVHKKSRLLTNKAVKKRLHGCFQNQRSTIGDIRYAKCXRVSSNFFRRGSVS LGHHHHHHRL | 8 |
| MASHINSNPNQLLLLYLKSTIGDIRCAXCXDFRHYRNTKYVFXTRHNRRTGYGS LGHHHHHHRL | 9 |

-continued

| Sequence | SEQ ID NO: |
|---|---|
| MASYYIHDIAVSAYSKRRGYHNIQVESLYPKIGDIRSAKCXTWRNHRHTXGSGS LGHHHHHHRL | 10 |
| MAHYSXNHXRHPLYPSVNHRXSYPRIGLLSRIGDIRSASCXLRCFRXRSTGSGS LGHHHHHHRL | 11 |
| MAHNLRTXRNKNLIXLAFLHAPILKSRRLVHIGDIRVAACTHXVDVAPXYGSGS LGHHHHHHRL | 12 |
| XYPNTLNNVYQKCNKYNVIGDIRXARCXHXEHFSSQDQPKSKHKRRYKGFGSLG HHHHHHRL | 13 |
| MALIHSRQLVYSKNYXCCLDIGDIRHVLRGKYNDHLFGNAIYRKGVKAFNGSGS LGHHHHHHRL | 14 |
| MADNEFKILXIAXLHKSKHRTYLDYLNLVWXIGDIRAFQXXLKTVLXEAKGSGS LGHHHHHHRL | 15 |
| MAFHHXPHFTXRLPLLRRNCIGDIRRLYSPLPRDPHANFKFSFVEPNANRGSGS LGHHHHHHGYR | 16 |
| MATDHNHSHRRPRREHLDXNXHYSRPXVANXIGDIRTFRRRYIQVXYHLXGSDS LGHHHHHHRL | 17 |
| MAHXSIPHHRKSIDDSLRHLIGDIRYRNRYLXRILYRTSHYKNYYCQHSIGSGS LGHHHHHHRL | 18 |
| MANLXXYKXVVNXTLFQWXATHRYSHFHNKCIGDIRTTXSWTRSXXXHAXGSGS LGHHHHHHRL | 19 |
| MATFSRYHTIGDIRHHTLKHHQSKGLQXRLIFLKRQFKAXGNCLRWKILFGSCS LGHHHHHHRL | 20 |
| MALNSNSCHXRVATPISSWKIGDIRARFVSYLHYTNFSFSXXKXKFFTKXGSGS LGHHHHHHRL | 21 |
| MANVFPQTDRSLERSQCLFEAFHSIVXHXESIGDIRLECLRITIVALRTTGSGS LGHHHHHHRL | 22 |
| MAIPNGYRAFNRADXLLLTRIGDIRNAHCXARCNYIYELRPLHHYRWSNRGSGS LGHHHHHHRL | 23 |
| MANTFSYHQKLKXGRHTDEILHTHXXHKKXXIGDIRYATCXKCVIKSHFXGSGS LGHHHHHHRL | 24 |
| MAIHKHLHIHNKKFSTFKSIIGDIRLAWCXNEYNIXPRCNSPRRFSYTAFGSGS LGHHHHHHRL | 25 |
| MAFKTNHTRCDHNSQHIVSQFQKPHLKRSRLIGDIRXAICXIKKHRXCHHGSGS LGHHHHHHRL | 26 |
| MAKISRRYHTFRRVLFRKRQIGDIRNAICXVLHHAVXYXQSKNNCKSXVXGSGS LGHHHHHHRL | 27 |
| MAFRLSYHNSFNGPVHRPHVFVHNXYRKGLRIGDIRFAPCXTHHLNSWSHGSGS LGHHHHHHRL | 28 |
| MAHWHRHHGHXIHYPYRFINLLFSPHXLDVVIGDIRKANCXWFLYSVAXIGSGS LGHHHHHHRL | 29 |
| MAHFDPYCRLYVPAYNSHTIYYHQKTAYYYLFIGDIRIDAVAENRSPYPLRGSG HHHHHHRL | 30 |
| MAFDHHHXLIGDIRNDHNDFYHVEDGFANVYIILYIIYSQTTSEVLIVSVGSGS LGHHHHHHRL | 31 |
| MAIXFAPRHIGDIRHPKQRTAHWKIKTAYPLKSLWKIRYRLKHIDRIFLSGSGS LGHHHHHHRL | 32 |
| MANXTLLQLKALRXSLSPLFLRLPLKASHASIGDIRIXKTRRGPSFIRWYGSGS LGHHHHHHRL | 33 |
| MAKFAICHTIGDIRFEFTIIYTPHKYLVXDHDRHVXSLSVXLXSLXNHSRGSGS LGHHHHHHRL | 34 |

-continued

| Sequence | SEQ ID NO: |
|---|---|
| MAKLKDKLNNXKXNTTNASAIGDIRIHANXLDVFLRNXHHKXTNYGRFLXGSGS LGHHHHHHRL | 35 |
| XPHYYHYNTXHXYYRHXHHSIGDIRSHFXPTKHIWLSGXLXLIHYKSSNNGSGS LGHHHHHHRL | 36 |
| MAHYTNNTLRPLARHHHFRLEQRFGRHLTSNIGDIRLNHVFHXXLRRYYVGSGS LGHHHHHHRL | 37 |
| MAKFHDKNSYKSKHKKYNXLIGDIRXFNSYHRXXNCNKLCHPXISWDLFIGSGS LGHHHHHHRL | 38 |
| MAYTEKHNGIGDIRPAICXNSKNQNHRCNHYQIKLYIHXLXRLPHNYRNS GSGSGLGHHHHHHRL | 39 |
| MALTLRYLKIGDIRLANCXTVFPHFLSKKFFENGHRNLARPCTFRRNRHL GSGSGLGHHHHHHRL | 40 |
| MAYHKHRVXHHHEDKATSLTSNLVRLRLKTRIGDIRRALCXLSKFRYLIN GSGSGLGHHHHHHRL | 41 |
| MALLHHLRXIGDIRPAHCXVSHQRRYVPISRKNVFFKRGFNSHPLRKILW GSGSGLGHHHHHHRL | 42 |
| MARFRHSNNYYLTPFLTPLKTLISLQLRYRLIGDIRNASYXHKFSNRNRF GSGSGLGHHHHHHRL | 43 |
| MAIFNQGYRIKAWNDLKDIAIGDIRHALCXLVLARIKLQRRXVKYKHDHR GSGSGLGHHHHHHRL | 44 |
| MAHQHHHPNYALXQRRLSIAIGDIRLAICXFAHLYHCYRKHLXANTIPXK GSGSGLGHHHHHHRL | 45 |
| MAFVTYQHXSQKNFRRYQILRNHFHPQNYRFIGDIRHALCXFIFKNLXRH GSGSGLGHHHHHHRL | 46 |
| MAAXKIRSKIGDIRTAVCXFXHRHHHHHILDPYYLKXIVXYYSLKSRITL GSGSGLGHHHHHHRL | 47 |
| MAFIKPCXXYLLPPTXLNLYIGDIRRAKCXEAXNNFHXNNKPLXATXPPH GSGSGLGHHHHHHRL | 48 |
| MAKDILKLRIPFATLSGHRNIGDIRHAYCXSLKRPYIQVYSYLNHLKVRF GSGSGLGHHHHHHRL | 49 |
| MATLHNIHDLNHYYRNLNTRIGDIRHATCXYFFXKLKLLKHNRFXDRAIY GSGSGLGHHHHHHRL | 50 |
| MAPYRINQQXNFPWSSALFQIGDIRHARCXDSCRRFTNIXRYVYLKRRXN GSGSGLGHHHHHHRL | 51 |
| MALFKPYPKIGDIRKARCXLQHTLHHRTNKQPSYRRRLKTLIPLFRRCXL GSGSGLGHHHHHHRL | 52 |
| MATNHLHRTIGDIRHAQCXIYLIYLVQNDQYKRNNRTFRLXLNPKLLKRF GSGSGLGHHHHHHRL | 53 |
| MATNSYYHHNPLXRRTHVVXTLKPXNFWAKXIGDIRRAHCXTTINXLKRR GSGSGLGHHHHHHRL | 54 |
| MAILLHVSTRSRYPHHHXAIIGDIRCASCXYPVLKWFYNFNRLKTYRKQF GSGSGLGHHHHHHRL | 55 |
| MAYRTHKLLHHHNDKWKSNIFPRIFVCHYYLIGDIRHARCXIPLEILRRY GSGSGLGHHHHHHRL | 56 |
| MAYSKHRFSFRHNNXLRDRKLIRKFSYHNHSIGDIRVANKFRYLHVFKFI GSGSGLGHHHHHHRL | 57 |
| MASIKLINQXXTTNPHLRLHIGDIRRLIKDLYXFRVYYRPTNSGRRLFVN GSGSGLGHHHHHHRL | 58 |
| MAHSHHHSPXIEFHSNGRLHIGDIRKFYADALXVLFFKXAFIDRIPFHDA GSGSGLGHHHHHHRL | 59 |

-continued

| Sequence | SEQ ID NO: |
|---|---|
| MANIYFCSRRTNFHNSCYLXIGDIRGLSIYHHIXIHNKLHLLIXYNLLXX GSGSGLGHHHHHHRL | 60 |
| MAIHYHHPIIGDIRLKHNXINAHTKHVPQKLYLDIKFRRLFGLYILRXLN GSGSGLGHHHHHHRL | 61 |
| MAILYHYHNIGDIRRSQRHLNXQXRLYVSTLLHSSHTLRRASITHRIRKF GSGSGLGHHHHHHRL | 62 |
| MATFSRYHTIGDIRHHTLKHHQSKGLQXRLIFLKRQFKAXGNCLRWKILF GSGSGLGHHHHHHRL | 63 |
| MAKYTHIHSIGDIRNTYRNKHKHXALNKTNWALFQQHHRXLIRLFYRRLL GSGSGLGHHHHHHRL | 64 |
| MALNKHKHLRNHTRHHSVPTIGDIRKRIHNLLHYLAGFRFFNQXHSKXGV GSGSGLGHHHHHHRL | 65 |
| MAYLHNHHNYSSNNKLHHLEIGDIRLIYQKYLRNPXFXTFLSRKHXNWQR GSGSGLGHHHHHHRL | 66 |
| MANLTAXSRIGDIRKHHFGRPLYLTKHGAYPRYHTRYKHLLTYRHHFPLI GSGSGLGHHHHHHRL | 67 |
| MAKHTHLRPXNFTQRLRKAHIGDIRLPRNISTSRIRTHIKFHLIRXHLRN GSGSGLGHHHHHHRL | 68 |
| MAFLLNHKRIGDIRKLPPLNLXATKTLTKERIRKIVNGFVQRLKGHSWWI GSGSGLGHHHHHHRL | 69 |
| MAIHHSYRGFTLRIPLTTNKIGDIRTAFPYPXLSHLFDRRRWKRGLHNWF GSGSGLGHHHHHHRL | 70 |

wherein X is the modified amino acid residue to which the oligosaccharide is linked.

In certain embodiments, the glycopeptide comprises the sequence IGDIR (SEQ ID NO:1) or IGDIRxA (SEQ ID NO:2), but does not comprise the sequence HHHHHHRL (SEQ ID NO:3); the sequence GHHHHHHRL (SEQ ID NO:4); the sequence GxGHHHHHHRL (SEQ ID NO:5), wherein x is any amino acid; the sequence GSGSLGHHHHHHRL (SEQ ID NO:6); and/or the sequence GSGSGLGHHHHHHRL (SEQ ID NO:7). Thus, additional exemplary glycopeptides containing (SEQ ID NO:1) and a modified amino acid residue to which the oligosaccharide is linked include, without limitation, the following sequences:

| Sequence | SEQ ID NO: |
|---|---|
| MAYFVHKKSRLLTNKAVKKRLHGCFQNQRSTIGDIRYAKCXRVSSNFFRRGSV | 71 |
| MASHINSNPNQLLLLYLKSTIGDIRCAXCXDFRHYRNTKYVFXTRHNRRTGY | 72 |
| MASYYIHDIAVSAYSKRRGYHNIQVESLYPKIGDIRSAKCXTWRNHRHTX | 73 |
| MAHYSXNHXRHPLYPSVNHRXSYPRIGLLSRIGDIRSASCXLRCFRXRST | 74 |
| MAHNLRTXRNKNLIXLAFLHAPILKSRRLVHIGDIRVAACTHXVDVAPXY | 75 |
| XYPNTLNNVYQKCNKYNVIGDIRXARCXHXEHFSSQDQPKSKHKRRYKGF | 76 |
| MALIHSRQLVYSKNYXCCLDIGDIRHVLRGKYNDHLFGNAIYRKGVKAFN | 77 |
| MADNEFKILXIAXLHKSKHRTYLDYLNLVWXIGDIRAFQXXLKTVLXEAK | 78 |
| MAFHHXPHFTXRLPLLRRNCIGDIRRLYSPLPRDPHANFKFSFVEPNANR | 79 |
| MATDHNHSHRRPRREHLDXNXHYSRPXVANXIGDIRTFRRRYIQVXYHLXGSD | 80 |
| MAHXSIPHHRKSIDDSLRHLIGDIRYRNRYLXRILYRTSHYKNYYCQHSI | 81 |
| MANLXXYKXVVNXTLFQWXATHRYSHFHNKCIGDIRTTXSWTRSXXXHAX | 82 |
| MATFSRYHTIGDIRHHTLKHHQSKGLQXRLIFLKRQFKAXGNCLRWKILFGSC | 83 |
| MALNSNSCHXRVATPISSWKIGDIRARFVSYLHYTNFSFSXXKXKFFTKX | 84 |

| Sequence | SEQ ID NO: |
|---|---|
| MANVFPQTDRSLERSQCLFEAFHSIVXHXESIGDIRLECLRITIVALRTT | 85 |
| MAIPNGYRAFNRADXLLLTRIGDIRNAHCXARCNYIYELRPLHHYRWSNR | 86 |
| MANTFSYHQKLKXGRHTDEILHTHXXHKKXXIGDIRYATCXKCVIKSHFX | 87 |
| MAIHKHLHIHNKKFSTFKSIIGDIRLAWCXNEYNIXPRCNSPRRFSYTAF | 88 |
| MAFKTNHTRCDHNSQHIVSQFQKPHLKRSRLIGDIRXAICXIKKHRXCHH | 89 |
| MAKISRRYHTFRRVLFRKRQIGDIRNAICXVLHHAVXYXQSKNNCKSXVX | 90 |
| MAFRLSYHNSFNGPVHRPHVFVHNXYRKGLRIGDIRFAPCXTHHLNSWSH | 91 |
| MAHWHRHHGHXIHYPYRFINLLFSPHXLDVVIGDIRKANCXWFLYSVAXI | 92 |
| MAHFDPYCRLYVPAYNSHTIYYHQKTAYYYLFIGDIRIDAVAENRSPYPLRGS | 93 |
| MAFDHHHXLIGDIRNDHNDFYHVEDGFANVYIILYIIYSQTTSEVLIVSV | 94 |
| MAIXFAPRHIGDIRHPKQRTAHWKIKTAYPLKSLWKIRYRLKHIDRIFLS | 95 |
| MANXTLLQLKALRXSLSPLFLRLPLKASHASIGDIRIXKTRRGPSFIRWY | 96 |
| MAKFAICHTIGDIRFEFTIIYTPHKYLVXDHDRHVXSLSVXLXSLXNHSR | 97 |
| MAKLKDKLNNXKXNTTNASAIGDIRIHANXLDVFLRNXHHKXTNYGRFLX | 98 |
| XPHYYHYNTXHXYYRHXHHSIGDIRSHFXPTKHIWLSGXLXLIHYKSSNN | 99 |
| MAHYTNNTLRPLARHHHFRLEQRFGRHLTSNIGDIRLNHVFHXXLRRYYV | 100 |
| MAKFHDKNSYKSKHKKYNXLIGDIRXFNSYHRXXNCNKLCHPXISWDLFI | 101 |
| MAYTEKHNGIGDIRPAICXNSKNQNHRCNHYQIKLYIHXLXRLPHNYRNS | 102 |
| MALTLRYLKIGDIRLANCXTVFPHFLSKKFFENGHRNLARPCTFRRNRHL | 103 |
| MAYHKHRVXHHHEDKATSLTSNLVRLRLKTRIGDIRRALCXLSKFRYLIN | 104 |
| MALLHHLRXIGDIRPAHCXVSHQRRYVPISRKNVFFKRGFNSHPLRKILW | 105 |
| MARFRHSNNYYLTPFLTPLKTLISLQLRYRLIGDIRNASYXHKFSNRNRF | 106 |
| MAIFNQGYRIKAWNDLKDIAIGDIRHALCXLVLARIKLQRRXVKYKHDHR | 107 |
| MAHQHHHPNYALXQRRLSIAIGDIRLAICXFAHLYHCYRKHLXANTIPXK | 108 |
| MAFVTYQHXSQKNFRRYQILRNHFHPQNYRFIGDIRHALCXFIFKNLXRH | 109 |
| MAAXKIRSKIGDIRTAVCXFXHRHHHHHILDPYYLKXIVXYYSLKSRITL | 110 |
| MAFIKPCXXYLLPPTXLNLYIGDIRRAKCXEAXNNFHXNNKPLXATXPPH | 111 |
| MAKDILKLRIPFATLSGHRNIGDIRHAYCXSLKRPYIQVYSYLNHLKVRF | 112 |
| MATLHNIHDLNHYYRNLNTRIGDIRHATCXYFFXKLKLLKHNRFXDRAIY | 113 |
| MAPYRINQQXNFPWSSALFQIGDIRHARCXDSCRRFTNIXRYVYLKRRXN | 114 |
| MALFKPYPKIGDIRKARCXLQHTLHHRTNKQPSYRRRLKTLIPLFRRCXL | 115 |
| MATNHLHRTIGDIRHAQCXIYLIYLVQNDQYKRNNRTFRLXLNPKLLKRF | 116 |
| MATNSYYHHNPLXRRTHVVXTLKPXNFWAKXIGDIRRAHCXTTINXLKRR | 117 |
| MAILLHVSTRSRYPHHHXAIIGDIRCASCXYPVLKWFYNFNRLKTYRKQF | 118 |
| MAYRTHKLLHHHNDKWKSNIFPRIFVCHYYLIGDIRHARCXIPLEILRRY | 119 |
| MAYSKHRFSFRHNNXLRDRKLIRKFSYHNHSIGDIRVANKFRYLHVFKFI | 120 |
| MASIKLINQXXTTNPHLRLHIGDIRRLIKDLYXFRVYYRPTNSGRRLFVN | 121 |
| MAHSHHHSPXIEFHSNGRLHIGDIRKFYADALXVLFFKXAFIDRIPFHDA | 122 |

-continued

| Sequence | SEQ ID NO: |
|---|---|
| MANIYFCSRRTNFHNSCYLXIGDIRGLSIYHHIXIHNKLHLLIXYNLLXX | 123 |
| MAIHYHHPIIGDIRLKHNXINAHTKHVPQKLYLDIKFRRLFGLYILRXLN | 124 |
| MAILYHYHNIGDIRRSQRHLNXQXRLYVSTLLHSSHTLRRASITHRIRKF | 125 |
| MATFSRYHTIGDIRHHTLKHHQSKGLQXRLIFLKRQFKAXGNCLRWKILF | 126 |
| MAKYTHIHSIGDIRNTYRNKHKHXALNKTNWALFQQHHRXLIRLFYRRLL | 127 |
| MALNKHKHLRNHTRHHSVPTIGDIRKRIHNLLHYLAGFRFFNQXHSKXGV | 128 |
| MAYLHNHHNYSSNNKLHHLEIGDIRLIYQKYLRNPXFXTFLSRKHXNWQR | 129 |
| MANLTAXSRIGDIRKHHFGRPLYLTKHGAYPRYHTRYKHLLTYRHHFPLI | 130 |
| MAKHTHLRPXNFTQRLRKAHIGDIRLPRNISTSRIRTHIKFHLIRXHLRN | 131 |
| MAFLLNHKRIGDIRKLPPLNLXATKTLTKERIRKIVNGFVQRLKGHSWWI | 132 |
| MAIHHSYRGFTLRIPLTTNKIGDIRTAFPYPXLSHLFDRRRWKRGLHNWF | 133 |

wherein X is the modified amino acid residue to which the oligosaccharide is linked.

In certain embodiments, the glycopeptide comprises a modified amino acid residue to which the oligosaccharide is linked, but does not comprise the sequence IGDIR (SEQ ID NO:1). Exemplary glycopeptides containing a modified amino acid residue to which the oligosaccharide is linked include, without limitation, the following sequences:

| Sequence | SEQ ID NO: |
|---|---|
| MAYFQNTSINNINALNQATQKNFFRIRLEIXTLNLVSKR YCNAXXHLLXXGFGSLGHHHHHHRL | 134 |
| MARFHSRSPFKDSHLFRNGTVGDIRSRAVHAQAEQRRGY LLVRLRGHRVGGLGSLGHHHHHHRL | 135 |
| MAKLKVCNXYAFSRPGWXIRKDIEFYYRINLVGDVRYAT CXRYGYLILTQGSGSLGHHHHHHRL | 136 |
| MATYHXTINXNXAYRXRTYSARNSIVSTENHIDDIRAAQ LGCXTNPKHLSFIGSGTHHHHHHRL | 137 |
| MANHKHTHISLKSIVQTHGGPHPNVARAANLLLEQLPVV RRRLQRRLLQRGLRSLGHHHHHHRL | 138 |
| XSNYVNSYLNTHLQLDQSTTIGDIHGLRKLGRYATESSF XRIHNISFLSHSGSGLGHHHHHHRL | 139 |
| MAIRKNFPXTFGHRPHLRVAHAQRAQHALLVLRRARRLL GSDQEVDAPGGRRGSGLGHHHHHHRL | 140 |
| MAHHYPNYHXRSHGDRLTLLRHLXSFLVDHKQILXFLLR XRKNHVSXXXTGSGSGLGHHHHHHRL | 141 |

wherein X is the modified amino acid residue to which the oligosaccharide is linked.

In certain embodiments, the glycopeptide comprises a modified amino acid residue to which the oligosaccharide is linked, does not comprises the sequence IGDIR (SEQ ID NO:1); the sequence IGDIRxA (SEQ ID NO:2); the sequence HHHHHHRL (SEQ ID NO:3); the sequence GHHHHHHRL (SEQ ID NO:4); the sequence GxGHHHHHHRL (SEQ ID NO:5), wherein x is any amino acid; the sequence GSGSLHHHHHHRL (SEQ ID NO:6); and/or the sequence GSGSGLGHHHHHHRL (SEQ ID NO:7). Thus, additional exemplary glycopeptides containing a modified amino acid residue to which the oligosaccharide is linked include, without limitation, the following sequences:

| Sequence | SEQ ID NO: |
|---|---|
| MAYFQNTSINNINALNQATQKNFFRIRLEIXTLNLVSKR YCNAXXHLLXXGF | 142 |
| MARFHSRSPFKDSHLFRNGTVGDIRSRAVHAQAEQRRGY LLVRLRGHRVGGL | 143 |
| MAKLKVCNXYAFSRPGWXIRKDIEFYYRINLVGDVRYAT CXRYGYLILTQ | 144 |
| MATYHXTINXNXAYRXRTYSARNSIVSTENHIDDIRAAQ CXTNPKHLSFIGSGT | 145 |
| MANHKHTHISLKSIVQTHGGPHPNVARAANLLLEQLPVV RRRLQRRLLQRGLR | 146 |
| XSNYVNSYLNTHLQLDQSTTIGDIHGLRKLGRYATESSF XRIHNISFLSH | 147 |
| MAIRKNFPXTFGHRPHLRVAHAQRAQHALLVLRRARRLL DQEVDAPGGRR | 148 |
| MAHHYPNYHXRSHGDRLTLLRHLXSFLVDHKQILXFLLR XRKNHVSXXXT | 149 |

wherein X is the modified amino acid residue to which the oligosaccharide is linked.

In some embodiments, the glycopeptide is a cyclic glycopeptide. Thus, the glycopeptide may comprise, without limitation, the following sequences:

| Sequence | SEQ ID NO: |
|---|---|
| linker<br>MAYFVHKKSRLLTNKAVKKRLHG**C**FQNQRSTIGDIRYAK**C**XRVSSNFFRRGSVSLGHHHHHHRL | 8 |
| linker<br>MASHINSNPNQLLLLYLKSTIGDIR**C**AX_____**C**XDFRHYRNTKYVFXTRHNRRTGYGSLGHHHHHHRL | 9 |
| Linker<br>MAHYSXNHXRHPLYPSVNHRXSYPRIGLLSRIGDIRSAS**C**XLR____**C**FRXRSTGSGSLGHHHHHHRL | 11 |
| Linker<br>XYPNTLNNVYQK**C**NKYNVIGDIRXAR**C**XHXEHFSSQDQPKSKHKRRYKGFGSLGHHHHHHRL | 13 |
| linker<br>MALIHSRQLVYSKNYX**C**________**C**LDIGDIRHVLRGKYNDHLFGNAIYRKGVKAFNGSGSLGHHHHHHRL | 14 |
| linker<br>MATFSRYHTIGDIRHHTLKHHQSKGLQXRLIFLKRQFKAXGN**C**LRWKILFGS**C**SLGHHHHHHRL | 20 |
| linker<br>MANVFPQTDRSLERSQ**C**LFEAFHSIVXHXESIGDIRLE**C**LRITIVALRTTGSGSLGHHHHHRL | 22 |
| linker<br>MAIPNGYRAFNRADXLLLTRIGDIRNAH**C**XAR___**C**NYIYELRPLHHYRWSNRGSGSLGHHHHHHRL | 23 |
| linker<br>MANTFSYHQKLKXGRHTDEILHTHXXHKKXXIGDIRYAT**C**XK____**C**VIKSHFXGSGSLGHHHHHHRL | 24 |
| linker<br>MAIHKHLHIHNKKFSTFKSIIGDIRLAW**C**XNEYNIXPR**C**NSPRRFSYTAFGSGSLGHHHHHHRL | 25 |
| linker<br>MAKISRRYHTFRRVLFRKRQIGDIRNAI**C**XVLHHAVXYXQSKNN**C**KSXVXGSGSLGHHHHHHRL | 27 |
| linker<br>MAKLKV**C**NXYAFSRPGWXIRKDIEFYYRINLVGDVRYAT**C**XRYGYLILTQGSGSLGHHHHHHRL | 136 |
| linker<br>MAKFHDKNSYKSKHKKYNXLIGDIRXFNSYHRXXN**C**NKL___**C**HPXISWDLFIGSGSLGHHHHHHRL | 38 |
| linker<br>MAYFVHKKSRLLTNKAVKKRLHG**C**FQNQRSTIGDIRYAK**C**XRVSSNFFRRGSV | 71 |
| linker<br>MASHINSNPNQLLLLYLKSTIGDIR**C**AX____**CX**DFRHYRNTKYVFXTRHNRRTGY | 72 |
| linker<br>MAHYSXNHXRHPLYPSVNHRXSYPRIGLLSRIGDIRSAS**C**XLR____**C**FRXRST | 74 |
| linker<br>XYPNTLNNVYQK**C**NKYNVIGDIRXAR**C**XHXEHFSSQDQPKSKHKRRYKGF | 76 |
| linker<br>MALIHSRQLVYSKNYX**C**________**C**LDIGDIRHVLRGKYNDHLFGNAIYRKGVKAFN | 77 |

-continued

| Sequence | SEQ ID NO: |
|---|---|
| linker<br>MATFSRYHTIGDIRHHTLKHHQSKGLQXRLIFLKRQFKAXGN**C**LRWKILFGS**C** | 83 |
| linker<br>MANVFPQTDRSLERSQ**C**LFEAFHSIVXHXESIGDIRLE**C**LRITIVALRTT | 85 |
| linker<br>MAIPNGYRAFNRADXLLLTRIGDIRNAH**C**XAR___**C**NYIYELRPLHHYRWSNR | 86 |
| linker<br>MANTFSYHQKLKXGRHTDEILHTHXXHKKXXIGDIRYAT**C**XK____**C**VIKSHFX | 87 |
| linker<br>MAIHKHLHIHNKKFSTFKSIIGDIRLAW**C**XNEYNIXPR**C**NSPRRFSYTAF | 88 |
| linker<br>MAKISRRYHTFRRVLFRKRQIGDIRNAI**C**XVLHHAVXYXQSKNN**C**KSXVX | 90 |
| linker<br>MAKFHDKNSYKSKHKKYNXLIGDIRXFNSYHRXXN**C**NKL___**C**HPXISWDLFI | 101 |
| linker<br>MAKLKV**C**NXYAFSRPGWXIRKDIEFYYRINLVGDVRYAT**C**XRYGYLILTQ | 144 |
| linker<br>MAYTEKHNGIGDIRPAI**C**XNSKNQNHR**C**NHYQIKLYIHXLXRLPHNYRNSGSGSGLGH<br>HHHHHRL | 39 |
| linker<br>MALTLRYLKIGDIRLAN**C**XTVFPHFLSKKFFENGHRNLARP**C**TFRRNRHLGSGSGLGH<br>HHHHHRL | 40 |
| linker<br>MAHQHHHPNYALXQRRLSIAIGDIRLAI**C**XFAHLYH**C**YRKHLXANTIPXKGSGSGLGH<br>HHHHHRL | 45 |
| linker<br>MAFIKP**C**XXYLLPPTXLNLYIGDIRRAK**C**XEAXNNFHXNNKPLXATXPPHGSGSGLGH<br>HHHHHRL | 48 |
| linker<br>MAPYRINQQXNFPWSSALFQIGDIRHAR**C**XDS_____**C**RRFTNIXRYVYLKRRXNGSG<br>SGLGHHHHHHRL | 51 |
| linker<br>MALFKPYPKIGDIRKAR**C**XLQHTLHHRTNKQPSYRRRLKTLIPLFRR**C**XLGSGSGLGH<br>HHHHHRL | 52 |
| linker<br>MAILLHVSTRSRYPHHHXAIIGDIR**C**AS______**C**XYPVLKWFYNFNRLKTYRKQFGS<br>GSGLGHHHHHHRL | 55 |
| linker<br>MAYRTHKLLHHHNDKWKSNIFPRIFV**C**HYYLIGDIRHAR**C**XIPLEILRRYGSGSGLGH<br>HHHHHRL | 56 |
| linker<br>MANIYF**C**SRRTNFHNS**C**YLXIGDIRGLSIYHHIXIHNKLHLLIXYNLLXXGSGSGLGH<br>HHHHHRL | 60 |
| linker<br>MAYTEKHNGIGDIRPAI**C**XNSKNQNHR**C**NHYQIKLYIHXLXRLPHNYRNS | 102 |
| linker<br>MALTLRYLKIGDIRLAN**C**XTVFPHFLSKKFFENGHRNLARP**C**TFRRNRHL | 103 |

-continued

| Sequence | SEQ ID NO: |
|---|---|
| linker<br>MAHQHHHPNYALXQRRLSIAIGDIRLAI**C**XFAHLYH**C**YRKHLXANTIPXK | 108 |
| linker<br>MAFIKP**C**XXYLLPPTXLNLYIGDIRRAK**C**XEAXNNFHXNNKPLXATXPPH | 111 |
| linker<br>MAPYRINQQXNFPWSSALFQIGDIRHAR**C**XDS______**C**RRFTNIXRYVYLKRRXN | 114 |
| linker<br>MALFKPYPKIGDIRKAR**C**XLQHTLHHRTNKQPSYRRRLKTLIPLFRR**C**XL | 115 |
| linker<br>MAILLHVSTRSRYPHHHXAIIGDIR**C**AS______**C**XYPVLKWFYNFNRLKTYRKQF | 118 |
| linker<br>MAYRTHKLLHHHNDKWKSNIFPRIFV**C**HYYLIGDIRHAR**C**XIPLEILRRY | 119 |
| linker<br>MANIYF**C**SRRTNFHNS**C**YLXIGDIRGLSIYHHIXIHNKLHLLIXYNLLXX | 123 |

wherein X is the modified amino acid residue to which the oligosaccharide is linked, and the Cys-Cys linker is one of the bis-alkylbenzene or bis-alkylpyridine groups described hereinafter.

In some embodiments, the monoclonal antibody PGT130 binds specifically to $Man_9GlcNAc_2$ glycans on HIV gp120 with an affinity comparable to the affinity of PGT130 binding to the glycopeptides of the invention. In other embodiments, the monoclonal antibody PGT130 binds specifically to $Man_8GlcNAc_2$ and/or $Man_9GlcNAc_2$ glycans on HIV gp120 with an affinity comparable to the affinity of PGT130 binding to the glycopeptides of the invention. By "comparable", it is intended that the variation is less than 50%, less than 40%, less than 30%, less than 20%, less than 10%, or less than 5% relative to the affinity of the binding mAb to gp120.

The glycopeptide may bind specifically to the carbohydrate-binding monoclonal antibody PGT130 with an affinity of less than 50 nm. For example, the glycopeptide may bind specifically to the carbohydrate-binding monoclonal antibody PGT130 with an affinity of less than 10 nM. In accordance with such embodiments, the glycopeptide comprises the sequence IGDIR (SEQ ID NO:1); the sequence IGDIRxA (SEQ ID NO:2), where x is any amino acid; the sequence HHHHHHRL (SEQ ID NO:3); the sequence GHHHHHHRL (SEQ ID NO:4); the sequence GxGHHHHHHRL (SEQ ID NO:5), wherein x is any amino acid; the sequence GSGSLGHHHHHHRL (SEQ ID NO:6); and/or the sequence GSGSGLGHHHHHHRL (SEQ ID NO:7.

In certain embodiments, the glycopeptide comprises the sequence IGDIR (SEQ ID NO:1) or IGDIRxA (SEQ ID NO:2), and a modified amino acid residue to which the oligosaccharide is linked. Exemplary glycopeptides containing (SEQ ID NO:1) and a modified amino acid residue to which the oligosaccharide is linked include, without limitation, the following sequences:

| Sequence | SEQ ID NO: |
|---|---|
| MANHSHGHNIGDIRDATCXLSNCYHYNNRRKNRFTLFTLL RILVQKSLFRGSGSGLGHHHHHHRL | 150 |
| MAIFNQGYRIKAWNDLKDIAIGDIRHALCXLVLARIKLQR RXVKYKHDHRGSGSGLGHHHHHHRL | 151 |
| MAIHHTHLNIGDIRFRHFPRRYRNNWXNFLFLVLRALTWK NRLAFFSNDHGSGSGLGHHHHHHRL | 152 |
| MAINXSIRLIGDIRPAQAQRGHLAPHARRVRHEVLGLVLE RLLVLRRLVRGSGSGLGHHHHHHRL | 153 |
| MAFLLNHKRIGDIRKLPPLNLXATKTLTKERIRKIVNGFV QRLKGHSWWIGSGSGLGHHHHHHRL | 154 |

wherein X is the modified amino acid residue to which the oligosaccharide is linked.

In certain embodiments, the glycopeptide comprises the sequence IGDIR (SEQ ID NO:1) or IGDIRxA (SEQ ID NO:2), but does not comprise the sequence HHHHHHRL (SEQ ID NO:3); the sequence GHHHHHHRL (SEQ ID NO:4); the sequence GxGHHHHHHRL (SEQ ID NO:5), wherein x is any amino acid; the sequence GSGSLGHHHHHHRL (SEQ ID NO:6); and/or the sequence GSGSGLGHHHHHHRL (SEQ ID NO:7). Thus, additional exemplary glycopeptides containing (SEQ ID NO:1) and a modified amino acid residue to which the oligosaccharide is linked include, without limitation, the following sequences:

| Sequence | SEQ ID NO: |
|---|---|
| MANHSHGHNIGDIRDATCXLSNCYHYNNRRKNRFTLFTL LRILVQKSLFR | 155 |
| MAIFNQGYRIKAWNDLKDIAIGDIRHALCXLVLARIKLQ RRXVKYKHDHR | 156 |

-continued

| Sequence | SEQ ID NO: |
|---|---|
| MAIHHTHLNIGDIRFRHFPRRYRNNWXNFLFLVLRALTW KNRLAFFSNDH | 157 |
| MAINXSIRLIGDIRPAQAQRGHLAPHARRVRHEVLGLVL ERLLVLRRLVR | 158 |
| MAFLLNHKRIGDIRKLPPLNLXATKTLTKERIRKIVNGF VQRLKGHSWWI | 159 |

wherein X is the modified amino acid residue to which the oligosaccharide is linked.

In certain embodiments, the glycopeptide comprises a modified amino acid residue to which the oligosaccharide is linked, but does not comprise the sequence IGDIR (SEQ ID NO:1). Exemplary glycopeptides containing a modified amino acid residue to which the oligosaccharide is linked include, without limitation, the following sequences:

| Sequence | SEQ ID NO: |
|---|---|
| MAYKKTFXDIGDSYGELHAQARRREAVRRLLRLVRHRVL LHLLRAVLHARGSGSGLGHHHHHHRL | 160 |
| MASSFRLHNXGPSRXRHWDRLLTIYSIGVSTLANSLRVL HGVAHRGRHLGGSGSGLGHHHHHHRL | 161 |
| MAYYNHPKLRQYLVKXLTRLRRYSYRELHDGDDHARQAH GRGRLLQDLVDRGSSGLGHHHHHHRL | 162 |
| MAYDPLHKASHSNHPQPYRYIGVIRHPLXRQSISQIFKI LLIRYLRKHRRGSGSGLGHHHHHHRL | 163 |

wherein X is the modified amino acid residue to which the oligosaccharide is linked.

In certain embodiments, the glycopeptide comprises a modified amino acid residue to which the oligosaccharide is linked, does not comprises the sequence IGDIR (SEQ ID NO:1); the sequence IGDIRxA (SEQ ID NO:2); the sequence HHHHHHRL (SEQ ID NO:3); the sequence GHHHHHHRL (SEQ ID NO:4); the sequence GxGHHHHHHRL (SEQ ID NO:5), wherein x is any amino acid; the sequence GSGSLGHHHHHHRL (SEQ ID NO:6); and/or the sequence GSGSGLGHHHHHHRL (SEQ ID NO:7). Thus, additional exemplary glycopeptides containing a modified amino acid residue to which the oligosaccharide is linked include, without limitation, the following sequences:

| Sequence | SEQ ID NO: |
|---|---|
| MAYKKTFXDIGDSYGELHAQARRREAVRRLLRLVRHRVL LHLLRAVLHAR | 164 |
| MASSFRLHNXGPSRXRHWDRLLTIYSIGVSTLANSLRVL HGVAHRGRHLG | 165 |
| MAYYNHPKLRQYLVKXLTRLRRYSYRELHDGDDHARQAH RGRLLQDLVDR | 166 |
| MAYDPLHKASHSNHPQPYRYIGVIRHPLXRQSISQIFKI LLIRYLRKHRR | 167 |

wherein X is the modified amino acid residue to which the oligosaccharide is linked.

In some embodiments, the glycopeptide is a cyclic glycopeptide. Thus, the glycopeptide may comprise, without limitation, the following sequences:

| Sequence | SEQ ID NO: |
|---|---|
| linker<br>MANHSHGHNIGDIRDATCXLSN____CYHYNNRRKNRFTLFTLLRILVQKSLFR GSGSGLGHHHHHHRL | 150 |
| linker<br>MANHSHGHNIGDIRDATCXLSN__CYHYNNRRKNRFTLFTLLRILVQKSLFR | 155 |

wherein X is the modified amino acid residue to which the oligosaccharide is linked, and the Cys-Cys linker is one of the bis-alkylbenzene or bis-alkylpyridine groups described hereinafter.

In some embodiments, the modified amino acid residue to which the oligosaccharide is linked is not at the N-terminal position of the glycopeptide. Thus, in some embodiments, the glycopeptide comprises the sequence IGDIR (SEQ ID NO:1), but does not comprise a modified amino acid residue to which the oligosaccharide is linked at the N-terminus. In certain embodiments, the glycopeptide does not comprise an N-terminal homopropargylglycine (alkyne) or L-allylglycine residue.

The cyclic glycopeptide may comprise a linker molecule between two cysteine side chains. In some embodiments, the linker molecule comprises

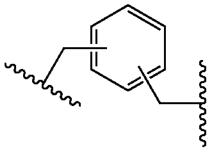 or 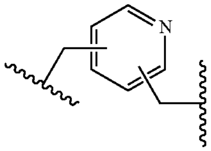 or

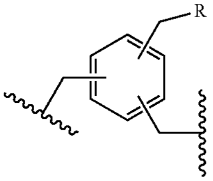

where R is an ester group (e.g., —C(O)O—$(CH_2)_n$—$CH_3$ where n is 0 to 6) or an immunogenic carrier molecule. The linkers are a reaction product of a dihalo reactant with a peptide containing at least two cysteine residues. Exemplary dihalo reactants include, without limitation, 1,4-dibromoxylene, 1,3-dibromoxylene, 1,2-dibromoxylene, 1,4-dichloroxylene, 1,3-dichloroxylene, 1,2-dichloroxylene, 2,6-bis(bromomethyl)pyridine, and 2,6-bis(chloromethyl)pyridine. Structurally similar linkers with different length alkyl chains can also be used, e.g., 1,4-bis(2-bromoethyl)benzene, 1,4-bis(3-bromobutyl)benzene, and 1,2-bis(2-bromoethyl)benzene.

These linkers can be reacted with the peptide to form a cyclized peptide prior to glycosylation using click reactions as described above. The cyclization reaction procedure can be carried according to the Examples herein.

A further aspect of the invention relates to a method of preparing glycopeptides that includes the steps of: providing an mRNA-displayed polypeptide having an N-terminal homopropargylglycine or allylglycine residue; treating the mRNA-displayed polypeptide with an enzyme suitable to remove the N-terminal homopropargylglycine or allylglycine residue from the polypeptide; and reacting the mRNA-displayed polypeptide recovered from the treating step with an oligosaccharide linked to a reactive moiety that is capable of reacting with a sidechain of one or more modified amino acids present in the polypeptide to thereby form a glycopeptide comprising one or more oligosaccharides linked to amino acid sidechains.

In one embodiment, the N-terminal homopropargylglycine or allylglycine residue is formylated, and the enzyme is a first treatment with peptide deformylase and a second treatment with methionine aminopeptidase. Exemplary conditions for carrying out the enzymatic treatments are described in the Examples.

In another embodiment, the peptide includes an enterokinase cleavage sequence (e.g., DYKDDDDK, SEQ ID NO:171) located within 1-10 residues of the N-terminus, and the enzyme is an enterokinase suitable to cleave the cleavage sequence and thereby remove the N-terminal homopropargylglycine or allylglycine residue. Exemplary conditions for carrying out the enzymatic treatments are described in the Examples.

As described herein, the optional cyclization step can also be carried out after the enzyme treatment but before glycosylation (i.e., reacting with the oligosaccharide via click reaction).

A further aspect of the invention relates to an immunogenic conjugate that includes a glycopeptide of the invention covalently or non-covalently bound to an immunogenic carrier molecule. Exemplary immunogenic carrier molecules include, without limitation, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

Any of a variety of conjugation methodologies can be utilized. See, e.g., Jennings et al., *J. Immunol.* 127:1011-8 (1981); Beuvery et al., *Infect. Immun* 40:39-45 (1993), each of which is hereby incorporated by reference in its entirety. In one approach terminal aldehyde groups can be generated through periodate oxidation, and the aldehydes are then reacted through reductive amination with free amino groups on the protein, mostly lysines, in the presence of sodium cyanoborohydride. In another approach, a carbodiimide reaction is performed to covalently link carboxylic groups to the lysine 6-amino groups on the carrier protein. The activation sites in this method are more random, compared to periodate activation.

A further aspect of the invention relates to a pharmaceutical composition that includes a pharmaceutically acceptable carrier and a glycopeptide or immunogenic conjugate of the invention. In certain embodiments, the glycopeptide is present. In other embodiments, the immunogenic conjugate is present.

Pharmaceutical compositions suitable for injectable or parental use (e.g., intravenous, intra-arterial, intramuscular, etc.) or intranasal use may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water, saline solutions, and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions. In some embodiments, the pharmaceutically acceptable carrier is a buffered saline solution.

The pharmaceutical compositions of the present invention may also be administered directly to the airways in the form of an aerosol. For use as aerosols, the compositions of the present invention in the form of a solution or suspension may be packaged in a pressurized aerosol container together with suitable propellants, for example, hydrocarbon propellants like propane, butane, or isobutane with conventional adjuvants. The pharmaceutical compositions of the present invention also may be administered in a non-pressurized form such as in a nebulizer or atomizer. Formulations suitable for intranasal nebulization or bronchial aerosolization delivery are also known and can be used in the present invention (see Lu & Hickey, *Exp. Rev. Vaccines* 6(2):213-226 (2007) and Alpar et al., *Adv. Drug Deliv. Rev.* 57(3): 411-30 (2005), which are hereby incorporated by reference in their entirety.

In certain embodiments, the pharmaceutical composition further comprises an adjuvant. For example, the pharmaceutical compositions of the present invention can also include an effective amount of a separate adjuvant. Suitable adjuvants for use in the present invention include, without limitation, aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid, Quil A, non-infective *Bordetella pertussis*, QS-21, monophosphoryl lipid A, an alpha-galactosylceramide derivative, or PamCys-type lipids.

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Adv. Drug Deliv. Rev.* 32:173-186 (1998), which is hereby incorporated by reference in its entirety) alone or optionally all combinations thereof are suitable for human administration.

The pharmaceutical compositions can also include one or more additives or preservatives, or both.

Effective amounts of the glycopeptide may vary depending upon many different factors, including mode of administration, target site, physiological state of the patient, other medications administered, and whether treatment is prophylactic or therapeutic. Treatment dosages need to be titrated to optimize safety and efficacy. The amount of glycopeptide immunogen depends on whether adjuvant is also administered, with higher dosages being required in the absence of adjuvant. The amount of a glycopeptide immunogen for administration sometimes varies from 1-5 mg per patient and more usually from 5-1000 μg per injection for human administration.

The glycopeptides, immunogenic conjugates, and pharmaceutical compositions can be incorporated into a delivery vehicle to facilitate administration. Such delivery vehicles include, but are not limited to, biodegradable microspheres (MARK E. KEEGAN & W. MARK SALTZMAN, Surface Modified Biodegradable Microspheres for DNA Vaccine Delivery, in DNA VACCINES: METHODS AND PROTOCOLS 107-113 (W. Mark Saltzman et al., eds., 2006), which is hereby incorporated by reference in its entirety), microparticles (Singh et al., *Expert Rev. Vaccine* 6(5):797-808 (2007), which is hereby incorporated by reference in its entirety), nanoparticles (Wendorf et al., *J. Pharm. Sci.* 95(12):2738-50 (2006) which is hereby incorporated by reference in its entirety), liposomes (U.S. Patent Application Publication No. 2007/0082043 to Dov et al. and Hayashi et al., *Biochem. Biophys. Res. Comm.* 261(3): 824-28 (1999), which are hereby incorporated by reference in their entirety), collagen minipellets (Lofthouse et al., *Vaccine* 19(30):4318-27 (2001), which is hereby incorporated by reference in its entirety), and cochleates (Gould-Fogerite et al., *Adv. Drug Deliv. Rev.* 32(3):273-87 (1998), which is hereby incorporated by reference in its entirety).

Another aspect of the invention relates to a method of inducing an immune response in an individual that involves administering to an individual a glycopeptide, an immunogenic conjugate, or a pharmaceutical composition of the present invention, wherein said administering is effective to induce a neutralizing immune response against a virus in an individual. The individual can be any mammal, particularly a human, although veterinary usage is also contemplated. This method is carried out by administering one of these active agents to an individual in a manner that is effective to induce an immune response against the glycopeptide. Because the glycopeptide mimics the native glycosylated epitope of a native target of the monoclonal antibody to which the glycopeptide was selected, certain glycopeptides can induce a carbohydrate-binding, neutralizing antibody response that is protective against a pathogen (e.g., viral pathogen) and certain other glycopeptides can induce a carbohydrate-binding, cytotoxic antibody response against a cancer cell that expresses a glycosylated antigen.

For each of these embodiments, administration of the glycopeptides, immunogenic conjugates, and/or pharmaceutical compositions can be carried orally, parenterally, subcutaneously, intravenously, intramuscularly, intraperitoneally, by intranasal instillation, by implantation, by intracavitary or intravesical instillation, intraarterially, intralesionally, transdermally, intra- or peri-tumorally, by application to mucous membranes, or by inhalation. Administration of these agents can be repeated periodically.

Exemplary viruses include, without limitation, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1 or HIV-2), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Acute Respiratory Syndrome (SARS Co-V), Tick-borne Encephalitis virus, Varicella zoster virus, Venezuelan Equine Encephalitis virus, Yellow Fever virus, Western Equine Encephalitis virus, and West Nile virus.

The use of one or more of the glycopeptides according to the present invention (e.g., SEQ ID NOs: 6-79) in an immunogenic conjugate or pharmaceutical composition is specifically contemplated for prophylactic or therapeutic treatment against HIV-1.

A further aspect of the invention relates to a method of inhibiting viral infection. This method involves administering to an individual a glycopeptide, and immunogenic conjugate, or a pharmaceutical composition according to the invention, wherein said administering is effective to induce a neutralizing immune response against a virus. For prophylactic treatment against viral infection, it is intended that the glycopeptides, immunogenic conjugates, and pharmaceutical compositions of the present invention can be administered prior to exposure of an individual to the virus and that the resulting immune response can inhibit or reduce the severity of the viral infection such that the virus can be eliminated from the individual. The glycopeptide, immunogenic conjugate, and pharmaceutical composition of the present invention can also be administered to an individual for therapeutic treatment. In accordance with one embodiment, it is intended that the composition(s) of the present invention can be administered to an individual who is already exposed to the virus. The resulting enhanced immune response can reduce the duration or severity of the existing viral infection, as well as minimize any harmful consequences of untreated viral infections. The composition(s) can also be administered in combination other therapeutic anti-viral regimen. In asymptomatic patients, treatment can begin at any age (e.g., 10, 20, 30 years of age). Treatment typically entails multiple dosages over a period of time. Treatment can be monitored by assaying antibody, or activated T-cell or B-cell responses to the therapeutic agent over time. If the response falls, a booster dosage is indicated.

In some embodiments, the pharmaceutical compositions of the present invention is present as a single dosage unit comprising about 1 μg to about 5 mg if the glycopeptide. However, the amount of a glycopeptide for administration sometimes varies from 5-1500 μg per dose for human administration. Occasionally, a higher dose of 1-2 mg per injection is used. Typically about 10, 20, 50, or 100 μg is used for each human dose. The mass of glycopeptide immunogen also depends on the mass ratio of immunogenic epitope within the glycopeptide immunogen to the mass of glycopeptide immunogen as a whole. Typically, $10^{-3}$ to $10^{-5}$ micromoles of immunogenic epitope are used for each microgram of glycopeptide immunogen. The timing of injections can vary significantly from once a day, to once a year, to once a decade. On any given day that a dosage of glycopeptide immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster administration at time intervals, such as 6 week intervals. Another regimen consists of an immunization followed by booster injections 1, 2, and 12 months later. Another regimen entails an administration every two months for a prolonged period in excess of 12 months. Alternatively, booster injections can be on an irregular basis as indicated by monitoring of immune response.

In certain embodiments, multiple doses are given over a period of time, each using a different immunogenic oligonucleotide in an appropriate amount, as indicated above.

A further aspect of the invention relates to a method for detecting a neutralizing antibody in serum. This method involves providing a glycopeptide of the invention, contacting the glycopeptide with serum from an individual, and detecting whether the glycopeptide binds specifically to an antibody present in the serum, wherein the detection of the antibody is carried out using a label.

Exemplary labels include, without limitation, a radiolabel, fluorescent label, enzymatic label, chemiluminescent marker, biotinyl group, an epitope recognized by a secondary reporter, a magnetic agent, or a toxin.

The detection step is preferably carried using a suitable assay format. Exemplary assays include, without limitation, ELISA, radioimmunoassay, gel-diffusion precipitation reaction assay, immunodiffusion assay, agglutination assay, fluorescent immunoassay, immunoelectrophoresis assay, surface plasmon resonance assay, or biolayer interferometry assay. In certainly of these assay formats, a secondary antibody is used to label the antibody bound specifically to the glycopeptide. Depending on the type of assay, the glycopeptide can be in the solution phase or coupled to a solid surface.

Using the demonstrated results presented in the accompanying Examples, the present application demonstrates that glycopeptides that are specifically bound by carbohydrate-binding monoclonal antibody PGT128, PGT130, or germline PGT128 can be prepared and it is expected that these will display higher affinity for the monoclonal antibody than the monoclonal antibody has for its binding partner.

EXAMPLES

The following examples are intended to illustrate practice of the invention, and are not intended to limit the scope of the claimed invention.

Materials and Methods for Examples 1-6

Materials

All synthetic DNA oligos were purchased from Integrated DNA Technologies. Oligos with a length of 50 bases or more were PAGE-purified (general procedure described below) before use. Stock solutions of individual dNTPs and NTPS were each obtained as a set from ThermoScientific. Restriction endonucleases were purchased from New England Biolabs.

All reagents and buffers, generally Molecular Biology grade, were purchased from Fisher Scientific, Ambion, or Sigma. All water used was either purified by a Milli-Q Ultrapure water purification system, or purchased RNA grade water (Fisherbrand, BP5611). Homemade buffers were sterilized by passage through 0.22 μm filters (Millipore). $Man_9GlcNAc_2$-azide and THPTA used in the click reaction were chemically synthesized.

All PCR amplification was performed on an Eppendorf Mastercycler Gradient thermal cycler. Quantitative absorbance measurements were performed on a NanoDrop 2000C (ThermoScientific) or NanoDrop OneC (ThermoScientific).

Precast SDS-PAGE gels (4-20% gradient) were purchased from Bio-Rad. All other SDS-PAGE gels were made using a Mini-PROTEAN® Tetra Handcast System (Bio-Rad). For 35S-cysteine-containing samples, gels were fixed, dried on chromatography paper, exposed to phosphorimaging screen and visualized using a Storm or Typhoon phosphorimager. For $^3$H-histidine-containing samples, gels were fixed, treated with NAMP100 fluorographic reagent (GE Healthcare), dried on chromatography paper, and exposed to film.

Samples for liquid scintillation counting were prepared in 20 mL scintillation vials (Fisherbrand, 03-337-23) with 2-15 mL of Econo-Safe Biodegradable Counting Cocktail (Atlantic Nuclear, 11175). Scintillation counting was performed on a Beckman LS6000TA scintillation counter.

A Voyager DE instrument was used for all MALDI-TOF-MS. Except where otherwise noted, the MALDI matrix used was α-cyano-4-hydroxycinnamic acid (CHCA; Sigma). CHCA was prepared as a 10 mg/mL solution in 0.1% TFA/MeCN and stored at −20° C. in between uses for up to a month.

Methods—Preselection Experiments

Cyclization of Free Peptide (Original Protocol)

Figure 3A:
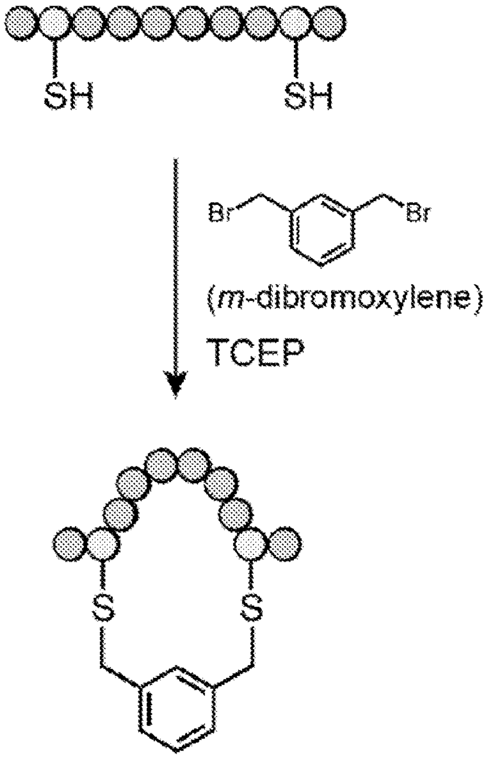
FIGS. 3A-3B illustrate peptide cyclization with m-dibromoxylene.
Figure 3B:
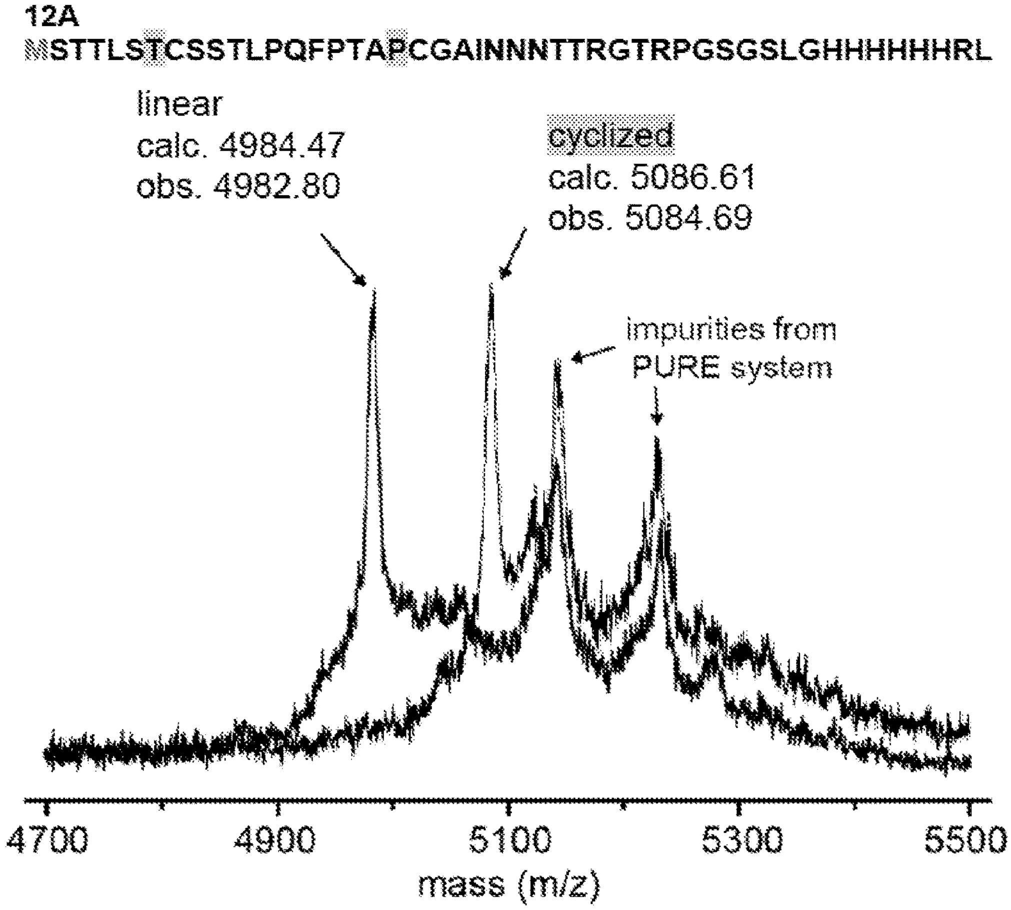

DNA for the 2G12 preselection sequence 12A, MSTTLSTCSSTLPQFPTAPCGAINNNTTRGTRPGSGSLGHHHHHHRL (SEQ ID NO:168) was PCR amplified from its plasmid using the forward primer Library-FP1 (5'-TAATACGACTCACTATAGGGTTAACTTTAGTAAGGAGG (SEQ ID NO:169)) and reverse primer (5'-CTAGCTACCTATAGCCGGTGGTGATGGTGATGGTGGCCTAAGC (SEQ ID NO:170)). The resulting DNA was transcribed using T7 polymerase, and the crude RNA was purified by 5% denaturing PAGE. 12A RNA was translated to peptide in the presence of $^{35}$S-cysteine. Crude peptides were split and purified with Ni-NTA agarose with or without cyclization while captured on resin. Ni-NTA agarose purification of peptides was used. The protocol used for cyclization while captured on resin is as follows. To 25 μL of crude translated peptide was added 100 μL of bind buffer (−BME; 50 mM Tris-HCl, pH 7.8, 300 mM NaCl) and 25 μL of Ni-NTA Agarose (Qiagen). The mixture was tumbled at room temperature for 1 hour. Then, the mixture was spun down at 21,000×g and the supernatant was carefully removed from the loosely-pelleted agarose. The resin was washed six times by resuspending with 200 μL of bind buffer with TCEP (50 mM Tris-HCl, pH 7.8, 300 mM NaCl, 0.2 mM TCEP), spinning down, and removing the supernatant. The resin was then washed twice with 200 μL of wash buffer with TCEP (50 mM Tris-HCl, pH 8.0, 0.2 mM TCEP). To the resin was then added 100 of cyclization buffer (40 mM Tris-HCl, pH 8.0, 0.2 mM TCEP, 5 mM m-dibromoxylene, 20% (v/v) MeCN), and the mixture was covered in foil and tumbled at room temperature for 30 minutes. The reaction was spun down and the supernatant was removed. Then, the resin was washed twice with 200 μL of bind buffer (+BME; 50 mM Tris-HCl, pH 7.8, 300 mM NaCl, 5 mM BME). The resin was resuspended in 100 μL of wash buffer (+BME; 50 mM Tris-HCl, pH 7.8, 5 mM BME) and transferred to an Ultra-free 0.22 μm centrifugal filter unit (Millipore). The tube was rinsed with 100 μL of wash buffer (+BME) and the rinse was added to the filter. The filter was then spun down at 10,000×g for 30 seconds. The resin in the filter was washed with 200 μL of wash buffer (+BME). To elute the peptide, 25 μL 0.2% TFA was added to the resin and allowed to sit at room temperature for 2 minutes before spinning down, collecting in a new tube. The elution step was carried out twice more, with each collected separately. The linear and cyclized peptides were analyzed by MALDI-TOF-MS (FIG. 3B).

Preparation of N-Terminal FLAG-Tag Sequences

Winners from round 10 of the 2G12 selection were prepared with N-terminal FLAG-tags as follows. A universal N-terminal fragment (Fragment 1) was generated that contained the N-terminal constant region, followed by a region that encoded for peptides with the FLAG-tag (DYKDDDDK, SEQ ID NO: 171) just after the N-terminal HPG. A second fragment (Fragment 2) encoded the individual peptide clone with a leading FLAG-tag sequence to overlap with Fragment 1 followed by a short spacer (GSG). Table 1 shows primers and fragments used to generate N-terminal FLAG-tag sequences.

Start II DNA Polymerase (ThermoScientific) in 1× Phusion HF Buffer. Using a thermal cycler, the reaction was initially heated to 98° C. for 30 seconds, followed by 25 cycles of 98° C. for 5 seconds, 54° C. for 10 seconds, and 72° C. for 10 seconds, then a final extension at 72° C. for 30 seconds. For Fragment 2, the appropriate wild-type plasmid (4 ng) was used as a template in PCR (40 μL) with 0.2 mM of each dNTP, 1 μM each of forward and reverse primer (Cut-Fr2-FP-sequence and Cut-Fr2-RP, respectively), and 0.02 U/μL of Phusion Hot Start II DNA Polymerase (ThermoScientific) in 1× Phusion HF Buffer. Using a thermal cycler, the reaction was initially heated to 98° C. for 30 seconds, followed by 25 cycles of 98° C. for 5 seconds, 59° C. for 10 seconds, and 72° C. for 10 seconds, then a final extension at 72° C. for 30 seconds. The crude PCR products for Fragment

TABLE 1

Primers and fragments to generate N-terminal FLAG-tag sequences.

| Name | Sequence (5' to 3') | SEQ ID NO: |
|---|---|---|
| Cut-Fr1-FP | CTCGGATCCTAATACGACTCACTATAGGGT | 172 |
| Cut-Fr1-RP-0 | TTTGTCATCGTCGTCTTTATAATCCATTTAGCTGTC CTCCTTAC | 173 |
| Cut-Fr2-FP-10F2 | GATTATAAAGACGACGATGACAAAGGCTCCGGTCAT CCGTACAACACGTCGCG | 174 |
| Cut-Fr2-FP-10F3 | GATTATAAAGACGACGATGACAAAGGCTCCGGTGAT ACACTACACCTTAAGCA | 175 |
| Cut-Fr2-FP-10F5 | GATTATAAAGACGACGATGACAAAGGCTCCGGTAGT CCACATCTCCCCGTACT | 176 |
| Cut-Fr2-FP-10F6 | GATTATAAAGACGACGATGACAAAGGCTCCGGTTTG ATGTTTATCCGCATTTA | 177 |
| Cut-Fr2-FP-10F8 | GATTATAAAGACGACGATGACAAAGGCTCCGGTTTA CTGAAAATGGTGGATCA | 178 |
| Cut-Fr2-FP-10F9 | GATTATAAAGACGACGATGACAAAGGCTCCGGTCGA TCAACACTTAATTCACT | 179 |
| Cut-Fr2-FP-10F12 | GATTATAAAGACGACGATGACAAAGGCTCCGGTTGC TATGTGACTGTTATTCC | 180 |
| Cut-Fr2-FP-10V1 | GATTATAAAGACGACGATGACAAAGGCTCCGGTGCC ACCAAGACCAACTGCAA | 181 |
| Cut-Fr2-FP-10V8 | GATTATAAAGACGACGATGACAAAGGCTCCGGTGTG TTGCCCACCATCATCTC | 182 |
| Cut-Fr2-FP-10V9 | GATTATAAAGACGACGATGACAAAGGCTCCGGTACC AGCATCCCCTACACCTA | 183 |
| Cut-Fr2-RP | CATGCTCGAGCTAGCTACCTATAGCCGGTG | 184 |
| Fragment 1 | **CTCGGATCCTAATACGACTCACTATAGGGT**TAACTT TA**GTAAGGAGGACAGCTAAATGGATTATAAAGACGA CGATGACAAA** | 185 |
| Fragment 2-10F2 | **GATTATAAAGACGACGATGACAAAGGCTCCGGTCAT CCGTACAACACGTCGCG**TACTTCAGCTATGATGGCC GCTCTGAAGATGCAAGTTACTGATATGTATGCCTTG GCCTTGTTCCATAGGATACTGGGCTCCGGTTCTCTG GGTCATCACCACCATCACCACCGGCTATAGGTAGCT AG**CTCGAGCATGCATCTAGAGGGCCCAATTCG** | 186 |

A representative example of Fragment 2 is shown with the sequence for 10F2. Fragment DNA from primers is shown in bold.

For Fragment 1, wild-type plasmid 10F2 (4 ng) was used as a template in PCR (40 μL) with 0.2 mM of each dNTP, 1 μM each of forward and reverse primer (Cut-Fr1-FP and Cut-Fr1-RP-0, respectively), and 0.02 U/μL of Phusion Hot 1 and each Fragment 2 were applied on a 2% agarose gel for purification. The fragment bands were visualized with a 254 nm handheld UV lamp, extracted using an x-tracta Gel Extractor tool (Promega), and transferred into a new, pre-massed 1.5 mL tube. The fragment bands were purified using EZNA Gel Extraction Kit (Omega Bio-tek), following the manufacturer's protocol and eluting with 50 μL of water.

Fragment 1 and each Fragment 2 were combined to generate the full DNA of each MFLAG-sequence for cloning. Each PCR (50 μL) was assembled with 0.2 mM of each dNTP, 1 of each purified fragment (Fragment 1 and the appropriate Fragment 2), 1 μM of Cut-Fr1-FP (forward primer), 1 μM of Cut-Fr2-RP (reverse primer), and 0.02 U/μL of Phusion Hot Start II DNA Polymerase (Thermo-Scientific) in 1× Phusion HF Buffer. Using a thermal cycler, the reaction was initially heated to 98° C. for 30 seconds, followed by 25 cycles of 98° C. for 5 seconds, 54° C. for 10 seconds, and 72° C. for 10 seconds, then a final extension at 72° C. for 30 seconds. The crude PCR mixtures were diluted with water to 300 μL, extracted with phenol/chloroform, and precipitated with ethanol followed by a 70% (v/v) ethanol wash. The pellets were used directly in a double-digestion reaction (40 μL) with XhoI and BamHI (20 U each) in 1× CutSmart Buffer. After incubation at 37° C. overnight, the digested inserts were run on 1% agarose gel and purified with a kit as before. After elution, the DNA inserts were quantified by absorbance using NanoDrop. Each MFLAG-sequence insert was cloned into an empty pCR2.1 vector and sequenced via Sanger sequencing.

TABLE 2

Sequences of MFLAG clones (full DNA and encoded peptides).

| Name | Sequence (5' to 3') | SEQ ID NO: |
|---|---|---|
| MFLAG-<br>10F2 | MDYKDDDDKGSGHPYNTSRTSAMMAALKMQVTDMYALALFHRILGSG<br>LGHHHHHHRL | 187 |
| | CATGATTACGCCAAGCTTGGTACCGAGCTCGGATCCTAATACGACTC<br>ACTATAGGGTTAACTTTAGTAAGGAGGACAGCTAAATGGATTATAAA<br>GACGACGATGACAAAGGCTCCGGTCATCCGTACAACACGTCGCGTAC<br>TTCAGCTATGATGGCCGCTCTGAAGATGCAAGTTACTGATATGTATG<br>CCTTGGCCTTGTTCCATAGGATACTGGGCTCCGGTTCTCTGGGTCAT<br>CACCACCATCACCACCGGCTATAGGTAGCTAGCTCGAGCATGCATCT<br>AGAGGGCCCAATTCG | 188 |
| MFLAG-<br>10F3 | MDYKDDDDKGSGDTLHLKQIGGMPNCITQQDVRMTSIPYTYTWPGSG<br>LGHHHHHHRL | 189 |
| | CATGATTACGCCAAGCTTGGTACCGAGCTCGGATCCTAATACGACTC<br>ACTATAGGGTTAACTTTAGTAAGGAGGACAGCTAAATGGATTATAAA<br>GACGACGATGACAAAGGCTCCGGTGATACACTACACCTTAAGCAGAT<br>CGGAGGAATGCCAAATTGCATCACTCAACAGGACGTACGAATGACAT<br>CCATTCCATATACCTATACATGGCCTGGCTCCGGTTCTCTGGGTCAT<br>CACCACCATCACCACCGGCTATAGGTAGCTAGCTCGAGCATGCATCT<br>AGAGGGCCCAATTCG | 190 |
| MFLAG-<br>10F5 | MDYKDDDDKGSGSPHLPVLLCKMVLNDGRRIVQMSCELPMVRRSGSG<br>LGHHHHHHRL | 191 |
| | CATGATTACGCCAAGCTTGGTACCGAGCTCGGATCCTAATACGACTC<br>ACTATAGGGTTAACTTTAGTAAGGAGGACAGCTAAATGGATTATAAA<br>GACGACGATGACAAAGGCTCCGGTAGTCCACATCTCCCCGTACTGTT<br>ATGTAAGATGGTCCTAAACGATGGTAGACGGATTGTTCAAATGTCTT<br>GTGACTGCCAATGGTTCGACGATCAGGCTCCGGTTCTCTGGGTCAT<br>CACCACCATCACCACCGGCTATAGGTAGCTAGCTCGAGCATGCATCT<br>AGAGGGCCCAATTCG | 192 |
| MFLAG-<br>10F6 | MDYKDDDDKGSGLMFIRIYPTRMQYVYHAPLLTMVRMSPTGPLIGSG<br>LGHHHHHHRL | 193 |
| | CATGATTACGCCAAGCTTGGTACCGAGCTCGGATCCTAATACGACTC<br>ACTATAGGGTTAACTTTAGTAAGGAGGACAGCTAAATGGATTATAAA<br>GACGACGATGACAAAGGCTCCGGTTTGATGTTTATCCGCATTTATCC<br>TACCCGCATGCAGTATGTCTATCACGCTCCTCTGCTTACGATGGTTC<br>GTATGTCCCCGACTGGTCCCCTAATCGGCTCCGGTTCTCTGGGTCAT<br>CACCACCATCACCACCGGCTATAGGTAGCTAGCTCGAGCATGCATCT<br>AGAGGGCCCAATTCG | 194 |
| MFLAG-<br>10F8† | MDYKDDDDKGSGLLKMVDQSRLMPVPGIGVTLHMRSIPYSYLPIGSG<br>LGHHHHHHRL | 195 |
| | CATGATTACGCCAAGCTTGGTACCGAGCTCGGATCCTAATACGACTC<br>ACTATAGGGTTAACTTTAGTAAGGAGGACAGCTAAATGGATTATAAA<br>GACGACGATGACAAAGGCTCCGGTTTACTGAAAATGGTGGATCAATC<br>GAGACTCATGCCCGTTCCCGGAATTGGGGTGACTTTGCATATGAGAT<br>CTATTCCTTATAGTTACTTACCAATAGGCTCCGGTTCTCTGGGTCAT<br>CACCACCATCACCACCGGCTATAGGTAGCTAGCTCGAGCATGCATCT<br>AGAGGGCCCAATTCG | 196 |
| MFLAG-<br>10F9 | MDYKDDDDKGSGRSTLNSLEYRMQYATEDPRIRMASIPYTYWWPGSG<br>LGHHHHHHRL | 197 |
| | CATGATTACGCCAAGCTTGGTACCGAGCTCGGATCCTAATACGACTC<br>ACTATAGGGTTAACTTTAGTAAGGAGGACAGCTAAATGGATTATAAA<br>GACGACGATGACAAAGGCTCCGGTCGATCAACACTTAATTCACTAGA<br>ATACCGAATGCAATATGCAACTGAGGACCCAAGGATACGCATGGCTA<br>GTATACCCTACACATATTGGTGGCCCGGCTCCGGTTCTCTGGGTCAT<br>CACCACCATCACCACCGGCTATAGGTAGCTAGCTCGAGCATGCATCT<br>AGAGGGCCCAATTCG | 198 |

TABLE 2 -continued

Sequences of MFLAG clones (full DNA and encoded peptides).

| Name | Sequence (5' to 3') | SEQ ID NO: |
|---|---|---|
| MFLAG-10F12 | MDYKDDDDKGSGCYVTVIPAMNMPEARLGIVCHMPGIRRGKALYGSG LGHHHHHHRL | 199 |
| | CATGATTACGCCAAGCTTGGTACCGAGCTCGGATCCTAATACGACTC ACTATAGGGTTAACTTTAGTAAGGAGGACAGCTAAATGGATTATAAA GACGACGATGACAAAGGCTCCGGTTGCTATGTGACTGTTATTCCGGC TATGAATATGCCGGAAGCTAGACTCGGCATTGTCTGCCACATGCCTG GGATCAGGCGTGGGAAGGCCTTGTACGGCTCCGGTTCTCTGGGTCAT CACCACCATCACCACCGGCTATAGGTAGCTAGCTCGAGCATGCATCT AGAGGGCCCAATTCG | 200 |
| MFLAG-10V1 | MDYKDDDDKGSGATKTNCKREKTMDNHVTIMRSIPWYTYRWLPNGSG LGHHHHHHRL | 201 |
| | CATGATTACGCCAAGCTTGGTACCGAGCTCGGATCCTAATACGACTC ACTATAGGGTTAACTTTAGTAAGGAGGACAGCTAAATGGATTATAAA GACGACGATGACAAAGGCTCCGGTGCCACCAAGACCAACTGCAAGCG GGAGAAGACCATGGACAACCACGTGACGATCATGAGGAGCATCCCGT GGTACACGTACCGCTGGTTGCCCAACGGCTCCGGTAGCTTAGGCCAC CATCACCATCACCACCGGCTATAGGTAGCTAGCTCGAGCATGCATCT AGAGGGCCCAATTCG | 202 |
| MFLAG-10V8 | MDYKDDDDKGSGVLPTIISTNVNPFRMLSIPTYTYLMPITWGEIGSG LGHHHHHHRL | 203 |
| | CATGATTACGCCAAGCTTGGTACCGAGCTCGGATCCTAATACGACTC ACTATAGGGTTAACTTTAGTAAGGAGGACAGCTAAATGGATTATAAA GACGACGATGACAAAGGCTCCGGTGTGTTGCCCACCATCATCTCGAC CAACGTGAACCCGTTCCGGATGCTCTCGATCCCGACCTACACGTACC TGATGCCCATCACGTGGGGCGAGATCGGCTCCGGTAGCTTAGGCCAC CATCACCATCACCACCGGCTATAGGTAGCTAGCTCGAGCATGCATCT AGAGGGCCCAATTCG | 204 |
| MFLAG-10V9 | MDYKDDDDKGSGTSIPYTYLNRSLWTNYRVNSWSMSKNVNVMPLGSG LGHHHHHHRL | 205 |
| | CATGATTACGCCAAGCTTGGTACCGAGCTCGGATCCTAATACGACTC ACTATAGGGTTAACTTTAGTAAGGAGGACAGCTAAATGGATTATAAA GACGACGATGACAAAGGCTCCGGTACCAGCATCCCCTACACCTACCT CAACCGCTCGCTGTGGACGAACTACCGCGTCAACAGCTGGAGCATGT CCAAGAACGTGAACGTGATGCCGTTGGGCTCCGGTAGCTTAGGCCAC CATCACCATTCACCACCGGCTATAGGTAGCTAGCTCGAGCATGCATC TAGAGGGCCCAATTCG | 206 |

†MFLAG-10F8 was not confirmed by sequencing.

The FLAG-tag amino acid sequence (DYKDDDDK, SEQ ID NO: 171) and the encoding DNA sequence are in bold.

Following sequence confirmation, PCR (50 μL) was assembled with confirmed plasmid template (5 ng) 0.2 mM of each dNTP, 1 μM of forward primer, 1 μM of reverse primer (FixL-RP-CHRL for Fixed library: 5'-CTAGCTACCTATAGCCGGTGGCAGTGGTGATGGTGGTGATGA (SEQ ID NO: 207); VarL-RP-CHRL for Variable library: 5'-CTAGCTACCTATAGCCGGTGGCAGTGGTGATGGTGATGGTGG (SEQ ID NO: 208)), and 0.02 U/μL of Phusion Hot Start II DNA Polymerase (ThermoScientific) in 1× Phusion HF Buffer. Using a thermal cycler, the reaction was initially heated to 98° C. for 30 seconds, followed by 25 cycles of 98° C. for 5 seconds, 64° C. for 10 seconds, and 72° C. for 10 seconds, then a final extension at 72° C. for 30 seconds. The crude PCR mixtures were diluted with water to 300 extracted with phenol/chloroform, and precipitated with ethanol followed by a 70% (v/v) ethanol wash. The DNAs were analyzed on a 1% agarose gel, compared to controls with known concentrations to approximate the yield for assembling T7 transcription. Template DNA (5 pmol) was used in T7 transcription. Crude transcripts were purified by 5% denaturing PAGE.

Enterokinase Experiments

Peptides MFLAG-10F6-CHRL, MFLAG-10F12-CHRL, MFLAG-10V1-CHRL, and MFLAG-10V8-CHRL were translated in the presence of $^{3}$H-histidine for radiolabeling from 25 pmol of RNA. Crude peptides were purified by Anti-FLAG affinity. ANTI-FLAG® M2 Affinity Gel (Sigma) was equilibrated as follows. The Anti-FLAG resin (25 μL) was resuspended in 500 μL of glycine-HCl pH 3.5 and spun down at 5,000×g for 1 minute. The supernatant was removed, and the wash with glycine-HCl was repeated twice more for a total of three washes. The Anti-FLAG resin was then washed with 500 μL of bind buffer (−BME) four times and resuspended in bind buffer (−BME) to a total volume of 125 μL and transferred to 25 of crude translated peptide. The mixture tumbled at room temperature for 1 hour. Then, the suspension was transferred to an Ultra-free 0.22 μm centrifugal filter unit (Millipore). The tube that contained the mixture was rinsed with 100 μL of bind buffer (−BME), and the rinse was transferred to the filter. The filter was spun down at 10,000×g for 30 seconds. Then, the resin was washed three times with 200 μL of bind buffer (−BME), followed by two washes with 200 of wash buffer (−BME). To elute the peptides, 25 μL 0.2% TFA was added to the resin and allowed to sit at room temperature for 2 minutes before spinning down, collecting in a new tube. A second elution was carried out and collected separately.

A cleavage reaction was assembled as follows. Eluted peptide (37.5 μL in 0.2% TFA) was neutralized with 6.6 μL of 1 M Tris-HCl, pH 7.8. Then, 5 μL of 10×rEK Cleavage Buffer was added, followed by 1 μL of 0.5 U/μL Tag-Off™ High-Activity rEK (Novagen, now discontinued). The reaction was incubated at room temperature overnight. Then, the peptides were dialyzed against 0.1% (v/v) Triton X-100 using a Slide-A-Lyzer™ MINI device (0.1 mL capacity, 3.5 kDa MWCO) (ThermoScientific) at room temperature overnight. The dialyzed peptides were retrieved from the devices, transferring to 0.5 mL centrifuge tubes. A portion was set aside for gel analysis, and the remaining peptide solutions were concentrated to dryness by speedvac for the click reaction.

The click reaction (5 μL) with $Man_9$-cyclohexyl-$N_3$ was carried out. Following the reaction, samples were diluted with water to 40 μL. The peptides were run on a 4-20% SDS-PAGE gel (Bio-Rad) before cleavage, after cleavage, and after the click reaction.

Preparation of PDF and MAP

Preparation of PDF/MAP Vectors. PDF/MAP were prepared based on a report from the Suga group (Kawakami et al., *Nature Chem. Biol.* 5:888 (2009), which is hereby incorporated by reference in its entirety). Vectors for MAP (pET-16b, Addgene) and PDF (pET-21a, Addgene) in plasmids that encoded the overexpression of aminoacyl tRNA synthetases were previously prepared. In order to obtain a plentiful amount of the plasmids to yield the vectors, a miniprep kit (Zymo) was used.

The freshly-prepared plasmids were digested with restriction endonucleases to generate the empty vectors as follows. A 200 μL double-digestion reaction was carried out for each. The pET-16b plasmid (for MAP) was combined with 20 μL of 10× CutSmart Buffer (1× final) and 4 μL each of NdeI and BamHI-HF (80 U of each enzyme), with water added to volume. An analogous reaction was prepared for the pET-21a plasmid (for PDF) using XhoI instead of BamHI-HF. The double-digestion reactions were incubated overnight at 37° C. In order to prevent recircularization of the vector, 10 μL of rSAP (Shrimp Alkaline Phosphatase, New England Biolabs) was added to each tube and the reactions were incubated at 37° C. for 30 minutes. Then, the crude reactions were diluted with water to 300 μL, extracted with phenol/chloroform, and precipitated with ethanol followed by a 70% (v/v) ethanol wash. The vectors were dissolved in water, quantified by measuring absorbance, and set aside for ligation of the inserts.

Preparation of PDF/MAP Inserts. First, genomic DNA from a K12 strain of *E. coli* was isolated (Cheng et al., *Biotechnol. Lett.* 28(1):55-59 (2006), which is hereby incorporated by reference in its entirety). A 15 mL culture tube containing 5 mL of LB was inoculated with XL10-Gold competent cells and the culture was grown overnight at 37° C. on a rotator. Two portions of culture (1 mL each) were transferred to 1.5 mL tubes and pelleted by centrifugation at 8,000×g for 2 minutes at ambient temperature. The supernatants were discarded, and the cell pellets were washed as follows. The pellets were resuspended in 400 μL of STE buffer (100 mM NaCl, 10 mM Tris-HCl, 1 mM EDTA, pH 8.0), spun down as before, and the supernatants were discarded. This wash was repeated once for a total of two washes. The washed pellets were resuspended in 200 μL of TE buffer (10 mM Tris-HCl, 1 mM EDTA, pH 8.0). Cells were lysed by addition of 100 μL of PCI (phenol/chloroform/isoamyl alcohol, 25:24:1 (v/v/v), VWR) with vortexing for 1 minute. The cloudy white mixtures were centrifuged at 13,000×g for 5 minutes, at which time the organic and aqueous layers had a white interface of denatured proteins in between. For each tube, a portion of the aqueous layer (160 μL) was transferred to a new 1.5 mL tube. TE buffer (40 μL) and chloroform (100 μL) were added and the mixture was briefly vortexed and spun down as before. A portion of the aqueous layer (160 μL) was transferred to a new 1.5 mL tube, and chloroform extraction was repeated several times, with gentle tapping and tube inversion instead of vortexing. Disappearance of the middle white protein layer indicated completion of chloroform extraction, after a total of 4 extractions. To the final aqueous layer (160 μL) in a new 1.5 mL tube was added 40 μL of TE buffer and 5 μL of RNase A (10 mg/mL). The mixture was incubated at 37° C. for 10 minutes to digest RNA. Then, 100 μL of chloroform was added to denature RNase A. The tube was mixed well and spun down as before. A portion of the aqueous layer (150 μL) was transferred to a new 1.5 mL tube for absorbance measurement and quantitation.

TABLE 3

PCR amplification primers for MAP and PDF.

| Name | Sequence 5' to 3' | SEQ ID NO: |
|---|---|---|
| MAP-FP | CGT**CA**↓**TATG**GCTATCTCAATCAAGACCCC | 209 |
| MAP-RP | AGCC**G**↓**GATCC**TTATTCGTCGTGCGAGATTA | 210 |
| PDF-FP | GCATA**CA**↓**TATG**TCAGTTTTGCAAGTGTTACATATTCCGG | 211 |
| PDF-RP | GGTG**C**↓**TCGAG**AGCCCGGGCTTTCAGACGAT | 212 |

Restriction endonuclease sites are in bold, with a downward arrow (↓) to indicate the location of the cut.

Primer sets for MAP or PDF (shown in Table 3) were used for PCR amplification of the desired genes from the isolated genomic DNA. The primers contained an annealing region for the protein of interest, as well as restriction endonuclease sites (shown in bold) for cloning. For each protein gene, PCR (50 μL) was assembled with the genomic DNA as template (20 ng) with 50 μM of each dNTP, 2 μM each of the forward and reverse primers, and 0.02 U/μL Phusion HF DNA Polymerase (ThermoScientific) in 1× Phusion HF Buffer. Using a thermal cycler, the reactions were initially heated to 98° C. for 30 seconds, followed by 30 cycles of 98° C. for 5 seconds, 62° C. for 10 seconds, and 72° C. for 15 seconds. The crude PCR mixtures were diluted with water to 300 μL, extracted with phenol/chloroform, and precipitated with ethanol followed by a 70% (v/v) ethanol wash. Pellets for the amplified MAP and PDF genes were dissolved in 42 μL of water and analyzed by 1% agarose gel.

Upon confirmation of amplification of MAP and PDF genes by gel, the DNAs were digested with restriction endonucleases to generate DNA inserts for ligation into the overexpression vectors described above. A 50 μL double-digestion reaction was carried out for each. MAP DNA (40 μL) was combined with 5 μL of 10× CutSmart Buffer (1× final) and 2.5 μL each of NdeI and BamHI-HF (50 U of each enzyme). An analogous reaction was prepared for PDF using XhoI instead of BamHI-HF. The double-digestion reactions were incubated overnight at 37° C. Then, the crude reactions were diluted with water to 300 μL, extracted with phenol/chloroform, and precipitated with ethanol followed by a 70% (v/v) ethanol wash.

The pellets for the MAP and PDF inserts were dissolved in 40 μL of water with 4 μL of 10× Orange G loading dye. The entire volume of each sample was loaded onto a 1% agarose gel for purification. Bands for the inserts were visualized with a 254 nm handheld UV lamp, extracted using x-tracta Gel Extractor tools (Promega), and transferred into new, pre-massed 1.5 mL tubes. The insert DNA bands were purified using EZNA Gel Extraction Kit (Omega Bio-tek) by following the manufacturer's protocol. After elution, the DNA inserts were quantified by absorbance using NanoDrop.

Cloning of PDF/MAP into Vectors. MAP and PDF plasmid construction was carried out by ligating the insert DNAs for each protein into its corresponding vector. Ligation reactions (5 μL each) were assembled by combining 2.5 μL of 2× Quick Ligase Buffer (1× final), 2 nM of vector, 6 nM of insert, 0.25 μL of T4 Quick DNA Ligase, and water to volume. Ligation reactions with vector only (no insert) were also prepared as negative controls. The ligation reactions were incubated at ambient temperature for 10 minutes, then chilled on ice. To each reaction was added 45 μL of XL10-Gold competent cells, and transformation was allowed to proceed on ice for 30 minutes. The cells were heat shocked at 42° C. for 30 seconds and immediately placed back on ice. Then, cells were transferred to 15 mL culture tubes with 1 mL of SOC medium (Super Optimal broth with Catabolite repression) and rotated at 37° C. for 1 hour. The cells were transferred to new 1.5 mL tubes and pelleted by centrifugation at 10,000×g for 1 minute. The supernatants were decanted, leaving ~100 μL of medium. Using a 200 μL pipettor, each of the pelleted cells was resuspended in the remaining medium, pipetted onto an LB/Amp agar plate, and spread with glass beads. The plates were grown overnight at 37° C. for colony formation. Three colonies each were picked from the MAP plate and the PDF plate for growth and plasmid miniprep. Each prepared plasmid was submitted for Sanger sequencing analysis (Genewiz) to confirm the insert was properly incorporated into the vector.

Expression Test

After confirmation of the correct sequences, a plasmid stock for each PDF and MAP were transformed into One Shot BL21 Star (DE3) cells (Invitrogen). For the reaction, 10 ng of plasmid was combined with 12 μL of cells and incubated on ice for 20 minutes. The cells were heat shocked at 42° C. for 30 seconds and immediately placed back on ice. Then, cells were transferred to 15 mL culture tubes with 100 μL of SOC medium and rotated at 37° C. for 1 hour. The cells were transferred to new 1.5 mL tubes and pelleted by centrifugation at 10,000×g for 1 minute. The supernatants were decanted and plated onto LB/Amp agar plates as before. The plates were grown overnight at 37° C. for colony formation. Four colonies from each plate were picked and used to inoculate 5 mL of LB/Amp in a 15 mL culture tube. The cultures were rotated at 37° C. for ~7 hours, at which time the OD600 of each was ~1.2. For each protein culture, two glycerol stocks were prepared. To a 1.5 mL sterile screw-cap tube with 500 μL autoclaved 30% glycerol was added 500 μL culture, for a final concentration of 15% glycerol. Each tube was immediately placed on dry ice to freeze, then stored at −80° C.

For each glycerol stock (four per protein), a portion of 5 mL of LB/Amp was inoculated in a 15 mL culture tube. The starter cultures were grown overnight by rotating at 37° C. Then, 100 μL of each starter culture was used to inoculate 5 mL of fresh LB/Amp in a 15 mL culture tube. An extra portion of 5 mL of LB/Amp was inoculated as well to monitor the approximate OD600 at various time points. The cultures were grown by rotating at 37° C. When the OD600 was ~0.6, 2 mL of culture was removed from each tube to save as the "pre-induced" culture. Each of the remaining 3 mL of cultures was induced with 3 μL of 1 M IPTG (isopropyl β-D-1-thiogalactoside) and allowed to rotate at 37° C. for 3.5 hours ("induced" cultures). The actual OD600 value was measured for each "pre-induced" and "induced" culture sample. A volume of each culture equivalent to OD600=0.8 was transferred to a 2 mL tube and pelleted by centrifugation at 21,000×g for 2.5 minutes. Supernatants were discarded and pellets were used for analysis by SDS-PAGE (pre-induced samples were stored at −20° C. before analysis).

Figure 4:
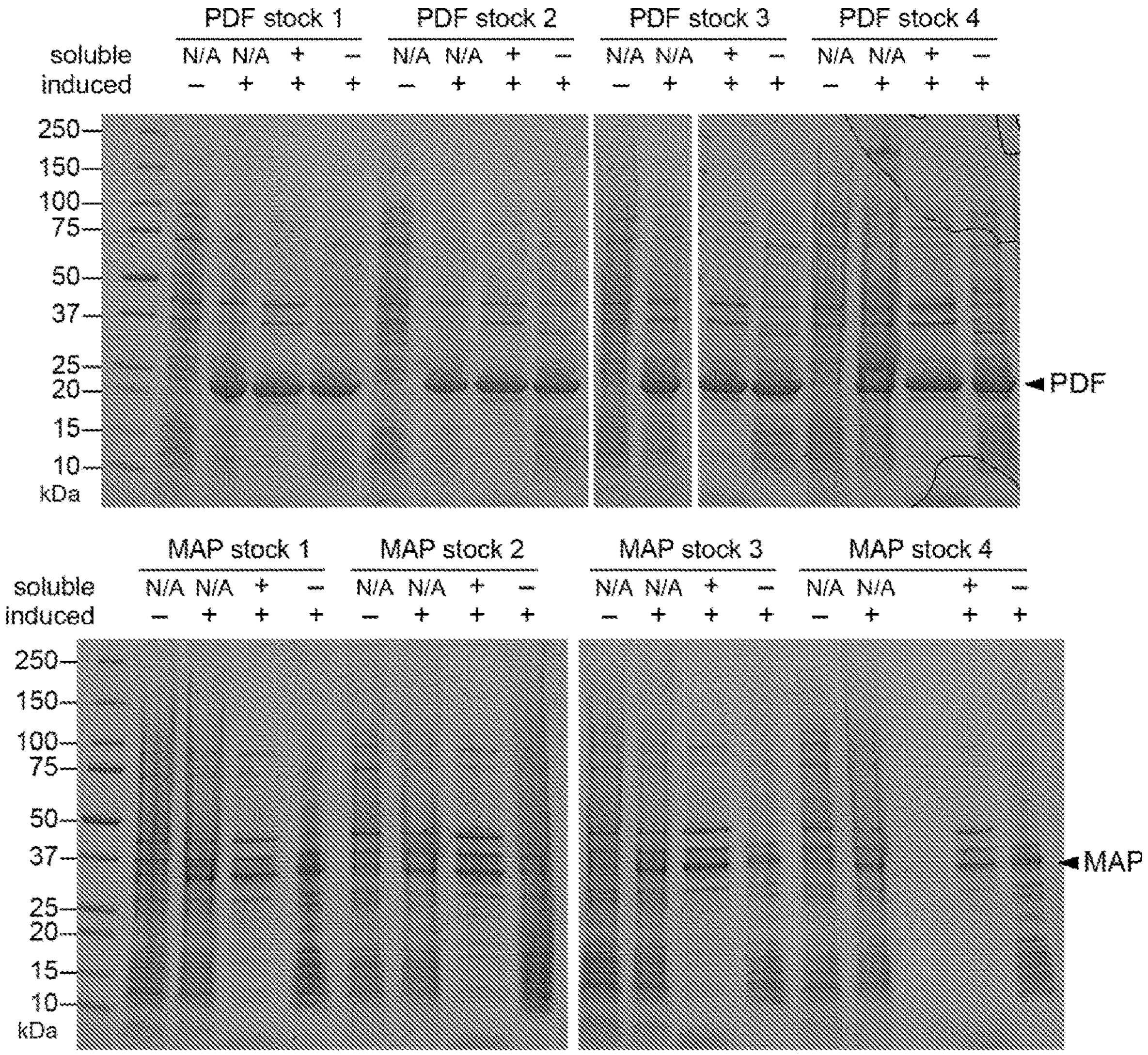
FIG. 4 shows the expression and solubility of PDF and MAP. Samples were run on 4-20% SDS-PAGE (Bio-Rad) and stained with Coomassie Brilliant Blue G-250 (Bio-Rad).

Each pellet was resuspended in 100 μL 1× Laemmli sample buffer with 2.5% (v/v) BME and heated to 95° C. for 10 minutes. After cooling to room temperature, 15 μL of each sample was loaded onto a 4-20% SDS-PAGE gel (Bio-Rad) to compare protein expression levels before and after induction. The glycerol stock(s) showing the greatest protein expression levels were designated for use in future experiments (FIG. 4). Expression levels were generally strong for PDF, while MAP expression levels were typically much lower than PDF.

Solubility Test

At the same time as the protein expression experiment, the solubility of each protein was also tested. For each culture, 1 mL of the remaining "induced" cells was transferred to a 2 mL tube and pelleted by centrifugation at 21,000×g for 3 minutes. The supernatants were discarded, and the pellets were resuspended in 50 μL of B-PER Bacterial Protein Extraction Reagent (ThermoScientific). Lysis was allowed to proceed at ambient temperature for 10 minutes. Then, the reactions were pelleted by centrifugation at 21,000×g for 10 minutes at 4° C. Each supernatant (soluble proteins) was transferred to a new 1.5 mL tube with 50 μL 2× Laemmli sample buffer with 5% (v/v) BME. To each pellet (insoluble proteins) was added 100 μL 1× Laemmli sample buffer with 2.5% (v/v) BME. Samples were heated to 95° C. for 10 minutes. After cooling to room temperature, 15 μL of each sample was loaded onto a 4-20% SDS-PAGE gel (Bio-Rad) to analyze protein solubility. Bands for both PDF and MAP were more prevalent in the soluble fraction, indicating the proteins are soluble and could be isolated from cells using the conditions described above (FIG. 4).

Second-Strand Synthesis

Short peptide sequences were used to test digestion with PDF/MAP. The DNAs for those sequences were prepared by second-strand synthesis. The oligos used are listed in Table 4, as well as the peptide sequences encoded by combinations thereof.

TABLE 4

Oligos for second-strand synthesis and encoded peptide sequences.

| Name | Sequence (5' to 3') | SEQ ID NO: |
|---|---|---|
| MH6C-1 | TAATACGACTCACTATAGGGTTAACTTTAGTAAGGAGG ACAGCTAAATGCACCACCATCACCATCACTGCAAA | 213 |
| MAH6C-1 | TAATACGACTCACTATAGGGTTAACTTTAGTAAGGAGG ACAGCTAAATGGCGCACCACCATCACCATCACTGCAAA | 214 |
| MH6C-2AAdeltaM | CTAGCTACCTATAGCCGGTGGCATTTATGGGTCAGACG CGCCGGGTCGATGTAGGCTTTGCAGTGATGGTGATGGT G | 215 |

TABLE 4 -continued

Oligos for second-strand synthesis and encoded peptide sequences.

| Name | Sequence (5' to 3') | SEQ ID NO: |
|---|---|---|
| MH6C-AAAM[a] | MHHHHHHCKAYIDPARLTHKCHRL | 216 |
| MAH6C-AAAM[b] | MAHHHHHHCKAYIDPARLTHKCHRL | 217 |

Peptide sequences are encoded by the following oligo combinations:
[a]MH6C-1 and MH6C-2AAdeltaM;
[b]MAH6C-1 and MH6C-2AAdeltaM.

Second-strand synthesis reactions (100 μL) were assembled by combining 10 μL of 10× Apex Buffer II (Genesee Scientific), 3 μL of 50 mM $MgCl_2$, 2 μL of 10 mM each dNTP mix, 1 μL of 100 μM oligo-1, 1 μL of 100 μM oligo-2, and 0.5 μL of Apex Hot Start Taq (Genesee Scientific). Using a thermal cycler, the reactions were heated at 98° C. for 10 minutes, 55° C. for 15 minutes, and 72° C. for 45 minutes. The crude PCR mixtures were diluted with water to 300 μL, extracted with phenol/chloroform, and precipitated with ethanol followed by a 70% (v/v) ethanol wash. The pellets were dissolved in 25 μL of water. The DNAs were analyzed on a 2% agarose gel, compared to controls with known concentrations to approximate the yield for assembling T7 transcription. DNA was transcribed, and the crude transcripts were purified by 8% denaturing PAGE for use in translation.

Note: It has been observed that T7 transcription sometimes fails to produce RNA from dsDNA generated by second-strand synthesis. It is hypothesized that T7 transcription may fail in cases when the composition of the resulting dsDNA is about 50% synthetic oligonucleotides. PCR amplification of the DNA produced from second-strand synthesis typically results in dsDNA that can be successfully transcribed.

Methods—Library Generation for Round 1 Selection

Extension of DNA Libraries

The antisense strands of the DNA libraries to be extended and used in this study were purchased from Integrated DNA Technologies (Ultramer® DNA Oligos, 4 nmol; summarized in Table 5). The lyophilized powders were dissolved in 100 μL of water and purified by denaturing PAGE. A portion of each library (40 μL) was purified, and the rest was stored at −20° C. The libraries were purified as follows. To 40 μL of library in water was added 60 μL of 8 M urea. The libraries were heated at 70° C. for 5 minutes before loading onto a pre-run 5% denaturing PAGE gel. The library bands were visualized with a 254 nm handheld UV lamp and cut out with fresh razors for electroelution with Elutrap Electroelution System (Whatman) with 0.5×TBE running buffer. The eluents were precipitated with isopropanol followed by a 70% (v/v) ethanol wash. The library pellets were dissolved in 26 μL of water and quantified using NanoDrop.

TABLE 5

Individual libraries for selection with PGT antibodies.

| Library | Name | Sequence 5' to 3'[a] | SEQ ID NO: |
|---|---|---|---|
| Heavily Biased | H-E-2 | AXXXXXXXIGDIRXAXCMXXXXXXXXXXXXXXXXXXXXXXXXXXXXXXX | 218 |
| | | GTGGTGATGACCCAGAGAACCGGAGCCSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNCATGCASNNCGCSNNACGAATATCGCCAATSNNSNNSNNSNNSNNSNNSNNCGCCATTTAGCTGTCCTCCTTACTAA | 219 |
| | H-M-2 | AXXXXXXXXXXXXXXXXXXIGDIRXAXCMXXXXXXXXXXXXXXXXXXXX | 220 |
| | | GTGGTGATGACCCAGAGAACCGGAGCCSNNSNNSNNSNNSNNSNNSNNSNNSNNSNNSNNSNNSNNSNNSNNSNNSNNSNNSNNSNNCATGCASNNCGCSNNACGAATATCGCCAATSNNSNNSNNSNNSNNSNNSNNSNNSNNSNNSNNSNNSNNSNNSNNSNNSNNSNNCGCCATTTAGCTGTCCTCCTTACTAA | 221 |
| | H-L-2 | AXXXXXXXXXXXXXXXXXXXXXXXXXXXXXIGDIRXAXCMXXXXXXXXX | 222 |
| | | GTGGTGATGACCCAGAGAACCGGAGCCSNNSNNSNNSNNSNNSNNSNNSNNSNNCATGCASNNCGCSNNACGAATATCGCCAATSNNSNNSNNSNNSNNSNNSNNSNNSNNSNNSNNSNNSNNSNNSNNSNNSNNSNNSNNSNNSNNSNNSNNSNNSNNSNNSNNSNNCGCCATTTAGCTGTCCTCCTTACTAA | 223 |
| Less Biased | L-E-3 | AXXXXXXXIGDIRXXXXXXXXXXXXXXXXXXXXXXXXXXXXXXXXXXXX | 224 |
| | | GTGATGGTGGCCTAAGCTACCGGAGCCSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNSNNACGAATATCGCCAATSNNSNNSNNSNNSNNSNNSNNCGCCATTTAGCTGTCCTCCTTACTAA | 225 |
| | L-M-3 | AXXXXXXXXXXXXXXXXXXIGDIRXXXXXXXXXXXXXXXXXXXXXXXXX | 226 |
| | | GTGATGGTGGCCTAAGCTACCGGAGCCSNNSNNSNNSNNSNNSNNSNNSNNSNNSNNSNNSNNSNNSNNSNNSNNSNNSNNSNNSNNSNNSNNSNNACGAATATCGCCAATSNNSNNSNNSNNSNNSNNSNNSNNSNNSNNSNNSNNSNNSNNSNNSNNSNNSNNCGCCATTTAGCTGTCCTCCTTACTAA | 227 |

TABLE 5 -continued

Individual libraries for selection with PGT antibodies.

| Library | Name | Sequence 5' to 3'[a] | SEQ ID NO: |
|---|---|---|---|
| | L-L-3 | AXXXXXXXXXXXXXXXXXXXXXXXXXXXXXIGDIRXXXXXXXXX<br>XXXXX | 228 |
| | | GTGATGGTGGCCTAAGCTACCGGAGCCSNNSNNSNNSNNSNNSN<br>NSNNSNNSNNSNNSNNSNNSNNSNNACGAATATCGCCAATSNNS<br>NNSNNSNNSNNSNNSNNSNNSNNSNNSNNSNNSNNSNNSNNSNN<br>SNNSNNSNNSNNSNNSNNSNNSNNSNNSNNSNNSNNSNNCGCCA<br>TTTAGCTGTCCTCCTTACTAA | 229 |
| | L-0-3 | AXXXXXXXXXXXXXXXXXXXXXXXXXXXXXXXXXXXXXXXXXXX<br>XXXXX | 230 |
| | | GTGATGGTGGCCTAAGCTACCGGAGCCSNNSNNSNNSNNSNNSN<br>NSNNSNNSNNSNNSNNSNNSNNSNNSNNSNNSNNSNNSNNSNNS<br>NNSNNSNNSNNSNNSNNSNNSNNSNNSNNSNNSNNSNNSNNSNN<br>SNNSNNSNNSNNSNNSNNSNNSNNSNNSNNSNNSNNSNNCGCCA<br>TTTAGCTGTCCTCCTTACTAA | 231 |

[a]Each peptide sequence is followed by -GSGSLGHTIFITITITIHRL (SEQ ID NO: 6). The Heavily Biased library comprises three individual libraries with the conserved IGDIRXAXCM (SEQ ID NO: 289) motif early (E), middle (M), or late (L) in the sequence. The Less Biased library comprises four individual libraries with the conserved IGDIR (SEQ ID NO: 1) motif early (E), middle (M), or late (L) in the sequence, or not at all (0). The resulting open reading frames of each individual library are shown, lacking the implicitly-cleaved N-terminal HPG. The antisense DNA sequences of each library, as ordered from IDT, are also shown.

The purified DNA templates were extended by PCR amplification (Table 4). For each library, PCR (1.2 mL) was performed with 15 nM of purified template (16 pmol), 0.2 mM of each dNTP, 1 μM of the forward extending primer (JB-HL-fwd-X: 5'-TAATACGACTCACTATAGGGT-TAACTTTAGTAAGGAGGACAGCTAA (SEQ ID NO:232), 1 μM of the reverse extending primer (Heavily Biased: 5'-CTAGCTACCTATAGCCGGTGGT-GATGGTGGTGATGACCCAGAGAAC (SEQ ID NO:233); Less Biased: 5'-CTAGCTACC-TATAGCCGGTGGTGATGGTGATGGTGGCCTAAGC-TAC (SEQ ID NO:234)), and 0.025 U/μL Taq DNA Polymerase (New England Biolabs) in 1× Standard Taq Buffer. The following PCR protocol was used: 5 cycles of 95° C. for 30 seconds, 57° C. for 15 seconds, and 68° C. for 15 seconds, followed by a final extension at 68° C. for 5 minutes. The crude PCR products for the Heavily Biased pool and for the Less Biased pool were combined on ice in 15 mL conical centrifuge tubes. The DNA solutions were extracted with phenol/chloroform, followed by 3 extractions with n-butanol to concentrate the DNA solution. The resulting DNA solution (~2-3 mL) was aliquoted into 2 mL microcentrifuge tubes and precipitated with isopropanol. The pellets were rinsed with 70% (v/v) ethanol and dissolved in 100 μL of water. The extended DNA library pools were analyzed on a 2% agarose gel. The yields were estimated to be 188-235 pmol based on comparisons to control samples with known concentrations.

TABLE 6

Extended library DNA sequences. The full sense DNA sequences after PCR with the extending primers are shown, with the added constant regions in bold.

| Library | Name | Sequence 5 to 3' | SEQ ID NO: |
|---|---|---|---|
| Heavily Biased | H-E-2 full | **TAATACGACTCACTATAGGGTTAACT**TTAGTAAGGAGGACAGC<br>TAAATGGCGNNSNNSNNSNNSNNSNNSNNSATTGGCGATATTC<br>GTNNSGCGNNSTGCATGNNSNNSNNSNNSNNSNNSNNSNNSNN<br>SNNSNNSNNSNNSNNSNNSNNSNNSNNSNNSNNSNNSNNSNNS<br>NNSNNSNNSNNSNNSNNSNNSNNSGGCTCCGGTTCTCTGGGTC<br>ATCACCAC**CATCACCACCGGCTATAGGTAGCTAG** | 235 |
| | H-M-2 full | **TAATACGACTCACTATAGGGTTAACT**TTAGTAAGGAGGACAGC<br>TAAATGGCGNNSNNSNNSNNSNNSNNSNNSNNSNNSNNSNNSN<br>NSNNSNNSNNSNNSNNSNNSATTGGCGATATTCGTNNSGCGNN<br>STGCATGNNSNNSNNSNNSNNSNNSNNSNNSNNSNNSNNSNNS<br>NNSNNSNNSNNSNNSNNSNNSNNSGGCTCCGGTTCTCTGGGTC<br>ATCACCAC**CATCACCACCGGCTATAGGTAGCTAG** | 236 |
| | H-L-2 full | **TAATACGACTCACTATAGGGTTAACT**TTAGTAAGGAGGACAGC<br>TAAATGGCGNNSNNSNNSNNSNNSNNSNNSNNSNNSNNSNNSN<br>NSNNSNNSNNSNNSNNSNNSNNSNNSNNSNNSNNSNNSNNSNN<br>SNNSNNSNNSATTGGCGATATTCGTNNSGCGNNSTGCATGNNS<br>NNSNNSNNSNNSNNSNNSNNSNNSGGCTCCGGTTCTCTGGGTC<br>ATCACCAC**CATCACCACCGGCTATAGGTAGCTAG** | 237 |
| Less Biased | L-E-3 full | **TAATACGACTCACTATAGGGTTAACT**TTAGTAAGGAGGACAGC<br>TAAATGGCGNNSNNSNNSNNSNNSNNSNNSATTGGCGATATTC<br>GTNNSNNSNNSNNSNNSNNSNNSNNSNNSNNSNNSNNSNNSNN<br>SNNSNNSNNSNNSNNSNNSNNSNNSNNSNNSNNSNNSNNSNNS<br>NNSNNSNNSNNSNNSNNSNNSNNSGGCTCCGGTAGCTTAGGCC<br>ACCATCAC**CATCACCACCGGCTATAGGTAGCTAG** | 238 |

TABLE 6 -continued

Extended library DNA sequences. The full sense DNA sequences after PCR with the extending primers are shown, with the added constant regions in bold.

| Library | Name | Sequence 5 to 3' | SEQ ID NO: |
|---|---|---|---|
| | L-M-3 full | **TAATACGACTCACTATAGGGTTAACT**TTAGTAAGGAGGACAGC<br>TAAATGGCGNNSNNSNNSNNSNNSNNSNNSNNSNNSNNSNNSN<br>NSNNSNNSNNSNNSNNSNNSATTGGCGATATTCGTNNSNNSNN<br>SNNSNNSNNSNNSNNSNNSNNSNNSNNSNNSNNSNNSNNSNNS<br>NNSNNSNNSNNSNNSNNSNNSNNSGGCTCCGGTAGCTTAGGCC<br>ACCATCAC**CATCACCACCGGCTATAGGTAGCTAG** | 239 |
| | L-L-3 full | **TAATACGACTCACTATAGGGTTAACT**TTAGTAAGGAGGACAGC<br>TAAATGGCGNNSNNSNNSNNSNNSNNSNNSNNSNNSNNSNNSN<br>NSNNSNNSNNSNNSNNSNNSNNSNNSNNSNNSNNSNNSNNSNN<br>SNNSNNSNNSATTGGCGATATTCGTNNSNNSNNSNNSNNSNNS<br>NNSNNSNNSNNSNNSNNSNNSNNSGGCTCCGGTAGCTTAGGCC<br>ACCATCAC**CATCACCACCGGCTATAGGTAGCTAG** | 240 |
| | L-0-3 full | **TAATACGACTCACTATAGGGTTAACT**TTAGTAAGGAGGACAGC<br>TAAATGGCGNNSNNSNNSNNSNNSNNSNNSNNSNNSNNSNNSN<br>NSNNSNNSNNSNNSNNSNNSNNSNNSNNSNNSNNSNNSNNSNN<br>SNNSNNSNNSNNSNNSNNSNNSNNSNNSNNSNNSNNSNNSNNS<br>NNSNNSNNSNNSNNSNNSNNSNNSGGCTCCGGTAGCTTAGGCC<br>ACCATCAC**CATCACCACCGGCTATAGGTAGCTAG** | 241 |

T7 Transcription

Several batches of T7 transcription were carried out in order to produce substantive quantities of RNA for subsequent steps. As a representative example, 75 pmol of library DNA was used for a T7 transcription reaction. The reaction was incubated at 37° C. overnight, DNA template was removed by incubation with Turbo DNase at 37° C. for 15 minutes and the reaction was quenched with EDTA. The crude transcripts were precipitated with isopropanol, followed by a 70% (v/v) ethanol rinse. The library RNA pellets were dissolved in 8 M urea and purified on a 5% denaturing PAGE gel. Note: The glass plates of the gel were soaked in 1 N NaOH for 1 hour, prior to use. The RNA bands were visualized with a 254 nm handheld UV lamp and cut out with fresh razors for electroelution with Elutrap Electroelution System (Whatman) with 0.5×TBE running buffer. The eluents were precipitated with isopropanol followed by a 70% (v/v) ethanol wash. The library pellets were dissolved in 140 of water and quantified by NanoDrop. In this representative experiment, yields were 2.5-3.7 nmol. The purified RNA was combined with other batches for puromycin modification.

Puromycin Modification

Purified library RNA (4.8 nmol) was subjected to puromycin modification via photo-crosslinking with psoralen. Reactions (1600 μL) were assembled on ice with 3 μM Library RNA and 7.5 μM XL-PSO oligonucleotide [(C6 psoralen)-2'-OMe(UAGCCGGUG)$(dA)_{15}$(Spacer $9)_2$dA $(dC)_2$—Puromycin, purchased from Keck] in 1× XL Buffer (10× XL buffer: 200 mM HEPES-KOH, 1 M KCl, 10 mM spermidine, 10 mM EDTA, pH 7.5). The reaction mixtures were aliquoted into 8-strip 0.2 mL PCR tubes (50 μL each) and annealed on a thermal cycler (Bio-Rad S1000). Reactions were heated at 70° C. for 3 minutes, then slowly cooled to 25° C. with a ramp of 0.1° C./s, incubated at 25° C. for 5 minutes, and then chilled at 4° C. The annealed solutions were transferred to a Costar 96-well plate (100 μL per well) and a sample (5 μL) was set aside for gel analysis. The plate was placed on an ice water bath prepared in an empty pipette-tip box lid. In the 4° C. room, a handheld UV lamp was placed on top of the plate to irradiate the solutions at 365 nm for 20 minutes. The solutions from the wells were combined and a sample (5 μL) was set aside for gel analysis. Then, the solutions were precipitated with isopropanol followed by a 70% (v/v) ethanol wash before denaturing PAGE purification. A 5% gel was used, and the bands were visualized by RNA Staining Solution (Abnova, discontinued). The crosslinked RNA ("XL-RNA") bands were cut out and electroeluted with Elutrap Electroelution System (Whatman) with 0.5×TBE running buffer. The eluents were collected and precipitated with ethanol followed by a 70% (v/v) ethanol wash. The XL-RNA pellets were dissolved in 100 μL of water and quantified by NanoDrop. Yields ranged from 1050-1695 pmol. The purified XL-RNA was analyzed on a 5% denaturing PAGE, with comparison to the saved samples of non-XL RNA and crude XL-RNA.

Translation

Purified XL-RNA was subjected to mRNA-display translation with the homemade PURE system. As a representative example, 1500 pmol of XL-RNA was used for a translation reaction (1500 μL) assembled, with the addition of 15 μM MAP, 6 μM PDF, and 100 μM $CoCl_2$, with 3.3 μM $^3$H-histidine for radiolabeling. The translation reactions were incubated at 37° C. for 30 minutes. Then, 450 μL (0.3 volumes) of a solution of 2.05 M KCl and 172 mM $Mg(OAc)_2$ were added. The mixtures were incubated at room temperature for 15 minutes and then stored at −20° C. overnight to allow for efficient fusion formation.

Oligo(dT) Purification and Cyclization

Using the 1500 μL translation plus 450 μL $Mg^{2+}/K^+$ added as a representative example, following is the general protocol used for oligo(dT) purification and cyclization. A sample of the crude translation was set aside (48 μL) for analytical purposes. Six portions of 250 each of Oligo $d(T)_{25}$ Magnetic Beads (New England Biolabs) were placed into 2 mL microcentrifuge tubes. The beads were equilibrated twice with 1 mL of 1× oligo(dT) binding buffer with high EDTA (20 mM Tris-HCl, 1 M NaCl, 50 mM EDTA, pH 8.0, 0.2% (v/v) Triton X-100, 5 mM BME). The beads were resuspended in 317 μL of 2× oligo(dT) binding buffer with high EDTA and 317 μL of crude translation was added to each. The suspensions were tumbled at room temperature for 30 minutes. The supernatants were removed, and each of the tubes with beads were washed four times with 1268 μL of oligo(dT) binding buffer with TCEP (20 mM Tris-HCl, 1 M NaCl, 10 mM EDTA, pH 8.0, 0.2% (v/v) Triton X-10, 0.5 mM TCEP). The beads were then washed three times with 1268 µL of oligo(dT) wash buffer with TCEP (20 mM Tris-HCl, 300 mM NaCl, 10 mM EDTA, pH 8.0, 0.1% (v/v) Tween-20, 0.5 mM TCEP). Then, 1268 µL of cyclization buffer (20 mM Tris-HCl, pH 8.0, 660 mM NaCl, 0.2% (v/v) Triton X-100, 0.5 mM TCEP, 3.3 mM m-dibromoxylene, 33% (v/v) MeCN) was added and the suspension was tumbled at room temperature for 30 minutes. The supernatant was removed and 1268 µL of cyclization wash buffer with BME (20 mM Tris-HCl, pH 8.0, 660 mM NaCl, 0.2% (v/v) Triton X-100, 10 mM BME, 33% (v/v) MeCN) was added. The suspension was tumbled at room temperature for 10 minutes to quench the reaction. The supernatant was removed, and the beads were washed twice with 1268 µL portions of oligo(dT) wash buffer with BME/no EDTA (20 mM Tris-HCl, 300 mM NaCl, 0.1% (v/v) Tween-20, 10 mM BME). mRNA-peptide fusions were eluted from the beads with 317 µL of 0.1% (v/v) Tween-20. The elution step was repeated five times.

Yield Calculations by Liquid Scintillation Counting

The yields of oligo(dT) purification and cyclization, as well as subsequent steps, were calculated using LSC measurements. As the random libraries had a varying number of histidine residues within each peptide sequence, the average number of histidine residues was estimated to complete the specific activity calculation. Each library had six fixed histidine residues as part of the affinity tag on the C-terminus. Then, the probability of a histidine residue appearing in the random region was calculated, as histidine is encoded by 1/32 NNS codons. With 40 random NNS codons in the Heavily Biased library, 1.25 random histidine residues would be present on average. The Less Biased library comprised three libraries with 43 random NNS codons and one library with 48 NNS codons. Assuming equal representation of the four pools within the Less Biased library, 1.38 histidine residues would be present in the random regions. Adding the six fixed histidine residues, the average number of histidine residues was 7.25 for the Heavily Biased library and 7.38 in the Less Biased library.

In the oligo(dT) purification and cyclization example described, the yields were 18.2 pmol and 12.9 pmol for the Heavily Biased and Less Biased libraries, respectively. The fusion formation (i.e. mRNA-peptides formed) is determined from the yield of oligo(dT) purification, with the theoretical yield as the pmol of input XL-RNA. In the representative case, 1500 pmol of XL-RNA were used in translation, corresponding to fusion formation rates of 1.2% and 0.9% for the Heavily Biased and Less Biased libraries, respectively.

Reverse Transcription

For each library, the first two eluent fractions from oligo(dT) purification and cyclization were combined, totaling 3.8 mL. The eluents were passed through an Ultra-free 0.22 µm centrifugal filter unit (Millipore) into 10 separate 1.5 mL microcentrifuge tubes to remove residual magnetic beads. A portion of the filtered eluents (50 µL total) were saved for LSC and SDS-PAGE. Then, the mRNA-peptide fusions were precipitated with isopropanol in the presence of linear acrylamide carrier, followed by a 70% (v/v) ethanol wash. The pellets were allowed to dry at room temperature before dissolving in 27.5 µL of 0.18% (v/v) Triton X-100, such that the final concentration of Triton X-100 in the 50 µL reaction would be 0.1%. To the dissolved fusions were then added 2.5 µL of a mix of 10 mM each dNTP to a final concentration of 0.5 mM each and 6.25 µL of 80 µM reverse transcription primer to a final concentration of 10 µM (for Heavily Biased, H-RT-RP: 5'-TTTTTTTTTTTTTTTGT-GATGGTGGTGATGACCCAGAG (SEQ ID NO:242); for Less Biased, L-RT-RP: 5'-TTTTTTTTTTTTTTTGT-GATGGTGATGGTGGCCTAAGC (SEQ ID NO:243)). The solutions were heated at 65° C. for 5 minutes on a metal heat block and then incubated on ice for >5 minutes. Then, 10 µL of 5× Reaction Buffer (ThermoScientific), 1.25 µL of 40 U/µL of RiboLock RNase Inhibitor (ThermoScientific), and 2.5 µL of 200 U/µL of RevertAid Reverse Transcriptase (ThermoScientific) were added, with final concentrations of 1×, 1 U/µL, and 10 U/µL, respectively. The reactions were incubated at 42° C. on a metal heat block for 30 minutes, chilled on ice, and then diluted to 200 µL with water. A total of 25 µL was saved for LSC and SDS-PAGE. Yields were 14.3 pmol and 10.1 pmol for the Heavily Biased and Less Biased libraries, respectively.

Note: For subsequent rounds of selection, the reverse transcription protocol was altered slightly from that described above. Instead of addition before heating at 65° C., the dNTP mix was added after (with Reaction Buffer, RiboLock, and RevertAid).

Ni-NTA Agarose Purification

The cDNA/mRNA-peptide fusions were precipitated with ethanol in the presence of linear acrylamide carrier for Ni-NTA affinity purification. Each of the pellets in the 10 tubes was dissolved in 17.5 µL of denaturing bind buffer (100 mM NaH$_2$PO$_4$, 10 mM Tris-HCl, 6 M guanidinium hydrochloride, pH 8.0, with 0.2% (v/v) Triton X-100, 5 mM BME). Then, 75 µL of HisPur™ Ni-NTA Resin (ThermoScientific) was equilibrated as follows: 600 µL of denaturing bind buffer was added to the resin, spun down at 21,000×g for 30 seconds, and the supernatant was removed. This wash was repeated once more. The resin was resuspended in 200 µL of denaturing bind buffer and divided into the 10 tubes with fusions (20 µL each) for a volume of 37.5 µL per tube (altogether: 375 µL). The suspensions were tumbled at room temperature for 1 hour. Then, each of the 10 suspensions were transferred into one Ultra-free 0.22 µm centrifugal filter unit (Millipore), and the filter was spun down at 2,000×g for 30 seconds to collect the flow-through fraction. The tubes containing the resin suspensions were rinsed with 15 µL of denaturing bind buffer each (total: 150 µL) and transferred to the filter unit. The filter was spun down at 2,000×g for 30 seconds. The tubes were rinsed with denaturing bind buffer once more. Then, the resins in the filter unit were washed with 150 µL of wash buffer (50 mM NaH$_2$PO$_4$ pH 8.0, 300 mM NaCl, 20 mM imidazole, 5 mM BME) and spun down at 2,000×g for 30 seconds. This wash was repeated twice more, with the last centrifugation at 10,000×g instead of 2,000 xg. The cDNA/mRNA-peptide fusions were eluted from the resins as follows: the filter was placed into a new 1.5 mL microcentrifuge tube and 75 µL of native elute buffer (50 mM NaH$_2$PO$_4$, 300 mM NaCl, 250 mM imidazole, pH 8.0, with 0.2% (v/v) Triton X-100, 5 mM BME) was added, and then the filter was spun down at 10,000×g for 30 seconds. The elution step was repeated twice more with collection of each eluent in a separate 1.5 mL microcentrifuge tube. A portion of the flow-through, washes, and eluents, as well as the filter with resin, were measured by LSC. The combined eluents of the Heavily Biased and Less Biased libraries contained 4.6 pmol and 4.0 pmol fusions, respectively, while the flow-through fractions contained 3.1 pmol and 2.0 pmol fusions, respectively. To improve recovery, imidazole can be omitted from the wash buffer.

Ni-NTA agarose purification was repeated to retrieve more cDNA/mRNA-peptides from the flow-through fractions. To the flow-through fraction (375 μL) was added 75 of fresh Ni-NTA resin. The suspension was tumbled at room temperature for 1 hour before transferring to a new centrifugal filter unit. Wash and elution steps were carried out as before. A portion of the flow-through, washes, and eluents, as well as the filter with resin, were measured by LSC. In the first eluent, another 1.1 pmol and 0.8 pmol of fusions were recovered for the Heavily Biased and Less Biased libraries, respectively.

Gel Filtration

All three eluents from Ni-NTA agarose purification, as well as the first eluent from resubjection, were desalted by gel filtration to remove imidazole. Per manufacturer's instructions, a NAPS column (GE Healthcare) was equilibrated with 10 mL of gel filtration buffer (10 mM Tris-HCl, pH 7.5, 1 mM EDTA pH 8.0, with 0.2% (v/v) Triton X-100 and 5 mM BME). The eluents (300 μL total) were then loaded onto the column and collected in a 1.5 mL tube as the first flow-through fraction. Then, 200 μL of gel filtration buffer was added and collected in a new 1.5 mL tube as the second flow-through fraction. The cDNA/mRNA-peptide fusions were then eluted from the column with 700 μL of gel filtration buffer, followed by a second elution (300 μL of gel filtration buffer), collected separately. Yields were 6.2 pmol and 5.1 pmol for the Heavily Biased and Less Biased libraries, respectively.

Nuclease-digestion of Fusions for SDS-PAGE

The efficiency of the click reaction was analyzed by SDS-PAGE of nuclease-digested peptides. Saved samples of combined non-glycosylated fusions and glycosylated fusions for batches 1-3 and batches 4-5 were separately precipitated with ethanol in the presence of linear acrylamide. The pellets were dried and dissolved in 4 μL of 200 mM $NH_4OAc$ pH 5.3. Then, 1 μL of 1 U/μL Nuclease $P_1$ from *Penicillium citrinum* (Sigma) was added and the samples were incubated at 37° C. for 1 hour. The reaction was quenched by addition of 2.5 μL of 1 M Tris-HCl, pH 7.8. Then, 7.5 μL of 2× Laemmli sample buffer with 5% BME was added to the samples for analysis on a 4-20% SDS-PAGE gel (Bio-Rad).

Click Reaction and Analysis of Fusions Batches

Three batches of fusion prep were carried out and subjected to the click reaction with $Man_9GlcNAc_2$—$N_3$. Then, all eight batches were resubjected to the click reaction to improve glycosylation efficiency. Each of the sample sets were separately analyzed by SDS-PAGE, as well as combined.

Preparation of Glycosylated Fusions for Selection Round 1

For each library, all glycosylated fusions from batches 1-8 were combined in a single 1.5 mL tube. The volume was reduced by speed-vac, and then the fusions were precipitated with isopropanol in the presence of linear acrylamide carried, followed by a 70% (v/v) ethanol wash. The pellets were dissolved in 153 μL 1× selection buffer (20 mM Tris-HCl, pH 7.5, 100 mM NaCl, 0.1% (v/v) Triton X-100). A portion of the library fusions were set aside (4.5 μL).

Round 1 Selection

To 148.5 μL of library fusions in 1× selection buffer were added PGT128, PGT130, and glPGT128 to final concentrations of 200 nM each, with 1× selection buffer added to 200 μL. The mixture was tumbled at room temperature for 1 hour. While tumbling, Dynabeads™ Protein G (Invitrogen) were equilibrated with 1× selection buffer as follows. For each library, 150 μL of Protein G bead suspension was transferred to a 1.5 mL microcentrifuge tube. The tube was placed on a magnetic rack for 1 minute to separate the beads from solution, and the supernatant was removed. Then, 600 μL of 1× selection buffer was added to the beads. The mixture was resuspended by gently vortexing, spun down briefly, and placed on a magnetic rack for 1 minute. The supernatant was removed, and this wash was repeated two more times. The final supernatant was removed just prior to addition of the incubated library/antibody mixture. The mixture was allowed to tumble at room temperature for 30 minutes to capture antibodies and bound library fusions. Then, the suspension was briefly spun down, placed on a magnetic rack, and the supernatant was removed and saved. To wash the beads, 200 μL of 1× selection buffer was added, gently vortexed, spun down briefly, placed on a magnetic rack for 1 minute, and the wash was removed and saved. This wash step was repeated twice more for a total of three washes, each saved separately. The beads were resuspended in 200 μL of PCR mix A (1× Standard Taq Buffer, 0.1 mM each dNTP, 0.1% (v/v) Triton X-100) for PCR-based cDNA recovery from beads, described later.

Determination of Fraction Bound. The bead mixture in PCR mix A was resuspended by pipet, and 4 μL was transferred to a new 1.5 mL tube with 50 μL denaturing elute buffer (10 mM Tris-HCl, pH 7.5, 1 mM EDTA pH 8.0, 0.2% SDS) to elute a small portion of fusions to measure the bound fraction. The suspension was heated at 95° C. for 5 minutes to denature antibodies, spun down briefly, placed on a magnetic rack for 1 minute, and the eluent was directly placed into a vial with liquid scintillation cocktail. The beads were washed with 50 of denaturing elute buffer, and the wash was placed into the same vial with liquid scintillation cocktail as the eluent. The beads were resuspended in 50 μL of denaturing elute buffer and placed into a separate vial with liquid scintillation cocktail for radioactivity measurements. The eluent with wash and the beads represented the "bound" fraction. Portions of the supernatant (4 μL) and washes (4 μL each) were measured by LSC as the "unbound" fraction. The tube in which the antibody and library fusions were incubated was also measured by LSC, but not included in calculations of fraction bound. The fraction bound was 18.1% for the Heavily Biased library and 14.8% for the Less Biased library.

Recovery of Bound cDNA from Round 1 Selection.

Another 400 μL of PCR mix A was added to dilute the bead-bound fraction. Pilot PCR experiments were carried out to determine the optimal PCR conditions for cDNA recovery. In experiments carried out by Satoru Horiya with similar libraries, a higher annealing temperature (73° C.) was preferable to the 62° C. annealing temperature we've typically used with these primer sets. Thus, a pilot PCR experiment was carried out to compare 62° C. to 73° C. as the annealing temperature within the following program: 94° C. for 5 minutes, n cycles of 94° C. for 30 seconds, 62° C. or 73° C. for 30 seconds, and 74° C. for 30 seconds. To 20 μL of beads in PCR mix A was added another 40 μL of PCR mix A. Then, 20 μL PCR mix B (1× Standard Taq Buffer, 0.1 mM each dNTP, 4 μM forward primer, 4 μM reverse primer, 0.1 U/μL Taq (New England Biolabs), 0.1% (v/v) Triton X-100) was added, such that the final concentrations were 1×Standard Taq Buffer, 0.1 mM each dNTP 1 μM forward primer (Library FP1: 5'-TAATACGACTCACTATAGGGTTAACTTTAGTAAGGAGG (SEQ ID NO: 169), 1 μM reverse primer (for Heavily Biased: 5'-CTAGCTACCTATAGCCGGTGGTGATGGTGGTGATGACCCAGAG (SEQ ID NO:244); for Less Biased: 5'-CTAGCTACCTATAGCCGGTGGTGATGGTGATGGTGGCCTAAGC (SEQ ID NO:170), 0.025 U/μL Taq, 0.1% (v/v) Triton X-100. For each annealing temperature, six aliquots of 6 μL each were prepared in individual 0.2 mL PCR tubes to remove samples at various cycle numbers. Just prior to placing on the thermal cycler to run the program described above, the samples were vortexed briefly to resuspend the beads. After 5 minutes of initial denaturation, the program was paused, and the samples were again vortexed to resuspend the beads. The program was continued, and sample tubes were removed at 12, 14, 16, 18, 20, and 22 cycles. Each cycle number for the two annealing temperatures tested were analyzed on a 6% acrylamide gel. As expected, cycling was much more rapid at 62° C. than 73° C., resulting in higher molecular weight bands with a reduction in the desired PCR product band at 249 base pairs.

With the annealing temperature set as 73° C., the cycles screened above were tested for 25 μL volume per tube in a pilot PCR experiment. However, increasing the volume of the bead suspension from 6 μL to 25 μL required a greater number of PCR cycles. Ultimately, large scale PCR was carried out with a total of 1.2 mL for each library, with 24 cycles for the Heavily Biased library, and 28 cycles for the Less Biased library. In order to maximize recovery of bound material, samples from pilot PCR experiments were subject to further PCR to achieve the same number of cycles.

PCR-amplified library samples were combined for the next round of selection as follows. Each crude PCR was spun down briefly, placed on a magnet for 1 minute, and the supernatant was transferred to a tube on ice. The beads in each tube were rinsed with 0.1% Triton X-100, spun down briefly, placed on a magnet for 1 minute, and the rinse was transferred to the same tube on ice. The recovered crude PCR samples were filtered through an Ultra-free 0.22 μm centrifugal filter unit (Millipore) to remove residual magnetic beads. Then, the filtered solutions (3 mL) were transferred to a 15 mL conical tube for phenol/chloroform extraction. The aqueous solution was then aliquoted into four 2 mL microcentrifuge tubes for isopropanol precipitation, followed by a 70% (v/v) ethanol wash. The DNA pellets were dissolved in a total of 151 μL of water and recombined. The approximate yields were estimated by comparing the band intensities of the Heavily Biased and Less Biased library DNA solutions to a sample with a known concentration on a 6% acrylamide gel. Recovery of each library was approximately 38 pmol each.

For the next round of selection, the pools were to be split for three parallel selections against PGT128, PGT130, and glPGT128 individually. Thus, a portion of the recovered DNA (12 pmol) was further amplified in order to obtain enough RNA for fusion preparation. Several pilot experiments were carried out to optimize conditions for PCR. Ultimately, a 50-fold dilution of recovered DNA with 8 cycles provided enough material for subsequent experiments (75 to 94 pmol), though higher molecular weight bands were present in the samples, indicating the samples were cycled too much.

Subsequent Rounds of Selection

Fusions were prepared for the subsequent rounds of selection in a similar manner as the fusions for the first round. Fusion formation was much more efficient in the second round (3.8-9.1% in round 2 vs. 0.5-2.1% in round 1), thus improving overall yields and reducing the amount of translation volume required. Volumes of the subsequent transformations and purifications were decreased accordingly, with the exception of the click reaction.

The volume of the selection step was adjusted in each round to ensure excess of the antibody over the library fusions. Thus, as the concentration of the antibody decreased through selection, the volume of selection increased. For instance, the selection volume was 4.8 mL for round 9 with 2.5 nM PGT128 (12 pmol) with 4.9 or 5.6 pmol of library fusions.

Negative Selection Against Immobilization Carrier. Negative selections against the immobilization carrier were done just prior to the selection step, as follows. Magnetic beads (Protein A/G or Streptavidin) were equilibrated with 1× selection buffer. Fusions in 1× selection buffer were added to the beads and tumbled at room temperature for 30 minutes. The supernatant was transferred to a new tube and the beads were washed twice with 1× selection buffer, combining with the supernatant. The unbound fraction was directly used for selection with target.

Negative Selection Against Non-Glycosylated Binders. Fusions from gel filtration were concentrated by speedvac and precipitated with alcohol in the presence of linear acrylamide carrier. The fusion pellets were dissolved in 1× selection buffer. Following negative selection against the immobilization carrier (described above), the fusions were incubated with 200 nM of antibody target for 1 hour at room temperature. The antibody-fusion complexes were captured on immobilization carrier for 30 minutes at room temperature. The supernatant was removed, and the beads were washed four times with 1× selection buffer. The combined supernatant and washes were filtered through a 0.22 μm Ultrafree centrifugal filter unit (Millipore) and precipitated for the click reaction.

Characterization of Selection Winners

Preparation of Preselection DNA for Sequencing

A sample of saved cDNA/mRNA-peptide fusions (after gel filtration) from the preparation for the first round of selection was PCR amplified for sequencing analysis. PCR (200 μL) of the cDNA/mRNA-peptide fusions (2.5 μL; 18-28 fmol) was performed with 0.1 mM of each dNTP, 1 μM each of forward primer and the appropriate reverse primer (described above), and 0.025 U/μL Taq DNA Polymerase (New England Biolabs) in 1× Standard Taq Buffer. The following PCR protocol was used: 94° C. for 5 minutes, then 12 cycles of 94° C. for 30 seconds, 66° C. for 30 seconds, and 74° C. for 30 seconds, followed by a final extension at 74° C. for 30 minutes. The crude PCR mixtures were diluted with water to 300 extracted with phenol/chloroform, and precipitated with ethanol followed by a 70% (v/v) ethanol wash. The pellets were dissolved in 21 μL of water. The library DNAs were analyzed on a 6% acrylamide gel, compared to controls with known concentrations to approximate the yield for Sanger sequencing.

The recovered preselection DNA was minimally PCR amplified to submit for Amplicon-EZ Next Generation Sequencing (NGS). PCR (250 μL) was performed with the recovered DNA (~0.6 pmol), 0.2 mM of each dNTP, 0.5 μM each of forward primer and the appropriate reverse primer (described above), and 0.02 U/μL Phusion HF DNA Polymerase (ThermoScientific) in 1× Phusion HF Buffer. The following PCR protocol was used: 98° C. for 30 seconds, followed by 3 cycles of 98° C. for 5 seconds, 66° C. for 10 seconds, and 72° C. for 15 seconds. The crude PCR products were purified using a PCR clean-up kit (New England Biolabs), following the manufacturer's instructions and then eluting with 11 μL of 10 mM Tris-HCl, pH 8.0. The purified DNA was quantified using NanoDrop and assessed for purity with an 8% acrylamide gel.

Sanger Sequencing

Preselection DNA and library DNA recovered from selection were cloned into plasmids, purified by a mini-prep kit (Zymo), and sent to Genewiz for Sanger sequencing. Preselection Sequences, round 10 selection sequences for PGT128, and round 7 selection sequences for PGT130 are shown in the tables 7, 8, and 9 below, respectively.

TABLE 7

Preselection sequences.

| Name | Sequence | SEQ ID NO: |
|---|---|---|
| H-pre-2 | MAPLKPKGSLATRAATFXSRIGDIRAAFCXFNGRASLLVLLFILR ALHVDGSGSLGHHHHHHRL | 245 |
| H-pre-6 | MANRTXYNHIRVNDWTHLAIXLLDEVRKQSCIGDIRRANCXPWKS SDQNEGSGSLGHHHHHHRL | 246 |
| H-pre-8 | MAPPTXACPIGDIRCAICXLPTKPPWFNPXARLDIANQHLSHTPN SHFTRGSGSLGHHHHHHRL | 247 |
| H-pre-10 | MAHFXSLRAASAAYNXXTNXITVTPSQVKHGIGDIRPAHCXYPPT XKVLDGSGSLGHHHHHHRL | 248 |
| H-pre-11 | MARR-- ALCIGDIREATCXLLFCQPFFIDHLHNFAKFHRQIHGHAITTTSG SGSLGHHHHHHRL | 249 |
| H-pre-12 | MAVPTKEAWSAPSPLKWKITYPHHSPXYPFTIGDIRHRRACPASP ASSTSAPVLWVITTITTGYR | 250 |
| L-pre-3 | MATYFPTTSIGDIRPYTGLPLVTQTXNTPINRLRNSYSLQNYRFH RKSPNGSGSLGHHHHHHRL | 251 |
| L-pre-5 | MAHPARFIYIGDIRGVPLDHXKHGFNNSTRLEPGGLSVCLHNHEC XNYWTGSGSLGHHHHHHRL | 252 |
| L-pre-6 | MAPLHIXVYIGDIRPYTIGDXRRSIQSIXDHSYLKCQNVXHCIDD HXLHVGSGSLGHHHHHHRL | 253 |
| L-pre-7 | MARYPTYEAIGDIRRYLASLQIRTQVLLKTLRQTTEHXQLIDQIT LVNXYGSGSLGHHHHHHRL | 254 |
| L-pre-8 | MAYSARRNFDVRSXYDSFSENRNTIQTRYYFIGDIRHQKKXTRSX TQLFLGSGSLGHHHHHHRL | 255 |
| L-pre-12 | MAFLTTCRLIGDIRRIYNYSITKGRLTSLIRQRRHRLKGQLNTLN LYKLXGSGSLGHHHHHHRL | 256 |

Sequences with a prefix of H are from the Heavily Biased Library, while sequences with the prefix of L are from the Less Biased library.

TABLE 8

Round 10 sequences-PGT128. Sequences with a prefix of 101 are from the Heavily Biased Library, while sequences with the prefix of 102 are from the Less Biased library.

| Name | Sequence | SEQ ID NO: |
|---|---|---|
| 101-1 | MAIPNGYRAFNRADXLLLTRIGDIRNAHCXARCNYIYELRPLHHY RWSNRGSGSLGHHHHHHRL | 23 |
| 101-2 | MANTFSYHQKLKXGRHTDEILHTHXXHKKXXIGDIRYATCXKCVI KSHFXGSGSLGHHHHHHRL | 24 |
| 101-4 | MAIHKHLHIHNKKFSTFKSIIGDIRLAWCXNEYNIXPRCNSPRRF SYTAFGSGSLGHHHHHHRL | 25 |
| 101-5 | MAFKTNHTRCDHNSQHIVSQFQKPHLKRSRLIGDIRXAICXIKKH RXCHHGSGSLGHHHHHHRL | 26 |
| 101-11 | MARFHSRSPFKDSHLFRNGTVGDIRSRAVHAQAEQRRGYLLVRLR GHRVGGLGSLGHHHHHHRL | 135 |
| 101-13 | MAKISRRYHTFRRVLFRKRQIGDIRNAICXVLHHAVXYXQSKNNC KSXVXGSGSLGHHHHHHRL | 27 |
| 101-15 | MAKLKVCNXYAFSRPGWXIRKDIEFYYRINLVGDVRYATCXRYGY LILTQGSGSLGHHHHHHRL | 136 |

TABLE 8 -continued

| Round 10 sequences-PGT128. Sequences with a prefix of 101 are from the Heavily Biased Library, while sequences with the prefix of 102 are from the Less Biased library. | | |
|---|---|---|
| Name | Sequence | SEQ ID NO: |
| 101-16 | MATYHXTINXNXAYRXRTYSARNSIVSTENHIDDIRAAQCXTNPK HLSFIGSGTLGHHHHHHRL | 137 |
| 101-19 | MAFRLSYHNSFNGPVHRPHVFVHNXYRKGLRIGDIRFAPCXTHHL NSWSHGSGSLGHHHHHHRL | 28 |
| 101-26 | MAHWHRHHGHXIHYPYRFINLLFSPHXLDVVIGDIRKANCXWFLY SVAXIGSGSLGHHHHHHRL | 29 |
| 101-30 | MAHFDPYCRLYVPAYNSHTIYYHQKTAYYYLFIGDIRIDAVAENR SPYPLRGSGHHHHHHRL | 30 |
| 102-2 | MAFDHHHXLIGDIRNDHNDFYHVEDGFANVYIILYIIYSQTTSEV LIVSVGSGSLGHHHHHHRL | 31 |
| 102-9 | MAIXFAPRHIGDIRHPKQRTAHWKIKTAYPLKSLWKIRYRLKHID RIFLSGSGSLGHHHHHHRL | 32 |
| 102-21 | MAIHNNSRIXDLLIIRHRWXIGDIRTTHILNNRKTXSSLIKRNSK NGXSIAPGSLGHHHHH--AIGS | 257 |
| 102-23 | MANXTLLQLKALRXSLSPLFLRLPLKASHASIGDIRIXKTRRGPS FIRWYGSGSLGHHHHHHRL | 33 |
| 102-28 | MAKFAICHTIGDIRFEFTIIYTPHKYLVMDHDRHVMSLSVMLMSL MNHSRGSGSLGHHHHHHRL | 258 |
| 102-33 | MAKLKDKLNNXKXNTTNASAIGDIRIHANXLDVFLRNXHHKXTNY GRFLXGSGSLGHHHHHHRL | 35 |
| 102-35 | XPHYYHYNTXHXYYRHXHHSIGDIRSHFXPTKHIWLSGXLXLIHY KSSNNGSGSLGHHHHHHRL | 36 |
| 102-36 | MANHKHTHISLKSIVQTHGGPHPNVARAANLLLEQLPVVRRRLQR RLLQRGLRSLGHHHHHHRL | 138 |
| 102-37 | MAKYLTTNRLHVLTRKTEGLYDHNVLTRPTRIGDIRXXLLNYRKT LQHFYGSGSLGHHHHHHRL | 259 |
| 102-38 | MAHYTNNTLRPLARHHHFRLEQRFGRHLTSNIGDIRLNHVFHXXL RRYYVGSGSLGHHHHHHRL | 37 |
| 102-39 | MAXFVYHSTHPNRYHNLTLHIGDIRQRTIQQERIRVFLLFNLNLL GKNKYGSGSLGPSPSPPAIGS | 260 |
| 102-43 | XSNYVNSYLNTHLQLDQSTTIGDIHGLRKLGRYATESSFXRIHNI SFLSHGSGSLGHHHHHHRL | 139 |
| 102-45 | MAKFHDKNSYKSKHKKYNXLIGDIRXFNSYHRXXNCNKLCHPXIS WDLFIGSGSLGHHHHHHRL | 38 |

TABLE 9

| Round 7 Sequences-PGT130. | | |
|---|---|---|
| Name | Sequence | SEQ ID NO: |
| 7H130-2 | MAIKLLPTRAFNQNKHQRPRIGDIRPAGCXTYLITHHKLKGIFKR KLTTLGSGSLGHHHHHHRL | 261 |
| 7H130-3 | MAFIKRNKHLDDTSRSRRHGIGDIRRAFCXIRKIVHPYLKWPRFK CIQRNGSGSLGHHHHHHRL | 262 |
| 7H130-4 | MALTXXXSFPRTTISSSIVPSFTHHAQWFCTIGDIRSAECXSXVH SLESTGSGSLGHHHHHHRL | 263 |
| 7H130-5 | MATSDYQRHIGDIRLACCXTSKCTWLICLRHPCLLSAARVPECLH ISRRFGSGSLGHHHHHHRL | 264 |

TABLE 9 -continued

| Round 7 Sequences-PGT130. | | |
|---|---|---|
| Name | Sequence | SEQ ID NO: |
| 7H130-6 | MANNTLFKTXRQGYLNPLKKFLQQRNLYPKFIGDVRTAPCXXNYI NSFYTGSGSLGHHHHHHRL | 265 |
| 7H130-7 | MASHNSRRKLLRNLAYLTIWXXTLLLKARIVIGDIRHAHCXEHNA NNAXIGSGSLGHHHHHHRL | 266 |
| 7H130-8 | MAVNLLQRQIGDIRXASCXLTLNTYKHYCTHSTDVXSLHTXRHLF CSPQGGYGSLGHHHHHHRL | 267 |
| 7H130-9 | MAINFSSIFKRCYHTKTPRPIGDIRNAHCXTXIKRLLQIDVLPWK LHYAIGSGSLGHHHHHHRL | 268 |
| 7H130-10 | MAHQIIDPIPTRTRAGRRTALAIFVWCXLKNFLAARLLPNRHTYA IHNGSGSLGHHHHHHRL | 269 |
| 7H130-12 | MAYHPYFICSXYHSFDKKXTKHRLSSLHKPTIGDIRHAYYXRALL LPKYFDSGSLGHHHHHHRL | 270 |
| 7L130-1 | MAINPNSKRRTRSRHYNGDHIGDIRAKHLSHRKITLLGIYRIRLK VALNLLRSLGHHHHHHRL | 271 |
| 7L130-2 | MASHADHLHHINAHHMDVWIIGDIRLIGHILRCKRVCLNNLRQSF RHSLSGSGSLGHHHHHHRLR | 272 |
| 7L130-3 | MAFNHHFPPYKFFEKIHTFRIGDIRSILFLRSLQRANHIKKHSPY FIKXFGSGSLGHHHHHHRL | 273 |
| 7L130-4 | MANFKLHRTVXTAIQNHVXHNKRKFILNISFIGDIRGRRKHPLQY RTNVVGSGSLGHHHHHHRL | 274 |
| 7L130-6 | MATNNQRHTYXNIPXXSCLRIGDIRSVXSLCTNRRCLDISVNPLX LNEHGGSGSLGHHHHHHRL | 275 |
| 7L130-7 | MACHHHNHIYKPREATYISPIGDIRKFLTLTLLKYQLFINRIYSK XHLSKGSGSLGHHHHHHRL | 276 |
| 7L130-8 | MAFIIPPRXKVPRYSPHSKLIGDIRRHSFLNLIHXKHVSYIPFSK WKKYCGSGCLGHHHHHHRL | 277 |
| 7L130-9 | MASNRNRRSKHNTHNEKLKLFYDQNQYNFHLIGDIRITHSSNKSS YLPTHGSGSLGHHHHHHRL | 278 |
| 7L130-10 | MANEYIHSNIGDIRGRHNRHRKNKLIQFAYTCYNXLVRNTTRRAI RNLVAGFGSLGHHHHHHRL | 279 |

Sequences with a prefix of 7H130 are from the Heavily Biased Library, while sequences with the prefix of 7L130 are from the Less Biased library.

Ribosomally-synthesized PGT128 Selection Winners

The winners of selection with PGT128 at round 9 based on Sanger sequencing were prepared by ribosomal synthesis for analysis. DNA was obtained via PCR amplification with the plasmids as templates. For each sequence, PCR (50 μL) was performed with 0.5 ng plasmid template, 0.2 mM of each dNTP, 1 μM each of forward primer and the appropriate reverse primer (described above), and 0.025 U/μL Taq DNA Polymerase (New England Biolabs) in 1× Standard Taq Buffer. The following PCR protocol was used: 94° C. for 5 minutes, then 19 cycles of 94° C. for 30 seconds, 66° C. for 30 seconds, and 74° C. for 30 seconds, followed by a final extension at 74° C. for 30 minutes. The crude PCR mixtures were diluted with water to 250 μL, extracted with phenol/chloroform, and precipitated with ethanol followed by a 70% (v/v) ethanol wash. The pellets were dissolved in 21 μL of water. T7 transcription was carried out using all of the amplified DNA, and the crude transcripts were purified by denaturing PAGE as previously described. RNA yields ranged from 294-904 pmol.

Non-radioactive Peptides. For analysis by MALDI-TOF-MS, translation (20 μL) was carried out in the presence of PDF/MAP, without addition of radioactivity. The crude peptides were purified by Ni-NTA agarose or, if the sequence contained two cysteine residues, was cyclized while captured on the Ni-NTA resin. Following is the updated protocol for cyclization on Ni-NTA agarose.

Cyclization of Peptide on Ni-NTA Agarose. To 50 μL of crude translated peptide was added 200 μL of bind buffer (−BME; 50 mM Tris-HCl, pH 8.0, 300 mM NaCl) and 50 μL of HisPur™ Ni-NTA Resin (ThermoScientific). The mixture was tumbled at room temperature for 1 hour. Then, the mixture was spun down at 21,000×g, and the supernatant was carefully removed from the loosely-pelleted resin. The resin was washed six times by resuspending with 400 μL of cyclization wash buffer with TCEP (50 mM Tris-HCl, pH 8.0, 300 mM NaCl, 0.5 mM TCEP), spinning down, and removing the supernatant. To the resin was then added 400 μL of cyclization buffer (50 mM Tris-HCl, pH 8.0, 300 mM NaCl, 0.5 mM TCEP, 3.3 mM m-dibromoxylene, 24.75% (v/v) MeCN), and the mixture was covered in foil and tumbled at room temperature for 30 minutes. The reaction was spun down and the supernatant was removed. To the resin was then added 400 μL of cyclization wash buffer with BME (50 mM Tris-HCl, pH 8.0, 300 mM NaCl, 10 mM BME, 33% (v/v) MeCN), and the mixture was tumbled at room temperature for 10 minutes. The reaction was spun down and the supernatant was removed. The resin was resuspended in 200 μL of wash buffer with BME (50 mM Tris-HCl, pH 8.0, 5 mM BME) and transferred to an Ultra-free 0.22 μm centrifugal filter unit (Millipore). The tube was rinsed with 200 μL of wash buffer with BME and the rinse was added to the filter. The filter was then spun down at 10,000×g for 30 seconds. The resin in the filter was washed with 400 μL of wash buffer with BME. To elute the peptide, 50 μL 0.2% TFA was added to the resin and allowed to sit at room temperature for 2 minutes before spinning down, collecting in a new tube. The elution step was carried out once more, with the eluent collected separately. A portion of each eluent in 0.2% TFA (1.5 μL) was analyzed by MALDI-TOF-MS.

Radioactive Peptides. For binding analysis, translation (50 μL) was carried out in the presence of PDF/MAP and $^3$H-histidine for radiolabeling. The crude peptides were purified by Ni-NTA agarose or, if the sequence contained two cysteine residues, was cyclized while captured on the Ni-NTA resin. The peptide eluents were combined and dialyzed as follows. To the combined eluents was added a solution of Triton X-100 in water for a final concentration of 0.1%. Then, the peptides were dialyzed against 0.1% (v/v) Triton X-100 using a Slide-A-Lyzer™ MINI device (0.1 mL capacity, 3.5 kDa MWCO) (ThermoScientific) at room temperature overnight. The dialyzed peptides were retrieved from the devices, transferring to 0.5 mL centrifuge tubes. The peptide solutions were concentrated to dryness by speedvac for the click reaction.

The click reaction (5 μL) with $Man_9GlcNAc_2$—$N_3$ was carried out as previously described. Following the reaction, samples were diluted with water to 30 μL. Upon observation of insoluble material in the tube, the solution was acidified with TFA to improve solubility. The glycosylated peptides were analyzed by 4-20% SDS-PAGE (Bio-Rad).

To neutralize the glycosylated peptides before binding assays, peptides were dialyzed against 0.1% (v/v) Triton X-100, as before. Then, 5× selection buffer was added to the peptide solutions to 1× overall.

Sequences were screened for their binding to PGT128 as follows. Each glycosylated peptide (20 fmol) was incubated with either 0 nM or 100 nM PGT128, diluted to 20 μL with 1× selection buffer, tumbling for 1 hour at room temperature. While tumbling, Dynabeads™ Protein G (Invitrogen) were equilibrated with 1× selection buffer as follows. Steps were carried out using a multi-channel pipettor where possible. For each sequence, 5 μL of Protein G bead suspension was transferred to a 0.2 mL PCR tube in a strip. Then, 40 μL of 1× selection buffer was added to the beads. The mixture was resuspended by gently vortexing, spun down briefly, and placed on a magnet for 1 minute. The supernatant was removed, and this wash was repeated two more times. The final supernatant was removed just prior to addition of the incubated peptide/antibody mixture. The mixture was allowed to tumble at room temperature for 30 minutes to capture antibodies and bound peptides. Then, the suspension was briefly spun down, placed on a magnet, and the supernatant was transferred to an individual 0.2 mL PCR tube. To wash the beads, 20 μL of 1× selection buffer was added, gently vortexed, spun down briefly, placed on a magnet for 1 minute, and the wash was transferred to the same PCR tube as the supernatant. This wash step was repeated twice more for a total of three washes, saved altogether with the supernatant as the "unbound" fraction. The beads were then resuspended in 40 μL of denaturing elute buffer. The suspension was heated at 95° C. for 5 minutes to denature antibodies, spun down briefly, placed on a magnet for 1 minute, and the eluent was transferred to an individual 0.2 mL PCR tube. The beads were washed with 40 μL of denaturing elute buffer, and the wash was placed into the same tube as the eluent. The combined eluent and wash represented the "bound" fraction. The beads were resuspended in 40 μL of denaturing elute buffer, vortexed, and directly placed into a vial with liquid scintillation cocktail for radioactivity measurements, though it was not included in calculations of fraction bound. Each of the tubes with the "unbound" and "bound" fractions were placed into vials for LSC. The tube in which the antibody and peptides were incubated were also measured by LSC, but not included in calculations of fraction bound.

PGT128 Affinity Purification

Cyclized and glycosylated peptides 91-8 (SEQ ID NO:74) and 91-12 (SEQ ID NO:76) (Heavily Biased library) were subject to PGT128 affinity purification. The sequences (0.3 μmol) were each incubated with 100 nM PGT128, diluted to 40 μL with 1× selection buffer, tumbling for 1 hour at room temperature. The antibody/peptide complexes were captured on equilibrated Protein G (10 μL) and washed as described previously. The bound fraction was then eluted as follows. The beads were resuspended in 10 μL of 1× selection buffer and heated at 70° C. for 30 minutes. Then, the suspension was chilled on ice for 5 minutes, and tumbled at room temperature for 10 minutes. The eluent was separated, and the beads were washed with 10 μL of 1× selection buffer. The wash was combined with the eluent as the "bound" fraction. The radioactivity of the "unbound" fraction and resuspended beads were measured by LSC, as well as a small portion of the eluted "bound" fraction.

Synthetic PGT128 Selection Winners

Peptides H-1 (SEQ ID NO:291) and H-22 (SEQ ID NO:306), two of the top sequences from the Heavily Biased library, were synthesized by the Pentelute Lab, MIT using their lab's automated rapid-flow peptide synthesizer. 100 mg of 0.18 mmol/g RINK amide ChemMatrix® resin was used for the synthesis. All Fmoc-deprotections were carried out with 20% (v/v) piperidine in DMF+1% (v/v) formic acid.

For each peptide, 90 mg of resin was cleaved/deprotected for 3 hours at room temperature with 5 mL of cleavage cocktail (87.5:5:5:2.5 TFA/phenol/H2O/TIPS) in a 15 mL conical centrifuge tube. The resin was spun down and the supernatant was filtered through a 0.45 μm filter and transferred to a new 15 mL tube. The resin tube was rinsed with another 5 mL portion of cleavage cocktail, spun down, and the supernatant was transferred to the same new tube. TFA was evaporated from the supernatant using N2 in the hood. Then, 10 mL of cold diethyl ether was added. The solution was vortexed and spun down to precipitate the peptide. The supernatant was decanted, and the peptide pellet was rinsed three times with 5 mL portions of cold diethyl ether. The peptide was dissolved in water and lyophilized overnight.

Then, 9 mg of crude peptide was reduced and cyclized as follows. Each peptide (1 mM final concentration) was dissolved in 200 mM $NH_4HCO_3$ with 10 mM TCEP for a reaction volume of 1332 μL. The reactions were tumbled at room temperature for 50 minutes. At that time, the reactions were buffer-exchanged to remove excess TCEP. Due to its poor solubility, H-1 (SEQ ID NO:291) was pelleted by centrifugation and the reagents were removed. The pellet was washed six times with 1 mL portions of 200 mM $NH_4HCO_3$. Portions of the H-22 reaction were transferred to Centricon-500 spin columns (MWCO 2 kDa) with 300 μL of 200 mM $NH_4HCO_3$. The filters were spun down and washed six times with 300 μL of 200 mM $NH_4HCO_3$. The solutions were then diluted to 1322 μL with 200 mM $NH_4HCO_3$, 5.95 mL of water, and 5.68 mL of MeCN in a 15 mL conical tube. Then, 529 μL of a solution of 5 mM m-dibromoxylene in MeCN was added, for a final concentration of 0.2 mM of m-dibromoxylene and 0.1 mM peptide. The cyclization reactions were tumbled at room temperature and monitored by LC-MS. After 40 minutes, H22 was complete. At that time, 132 μL of 5 mM m-dibromoxylene in MeCN was added to the H-1 reaction to push it to completion (total reaction time: 140 minutes). The reactions were quenched by lowering the pH with formic acid. The solutions were concentrated under reduced pressure and lyophilized overnight.

Crude cyclized peptides were purified by HPLC on a Waters Symmetry 300 C4 column (4.6×250 mm, 5 μm particle size) following a 90% A/10% B to 60% A/40% B gradient over 40 minutes with a flow rate of 4 mL/min, where solvent A was water/0.1% formic acid and solvent B was acetonitrile/0.1% formic acid. For each, 2 mg of pure cyclized peptide was obtained from 8 mg of crude.

Figures 5A, 5B:
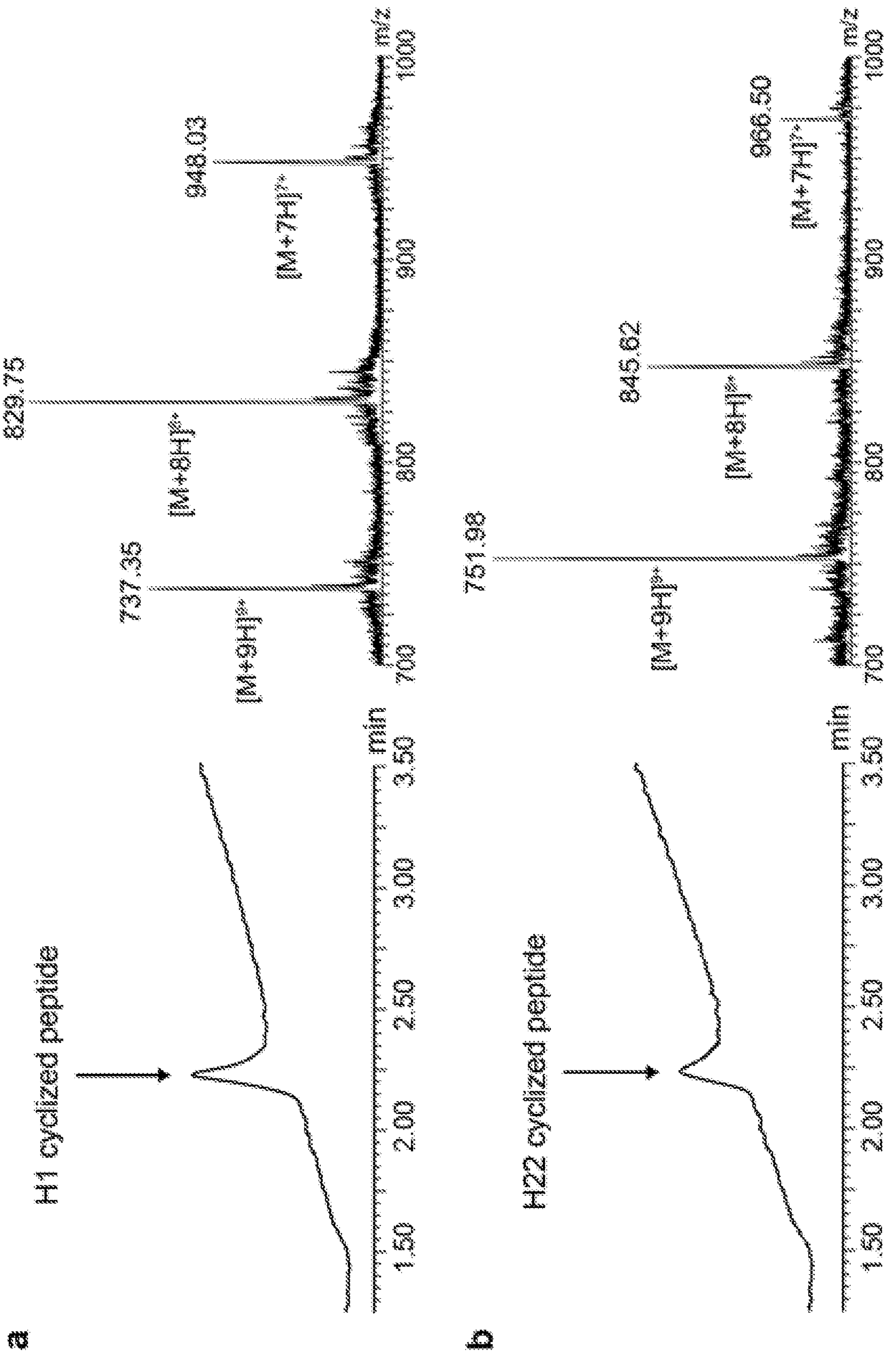
FIGS. 5A-5C shows LC-MS of pure cyclized peptides.

H-1 cyclized peptide. ESI-LRMS: observed base peaks, 737.35 $[M+9H]^{9+}$, 829.75 $[M+8H]^{8+}$, 948.03 $[M+7H]^{7+}$, 1106.04 $[M+6H]^{6+}$, corresponding to 6629.15 observed average mass, calculated average mass for $C_{293}H_{445}N_{93}O_{79}S_3$: 6626.28 (FIG. 5A).

H-22 cyclized peptide. ESI-LRMS: observed base peaks, 751.98 $[M+9H]^{9+}$, 845.62 $[M+8H]^{8+}$, 966.50 $[M+7H]^{7+}$, 1127.70 $[M+6H]^{6+}$, corresponding to 6758.62 observed average mass, calculated average mass for $C_{307}H_{495}N_{97}O_{70}S_3$: 6756.73 (FIG. 5B).

The click reaction was then carried out on cyclized peptide H22 with 2.2 equiv. $Man_9GlcNAc_2—N_3$, 2.5 equiv. CuSO4, 3 equiv. THPTA, and 50 equiv. Sodium ascorbate. The glycosylation was monitored by LC-MS and was mostly complete after 5 minutes. After 1 hour, the reaction was diluted with formic acid and purified by HPLC as described above to yield 0.5 mg of pure cyclized glycopeptide.

Figure 5C:
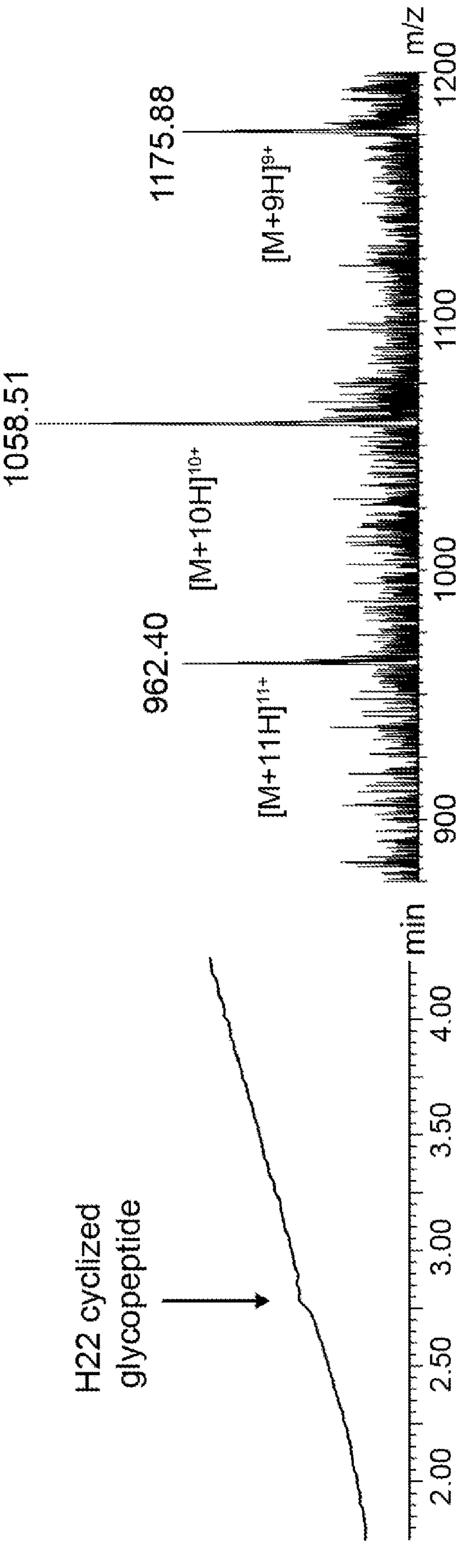

H22 cyclized glycopeptide. ESI-LRMS: observed base peaks, 1175.88 $[M+11H]^{11+}$, 1058.51 $[M+10H]^{10+}$, 1175.88 $[M+9H]^{9+}$, corresponding to 10,574.81 observed average mass, calculated average mass for $C_{447}H_{729}N_{107}O_{180}S_3$: 10,572.04 (FIG. 5C).

Example 1—Second-Generation mRNA Display Library Design for the Directed Evolution of Glycopeptides Applicant sought to apply glycopeptide mRNA display selection to evolve epitopes of PGT antibodies. Using new targets, changes were made to mRNA displayed-glycopeptide libraries, including N-terminal HPG removal and cyclization. The examples presented herein describe second-generation libraries and selection against PGT128 and clonally-related PGT130.

Figures 6A, 6B:
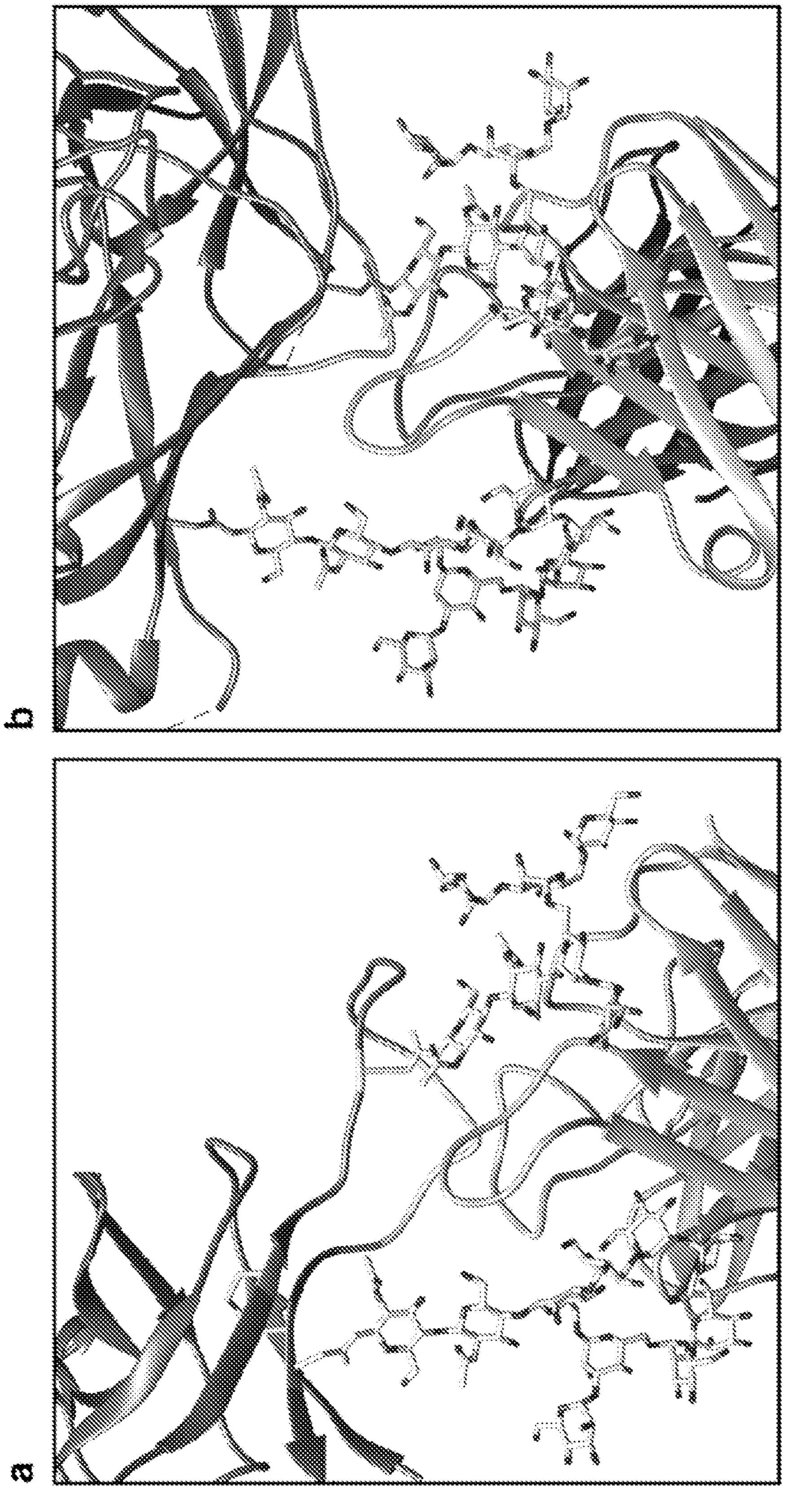
FIGS. 6A-6B illustrate PGT128 bound to HIV Env constructs.

Library Design Considerations. One of the most critical aspects of an mRNA display selection is the design of the library. The known, key elements of the PGT128 interaction with gp120 were focused on for library designs. Based on the crystal structure of PGT128 Fab with an engineered monomeric gp120 construct of its outer domain (FIG. 6A), the PGT128 epitope is characterized by two high-mannose carbohydrates (corresponding to positions N301 and N332) and a peptide motif (IGDIR) within the V3 loop (Pejchal et al., *Science* 334(6059):1097 (2011), which is hereby incorporated by reference in its entirety). A similar interaction was observed in a later crystal structure of PGT128 Fab bound to BG505.SOSIP gp140 trimer (FIG. 6B)(Kong et al., *Acta Crystallogr. D Biol. Crystallogr.* 71:2099-2108 (2015), which is hereby incorporated by reference in its entirety). PGT128 extends itself between the two carbohydrates to reach the tip of the V3 loop, which contains the highly-conserved IGDIR peptide motif.

PGT130, a member of the PGT128 family, interacts with gp120 in a distinct, but similar manner to PGT128 (Doores et al., *J. Virol.* 89(2):1105-1118 (2015), which is hereby incorporated by reference in its entirety). Although PGT130 exhibits lower potency and neutralization breadth than PGT128, it accommodates a glycan at the N334 position instead of the N332 position. Evolution of both PGT128 and PGT130 epitope mimics could provide a broader defense against gp120 isoforms.

It has also been hypothesized that elicitation of the desired bnAb response could be more achievable if the antigen could bind to the germline precursor to a bnAb (Chen et al., *Biochem. Biophys. Res. Comm.* 417 (4), 1164-1169 (2012) and Xiao et al., *Biochem. Biophys. Res. Comm.* 390(3):404-409 (2009), which are hereby incorporated by reference in their entirety). The antibody response begins with germline B cells that bind with lower affinity to the target antigen but that eventually mutate to the mature, high affinity antibody, a process called "affinity maturation". This process typically yields bnAbs with unusual features, such as long CDR loops (PGT128) and domain-exchange (2G12) (Calarese et al., *Science* 300(5628):2065 (2003) and Pejchal et al., *Science* 334(6059):1097 (2011), which are hereby incorporated by reference in their entirety). Thus, there is great interest in evolving peptides or glycopeptides that can bind the germline precursor to PGT128 and PGT130, glPGT128.

Overall, it was envisioned that a good PGT128 epitope mimic may be a cyclic peptide containing the conserved IGDIR (SEQ ID NO:1) peptide motif and two $Man_9GlcNAc_2$ carbohydrates. The $Man_9GlcNAc_2$ carbohydrates could be attached via click reaction with $Man_9GlcNAc_2—N_3$. Incorporation of these elements into libraries resulted in new features and improvements to library design and generation process.

Library Cyclization. Peptide cyclization was considered a desirable feature to increase potential of library members to best mimic the PGT128 epitope. Cyclization confers rigidity to peptides, possibly enhancing specificity and affinity for the target (Driggers et al., *Nature Rev. Drug Disc.* 7:608 (2008), which is hereby incorporated by reference in its entirety). To cyclize library peptides, the bis-alkylating agent m-dibromoxylene, which has been shown to rapidly form a Cys-to-Cys crosslink that would be stable under reducing conditions, was used (FIG. 3A)(Timmerman et al., *ChemBioChem* 6(5): 821-824 (2005); Seebeck et al., *J. Am. Chem. Soc.* 128(22):7150-7151 (2006); and Jo et al., *J. Am. Chem. Soc.* 134(42):17704-17713 (2012), which are hereby incorporated by reference in their entirety). This method has been successfully implemented in library generation of mRNA display selections (Guillen et al., *J. Am. Chem. Soc.* 134(25):10469-10477 (2012); White et al., *ACS Chem. Biol.* 10(5):1198-1208 (2015); and Hacker et al., *ACS Chem. Biol.* 12(3):795-804 (2017), which are hereby incorporated by reference in their entirety)

The use of m-dibromoxylene was optimized. Addition of fresh cyclization reagents while peptides are captured on a solid support provides a facile route to cyclization. To confirm the success of cyclization, a ribosomally-synthesized test peptide was purified by Ni-NTA and, while captured on resin, cyclized by treatment with m-dibromoxylene and TCEP in a pH 8 buffer. Analysis of the eluent by MALDI-TOF-MS confirmed full conversion of the linear peptide to the cyclized peptide (FIG. 3B).

N-terminal HPG Removal: Enterokinase. The desired $Man_9GlcNAc_2$ carbohydrates were installed into peptide libraries using established click reaction of the carbohydrate azide with the unnatural, alkynyl amino acid HPG (Horiya et al., *J. Am. Chem. Soc.* 136(14):5407-5415 (2014), which is hereby incorporated by reference in its entirety). As an analogue of Met, HPG is incorporated at the AUG start codon, thereby enforcing a requirement that a large sugar is located at the N-terminus. Although the 2G12 selection was not affected by this requirement in any obvious manner, it was postulated that the presence of an N-terminal carbohydrate could have a negative impact in selections against PGT antibodies. While 2G12 recognizes the "tips" of oligomannose carbohydrates, PGT128 penetrates deeper into gp120 to bind carbohydrates' $GlcNAc_2$ core and structural elements (peptide) (Calarese et al., *Science* 300(5628):2065 (2003) and Pejchal et al., *Science* 334(6059):1097 (2011), which are hereby incorporated by reference in their entirety). This interaction requires a specific arrangement of a peptide epitope flanked by carbohydrates. It was feared that fixed N-terminal carbohydrate might be floppy and add a non-specific element that could compete with the desired carbohydrate/peptide arrangements. Thus, it was sought to remove the N-terminal HPG in order to increase the percentage of "high quality" sequences.

Figures 7A, 7B, 7C:
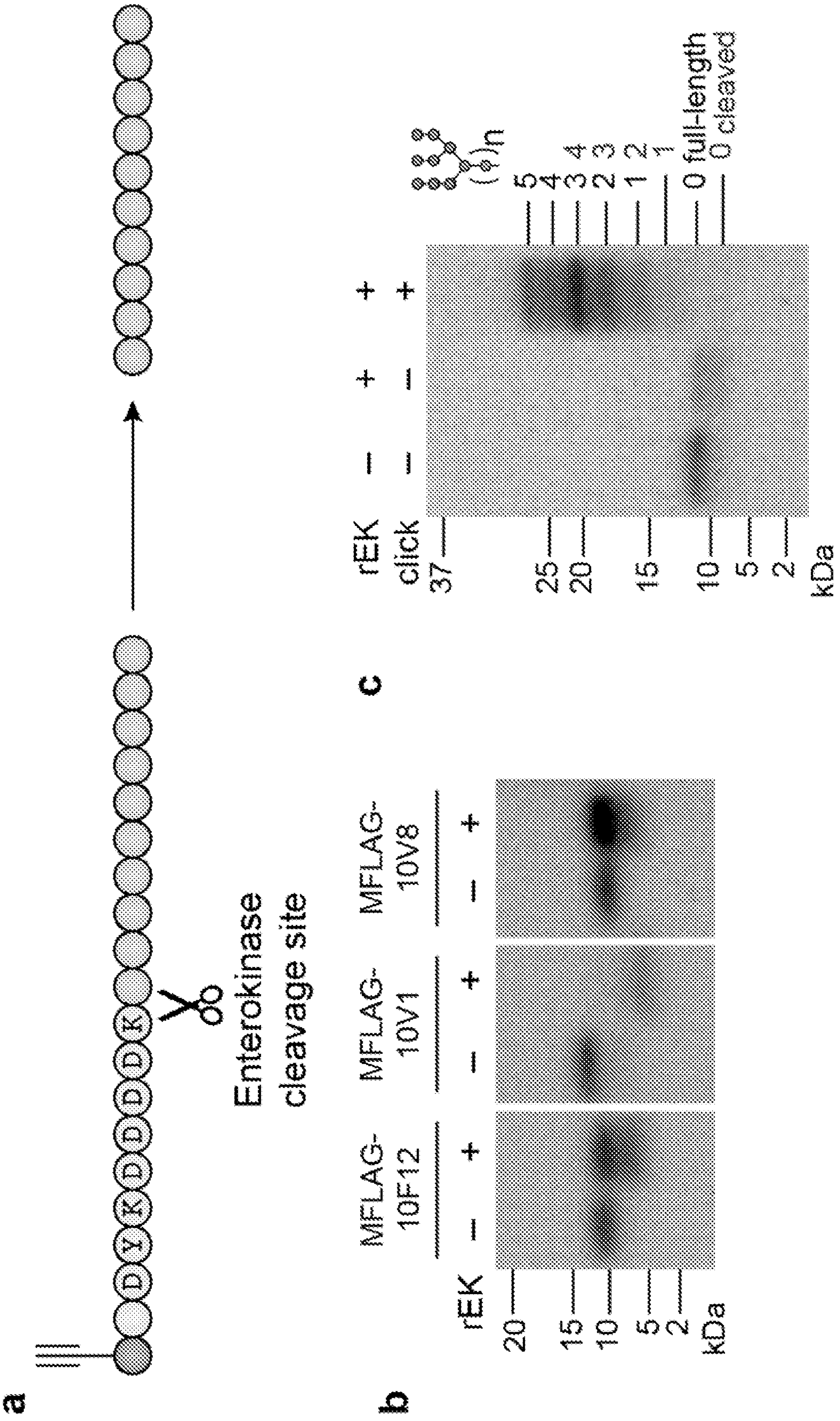
FIGS. 7A-7C illustrate the removal of N-terminal HPG with enterokinase.

The strategy for N-terminal HPG removal was based on proteolytic cleavage after translation. Initially, the use of enterokinase, an enzyme that recognizes the sequence DDDDK (SEQ ID NO: 194) and cleaves the peptide after the lysine residue, was pursued. By incorporating a FLAG-tag (DYKDDDDK, SEQ ID NO:171) at the N-terminus of the peptides, affinity purification by Anti-FLAG could be followed by enterokinase treatment to yield highly pure peptides lacking the N-terminal HPG (FIG. 7A).

To test enterokinase cleavage, several of the winners from round 10 of the 2G12 selection with FLAG-tags inserted at the N-terminus were prepared. Anti-FLAG-purified, $^3$H-histidine-labeled peptides were prepared with commercially-available recombinant enterokinase, Tag-Off™ High-Activity rEK (Novagen, now discontinued) and analyzed the reactions by SDS-PAGE (FIG. 7B). Upon treatment with rEK, FLAG-10V1 showed full conversion to the cleaved product, though FLAG-10F12 and FLAG-10V8 were not digested well, suggesting some sequence dependence of rEK activity. To confirm the bands were rEK cleavage product, peptides were analyzed by MALDI-TOF-MS. Unfortunately, signals were generally weak, as yields following Anti-FLAG purification were typically very low.

FLAG-10F6 was treated with rEK and the cleaved peptide was subjected to the click reaction with $Man_9$-cyclohexyl-azide. The rEK reaction was incomplete, as well as the click reaction, revealing overlapping sets of bands in the SDS-PAGE gel that was assessed for full-length peptide with 5 glycosylation sites and the cleaved peptide with 4 glycosylation sites (FIG. 7C).

Use of enterokinase for N-terminal HPG removal was unpredictable and difficult to monitor based on complicated shifts of SDS-PAGE gel bands and low signals in MALDI-TOF-MS. Ultimately, an alternative proteolytic strategy was used to remove the N-terminal HPG that provided a cleaner view of SDS-PAGE gel band shifts.

Figure 8A:
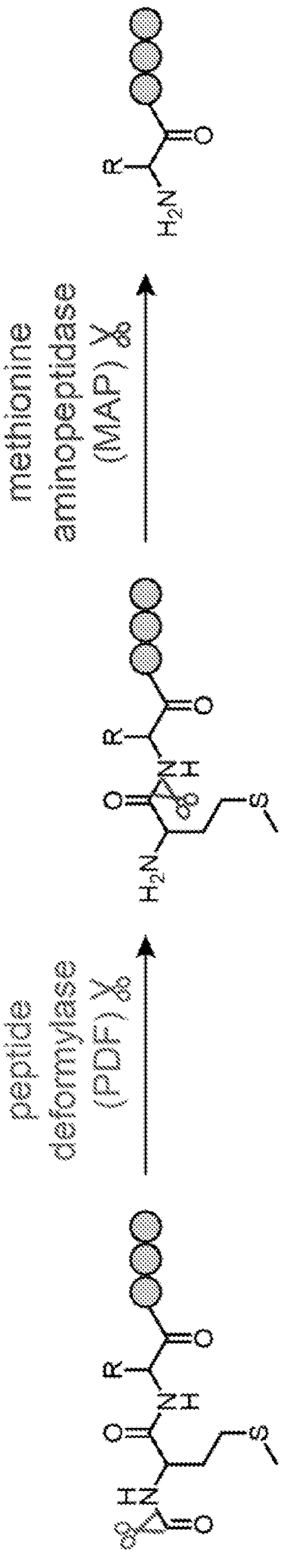
FIGS. 8A-8B illustrate N-terminal processing with PDF/MAP.
Figure 8B:
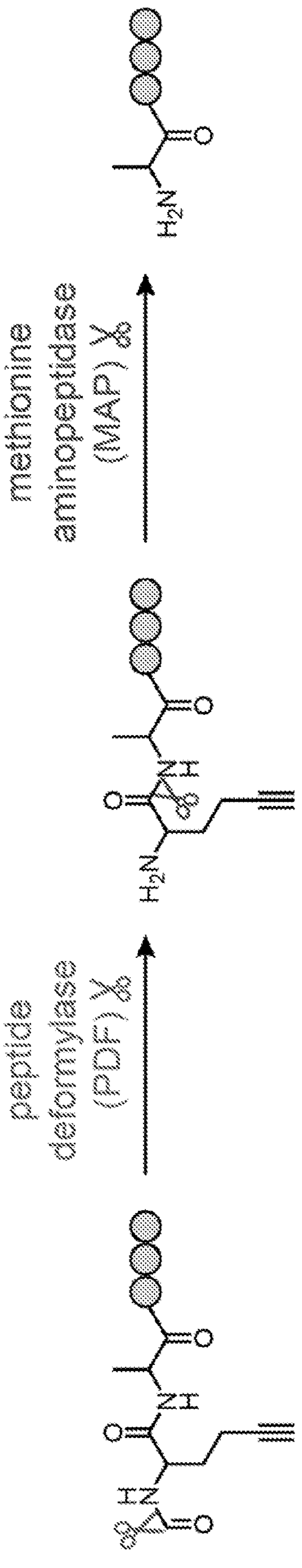

N-terminal HPG Removal: Methionine Aminopeptidase and Peptide Deformylase. Ribosomal protein synthesis is initiated by N-formylmethionine in prokaryotes. As shown in FIGS. 8A-8B, peptide deformylase (PDF) processes the N-terminal formyl group and, in most cases, the resulting methionine is processed by methionine aminopeptidase (MAP). It has been previously reported that MAP can also cleave non-canonical amino acid analogues of methionine, including HPG (Wang et al., *ChemBioChem* 9(2):324-330 (2008), which is hereby incorporated by reference in its entirety). It was anticipated that PDF/MAP could be included in the PURE system translation, as processing by the pair is a co-translational event (Kendall et al., *J. Biol. Chem.* 267(29):20667-20673 (1992), which is hereby incorporated by reference in its entirety). Indeed, the Suga group has previously included PDF/MAP in their own in vitro translation system to process N-formylmethionine (Kawakami et al., *Nature Chem. Biol.* 5:888 (2009), which is hereby incorporated by reference in its entirety.

There is sequence-dependence for MAP processing of Met: a small amino acid side-chain in the second position is required (Ben-Bassat et al., *J. Bacteriol.* 169(2):751 (1987); Hirel et al., *Proc. Nat. Acad. Sci. U.S.A.* 86(21):8247 (1989); and Xiao et al., *Biochem.* 49(26):5588-5599 (2010), which are hereby incorporated by reference in its entirety). Although the sequence-dependence for MAP processing of non-canonical amino acids is not well-studied, there are examples of a preference for alanine in the second position (Wang et al., *ChemBioChem* 9(2):324-330 (2008) and Abdeljabbar et al., *ChemComm.* 50(94):14900-14903 (2014), which are hereby incorporated by reference in their entirety). A selection method was designed to profile the sequence requirements for MAP processing of HPG. For the purposes of selection against PGT128, a fixed alanine was included in the second position.

Figure 9:
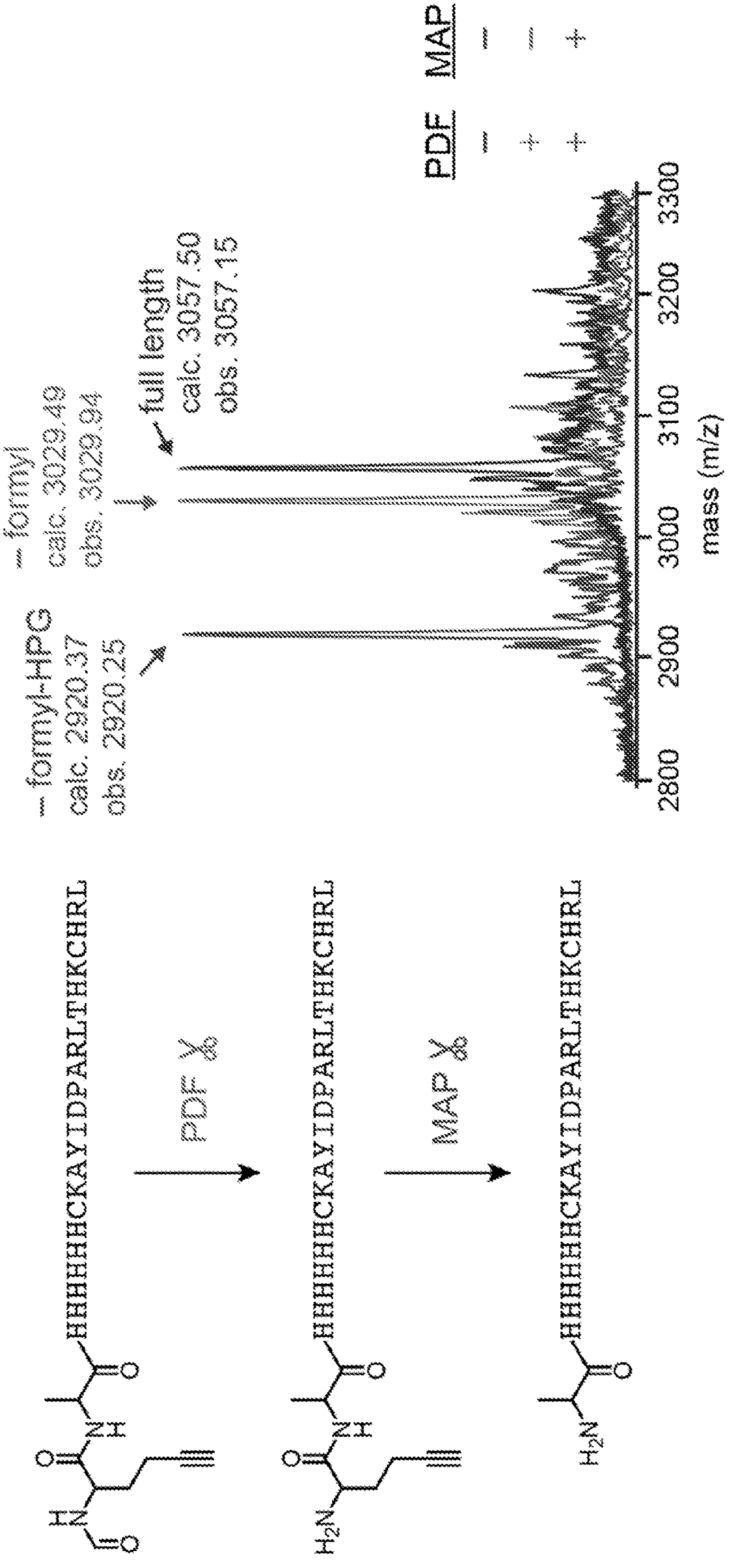
FIG. 9 shows MALDI-TOF-MS analysis of an exemplary peptide (SEQ ID NO: 216) with N-terminal formylated HPG treated with (i) PDF and (ii) MAP.

PDF and MAP were prepared from *E. coli* (strain K12) for experiments (Kawakami et al., *Nature Chem. Biol.* 5:888 (2009), which is hereby incorporated by reference in its entirety). Test sequences were translated in the absence or presence of 6 μM PDF and/or 15 μM MAP, with $Co^{2+}$ (100 μM $CoCl_2$) as a cofactor. The resulting peptides were purified by affinity for Ni-NTA and analyzed by MALDI-TOF-MS (FIG. 9). Test sequence MAH6CΔM, with alanine in the second position, was fully processed by PDF, followed by successful processing by MAP. Sequence MH6CΔM, with histidine in the second position, was fully processed by PDF, but was unaffected by MAP, consistent with previous literature reports that histidine is a poor second amino acid (Wang et al., *ChemBioChem* 9(2):324-330 (2008), which is hereby incorporated by reference in its entirety).

Figures 10A, 10B, 10C:
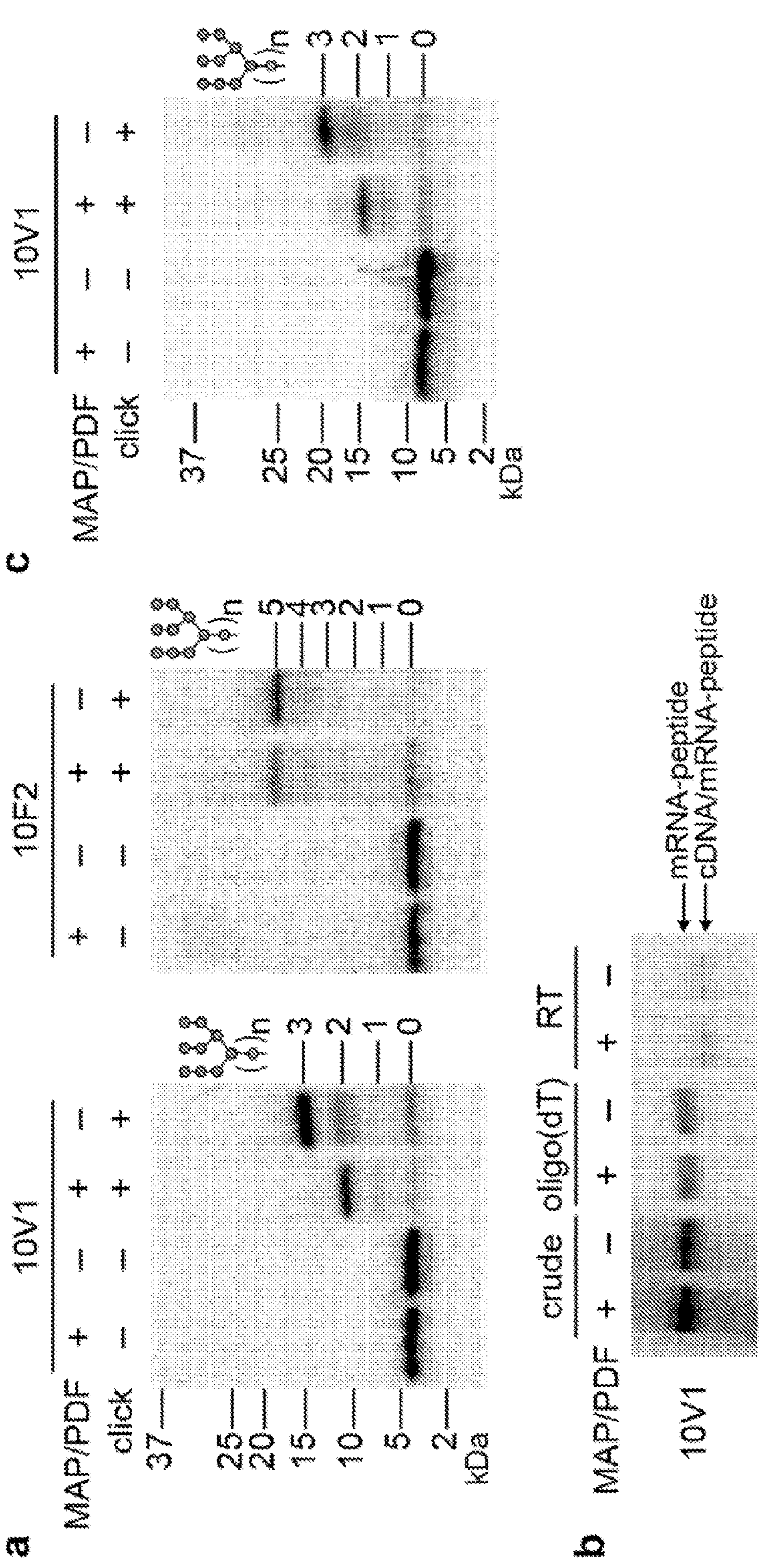
FIGS. 10A-10C show PDF/MAP processing analysis by SDS-PAGE.

Using SDS-PAGE, the glycosylation profiles of peptide 10V1 (MATKTNCKREKTXDNHVTIXRSIPWYTYRWLPNGSGSGCG, SEQ ID NO:339), a sequence selected by 2G12 that has alanine in the second position, translated with or without PDF/MAP and subjected to the click reaction with Many-cyclohexyl-azide was analyzed (FIG. 10A). All three glycosylation sites of 10V1 were filled without MAP, while only two were filled with MAP treatment. In contrast, the 2G12-clone 10F2 (MHPYNTSRTSAXXAALKMXQVTDXYALALFHRILGSGSGCG, SEQ ID NO: 288) has a histidine in the second position, and the number of glycosylations was the same with and without PDF/MAP. To confirm MAP treatment is compatible with selection conditions, 10V1 was prepared as an mRNA-peptide fusion in the presence or absence of PDF/MAP in translation. Fusion integrity was comparable by SDS-PAGE, indicating PDF/MAP do not affect fusion formation or degrade mRNA (FIG. 10B). Then, the 10V1 mRNA-peptides were glycosylated with Many-cyclohexyl-azide and nuclease-digested for SDS-PAGE analysis of the resulting peptides (FIG. 10C). Again, all three glycosylation sites of 10V1 were filled without MAP, while only two were filled with MAP treatment, suggesting MAP cleavage was still effective during mRNA display translation.

Overall, PDF/MAP effectively cleaved the N-terminal formyl-HPG of sequences with an alanine in the second position. This enzyme pair could be easily added to the PURE system translation mixture without negative consequences to the translation efficiency of peptides or mRNA-peptides. Consequently, PDF and MAP were utilized in selections with PGT antibodies.

Figure 11:
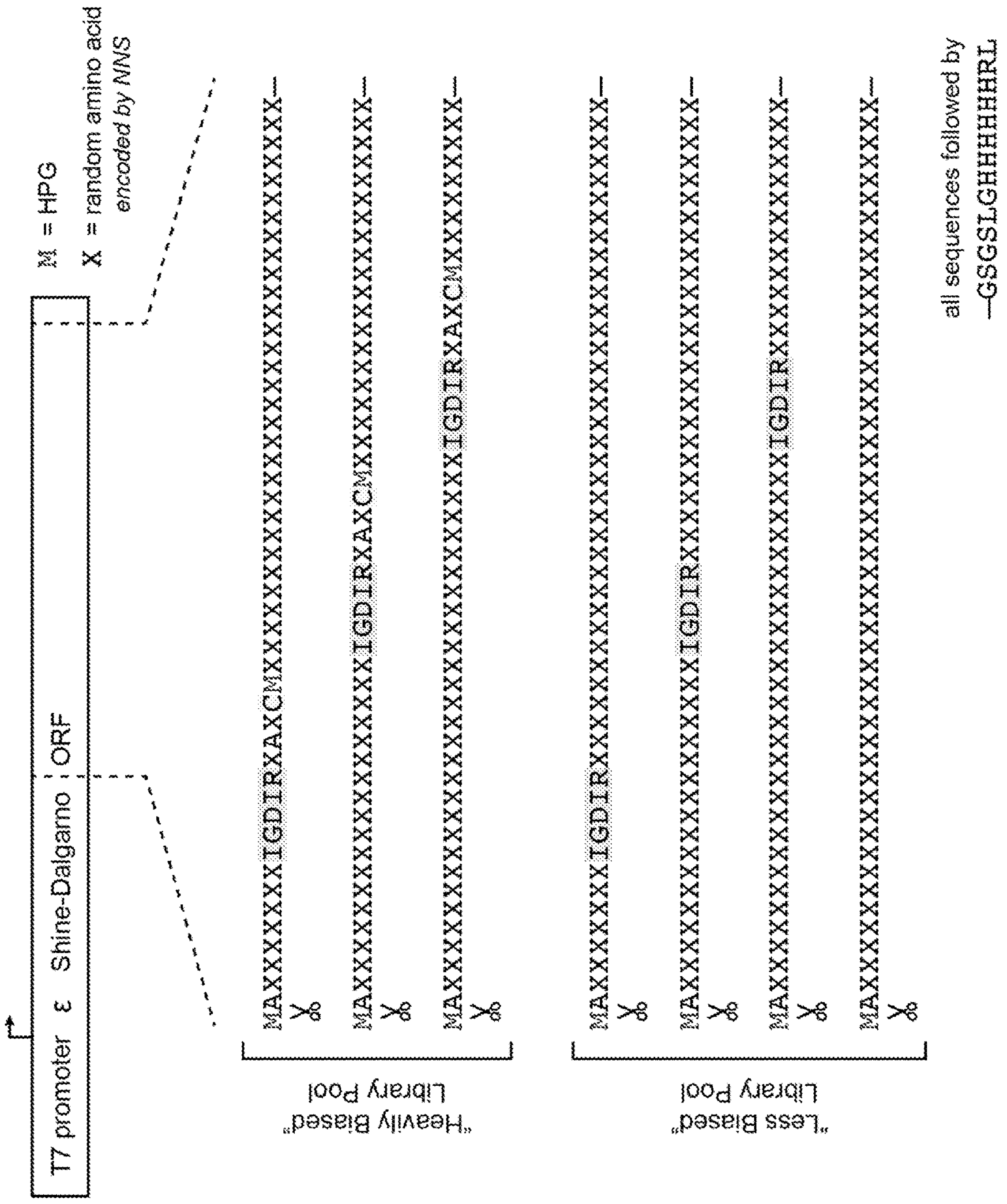
FIG. 11 illustrates the library designs for selection with PGT128. The "Heavily Biased" library pool includes SEQ ID NOS: 330-332 (from top to bottom) and the "Less Biased" pool includes SEQ ID NOS: 333-336 (from top to bottom).

Library Design. With validation of the approaches to cyclize the libraries and remove the N-terminal HPG, two sets of distinct DNA library pools encoding random 49-mer peptides for use in selections with PGT128 and PGT130 were designed (FIG. 11). Following the N-terminal constant region (T7 promoter, Epsilon, Shine-Dalgarno, etc.), the open reading frame of both libraries began with the required HPG, followed by a fixed alanine for efficient PDF/MAP processing (Wang et al., *ChemBioChem* 9(2):324-330 (2008), which is hereby incorporated by reference in its entirety). Following the random region encoding 48 amino acids was a flexible amino acid spacer and $His_6$-tag, plus the annealing region for crosslinking of the puromycin-containing oligonucleotide. Codon degeneracy was exploited in the C-terminal constant region to design orthogonal primers for the two library pools.

Figure 12:
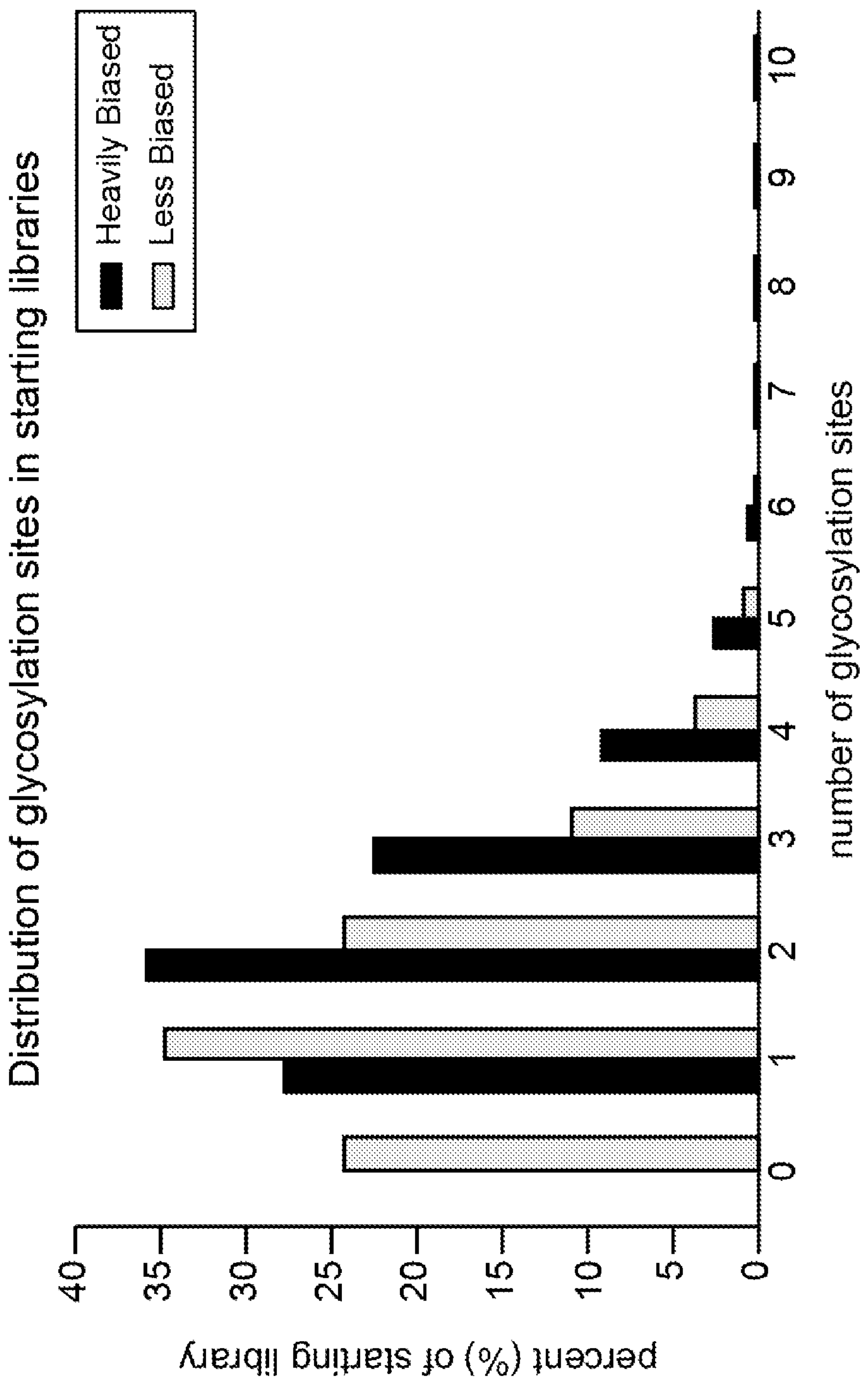
FIG. 12 is a graph showing the expected distribution of multivalency in each starting library. The Heavily Biased library (black) contains a fixed glycosylation site, while the Less Biased library (gray) does not.

The "Heavily Biased" library contained a peptide motif with conserved HIV elements: IGDIRxAxCX (SEQ ID NO:280), where x is a random amino acid and X is HPG. Three separate DNA libraries were compiled, with the conserved HIV elements incorporated in three different positions within the random region: early, middle, or late. Incorporation of the fixed cysteine residue allowed for potential cyclization with a random cysteine. The fixed HPG guaranteed a glycosylation site from click reaction with $Man_9GlcNAc_2$. The "Less Biased" library contained a minimal HIV motif: IGDIR (SEQ ID NO:1). The pool comprised four distinct libraries, with the IGDIR (SEQ ID NO:1) motif incorporated in the random region early, middle, late, or not at all. All random amino acids (x) were encoded by NNS, where N is any nucleotide and S is G or C. Use of NNS increased the probability of an AUG, which encodes the alkynyl glycosylation site, occurring at a given position from 1/64 (NNN) to 1/32. The distribution of glycosylation sites for each library was calculated based on the number of random positions (FIG. 12) (Temme et al., *Curr. Protoc. Chem. Biol.* 7(2):73-92 (2015), which is hereby incorporated by reference in its entirety). With one fixed HPG and 40 random amino acid positions, 59% of the starting Heavily Biased library is expected to have two or three glycosylation sites. In the Less Biased library, comprising three libraries with 43 random amino acids and one library with 48, 35.5% of the pool is expected to have two or three glycosylation sites.

Figure 13:
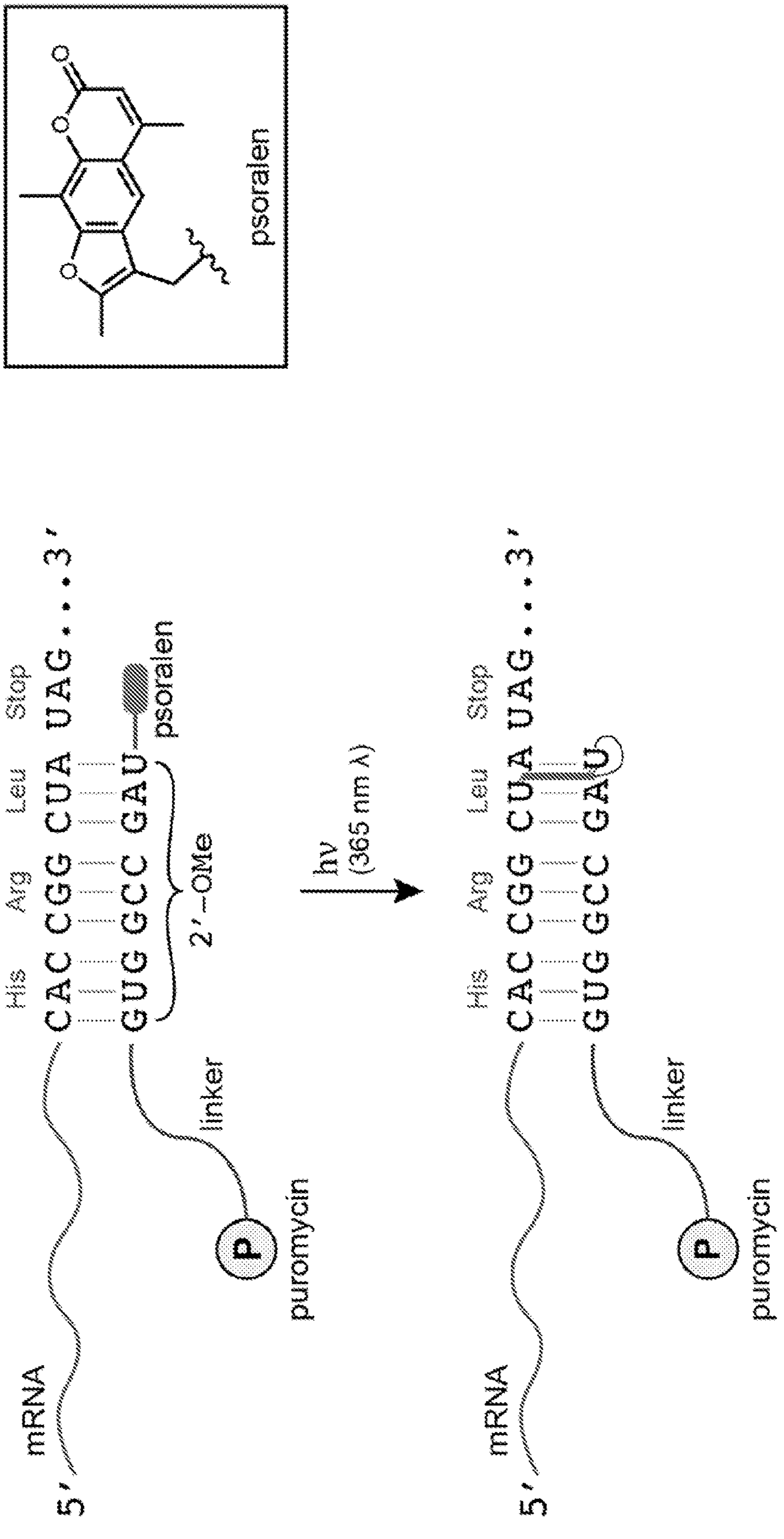
FIG. 13 illustrates the modification of mRNA with puromycin-containing oligonucleotide (SEQ ID NO:337).

Library Generation. To create each library pool with fixed elements in various locations, separate DNA libraries were purchased and combined. The desired DNA lengths were 249 bases, longer than the limitations quoted by commercial suppliers. To generate the full-length DNAs, the libraries were purchased with partial constant sequences and extended by PCR. Minimal cycling was used in order to keep the copy number of each sequence low, as the library diversity stems from the input DNA libraries. Higher affinity binders to PGT antibodies were expected by maintaining a higher sequence diversity of the starting library (Wilson et al., *Proc. Nat. Acad. Sci. U.S.A.* 98(7):3750 (2001), which is hereby incorporated by reference in its entirety). Each DNA library was extended by PCR separately and recombined for T7 transcription, followed by puromycin attachment via crosslinking to a puromycin-containing oligonucleotide. The puromycin oligonucleotide contained an annealing site for the 3'-end of the library mRNA. Upon treatment with longwave UV light (320-380 nm), the psoralen moiety in the puromycin oligonucleotide can undergo a photochemical reaction with the uracil base in the mRNA (FIG. 13) (Kurz et al., *Nucleic Acids Res.* 28(18):e83-e83 (2000), which is hereby incorporated by reference in its entirety). Typically, the photo-crosslinking reaction proceeded to 30-50% completion; the desired crosslinked RNA band was isolated during gel purification.

Translation was carried out in the presence of PDF/MAP for N-terminal HPG removal, with $^3$H-histidine for radiolabeling. mRNA-peptide fusion formation was encouraged by addition of $Mg(OAc)_2$ and KCl at room temperature, followed by incubation at −20° C. overnight (Liu et al. "Optimized Synthesis of RNA-Protein Fusions for in vitro Protein Selection," In *Methods in Enzymology*, Academic Press: 2000; Vol. 318, pp 268-293, which is hereby incorporated by reference in its entirety). In addition to the desired mRNA-peptides, the crude translation mixtures contained free peptides and non-fused crosslinked RNA. In order to improve the accuracy of quantitation based on liquid scintillation counting, it was found helpful to remove free peptides, as the C-terminal $His_6$-tags would be labeled with $^3$H-histidine. Upon incubation with oligo(dT) magnetic beads, mRNA-peptide fusions are captured, as well as non-fused crosslinked RNA, due to the $(dA)_{15}$ stretch in the puromycin oligonucleotide. The majority of free peptides were removed by this method, though it was desireable to use purified crosslinked RNA (removing non-crosslinked RNA) to reduce the overall generation of free peptides in translation. While captured on oligo(dT) magnetic beads, libraries were exposed to cyclization reagents. The eluted fractions were measured to determine the fusion formation based on input crosslinked RNA. Over several prepared translation batches mRNA-peptide fusions typically formed from 0.5-2.1% of the input crosslinked RNA.

Non-fused crosslinked RNA was removed by Ni-NTA affinity purification. Initially, Ni-NTA purification was attempted prior to reverse transcription in a procedure similar to that used for 2G12 selection, as the presence of non-fused crosslinked RNA necessitated a larger reaction volume (Horiya et al., *J. Am. Chem. Soc.* 136(14):5407-5415 (2014), which is hereby incorporated by reference in its entirety). Unfortunately, excessive loss of mRNA-peptide fusions (based on radioactivity) were noticed when purifying with Ni-NTA prior to reverse transcription. Addition of the cDNA strand during reverse transcription improved the solubility of the fusions; ultimately, reverse transcription was carried out prior to Ni-NTA purification. Even after this improvement, up to half of the input mRNA-peptides were present in the unbound fraction during Ni-NTA purification. Thus, the unbound fraction was resubjected to Ni-NTA purification to increase yields.

Figures 14A, 14B:
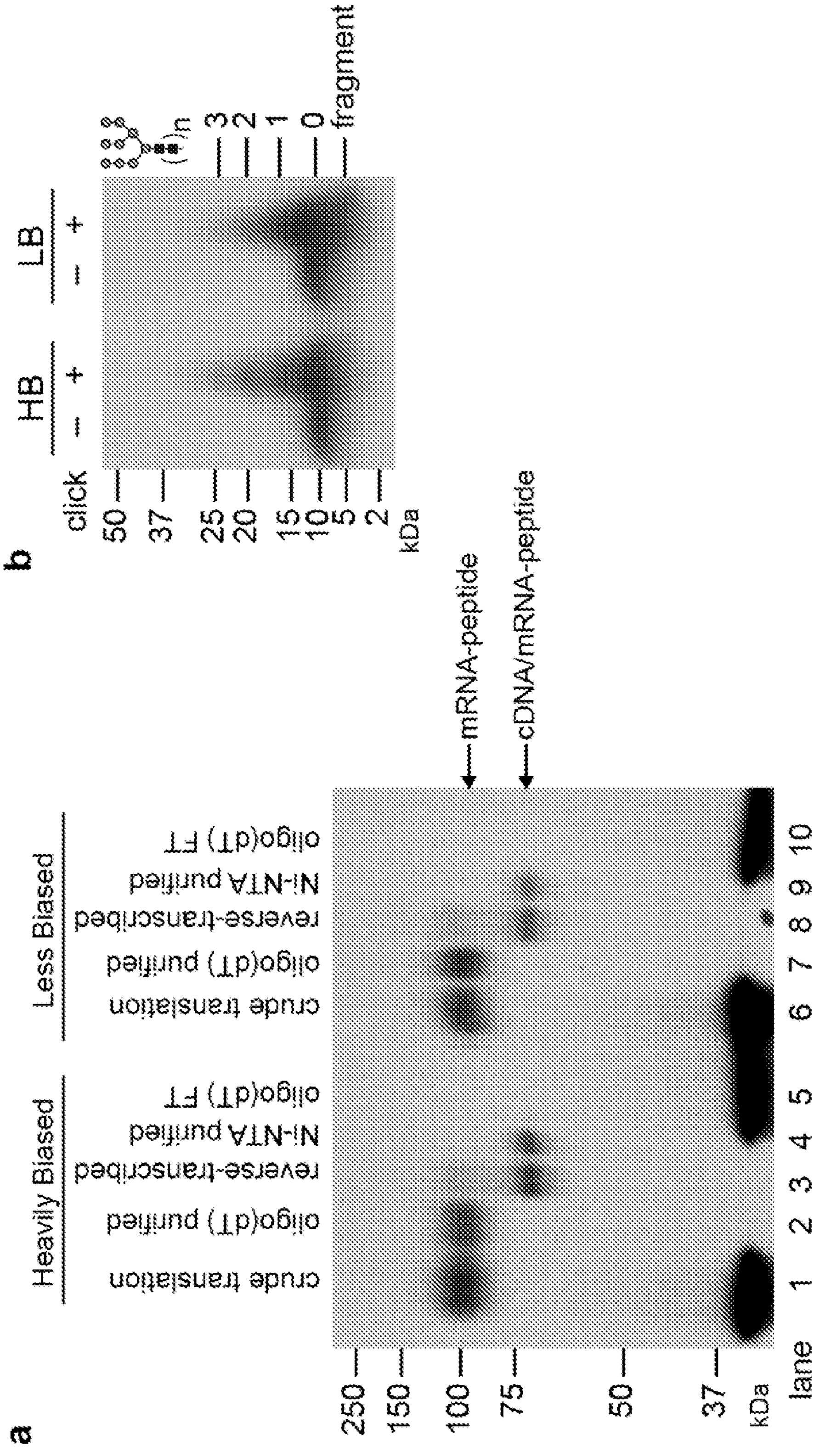
FIGS. 14A-14B shows the results of round 1 library generation.

At this point, each step of the process was verified by SDS-PAGE analysis (FIG. 14A). In lanes 1 and 6, the crude translations contain the desired mRNA-peptides (~100 kDa), as well as a poorly-resolved band under 37 kDa. The band under 37 kDa contains free peptides and potentially other small radioactive impurities, such as tRNA loaded with $^3$H-histidine. Oligo(dT) purification successfully removes free peptides, as lanes 2 and 7 contain just the mRNA-peptide bands. However, as mentioned earlier, oligo (dT) purification with magnetic beads fails to remove all peptide if non-crosslinked RNA is present. The flow-through of oligo(dT) purification (lanes 5 and 10) contains only the lower free peptide band, suggesting all mRNA-peptide fusions were successfully captured onto the oligo(dT) magnetic beads. The cDNA/mRNA-peptides resulting from reverse transcription migrate faster than the mRNA-peptides, as shown in lanes 3 and 8. After Ni-NTA purification (lanes 4 and 9), the cDNA/mRNA-peptide band is fainter, correlating to the loss of material from Ni-NTA purification noticed by liquid scintillation counting (LSC) measurements.

After verifying prior steps, the click reaction with $Man_9GlcNAc_2$-azide was carried out. Based on SDS-PAGE analysis of nuclease-digested fusions, the efficiency of the reaction was very low (FIG. 14B). The Heavily Biased library pool had fixed HPG residues in the sequences, yet the majority of peptides were not glycosylated at all. The Less Biased library pool was mostly non-glycosylated with a lower band was observed in the SDS-PAGE gel, indicating peptide fragments were present. To improve glycosylation efficiency, fusions were resubjected to click reaction conditions.

Libraries for the first round of selection were prepared over several batches to afford the desired quantities for selection. As mentioned previously, mRNA-peptides were easily lost due to poor solubility and/or sticking to tubes. After reverse transcription, the cDNA/mRNA-peptides exhibited slightly better properties, though still presented challenges in terms of handling. Minimal transfer of fusions between tubes reduced loss due to apparent sticking to tubes.

Example 2—Directed Evolution of Second-Generation mRNA Display Libraries Against HIV Broadly Neutralizing PGT Antibodies Round 1 Selection. The glycosylated fusions from several batches were combined for the first round of selection with three targets simultaneously: PGT128, PGT130, and glPGT128. A total of 7.3 pmol Heavily Biased library fusions and 6.8 pmol Less Biased library fusions were used, corresponding to $4.4\times10^{12}$ and $4.1\times10^{12}$ sequences, respectively. Library fusions were incubated with 200 nM of each antibody and captured on Protein G magnetic beads. Based on radioactivity measurements, 18.1% of the Heavily Biased library fusions and 14.8% of the Less Biased library fusions were bound. Even accounting for inclusion of three targets simultaneously, the fractions bound were unexpectedly high.

cDNA of the bound library fusions was recovered by direct PCR amplification from the magnetic beads. For subsequent rounds of selection, the recovered DNA of each library from the round 1 selection was split for individual selections with PGT128, PGT130, and glPGT128.

PGT128 Selection. A portion of the recovered round 1 DNA was prepared for selection against PGT128. PGT128 IgG was used as the target from rounds 2-10 of selection, while biotinylated PGT128 Fab was used in rounds 11-12. The progress of the selection was monitored by measuring the fraction bound to the target in each round, as summarized in FIG. 15A. Increased selection pressure was gradually applied throughout the selection. In addition to decreasing the concentration of target, the selection temperature was increased from room temperature to 37° C. in rounds 6-10. For rounds 11-12 with PGT128 Fab, the selection was carried out at room temperature.

In each of rounds 2-12, a negative selection was carried out against the immobilization carrier by incubating library fusions with empty magnetic beads (Protein A/G, Streptavidin) and discarding the bound fusions (bead binders). As glycosylation is a key part of the binding interaction with PGT128, non-glycosylated binders were removed in rounds 6-8 and rounds 11-12. Before the click reaction, library fusions were incubated with PGT128 (IgG or Fab) and the unbound fraction was carried on through the rest of the round. The fraction of the libraries that bound to PGT128 without glycosylation was typically under 0.5% in each round, indicating the carbohydrates were the main elements for binding.

Figures 15A, 15B, 15C:
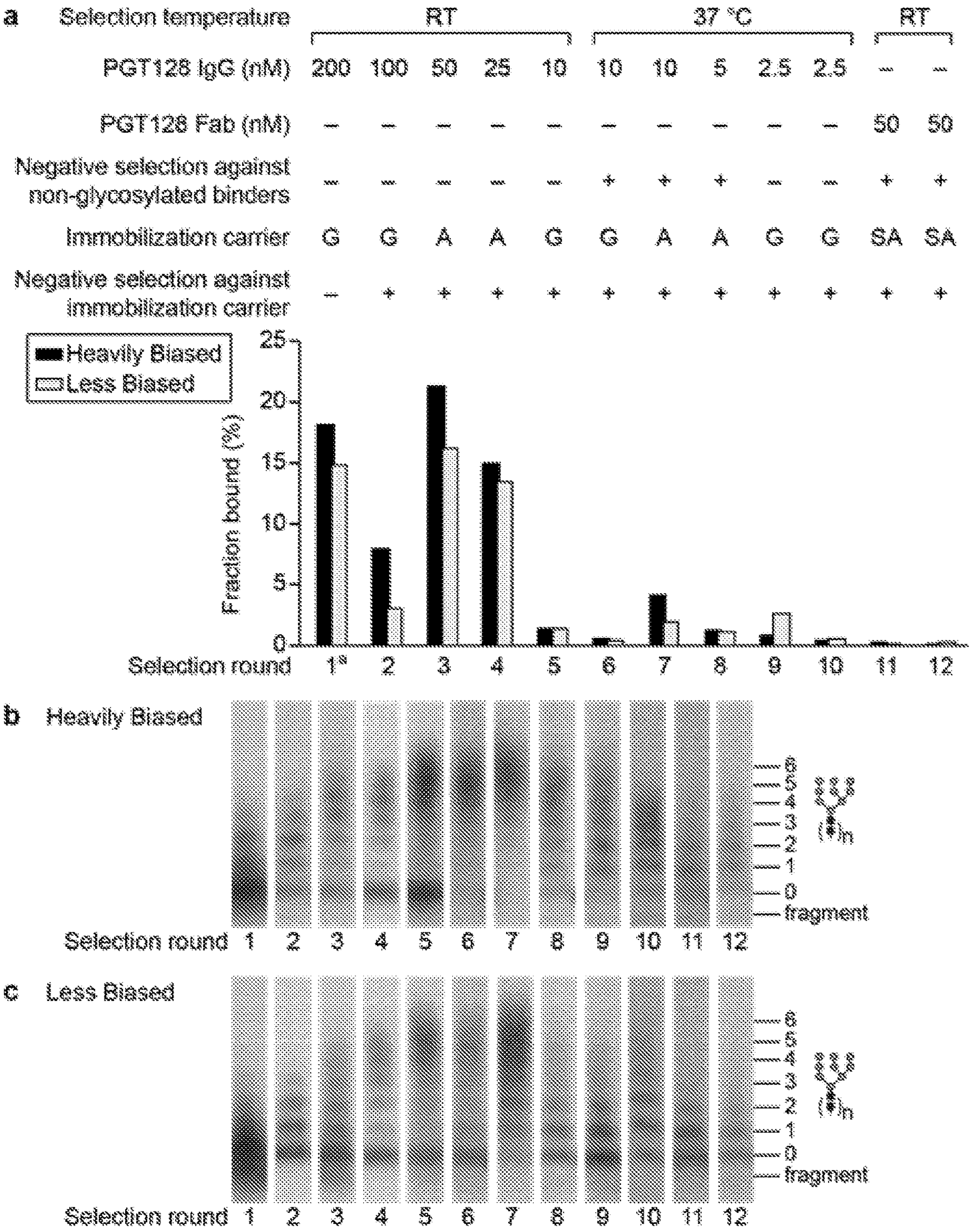
FIGS. 15A-15C show a summary of PGT128 selection progress.

The multivalency of the library populations in each round was monitored by SDS-PAGE (FIGS. 15B-15C). The multivalency increased through each round, from mostly 0-2 glycosylations to 5-6 or more. This trend was also observed during selection with 2G12; in that case, it was found that increasing the selection temperature from room temperature to 37° C. caused a remarkable downward shift in the multivalency of the populations (Horiya et al., *J. Am. Chem. Soc.* 136(14):5407-5415 (2014), which is hereby incorporated by reference in its entirety). Based on this observation, the selection temperature was raised to 37° C. in round 6 in hopes that the library populations would shift to lower multivalency. Indeed, a similar effect was observed.

The recovered DNA from each library were sequenced via Sanger sequencing after round 9 (Table 10). Despite SDS-PAGE estimates of 1-4 or 0-3 glycosylation sites for the Heavily Biased and Less Biased libraries, respectively, the number of glycosylation sites in the sequences varied greatly, ranging anywhere from 0 to 10. Only one sequence appeared twice, and it contained an undesirable 10 glycosylation sites. Interestingly, 22 out of 24 sequences from the Less Biased library contained the IGDIR (SEQ ID NO:1) motif, indicating there may have been some enrichment for sequences including this motif

TABLE 10

Round 9 PGT128 selection winners.

| ID | Peptide Sequence[a] | SEQ ID NO: |
|---|---|---|
| 91-1 | MAYFVHKKSRLLTNKAVKKRLHGCFQNQRSTIGDIRYAKCXRVSSNFFRR | 281 |
| 91-2 | MAPHQHRHLIGDIRRAWCXARVPNVNAHHSFKTXTRLXVFTPWIWARNKV | 282 |
| 91-3 | MAKFIHTRXPHKALRRIHPIIGDIRRDXHHNXRRRLRXNIRNTYLRFRRR | 283 |
| 91-5 | MASHINSNPNQLLLLYLKSTIGDIRCAXCXDFRHYRNTKYVFXTRHNRRT | 284 |
| 91-6 | MASYYIHDIAVSAYSKRRGYHNIQVESLYPKIGDIRSAKCXTWRNHRHTX | 73 |

TABLE 10 -continued

Round 9 PGT128 selection winners.

| ID | Peptide Sequence[a] | SEQ ID NO: |
|---|---|---|
| 91-7 | MAYYSGPKTIGDIRQTSHXRFXSYRYNXRRLPNAVRGDYHWIRILINRLR | 285 |
| 91-8 | MAHYSXNHXRHPLYPSVNHRXSYPRIGLLSRIGDIRSASCXLRCFRXRST | 74 |
| 91-9 | MAHNLRTXRNKNLIXLAFLHAPILKSRRLVHIGDIRVAACTHXVDVAPXY | 75 |
| 91-12 | XYPNTLNNVYQKCNKYNVIGDIRXARCXHXEHFSSQDQPKSKHKRRYKGF | 76 |
| 92-1 | MALIHSRQLVYSKNYXCCLDIGDIRHVLRGKYNDHLFGNAIYRKGVKAFN | 77 |
| 92-2 | MADNEFKILXIAXLHKSKHRTYLDYLNLVWXIGDIRAFQXXLKTVLXEAK | 78 |
| 92-3 | MAFHHXPHFTXRLPLLRRNCIGDIRRLYSPLPRDPHANFKFSFVEPNANR | 79 |
| 92-4 | MATDHNHSHRRPRREHLDXNXHYSRPXVANXIGDIRTFRRRYIQVXYHLX | 286 |
| 92-5 | MAHXSIPHHRKSIDDSLRHLIGDIRYRNRYLXRILYRTSHYKNYYCQHSI | 81 |
| 92-6[b] | MANLXXYKXVVNXTLFQWXATHRYSHFHNKCIGDIRTTXSWTRSXXXHAX | 82 |
| 92-8 | MATFSRYHTIGDIRHHTLKHHQSKGLQXRLIFLKRQFKAXGNCLRWKILF | 126 |
| 92-9 | MAYFQNTSINNINALNQATQKNFFRIRLEIXTLNLVSKRYCNAXXHLLXX | 287 |
| 92-10 | MALNSNSCHXRVATPISSWKIGDIRARFVSYLHYTNFSFSXXKXKFFTKX | 84 |
| 92-11 | MANVFPQTDRSLERSQCLFEAFHSIVXHXESIGDIRLECLRITIVALRTT | 85 |

[a]Only the random region of each peptide is shown. All peptides are followed by the constant sequence: -GSGSGLGHHHHHHRL (SEQ ID NO: 7); however, in some cases, there were mutations in this region. M denotes HPG, encoded by the AUG codon; a X denotes a potential $Man_9$ glycosylation site. Cysteine residues are denoted with a C. The fixed peptide sequences (IGDIRxAxCM (SEQ ID NO: 289) or IGDIR (SEQ ID NO: 1)) are present in each of the selections except 92-9 (SEQ ID NO: 287). [b]The sequence for 92-6 appeared twice. Sequences with a prefix of 91 are from the Heavily Biased Library, while sequences with the prefix of 92 are from the Less Biased library.

Several of the round 9 winning sequences were ribosomally-synthesized for binding analysis. Each sequence with two cysteine residues was subjected to cyclization during Ni-NTA affinity purification. The purified peptides were glycosylated via click reaction with $Man_9GlcNAc_2$—$N_3$ and screened for binding to 100 nM PGT128.

Figures 16A, 16B, 16C:
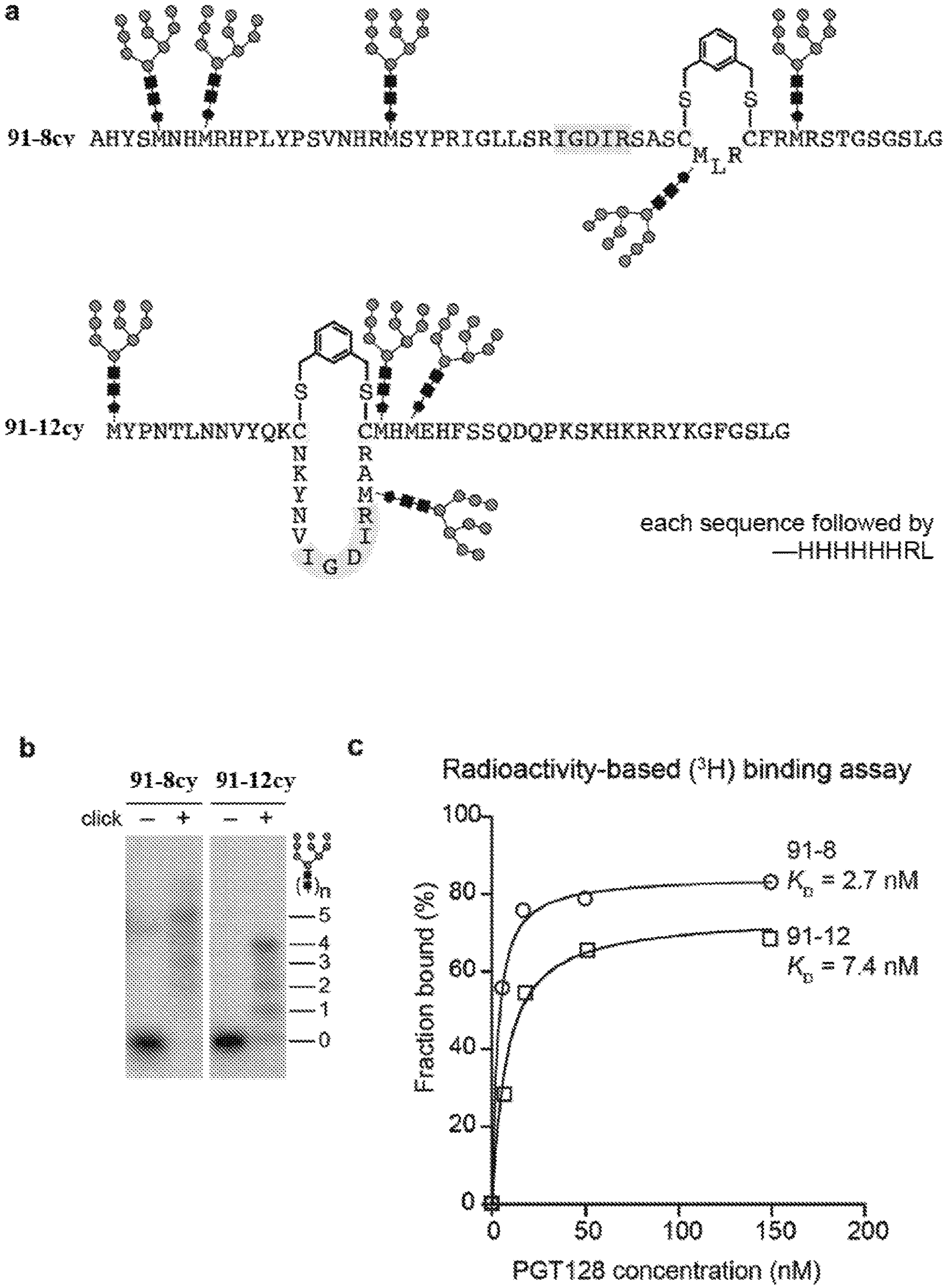
FIGS. 16A-16C show binding analysis of round 9 PGT128 sequences.

Cyclized sequences 91-8 (SEQ ID NO:74) and 91-12 (SEQ ID NO:76) (FIG. 16A) from the round 9 Heavily Biased library exhibited binding in preliminary screens (33-35 nM) and were investigated further; however, the glycosylation of the peptides was not complete. In order to enrich the mixture for those sequences with full glycosylation, a similar strategy to that which was found successful for removing incompletely-glycosylated peptides from the 2G12 selection was employed: affinity purification with target (Horiya et al., *J. Am. Chem. Soc.* 136(14):5407-5415 (2014), which is hereby incorporated by reference in its entirety). The peptides were pre-incubated with 100 nM PGT128 and captured on Protein G magnetic beads. The bound fractions were eluted from the beads using heat and carried onto a binding assay. 91-8cy and 91-12cy bound with $K_D$'s of 2.73±0.36 and 7.41±1.29, respectively (FIGS. 16B-16C). Each of the maximum fractions bound increased following affinity purification. For 91-8cy, the maximum fraction bound increased from 69% to 85%; for 91-12cy, the maximum fraction bound increased from 54% to 74%.

Although nanomolar binders were identified from the PGT128 selection sequences in round 9, there were no signs of convergence based on available Sanger sequence information. Selection was continued and next generation sequencing (NGS) was used to gain a broader view of the library populations and changes from round to round. The recovered library DNA from rounds 7-12, as well as preselection DNA (round 0), were submitted for Amplicon-EZ NGS (Genewiz). Data was analyzed for each library over several rounds.

Figures 17A, 17B:
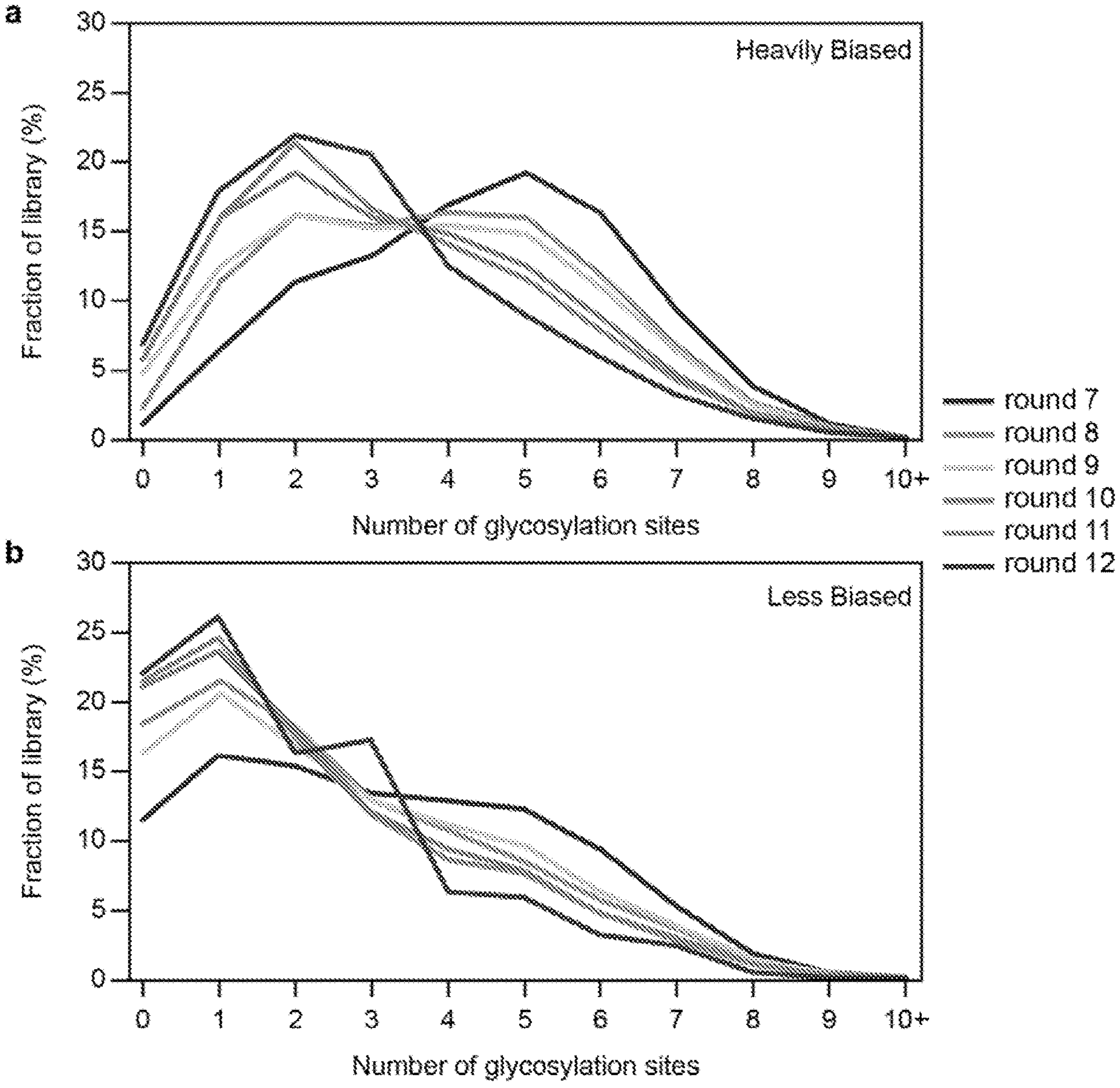
FIGS. 17A-17B show NGS analysis of multivalency through PGT128 selection for the Heavily Biased library (FIG. 17A) and the Less Biased library (FIG. 17B).

Overall, multivalency decreased in latter rounds of selection (FIG. 17A-17B), consistent with the library glycosylation patterns observed by SDS-PAGE. The average numbers of HPG's found in the sequences shifted from 4.5 and 3.2 in round 7 to 3 and 2.1 in round 12 for the Heavily Biased and Less Biased libraries.

Figures 18A, 18B:
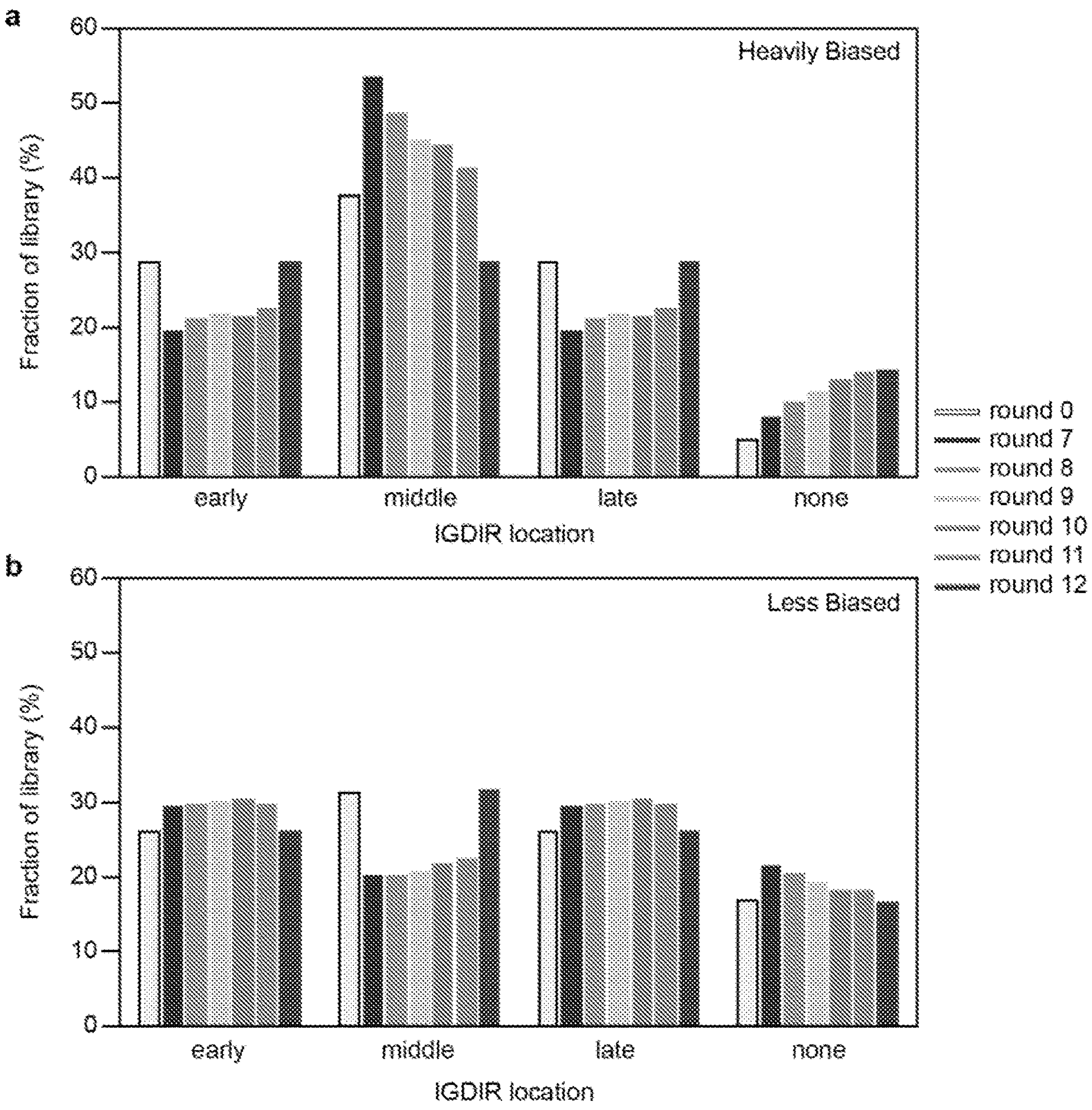
FIGS. 18A-18B show NGS analysis of IGDIR location through PGT128 selection for the Heavily Biased library (FIG. 18A) and the Less Biased library (FIG. 18B).

The general positions of the IGDIR (SEQ ID NO:1) sequence (early, middle, late, none) were analyzed within each library as well (FIGS. 18A-18B). Interestingly, having an IGDIR (SEQ ID NO:1) located in the middle of the sequence was prevalent in round 7 in the Heavily Biased library, but steadily decreased through round 12 (FIG. 18A). In the Less Biased library, the IGDIR (SEQ ID NO:1) location remained steady until a fairly sharp increase in round 12 for the middle position.

Example 3—Identification of a Peptide Consensus Motif in Selected Glycopeptides Upon examination of sequences individually, many point mutations were identified. These point mutations could be derived from sequencing read errors, PCR over several rounds of selection to regenerate the libraries, and/or PCR to generate samples for sequencing analysis. In order to account for these mutations, sequences were clustered into families of closely-related sequences. These clusters were generated by grouping all sequences with up to two amino acid differences from a representative sequence within the sequencing data. The representative sequence was chosen to maximize the number of sequences that could fit into the cluster.

For each cluster, a consensus sequence was assigned. Each consensus sequence was built position by position, based on which residue was most frequent at that position. In the event of a tie, the residue letter occurring earlier in the alphabet was chosen. As there are 20 amino For each cluster, a consensus sequence was assigned. Each consensus sequence was built position by position, based on which residue was most frequent at that position. In the event of a tie, the residue letter occurring earlier in the alphabet was chosen. As there are 20 amino acids, the consensus residue chosen would be present in more than 5% of the sequences. The consensus sequence could thus differ from the representative sequence chosen to create the cluster.

Cluster strength, or the sameness of the sequences within the cluster, was then evaluated based on the percent of sequences within the cluster having the consensus residue at a certain position. Each position was assigned a letter or number that represented a percentage range. The score range is as follows, where x is the consensus residue:

| |
|---|
| 0: x <= 85% |
| 1: 85% < x <= 86% |
| 2: 86% < x <= 87% |
| 3: 87% < x <= 88% |
| 4: 88% < x <= 89% |
| 5: 89% < x <= 90% |
| 6: 90% < x <= 90% |
| 7: 91% < x <= 92% |
| 8: 92% < x <= 93% |
| 9: 93% < x <= 94% |
| a: 94% < x <= 95% |
| b: 95% < x <= 96% |
| c: 96% < x <= 97% |

-continued

| |
|---|
| d: 97% < x <= 98% |
| e: 98% < x <= 99% |
| f: 99% < x <= 100% |

With this score guide, the most abundant cluster in the Heavily Biased library in round 12 was evaluated as follows, excluding N-terminal and C-terminal constant peptides:

Cluster 1—Heavily Biased, PGT128 Round 12

Representative (SEQ ID NO: 290)

YTEKHNGIGDIRPAICXNSKNQNYRCNHYQIKLYIHXLXRLSHNYRNS

Consensus (SEQ ID NO: 291)

YTEKHNGIGDIRPAICXNSKNQNHRCNHYQIKLYIHXLXRLPHNYRNS

Strength ebc7dacdddededdebcda6eb8eeebded5eeebeedbdbdcbdcd

For this cluster, the representative sequence and consensus sequence are not the same; the two differ in two locations (bold). Typically, the consensus sequence is also the most abundant sequence, as it is here.

The most abundant sequence clusters in each round were identified. The top cluster in round 7 only accounted for up to 0.23% of the total library population in the Less Biased library (just 70 sequences out of 30,793). The most abundant in round 7 for the Heavily Biased library was even less. With such few sequencing reads, these data have a lot of error. Still, it was apparent that the selection was not converged at this point. However, the fraction of library taken up by top sequences increased through each round.

Figure 19:
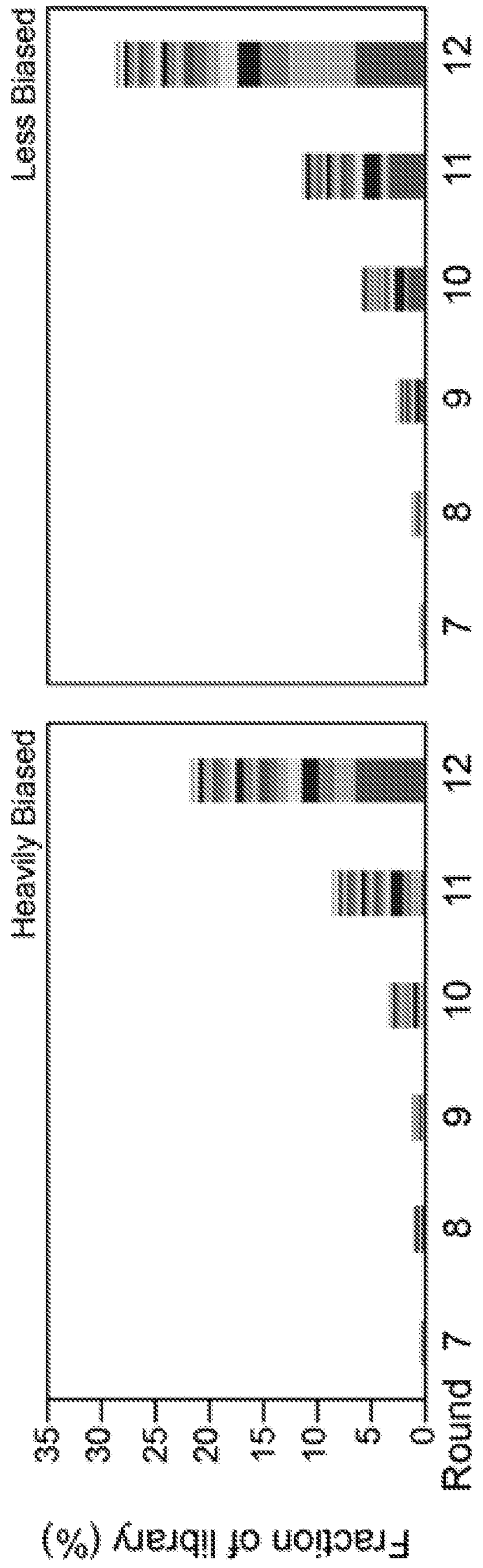
FIG. 19 shows bar graphs showing the enrichment of the top 20 most abundant sequence clusters in PGT128 selection. Each bar represents an individual sequence, with the height relative to its portion of the library.

The top 20 clusters are summarized in Table 11, with the consensus sequence and strength score. Starting from round 7, a clear increase in these clusters can be observed from round to round, though some clusters were not detected in earlier rounds (FIG. 19).

TABLE 11

Top 20 most abundant sequence clusters in round 12 of PGT128 selection for the Heavily Biased and Less Biased libraries.

| ID | Consensus sequence and score[a] | SEQ ID NO: | % of all sequences |
|---|---|---|---|
| | Heavily Biased | | |
| H-1 | YTEKHNGIGDIRPAICXNSKNQNHRCNHYQIKLYIHXLXRLPHNYRNS<br>ebc7dacdddededdebcda6eb8eeecded6eeebeedbdbdcbdcd | 291 | 6.47 |
| H_H | LTLRYLKIGDIRLANCXTVFPHFLSKKFFENGHRNLARPCTFRRNRHL<br>ccddededeecdcddcdcededdecddcdcddddcdddddbddccddd | 292 | 1.79 |
| H-52 | YHKHRVXHHHEDKATSLTSNLVRLRLKTRIGDIRRALCXLSKFRYLIN<br>eeceedcdddcccdddddcdccddecc8bddee8dce8cdddcceeec | 293 | 1.61 |
| H-14 | LLHHLRXIGDIRPAHCXVSHQRRYVPIsRKNvFFKRGFNsHpLRKILTA7<br>eeeceeededcdeeeccddcdedbbecdcdedddcde4ac6deecddd | 294 | 1.59 |
| H-25 | RFRHSNNYYLTPFLTPLKTLISLQLRYRLIGDIRNASYXHKFSNRNRF<br>dddeddceeeeeddeeeddddaeddecedddecedcc0acdcdd8ced | 295 | 1.24 |
| H-5 | HQTHSYRIGDIRIAHLHGQPHAPVQGLPpvLRRRRELQvpLRARALLV<br>ddddde eeddddeddeeeddecdddeeeeedeeee0Odddeddedeeb | 296 | 1.00 |
| H-66 | IFNQGYRIKATA7NDLKDIAIGDIRHALCXLVLARIKLQRRxvKyKHDHR<br>debbeeeddd8cdd0bbdde0bdea98cdaeeed75edccec8cdadd | 297 | 0.88 |
| H-9 | HQHHHPNYALXQRRLSIAIGDIRLAICXFAHLyHcyRKHLxANTIPXK<br>deddddddceccbdddc8dddbcededbccebedcbeddecdbbccdcd | 298 | 0.79 |
| H-36 | FVTYQHXSQKNFRRYQILRNHFHPQNYRFIGDIRHALCXFIFKNLXRH<br>cddeddcddddddecbbeededecdcddcdeddeddebccdcddddec | 299 | 0.76 |
| H-103 | RLHHNIHSHPQKYLEHPLAHLAGHVLGRHHTA7RyssmivHGHRvRHLDQ<br>ec9eddeeceedeeed0eeeeeddddd8eddededddddccccddeddcd | 300 | 0.68 |

TABLE 11 -continued

Top 20 most abundant sequence clusters in round 12 of PGT128 selection for the Heavily Biased and Less Biased libraries.

| ID | Consensus sequence and score[a] | SEQ ID NO: | % of all sequences |
|---|---|---|---|
| H-375 | AXKIRSKIGDIRTAVCXFXHRHHHHHILDPYYLKXIVXYYSLKSRITL<br>ccdededcdaddd7d8ebddeddde99998d9a97999da9999a889 | 301 | 0.67 |
| H-42 | FIKPCXXYLLPPTXLNLYIGDIRRAKCXEAXNNFHXNNKPLXATXPPH<br>bdeed0dee0eeddddddde6debddeeeedeadddbccdecccb8dbd | 302 | 0.66 |
| H-443 | KDILKLRIPFATLSGHRNIGDIRHAYCXSLKRPYIQVYSYLNHLKVRF<br>ebddddeceedcd8ccec9eddeddd8bcceeddddeedeedeeddec | 303 | 0.57 |
| H-158 | TLHNIHDLNHYYRNLNTRIGDIRHATCxyppxKLKLLKHNRpxDRAIY<br>bebdedddcdeedcc0debdcdeddd2ddbdcdedbed5cdddcdddd | 304 | 0.55 |
| H-221 | PYRINQQXNFPTAWSSALFQIGDIRHARCXDscRRFTNIXRyvyLKRRXN<br>eeeedbb9dcebebccd9dd9dedcddacbcedd8dc5eedeedeecb | 305 | 0.47 |
| H-22 | LFKPYPKIGDIRKARCXLQHTLHHRTNKQpsyRRRLKTLipLFRRCXL<br>eccbedcdedbdeeddcdcedecdeedceedecedecce9cbbeedce | 306 | 0.46 |
| H-247 | INHLHRTIGDIRHAQCXIYLIYLVQNDQyKRNNRTFRLxi,NpKLLKRF<br>deeea4ddddeeddcebeeeddfdecdcdaeddeededbecddeeced | 307 | 0.45 |
| H-61 | TNSYYHHNPLXRRTHVVXTLKPXNFTNAKXIGDIRRAHCXTTINXLKRR<br>dccedeecddccddccd9ed8dcbddccbdccacceeeeebabac8dd | 308 | 0.43 |
| H-13 | ILLHVSTRSRYPHHHXAIIGDIRCASCXypvLKTA7FyNFNRLKTyRKQF<br>edddbceddeeeeddbecbedbdecdd7cddeadbcdcddebacdbde | 309 | 0.41 |
| H-74 | YRTHKLLHHHNDKTNKSNIFPRIFVCHyyLIGDIRHARcxipLEILRRY<br>dddbdadecdbebb5ddaddcbdeddee8dcddecddd9cdecdddde | 310 | 0.41 |
| | Less Biased | | |
| L-8 | YSKHRFSFRHNNXLRDRKLIRKFSYHNHSIGDIRVANKFRYLHVFKFI<br>edbedcdddccccceecdddddddb9ededdeddddddecdccddddcdd4 | 311 | 6.48 |
| L-1 | SIKLINQXXTTNPHLRLHIGDIRRLIKDLyxpRvyyRpiusGRRLFVN<br>edecddcbadedeeeeeeeeeeeeeeeeeee0ededeeddddddeddddd | 312 | 6.05 |
| L-52 | HSHHHSPXIEFHSNGRLHIGDIRKFyADALXVLFFKXAFIDRIpFHDA<br>edededeeddbccc9edeeeeeeeeeeeeeeedebddddededcccce | 313 | 2.82 |
| L-67 | NIYFCSRRINFHNSCYLXIGDIRGLSiyHHixiHNKLHLLixyNLLXX<br>dddbcdddddcc7eceeddeddeedc9dcccdccbddcceccdceddd | 314 | 2.02 |
| L-11 | IHLLPLRHNRRSHNRPSRLSTA7QKNDYFKSIGDIRATYTA7LRHNFLYRLS<br>eedeeeddddeecdedee9edddbecdddeedeeddeeeddddeeec | 315 | 1.71 |
| L-61 | HVVVLHHSGFHGNRFSRLPKLLRNQHYQNIGDIRRLYNTNIPYTKRYFQ<br>dddadcdbcbccadcdcbddeedc0dd3dddccedad90cdcdddd9a | 316 | 1.29 |
| L-2 | IHYHHPIIGDIRLKHNXINAHTKHVPQKLYLDIKFRRLFGLYILRXLN<br>eddeddddeddedcd9b0bdedcdcea0ccd9bddeedcddededbed | 317 | 1.03 |
| L-120 | IRKNFPXTFGHRPHLRVAHAQRAQHALLvLRRARRLLDQEvDApGGRR<br>eecdde8cddddcdedcdeecddedddeeecbeeeecaceadeebee | 318 | |
| L-65 | ILYHYHNIGDIRRSQRHLNXQXRLYVSTLLHSSHTLRRASITHRIRKF<br>ecccddbddcddcdddcedcc9edcd6cebd7dddddddddbeedd8c | 319 | 0.74 |
| L-44 | TFSRYHTIGDIRHHTLKHHQSKGLQXRLIFLKRQFKAxGNcLRTNKILF<br>dedeeeeeeeeedcddeeedebedccdebcdcddddebdcceddddd | 320 | 0.69 |
| L-272 | TKDYRQKVRKIFSHHITKIGDIRLAEHQHFAKsRLLKGFvRARNRVRY<br>eecedeeddcded8edddeeeddeede6eeeeddeddd0edd0deddb | 321 | |
| L-128 | HHYPNYHXRSHGDRLILLRHLXSFLVDHKQILxFLLRxRKNHvsxXXT<br>bddc95dcecddce9ddedcddbddc7dcdcdbcddecebdd9bddd9 | 322 | |
| L-4 | KYTHIHSIGDIRNTYRNKHKHXALNKTNTNALFQQHHRXLIRLFYRRLL<br>ddadbdedcddddcddbcdcd8ddc8bcdb77dcdcdbdddcdddcee | 323 | 0.51 |
| L-15 | LNKHKHLRNHTRHHSVPTIGDIRKRIHNLLHyLAGFRFFNQxHsKXGV<br>eddedeeede4cedbe7deedddbeddcddbddecdeeddeb9cbbc7 | 324 | 0.50 |
| L-182 | IRNQTKKIGDIRGHHRTKPQYFEHpFVDLyKHyQyRvFHRGyLKLFRE<br>dddeddedeeeeededeceddddcdceed7cdedeedddedeeedee5 | 325 | |
| L-310 Y | LHNHHNYSSNNKLHHLEIGDIRLIyQKyLRNpxFxTFLsRKHxNyaQR<br>ddeded0d2d4cdddddcddbcdecd9bedecaccbc4dcdcdbbdbd | 326 | |
| L-1079 | NLTAXSRIGDIRKHHFGRPLYLTKHGAYPRYHTRYKHLLTYRHHFPLI<br>eeefffffedeeeeeeddeeedeedd9deeeecddbddedeeacedee | 327 | 0.42 |
| L-98 | KHTHLRPXNFTQRLRKAHIGDIRLpRNisTsRIRTHIKFHLIRxHLRN<br>eedecde0da6ccddbeadccb7c0ecdbddce9dceecdfdccadcc | 328 | 0.42 |
| L-43 | FLLNHKRIGDIRKLPPLNLXATKILTKERIRKivNGFvQRLKGHsTANVI<br>deeddddddddedeedeeedbdddddde7ededcdbdcd6dddadeddc | 329 | 0.39 |
| L-160 | IHHSYRGFTLRIPLTINKIGDIRTAFPypxLsHLFDRRRTNKRGLHNTA7F<br>dedeededdeebeddcceedeeedededdd39eec9dcde4dedddec | 340 | 0.37 |

[a]Each consensus sequence is cropped to show the individual random region, with the N-terminal processed HPG and fixed alanine, as well as the C-terminal -GSGSGLGHHHHHHRL (SEQ ID NO: 7), removed A X denotes a potential $Man_9$ glycosylation site. Cysteine residues are denoted with a C. The fixed peptide sequences (IGDIRxAxCM (SEQ ID NO: 289) or IGDIR (SEQ ID NO: 1)) are present in each of the selections except H-103 (SEQ ID NO: 300), L-120 (SEQ ID NO: 318), and L-128 (SEQ ID NO: 322).

Example 4—Confirmation of PGT128 Binding Affinity to Selected Glycopeptides Using BioLayer Interferometry Two of these sequences from the Heavily Biased library, clusters 1 and 22, have been prepared for binding analysis using BioLayer Interferometry (BLI). The peptides of interest, "H-1" and "H-22", are 54-mers and contain two internal cysteines for cyclization. Peptides were synthesized using automated rapid flow-based SPPS synthesizer, which has very successfully been used to synthesize other long peptides (>100 residues) (Mijalis et al., *Nature Chem. Biol.* 13(5):464-+(2017), which is hereby incorporated by reference in its entirety). A biotinyl-lysine residue was incorporated on the C-terminus for capture of the peptides on a streptavidin BLI sensor. The cysteines were protected with disulfides (–StBu) for selective unmasking just prior to cyclization with m-dibromoxylene.

Figure 20:
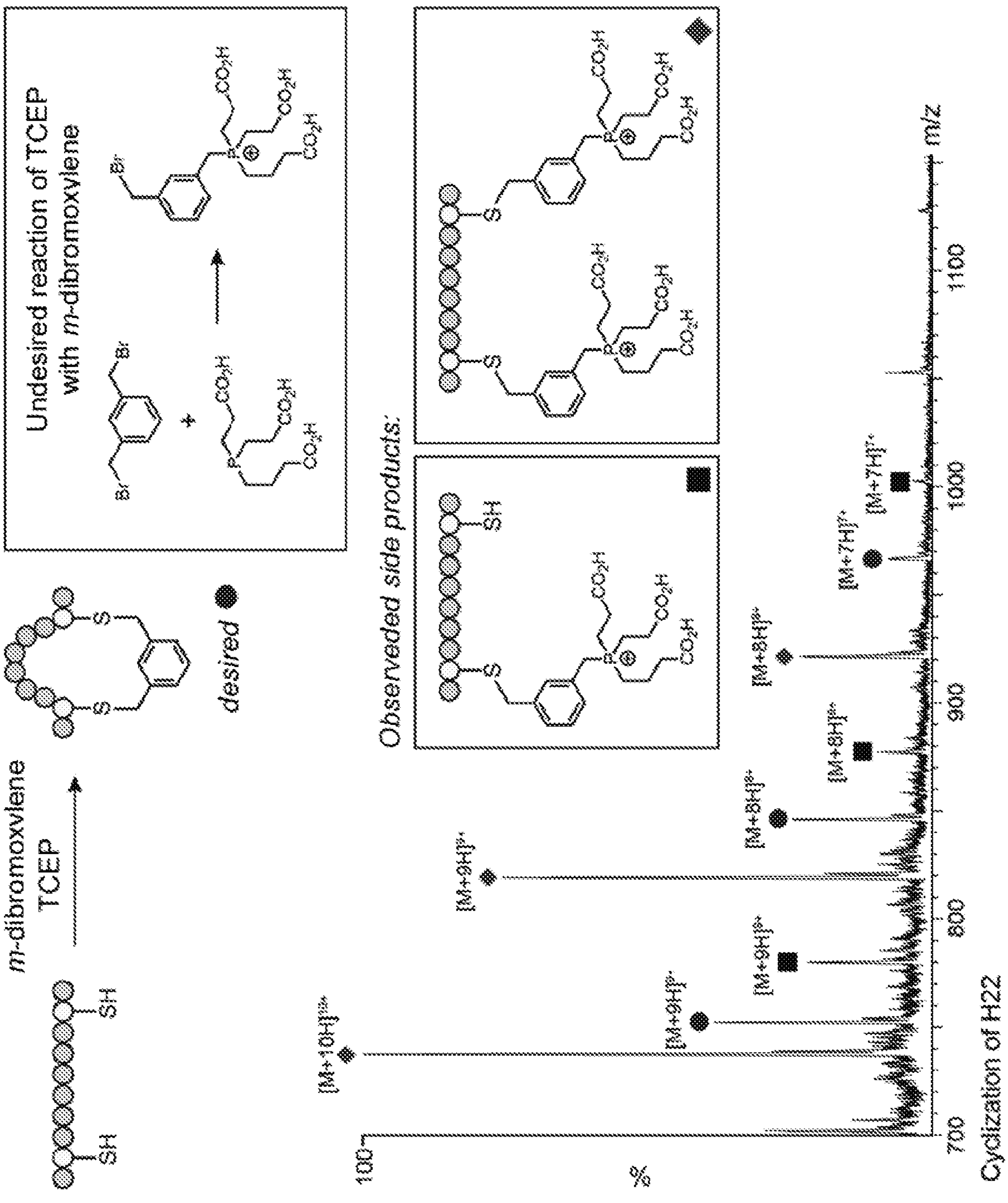
FIG. 20 illustrates an undesired side reaction during cyclization. TCEP reacts with m-dibromoxylene to form a (TCEP)-xylyl adduct which can be attacked by peptide cysteine residues. In the cyclization of H-22 (SEQ ID NO:306), the major product identified in ESI+MS is bis-(TCEP)-xylyl (purple diamond). The desired cyclized product is also observed (red circle), as well as mono-(TCEP)-xylyl (blue square).

Analysis of the crude peptides following resin cleavage and deprotection of all side chains (except —StBu) revealed the synthesis proceeded smoothly, with the main peak in LC-MS corresponding to the desired product. The crude peptides were then reduced with TCEP at pH 8.0 and diluted for cyclization. The reduction proceeded smoothly; however, excess TCEP reacted with m-dibromoxylene to form undesired (TCEP)-xylyl adducts that added to free cysteines during cyclization (FIG. 20). Removal of TCEP prior to addition of dibromoxylene greatly diminished this side reaction, allowing for efficient cyclization. The crude peptides were purified by HPLC prior to the click reaction with $Man_9GlcNAc_2$—$N_3$. The reaction proceeded smoothly to full conversion for H-22 but was only 60% complete for H-1.

Example 5—PGT130 Selection

A portion of the recovered round 1 DNA was prepared for selection against PGT130. The progress for 10 rounds of selection was monitored by measuring the fraction bound to the target in each round, as summarized in FIG. 21A. Increased selection pressure was gradually applied throughout the selection. In addition to decreasing the concentration of target, the selection temperature was increased from room temperature to 37° C. in rounds 6-10.

In each of rounds 2-10, a negative selection was carried out against the immobilization carrier by incubating library fusions with empty magnetic beads (Protein A/G) and discarding the bound fusions (bead binders). As PGT130 is known to bind glycans, non-glycosylated binders were removed in rounds 6-8. Before the click reaction, library fusions were incubated with PGT130 and the unbound fraction was carried on through the rest of the round. Interestingly, the fraction of the libraries that bound to PGT130 without glycosylation (4.2-16.1%) was much higher than that observed for PGT128.

Figures 21A, 21B, 21C:
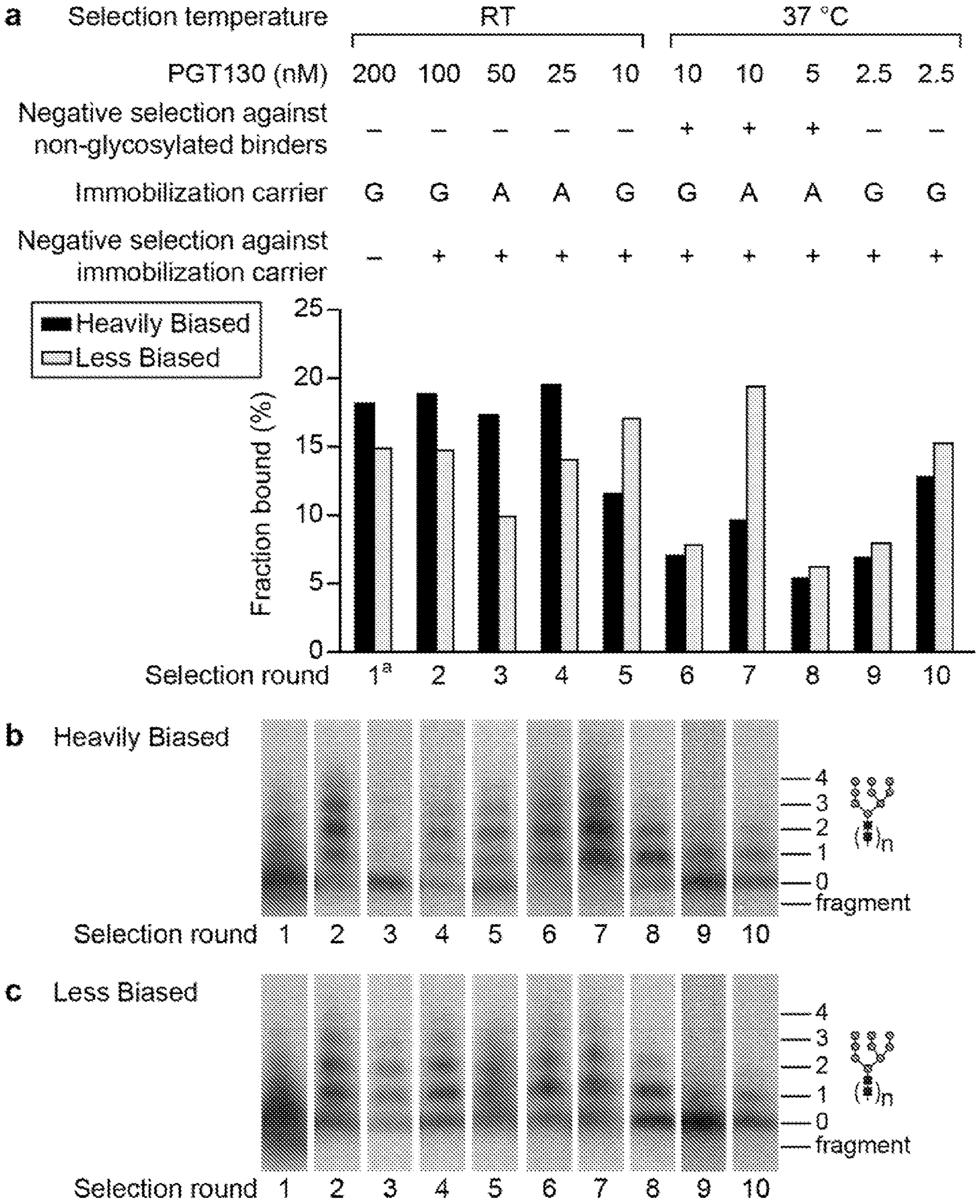
FIGS. 21A-21C shows a summary of PGT130 selection progress.

The multivalency of the library populations in each round was monitored by SDS-PAGE (FIGS. 21B-21C). In contrast to the dramatic increase in multivalency observed in the PGT128 selection, the PGT130 libraries remained low-valent, typically around 1-3 glycosylations. After the 37° C. selections, the library multivalency decreased to around 0-1 glycosylations. It may be that peptides bind to PGT130 with little or no dependence on glycans, as the libraries were able to bind PGT130 to a high degree before glycosylation.

Figures 22A, 22B:
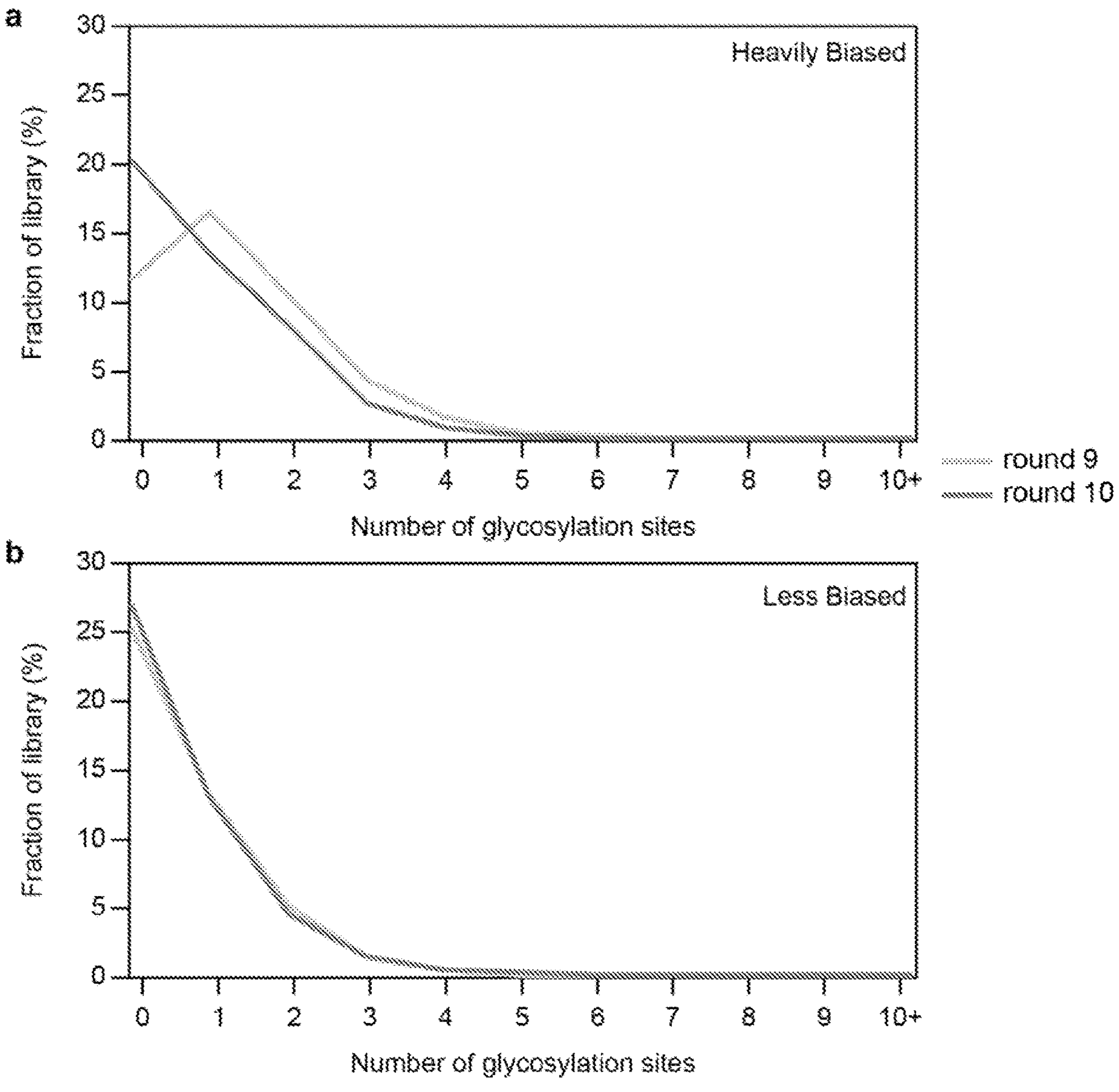
FIGS. 22A-22B shows NGS analysis of PGT130 selection for the Heavily Biased library (FIG. 22A) and the Less Biased library (FIG. 22B).

The PGT130 libraries from rounds 9 and 10 were sequenced by Amplicon-EZ NGS. Consistent with the SDS-PAGE analysis, the libraries predominantly contained sequences with one or no glycosylation sites (FIGS. 22A-22B).

At round 10, the top clusters for the PGT130 libraries comprise a larger fraction of the overall library than the PGT128 libraries at round 12, indicating a higher level of convergence in the libraries. The top 10 sequence clusters for the Heavily Biased and Less Biased libraries are listed in Table 12.

TABLE 12

Top 20 most abundant sequence clusters in round 12 of PGT130 selection for the Heavily Biased and Less Biased libraries.

| ID | Sequence | SEQ ID NO: | % of all sequences |
|---|---|---|---|
| | Heavily Biased | | |
| H-3 | FRSNDPKIGDIRHELHVAHPVDVVLLRLLRRVLAVHLAQHVVVALRHR<br>ddcdcdddddddcce9debeedcbeeeeeeeeeeeceedee8deeede | 341 | 18.98 |
| H-37 | NHSHGHNIGDIRDATCXLSNCYHYNNRRKNRFTLFILLRILVQKSLER<br>aecedddecddeeeddbeecdece9deeeddcefdbffecedae8dce | 342 | 1.21 |
| H-67 | QLYNLKVIGDIRRRGLHVRRLVALAHHVRDRLHLARRLLHLHHGVRLG<br>d3eefdefdddeedecbefdecdeed9cecdeededdd9edcdecccf | 343 | 1.10 |
| H-53 | IFNQGYRIKATA7NDLKDIAIGDIRHALCXLVLARIKLQRRXVKYKHDHR<br>eedededdde dadd0bcedd0fddcd95eceeddadddd5dcdedcdf | 297 | 1.04 |
| H-36 | YKKTFXDIGDSYGELHAQARRREAVRRLLRLVRHRVLLHLLRAVLHAR<br>fdeeceeccddddfdebdfcffcdceebededddeeeefdeefceded | 344 | 1.00 |
| H-50 | RSIHSQKIGDIRKGALHARVVRPVEQRQPLRVLLARVHRLADVLALLH<br>3edddadedeebe8dddeccadcdeaebbffdffefcdeeadcefeee | 345 | 0.88 |
| H-74 | SSFRLHNXGPSRXRHTAMRLLTIYSIGVSTLANSLRVLHGVAHRGRHLG<br>eeecffedbdeeddedeeeededceccdfeedbeeeee6beddeddde | 346 | 0.86 |
| H-47 | LKNLVQLIGDIRRGLHEHLHLALAGQRDDQLLLVLLVHRVHRGAHRHR<br>ddcdcdeeeedfdceb4eeddeddebdeecdffeeeceeeeededd9d | 347 | 0.84 |
| H-7 | YYNHPKLRQYLVKXLTRLRRYSYRELHDGDDHARQAHRGRLLQDLVDR<br>eeddbcbf9eeed0eeeeeeecebecbcfceceedccfefeefbfead | 348 | 0.80 |
| H-84 | LTVRTQLHHHHAQRPGDLLALVLLLRPRHTNRYSYRVVHARPQGRHDHR<br>ecefbeeeedebbdddbefeedeeefdeeeebaeedeceedecdcace | 349 | 0.79 |

TABLE 12 -continued

Top 20 most abundant sequence clusters in round 12 of PGT130 selection for the Heavily Biased and Less Biased libraries.

| ID | Sequence | SEQ ID NO: | % of all sequences |
|---|---|---|---|
| | Less Biased | | |
| L-4 | IQHHNFFPRTSRYIYPRRIGDIRPILRQNIFHHLKKFLHVVKTRYFSF<br>ededddededcbcaedeceddeddde8cddcaedccddccddd9bdd | 350 | 5.1 |
| L-35 | IHHTHLNIGDIRFRHFPRRYRNNTA7XNFLFLVLRALTTA7KNRLAFFSNDH<br>edddeedeeddeeeedeeeddaec8ddceeeedde9ddddcceeddbb | 351 | 2.2 |
| L-73 | INPNSKRRTRSRHYNGDHIGDIRAKHLSHRKITLLGIYRIRLKVALNL<br>eeeedcdddddceedbbddddeeddddadeeeddeeeeeeeeededece | 352 | 1.8 |
| L-124 | YITHSPHIGDIRHSKSLLLERNHGLLELLRLLVRVGRQEVRVHDVQHR<br>edeececedddecdbddedcdccceeddfececedcddccebc9ccde | 353 | 1.1 |
| L-140 | INXSIRLIGDIRPAQAQRGHLAPHARRVRHEVLGLVLERLLVLRRLVR<br>ae9ceeeedbddeddddeeefeddddeddd9dededecdeedfeddce | 354 | 1.0 |
| L-37 | NHIHLSDIGDIRHLKNEHNTYYNKKRLISVLEFLSLTNQLRFLAKNEYL<br>ddeeeecdddcedeeddddeeddeeeedbdeaddcdd9cdadaecddc | 355 | 0.9 |
| L-47 | DSHPYNIIRYSFQPPHLHEELLPQRRLLRGVHVQGVHPVVRLLHRVQR<br>ccdcededed8dadeeebd9deeeeefeeddedcddeecceeedeebd | 356 | 0.9 |
| L-64 | IRTRVSQIGDIRHDLKRNTTIFKNALFLIYLIKTYNRKNYHLKNLKDL<br>f9bdddbddefedceded5bedecdeceedeedbdbdccedeedeece | 357 | 0.7 |
| L-103 | FLLNHKRIGDIRKLPPLNLXATKILTKERIRKIVNGFVQRLKGHSTANNI<br>edfddeefefecedeeeedaadddddccdeecdcbeddceeedccedd | 329 | 0.6 |
| L-187 | YDPLHKASHSNHPQPYRYIGVIRHPLXRQSISQIFKILLIRYLRKHRR<br>ed9edcebcddcccedeecedcedceldcadcbedeceedbdeecccb | 358 | 0.6 |

[a]Each consensus sequence is cropped to show the individual random region, with the N-terminal processed HPG and fixed alanine, as well as the C-terminal -GSGSGLGHHHHHHRL (SEQ ID NO: 7), removed. A X denotes a potential $Man_9$ glycosylation site. Cysteine residues are denoted with a C. The fixed peptide sequences (IGDIRxAxCM (SEQ ID NO: 289) or IGDIR (SEQ ID NO: 1)) are present in each of the selections except H-36 (SEQ ID NO: 344), H-74 (SEQ ID NO: 346), H-7 (SEQ ID NO: 348), H-84 (SEQ ID NO: 349), L-47 (SEQ ID NO: 356), and L-187 (SEQ ID NO: 358).

Many of the sequences in the Heavily Biased library appear to have mutated away from the fixed IGDIRxAxCM (SEQ ID NO:289) sequence, with only two of the top 10 still containing the full motif with the glycosylation site. This may also be related to the apparent lack of dependence on glycosylation compared to PGT128.

Example 6—glPGT128 Selection

A portion of the recovered round 1 DNA was prepared for selection against glPGT128. In round 2 of selection, 0.28% and 0.45% of the Heavily Biased and Less Biased libraries, respectively, bound to 200 nM glPGT128. The same concentration of glPGT128 was used in round 3, and the binding was just 0.25% for the Heavily Biased library and 0.54% for the Less Biased library. The selection against glPGT128 is in progress.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A glycopeptide comprising one or more modified amino acid residues having a sidechain comprising an oligosaccharide, wherein the glycopeptide comprises IGDIR (SEQ ID NO: 1) or IGDIRxA (SEQ ID NO: 2), wherein the modified amino acid comprises homopropargylglycine, p-azido-phenylalanine, p-ethynyl-phenylalanine, or L-allyl glycine, wherein the glycopeptide binds specifically to carbohydrate-binding monoclonal antibody PGT128 with an affinity of less than 100 nM.

2. The glycopeptide according to claim 1, wherein the glycopeptide comprises from 2 to 5 of said modified amino acid residues.

3. The glycopeptide according to claim 1, wherein the oligosaccharide is a branched oligosaccharide.

4. The glycopeptide according to claim 3, wherein the branched oligosaccharide consists of 9 mannose moieties and 2 N-Acetylglucosamine moieties.

5. The glycopeptide according to claim 1, wherein modified amino acid comprises a linker molecule between the polypeptide chain and the monosaccharide or oligosaccharide, the linker molecule comprising

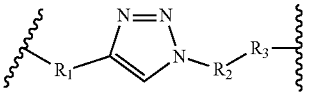

or

-continued

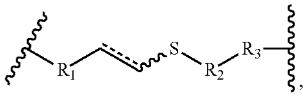

, wherein each of $R_1$ and $R_2$ is optionally a direct link or independently selected from the group consisting of a linear or branched $C_1$ to $C_{18}$ hydrocarbon that is saturated or mono- or poly-unsaturated, optionally interrupted by one or more non-adjacent —O—, —C(=O)—, or —$NR_4$—; a substituted or unsubstituted $C_3$ to $C_{10}$ cycloalkanediyl, a substituted or unsubstituted aryl diradical; a substituted or unsubstituted heteroaryl diradical; a monosaccharide diradical; or a disaccharide diradical;

$R_3$ is optional and can be —O—, —S—, or —$NR_4$—; and $R_4$ is H or a $C_1$ to $C_{10}$ alkyl.

6. The glycopeptide according to claim 1, wherein the glycopeptide binds specifically to monoclonal antibody PGT128 with an affinity of less than 50 nM.

7. The glycopeptide according to claim 1, wherein the monoclonal antibody PGT128 binds specifically to $Man_9GlcNAc_2$ glycans on HIV gp120 with an affinity comparable to the affinity of PGT128 binding to said glycopeptide.

8. The glycopeptide according to claim 1, wherein said glycopeptide comprises the sequence of SEQ ID NO: 20, 39, 40, 41, 42, 43, 44, 45, 46, 52, 57, 58, 69, 60, 61, 62, 63, 83, 102, 103, 104, 105, 106, 107, 108, 109, 115, 120, 121, 122, 123, 124, 125 or 126, wherein X is the modified amino acid residue to which the oligosaccharide is linked.

9. The glycopeptide according to claim 1, wherein the glycopeptide is a cyclic glycopeptide and wherein the glycopeptide comprises linker
MATFSRYHTIGDIRHHTLKHHQSKGLQXRLIFLKRQFKAXGNCLRWKILFGSCSLGHHHHHHRL (SEQ ID NO: 20), linker
MATFSRYHTIGDIRHHTLKHHQSKGLQXRLIFLKRQFKAXGNCLRWILFGSC(SEQ ID NO: 83), linker
MAYTEKHNGIGDIRPAICXNSKNQNHRCNHYQIKLYIHXLXLRLPHNYRNSGSGSGLGHHHHHHRL (SEQ ID NO: 39), linker
MALTLRYLKIGDIRLANCXTVFPHFLSKKFFENGHRNLARPCTFRRNRHLGSGSGLGHHHHHHRL (SEQ ID NO: 40), linker
MAHQHHHPNYALXQRRLSIAIGDIRLAICXFAHLYHCYRKHLXANTIPXKGSGSGLGHHHHHHRL (SEQ ID NO; 45), linker
MALFKPYPKIGDIRKARCXLQHTLHHRTNKQPSYRRRLKTLIPLFRRCXLGSGSGLGHHHHHHRL (SEQ ID NO: 52), linker
MANIYFCSRRTNFHNSCYLXIGDIRGLSIYHHIXIHNKLHLLIXNLLXXGSGSGLGHHHHHHRL (SEQ ID NO: 60), linker
MAYTEKHNGIGDIRPAICXNSKNQNHRCNHYQIKLYIHXLXLRLPHNYRNS (SEQ ID NO: 102), linker
MALTLRYLKIGDIRLANCXTVFPHFLSKKFFENGHRNLARPCTFRRNRHL (SEQ ID NO: 103), linker
MAHQHHHPNYALXQRRLSIAIGDIRLAICXFAHLYHCYRKHLXANTIPXK (SEQ ID NO: 108), -continued linker MALFKPYPKIGDIRKARCXLQHTLHHRTNKQPSYRRRLKTLIPLFRRCXL (SEQ ID NO: 115), or linker

MANIYFCSRRTNFHNSCYLXIGDIRGLSIYHHIXIHNKLHLLIXNLLXX (SEQ ID NO: 123), wherein X is the modified amino acid residue to which the oligosaccharide is linked, and the Cys-Cys linker is a bis-alkylbenzene group or bis-alkylpyridine group.

10. The glycopeptide according to claim 1, wherein the glycopeptide comprises a modified amino acid residue to which the oligosaccharide is linked.

11. The glycopeptide according to claim 1, wherein the glycopeptide is a cyclic glycopeptide and wherein the glycopeptide comprises a linker molecule between two cysteine sidechains.

12. The glycopeptide according to claim 11, wherein the linker molecule comprises

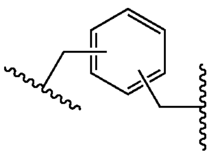

or

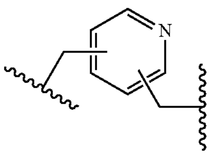

or

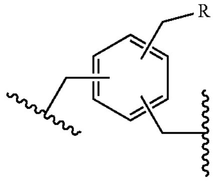

where R is (i) $-C(O)O-(CH_2)_n-CH_3$, where n is 0 to 6 or (ii) an immunogenic carrier molecule.

13. An immunogenic conjugate comprising a glycopeptide according to claim 1 covalently or non-covalently bound to an immunogenic carrier molecule.

14. A pharmaceutical composition comprising a pharmaceutically acceptable carrier and a glycopeptide according to claim 1.

15. A method of inducing an immune response in an individual comprising:

administering to an individual a glycopeptide according to claim 1, wherein said administering is effective to induce an immune response against the glycopeptide.

16. A method of inhibiting viral infection comprising:

administering to an individual a glycopeptide according to claim 1, wherein said administering is effective to induce a neutralizing immune response against a virus pathogen.

17. A method for detecting a neutralizing antibody in serum comprising:

providing a glycopeptide according to claim 1;

contacting the glycopeptide with serum from an individual; and detecting whether the glycopeptide binds specifically to an antibody present in the serum, wherein said detecting is carried out using a label.

18. A glycopeptide comprising one or more modified amino acid residues having a sidechain comprising an oligosaccharide, wherein the glycopeptide binds specifically to carbohydrate-binding monoclonal antibody PGT128, PGT130, or germline PGT128 with an affinity of less than 100 nM, wherein the glycopeptide comprises the sequence of SEQ ID NO: 140 or SEQ ID NO: 148.

* * * * *

SEQUENCE LISTING

```
<160> NUMBER OF SEQ ID NOS: 358

<210> SEQ ID NO 1
<211> LENGTH: 5
<212> TYPE: PRT
<213> ORGANISM: Artificial Sequence
<220> FEATURE:
<223> OTHER INFORMATION: Peptide

<400> SEQUENCE: 1

Ile Gly Asp Ile Arg
1               5


<210> SEQ ID NO 2
<211> LENGTH: 7
<212> TYPE: PRT
<213> ORGANISM: Artificial Sequence
<220> FEATURE:
<223> OTHER INFORMATION: Peptide
```

<220> FEATURE:
<221> NAME/KEY: misc_feature
<222> LOCATION: (6)..(6)
<223> OTHER INFORMATION: Xaa can be any naturally occurring amino acid

<400> SEQUENCE: 2

Ile Gly Asp Ile Arg Xaa Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Peptide

<400> SEQUENCE: 3

His His His His His His Arg Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Peptide

<400> SEQUENCE: 4

Gly His His His His His His Arg Leu
1               5

<210> SEQ ID NO 5
<211> LENGTH: 11
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 5

Gly Xaa Gly His His His His His His Arg Leu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Peptide

<400> SEQUENCE: 6

Gly Ser Gly Ser Leu Gly His His His His His His Arg Leu
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Peptide

<400> SEQUENCE: 7

Gly Ser Gly Ser Gly Leu Gly His His His His His His Arg Leu
1               5                   10                  15

```
<210> SEQ ID NO 8
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 8

Met Ala Tyr Phe Val His Lys Lys Ser Arg Leu Leu Thr Asn Lys Ala
1               5                   10                  15

Val Lys Lys Arg Leu His Gly Cys Phe Gln Asn Gln Arg Ser Thr Ile
            20                  25                  30

Gly Asp Ile Arg Tyr Ala Lys Cys Xaa Arg Val Ser Ser Asn Phe Phe
        35                  40                  45

Arg Arg Gly Ser Val Ser Leu Gly His His His His His His Arg Leu
    50                  55                  60


<210> SEQ ID NO 9
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (28)..(28)
<223> OTHER INFORMATION: Xaa at position 28 is a glycosylated derivative
      of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine

<400> SEQUENCE: 9

Met Ala Ser His Ile Asn Ser Asn Pro Asn Gln Leu Leu Leu Leu Tyr
1               5                   10                  15

Leu Lys Ser Thr Ile Gly Asp Ile Arg Cys Ala Xaa Cys Xaa Asp Phe
            20                  25                  30

Arg His Tyr Arg Asn Thr Lys Tyr Val Phe Xaa Thr Arg His Asn Arg
        35                  40                  45

Arg Thr Gly Tyr Gly Ser Leu Gly His His His His His His Arg Leu
    50                  55                  60


<210> SEQ ID NO 10
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (50)..(50)
```

```
<223> OTHER INFORMATION: Xaa at position 50 is a glycosylated derivative
      of homopropargylglycine or homopropargylglycine

<400> SEQUENCE: 10

Met Ala Ser Tyr Tyr Ile His Asp Ile Ala Val Ser Ala Tyr Ser Lys
1               5                   10                  15

Arg Arg Gly Tyr His Asn Ile Gln Val Glu Ser Leu Tyr Pro Lys Ile
            20                  25                  30

Gly Asp Ile Arg Ser Ala Lys Cys Xaa Thr Trp Arg Asn His Arg His
        35                  40                  45

Thr Xaa Gly Ser Gly Ser Leu Gly His His His His His His Arg Leu
    50                  55                  60


<210> SEQ ID NO 11
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (6)..(6)
<223> OTHER INFORMATION: Xaa at position 6 is a glycosylated derivative
      of homopropargylglycine or homopropargylglycine
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative
      of homopropargylglycine or homopropargylglycine

<400> SEQUENCE: 11

Met Ala His Tyr Ser Xaa Asn His Xaa Arg His Pro Leu Tyr Pro Ser
1               5                   10                  15

Val Asn His Arg Xaa Ser Tyr Pro Arg Ile Gly Leu Leu Ser Arg Ile
            20                  25                  30

Gly Asp Ile Arg Ser Ala Ser Cys Xaa Leu Arg Cys Phe Arg Xaa Arg
        35                  40                  45

Ser Thr Gly Ser Gly Ser Leu Gly His His His His His His Arg Leu
    50                  55                  60


<210> SEQ ID NO 12
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: Xaa at position 8 is a glycosylated derivative
      of homopropargylglycine or homopropargylglycine
<220> FEATURE:
<221> NAME/KEY: MISC_FEATURE
<222> LOCATION: (15)..(15)
```

<223> OTHER INFORMATION: Xaa at position 15 is a glycosylated derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 12

```
Met Ala His Asn Leu Arg Thr Xaa Arg Asn Lys Asn Leu Ile Xaa Leu
1               5                   10                  15

Ala Phe Leu His Ala Pro Ile Leu Lys Ser Arg Arg Leu Val His Ile
            20                  25                  30

Gly Asp Ile Arg Val Ala Ala Cys Thr His Xaa Val Asp Val Ala Pro
        35                  40                  45

Xaa Tyr Gly Ser Gly Ser Leu Gly His His His His His His Arg Leu
    50                  55                  60
```

<210> SEQ ID NO 13
<211> LENGTH: 62
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa at position 1 is a glycosylated derivative of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 13

```
Xaa Tyr Pro Asn Thr Leu Asn Asn Val Tyr Gln Lys Cys Asn Lys Tyr
1               5                   10                  15

Asn Val Ile Gly Asp Ile Arg Xaa Ala Arg Cys Xaa His Xaa Glu His
            20                  25                  30

Phe Ser Ser Gln Asp Gln Pro Lys Ser Lys His Lys Arg Arg Tyr Lys
        35                  40                  45

Gly Phe Gly Ser Leu Gly His His His His His His Arg Leu
    50                  55                  60
```

<210> SEQ ID NO 14
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (16)..(16)

```
<223> OTHER INFORMATION: Xaa at position 16 is a glycosylated derivative
      of homopropargylglycine or homopropargylglycine

<400> SEQUENCE: 14

Met Ala Leu Ile His Ser Arg Gln Leu Val Tyr Ser Lys Asn Tyr Xaa
1               5                   10                  15

Cys Cys Leu Asp Ile Gly Asp Ile Arg His Val Leu Arg Gly Lys Tyr
            20                  25                  30

Asn Asp His Leu Phe Gly Asn Ala Ile Tyr Arg Lys Gly Val Lys Ala
        35                  40                  45

Phe Asn Gly Ser Gly Ser Leu Gly His His His His His His Arg Leu
    50                  55                  60


<210> SEQ ID NO 15
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative
      of homopropargylglycine or homopropargylglycine
<220> FEATURE:
<221> NAME/KEY: MISC_FEATURE
<222> LOCATION: (40)..(41)
<223> OTHER INFORMATION: Xaa at positions 40-41 is a glycosylated
      derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative
      of homopropargylglycine or homopropargylglycine

<400> SEQUENCE: 15

Met Ala Asp Asn Glu Phe Lys Ile Leu Xaa Ile Ala Xaa Leu His Lys
1               5                   10                  15

Ser Lys His Arg Thr Tyr Leu Asp Tyr Leu Asn Leu Val Trp Xaa Ile
            20                  25                  30

Gly Asp Ile Arg Ala Phe Gln Xaa Xaa Leu Lys Thr Val Leu Xaa Glu
        35                  40                  45

Ala Lys Gly Ser Gly Ser Leu Gly His His His His His His Arg Leu
    50                  55                  60


<210> SEQ ID NO 16
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (6)..(6)
<223> OTHER INFORMATION: Xaa at position 6 is a glycosylated derivative
      of homopropargylglycine or homopropargylglycine
<220> FEATURE:
<221> NAME/KEY: MISC_FEATURE
<222> LOCATION: (11)..(11)
```

-continued

<223> OTHER INFORMATION: Xaa at position 11 is a glycosylated derivative of homopropargylglycine or homopropargylglycine

<400> SEQUENCE: 16

```
Met Ala Phe His His Xaa Pro His Phe Thr Xaa Arg Leu Pro Leu Leu
1               5                   10                  15

Arg Arg Asn Cys Ile Gly Asp Ile Arg Arg Leu Tyr Ser Pro Leu Pro
            20                  25                  30

Arg Asp Pro His Ala Asn Phe Lys Phe Ser Phe Val Glu Pro Asn Ala
        35                  40                  45

Asn Arg Gly Ser Gly Ser Leu Gly His His His His His His Gly Tyr
    50                  55                  60

Arg
65
```

<210> SEQ ID NO 17
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (27)..(27)
<223> OTHER INFORMATION: Xaa at position 27 is a glycosylated derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 17

```
Met Ala Thr Asp His Asn His Ser His Arg Arg Pro Arg Arg Glu His
1               5                   10                  15

Leu Asp Xaa Asn Xaa His Tyr Ser Arg Pro Xaa Val Ala Asn Xaa Ile
            20                  25                  30

Gly Asp Ile Arg Thr Phe Arg Arg Arg Tyr Ile Gln Val Xaa Tyr His
        35                  40                  45

Leu Xaa Gly Ser Asp Ser Leu Gly His His His His His His Arg Leu
    50                  55                  60
```

<210> SEQ ID NO 18
<211> LENGTH: 64
<212> TYPE: PRT
<213> ORGANISM: Artificial Sequence
<220> FEATURE:
<223> OTHER INFORMATION: Peptide -continued

```
<220> FEATURE:
<221> NAME/KEY: MISC_FEATURE
<222> LOCATION: (4)..(4)
<223> OTHER INFORMATION: Xaa at position 4 is a glycosylated derivative
      of homopropargylglycine or homopropargylglycine
<220> FEATURE:
<221> NAME/KEY: MISC_FEATURE
<222> LOCATION: (32)..(32)
<223> OTHER INFORMATION: Xaa at position 32 is a glycosylated derivative
      of homopropargylglycine or homopropargylglycine

<400> SEQUENCE: 18

Met Ala His Xaa Ser Ile Pro His His Arg Lys Ser Ile Asp Asp Ser
1               5                   10                  15

Leu Arg His Leu Ile Gly Asp Ile Arg Tyr Arg Asn Arg Tyr Leu Xaa
            20                  25                  30

Arg Ile Leu Tyr Arg Thr Ser His Tyr Lys Asn Tyr Tyr Cys Gln His
        35                  40                  45

Ser Ile Gly Ser Gly Ser Leu Gly His His His His His His Arg Leu
    50                  55                  60


<210> SEQ ID NO 19
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (5)..(6)
<223> OTHER INFORMATION: Xaa at positions 5-6 is a glycosylated
      derivative of homopropargylglycine or homopropargylglycine
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (45)..(47)
<223> OTHER INFORMATION: Xaa at positions 45-47 is a glycosylated
      derivative of homopropargylglycine or homopropargylglycine
<220> FEATURE:
<221> NAME/KEY: MISC_FEATURE
<222> LOCATION: (50)..(50)
<223> OTHER INFORMATION: Xaa at positions 50 is a glycosylated
      derivative of homopropargylglycine or homopropargylglycine

<400> SEQUENCE: 19

Met Ala Asn Leu Xaa Xaa Tyr Lys Xaa Val Val Asn Xaa Thr Leu Phe
1               5                   10                  15

Gln Trp Xaa Ala Thr His Arg Tyr Ser His Phe His Asn Lys Cys Ile
            20                  25                  30

Gly Asp Ile Arg Thr Thr Xaa Ser Trp Thr Arg Ser Xaa Xaa Xaa His
        35                  40                  45
```

```
Ala Xaa Gly Ser Gly Ser Leu Gly His His His His His His Arg Leu
    50                  55                  60


<210> SEQ ID NO 20
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (28)..(28)
<223> OTHER INFORMATION: Xaa at position 28 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine

<400> SEQUENCE: 20

Met Ala Thr Phe Ser Arg Tyr His Thr Ile Gly Asp Ile Arg His His
1               5                   10                  15

Thr Leu Lys His His Gln Ser Lys Gly Leu Gln Xaa Arg Leu Ile Phe
            20                  25                  30

Leu Lys Arg Gln Phe Lys Ala Xaa Gly Asn Cys Leu Arg Trp Lys Ile
        35                  40                  45

Leu Phe Gly Ser Cys Ser Leu Gly His His His His His His Arg Leu
    50                  55                  60


<210> SEQ ID NO 21
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (41)..(42)
<223> OTHER INFORMATION: Xaa at positions 41-42 is a glycosylated
      derivative of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative
      of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative
      of homopropargylglycine or homopropargylglycine

<400> SEQUENCE: 21

Met Ala Leu Asn Ser Asn Ser Cys His Xaa Arg Val Ala Thr Pro Ile
1               5                   10                  15

Ser Ser Trp Lys Ile Gly Asp Ile Arg Ala Arg Phe Val Ser Tyr Leu
            20                  25                  30

His Tyr Thr Asn Phe Ser Phe Ser Xaa Xaa Lys Xaa Lys Phe Phe Thr
        35                  40                  45

Lys Xaa Gly Ser Gly Ser Leu Gly His His His His His His Arg Leu
    50                  55                  60


<210> SEQ ID NO 22
```

```
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (27)..(27)
<223> OTHER INFORMATION: Xaa at position 27 is a glycosylated derivative
      of homopropargylglycine or homopropargylglycine
<220> FEATURE:
<221> NAME/KEY: MISC_FEATURE
<222> LOCATION: (29)..(29)
<223> OTHER INFORMATION: Xaa at position 29 is a glycosylated derivative
      of homopropargylglycine or homopropargylglycine

<400> SEQUENCE: 22

Met Ala Asn Val Phe Pro Gln Thr Asp Arg Ser Leu Glu Arg Ser Gln
1               5                   10                  15

Cys Leu Phe Glu Ala Phe His Ser Ile Val Xaa His Xaa Glu Ser Ile
            20                  25                  30

Gly Asp Ile Arg Leu Glu Cys Leu Arg Ile Thr Ile Val Ala Leu Arg
        35                  40                  45

Thr Thr Gly Ser Gly Ser Leu Gly His His His His His His Arg Leu
    50                  55                  60


<210> SEQ ID NO 23
<211> LENGTH: 64
<212> TYPE: PRT
<213> ORGANISM: Artificial Sequence
<220> FEATURE:
<223> OTHER INFORMATION: 101-1
<220> FEATURE:
<221> NAME/KEY: MISC_FEATURE
<222> LOCATION: (15)..(15)
<223> OTHER INFORMATION: Xaa at position 15 is a glycosylated derivative
      of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine

<400> SEQUENCE: 23

Met Ala Ile Pro Asn Gly Tyr Arg Ala Phe Asn Arg Ala Asp Xaa Leu
1               5                   10                  15

Leu Leu Thr Arg Ile Gly Asp Ile Arg Asn Ala His Cys Xaa Ala Arg
            20                  25                  30

Cys Asn Tyr Ile Tyr Glu Leu Arg Pro Leu His His Tyr Arg Trp Ser
        35                  40                  45

Asn Arg Gly Ser Gly Ser Leu Gly His His His His His His Arg Leu
    50                  55                  60


<210> SEQ ID NO 24
<211> LENGTH: 64
<212> TYPE: PRT
<213> ORGANISM: Artificial Sequence
<220> FEATURE:
<223> OTHER INFORMATION: 101-2
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (25)..(26)
<223> OTHER INFORMATION: Xaa at positions 25-26 is a glycosylated
      derivative of homopropargylglycine or homopropargylglycine
```

<220> FEATURE:
<221> NAME/KEY: MISC_FEATURE
<222> LOCATION: (30)..(31)
<223> OTHER INFORMATION: Xaa at positions 30-31 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 24

Met Ala Asn Thr Phe Ser Tyr His Gln Lys Leu Lys Xaa Gly Arg His
1               5                   10                  15

Thr Asp Glu Ile Leu His Thr His Xaa Xaa His Lys Lys Xaa Xaa Ile
            20                  25                  30

Gly Asp Ile Arg Tyr Ala Thr Cys Xaa Lys Cys Val Ile Lys Ser His
        35                  40                  45

Phe Xaa Gly Ser Gly Ser Leu Gly His His His His His His Arg Leu
    50                  55                  60

<210> SEQ ID NO 25
<211> LENGTH: 64
<212> TYPE: PRT
<213> ORGANISM: Artificial Sequence
<220> FEATURE:
<223> OTHER INFORMATION: 101-4
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative of homopropargylglycine or homopropargylglycine

<400> SEQUENCE: 25

Met Ala Ile His Lys His Leu His Ile His Asn Lys Lys Phe Ser Thr
1               5                   10                  15

Phe Lys Ser Ile Ile Gly Asp Ile Arg Leu Ala Trp Cys Xaa Asn Glu
            20                  25                  30

Tyr Asn Ile Xaa Pro Arg Cys Asn Ser Pro Arg Arg Phe Ser Tyr Thr
        35                  40                  45

Ala Phe Gly Ser Gly Ser Leu Gly His His His His His His Arg Leu
    50                  55                  60

<210> SEQ ID NO 26
<211> LENGTH: 64
<212> TYPE: PRT
<213> ORGANISM: Artificial Sequence
<220> FEATURE:
<223> OTHER INFORMATION: 101-5
<220> FEATURE:
<221> NAME/KEY: MISC_FEATURE
<222> LOCATION: (37)..(37)
<223> OTHER INFORMATION: Xaa at position 37 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

```
<220> FEATURE:
<221> NAME/KEY: MISC_FEATURE
<222> LOCATION: (47)..(47)
<223> OTHER INFORMATION: Xaa at position 47 is a glycosylated derivative
      of homopropargylglycine or homopropargylglycine

<400> SEQUENCE: 26

Met Ala Phe Lys Thr Asn His Thr Arg Cys Asp His Asn Ser Gln His
1               5                   10                  15

Ile Val Ser Gln Phe Gln Lys Pro His Leu Lys Arg Ser Arg Leu Ile
            20                  25                  30

Gly Asp Ile Arg Xaa Ala Ile Cys Xaa Ile Lys Lys His Arg Xaa Cys
        35                  40                  45

His His Gly Ser Gly Ser Leu Gly His His His His His His Arg Leu
    50                  55                  60


<210> SEQ ID NO 27
<211> LENGTH: 64
<212> TYPE: PRT
<213> ORGANISM: Artificial Sequence
<220> FEATURE:
<223> OTHER INFORMATION: 101-13
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative
      of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative
      of homopropargylglycine or homopropargylglycine

<400> SEQUENCE: 27

Met Ala Lys Ile Ser Arg Arg Tyr His Thr Phe Arg Arg Val Leu Phe
1               5                   10                  15

Arg Lys Arg Gln Ile Gly Asp Ile Arg Asn Ala Ile Cys Xaa Val Leu
            20                  25                  30

His His Ala Val Xaa Tyr Xaa Gln Ser Lys Asn Asn Cys Lys Ser Xaa
        35                  40                  45

Val Xaa Gly Ser Gly Ser Leu Gly His His His His His His Arg Leu
    50                  55                  60


<210> SEQ ID NO 28
<211> LENGTH: 64
<212> TYPE: PRT
<213> ORGANISM: Artificial Sequence
<220> FEATURE:
<223> OTHER INFORMATION: 101-19
<220> FEATURE:
<221> NAME/KEY: MISC_FEATURE
<222> LOCATION: (25)..(25)
<223> OTHER INFORMATION: Xaa at position 25 is a glycosylated derivative
      of homopropargylglycine or homopropargylglycine
```

```
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 28

Met Ala Phe Arg Leu Ser Tyr His Asn Ser Phe Asn Gly Pro Val His
1               5                   10                  15

Arg Pro His Val Phe Val His Asn Xaa Tyr Arg Lys Gly Leu Arg Ile
            20                  25                  30

Gly Asp Ile Arg Phe Ala Pro Cys Xaa Thr His His Leu Asn Ser Trp
        35                  40                  45

Ser His Gly Ser Gly Ser Leu Gly His His His His His His Arg Leu
    50                  55                  60


<210> SEQ ID NO 29
<211> LENGTH: 64
<212> TYPE: PRT
<213> ORGANISM: Artificial Sequence
<220> FEATURE:
<223> OTHER INFORMATION: 101-26
<220> FEATURE:
<221> NAME/KEY: MISC_FEATURE
<222> LOCATION: (11)..(11)
<223> OTHER INFORMATION: Xaa at position 11 is a glycosylated derivative
      of homopropargylglycine or homopropargylglycine
<220> FEATURE:
<221> NAME/KEY: MISC_FEATURE
<222> LOCATION: (27)..(27)
<223> OTHER INFORMATION: Xaa at position 27 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative
      of homopropargylglycine or homopropargylglycine

<400> SEQUENCE: 29

Met Ala His Trp His Arg His His Gly His Xaa Ile His Tyr Pro Tyr
1               5                   10                  15

Arg Phe Ile Asn Leu Leu Phe Ser Pro His Xaa Leu Asp Val Val Ile
            20                  25                  30

Gly Asp Ile Arg Lys Ala Asn Cys Xaa Trp Phe Leu Tyr Ser Val Ala
        35                  40                  45

Xaa Ile Gly Ser Gly Ser Leu Gly His His His His His His Arg Leu
    50                  55                  60


<210> SEQ ID NO 30
<211> LENGTH: 62
<212> TYPE: PRT
<213> ORGANISM: Artificial Sequence
<220> FEATURE:
<223> OTHER INFORMATION: 101-30

<400> SEQUENCE: 30

Met Ala His Phe Asp Pro Tyr Cys Arg Leu Tyr Val Pro Ala Tyr Asn
1               5                   10                  15

Ser His Thr Ile Tyr Tyr His Gln Lys Thr Ala Tyr Tyr Tyr Leu Phe
            20                  25                  30
```

```
Ile Gly Asp Ile Arg Ile Asp Ala Val Ala Glu Asn Arg Ser Pro Tyr
        35                  40                  45

Pro Leu Arg Gly Ser Gly His His His His His His Arg Leu
    50                  55                  60


<210> SEQ ID NO 31
<211> LENGTH: 64
<212> TYPE: PRT
<213> ORGANISM: Artificial Sequence
<220> FEATURE:
<223> OTHER INFORMATION: 101-2
<220> FEATURE:
<221> NAME/KEY: MISC_FEATURE
<222> LOCATION: (8)..(8)
<223> OTHER INFORMATION: Xaa at position 8 is a glycosylated derivative
      of homopropargylglycine or homopropargylglycine

<400> SEQUENCE: 31

Met Ala Phe Asp His His His Xaa Leu Ile Gly Asp Ile Arg Asn Asp
1               5                   10                  15

His Asn Asp Phe Tyr His Val Glu Asp Gly Phe Ala Asn Val Tyr Ile
            20                  25                  30

Ile Leu Tyr Ile Ile Tyr Ser Gln Thr Thr Ser Glu Val Leu Ile Val
        35                  40                  45

Ser Val Gly Ser Gly Ser Leu Gly His His His His His His Arg Leu
    50                  55                  60


<210> SEQ ID NO 32
<211> LENGTH: 64
<212> TYPE: PRT
<213> ORGANISM: Artificial Sequence
<220> FEATURE:
<223> OTHER INFORMATION: 102-9
<220> FEATURE:
<221> NAME/KEY: MISC_FEATURE
<222> LOCATION: (4)..(4)
<223> OTHER INFORMATION: Xaa at position 4 is a glycosylated derivative
      of homopropargylglycine or homopropargylglycine

<400> SEQUENCE: 32

Met Ala Ile Xaa Phe Ala Pro Arg His Ile Gly Asp Ile Arg His Pro
1               5                   10                  15

Lys Gln Arg Thr Ala His Trp Lys Ile Lys Thr Ala Tyr Pro Leu Lys
            20                  25                  30

Ser Leu Trp Lys Ile Arg Tyr Arg Leu Lys His Ile Asp Arg Ile Phe
        35                  40                  45

Leu Ser Gly Ser Gly Ser Leu Gly His His His His His His Arg Leu
    50                  55                  60


<210> SEQ ID NO 33
<211> LENGTH: 64
<212> TYPE: PRT
<213> ORGANISM: Artificial Sequence
<220> FEATURE:
<223> OTHER INFORMATION: 102-23
<220> FEATURE:
<221> NAME/KEY: MISC_FEATURE
<222> LOCATION: (4)..(4)
<223> OTHER INFORMATION: Xaa at position 4 is a glycosylated derivative
      of homopropargylglycine or homopropargylglycine
<220> FEATURE:
<221> NAME/KEY: MISC_FEATURE
<222> LOCATION: (14)..(14)
<223> OTHER INFORMATION: Xaa at position 14 is a glycosylated derivative
      of homopropargylglycine or homopropargylglycine
<220> FEATURE:
```

<221> NAME/KEY: MISC_FEATURE
<222> LOCATION: (38)..(38)
<223> OTHER INFORMATION: Xaa at position 38 is a glycosylated derivative
      of homopropargylglycine or homopropargylglycine

<400> SEQUENCE: 33

Met Ala Asn Xaa Thr Leu Leu Gln Leu Lys Ala Leu Arg Xaa Ser Leu
1               5                   10                  15

Ser Pro Leu Phe Leu Arg Leu Pro Leu Lys Ala Ser His Ala Ser Ile
            20                  25                  30

Gly Asp Ile Arg Ile Xaa Lys Thr Arg Arg Gly Pro Ser Phe Ile Arg
        35                  40                  45

Trp Tyr Gly Ser Gly Ser Leu Gly His His His His His His Arg Leu
    50                  55                  60

<210> SEQ ID NO 34
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (29)..(29)
<223> OTHER INFORMATION: Xaa at position 29 is a glycosylated derivative
      of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 34

Met Ala Lys Phe Ala Ile Cys His Thr Ile Gly Asp Ile Arg Phe Glu
1               5                   10                  15

Phe Thr Ile Ile Tyr Thr Pro His Lys Tyr Leu Val Xaa Asp His Asp
            20                  25                  30

Arg His Val Xaa Ser Leu Ser Val Xaa Leu Xaa Ser Leu Xaa Asn His
        35                  40                  45

Ser Arg Gly Ser Gly Ser Leu Gly His His His His His His Arg Leu
    50                  55                  60

<210> SEQ ID NO 35
<211> LENGTH: 64
<212> TYPE: PRT
<213> ORGANISM: Artificial Sequence
<220> FEATURE:
<223> OTHER INFORMATION: 102-33
<220> FEATURE:
<221> NAME/KEY: MISC_FEATURE
<222> LOCATION: (11)..(11)
<223> OTHER INFORMATION: Xaa at position 11 is a glycosylated derivative
      of homopropargylglycine or homopropargylglycine
<220> FEATURE:

```
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative
      of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative
      of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative
      of homopropargylglycine or homopropargylglycine

<400> SEQUENCE: 35

Met Ala Lys Leu Lys Asp Lys Leu Asn Asn Xaa Lys Xaa Asn Thr Thr
1               5                   10                  15

Asn Ala Ser Ala Ile Gly Asp Ile Arg Ile His Ala Asn Xaa Leu Asp
            20                  25                  30

Val Phe Leu Arg Asn Xaa His His Lys Xaa Thr Asn Tyr Gly Arg Phe
        35                  40                  45

Leu Xaa Gly Ser Gly Ser Leu Gly His His His His His His Arg Leu
    50                  55                  60


<210> SEQ ID NO 36
<211> LENGTH: 64
<212> TYPE: PRT
<213> ORGANISM: Artificial Sequence
<220> FEATURE:
<223> OTHER INFORMATION: 102-35
<220> FEATURE:
<221> NAME/KEY: MISC_FEATURE
<222> LOCATION: (1)..(1)
<223> OTHER INFORMATION: Xaa at position 1 is a glycosylated derivative
      of homopropargylglycine or homopropargylglycine
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (12)..(12)
<223> OTHER INFORMATION: Xaa at position 12 is a glycosylated derivative
      of homopropargylglycine or homopropargylglycine
<220> FEATURE:
<221> NAME/KEY: MISC_FEATURE
<222> LOCATION: (17)..(17)
<223> OTHER INFORMATION: Xaa at position 17 is a glycosylated derivative
      of homopropargylglycine or homopropargylglycine
<220> FEATURE:
<221> NAME/KEY: MISC_FEATURE
<222> LOCATION: (29)..(29)
<223> OTHER INFORMATION: Xaa at position 29 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (41)..(41)
```

```
<223> OTHER INFORMATION: Xaa at position 41 is a glycosylated derivative
      of homopropargylglycine or homopropargylglycine

<400> SEQUENCE: 36

Xaa Pro His Tyr Tyr His Tyr Asn Thr Xaa His Xaa Tyr Tyr Arg His
1               5                   10                  15

Xaa His His Ser Ile Gly Asp Ile Arg Ser His Phe Xaa Pro Thr Lys
            20                  25                  30

His Ile Trp Leu Ser Gly Xaa Leu Xaa Leu Ile His Tyr Lys Ser Ser
        35                  40                  45

Asn Asn Gly Ser Gly Ser Leu Gly His His His His His His Arg Leu
    50                  55                  60


<210> SEQ ID NO 37
<211> LENGTH: 64
<212> TYPE: PRT
<213> ORGANISM: Artificial Sequence
<220> FEATURE:
<223> OTHER INFORMATION: 102-38
<220> FEATURE:
<221> NAME/KEY: MISC_FEATURE
<222> LOCATION: (43)..(44)
<223> OTHER INFORMATION: Xaa at positions 43-44 is a glycosylated
      derivative of homopropargylglycine or homopropargylglycine

<400> SEQUENCE: 37

Met Ala His Tyr Thr Asn Asn Thr Leu Arg Pro Leu Ala Arg His His
1               5                   10                  15

His Phe Arg Leu Glu Gln Arg Phe Gly Arg His Leu Thr Ser Asn Ile
            20                  25                  30

Gly Asp Ile Arg Leu Asn His Val Phe His Xaa Xaa Leu Arg Arg Tyr
        35                  40                  45

Tyr Val Gly Ser Gly Ser Leu Gly His His His His His His Arg Leu
    50                  55                  60


<210> SEQ ID NO 38
<211> LENGTH: 64
<212> TYPE: PRT
<213> ORGANISM: Artificial Sequence
<220> FEATURE:
<223> OTHER INFORMATION: 102-45
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
<221> NAME/KEY: MISC_FEATURE
<222> LOCATION: (26)..(26)
<223> OTHER INFORMATION: Xaa at position 26 is a glycosylated derivative
      of homopropargylglycine or homopropargylglycine
<220> FEATURE:
<221> NAME/KEY: MISC_FEATURE
<222> LOCATION: (33)..(34)
<223> OTHER INFORMATION: Xaa at positions 33-34 is a glycosylated
      derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine

<400> SEQUENCE: 38

Met Ala Lys Phe His Asp Lys Asn Ser Tyr Lys Ser Lys His Lys Lys
1               5                   10                  15

Tyr Asn Xaa Leu Ile Gly Asp Ile Arg Xaa Phe Asn Ser Tyr His Arg
            20                  25                  30
```

```
Xaa Xaa Asn Cys Asn Lys Leu Cys His Pro Xaa Ile Ser Trp Asp Leu
        35                  40                  45

Phe Ile Gly Ser Gly Ser Leu Gly His His His His His His Arg Leu
    50                  55                  60


<210> SEQ ID NO 39
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 39

Met Ala Tyr Thr Glu Lys His Asn Gly Ile Gly Asp Ile Arg Pro Ala
1               5                   10                  15

Ile Cys Xaa Asn Ser Lys Asn Gln Asn His Arg Cys Asn His Tyr Gln
            20                  25                  30

Ile Lys Leu Tyr Ile His Xaa Leu Xaa Arg Leu Pro His Asn Tyr Arg
        35                  40                  45

Asn Ser Gly Ser Gly Ser Gly Leu Gly His His His His His His Arg
    50                  55                  60

Leu
65


<210> SEQ ID NO 40
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine

<400> SEQUENCE: 40

Met Ala Leu Thr Leu Arg Tyr Leu Lys Ile Gly Asp Ile Arg Leu Ala
1               5                   10                  15

Asn Cys Xaa Thr Val Phe Pro His Phe Leu Ser Lys Lys Phe Phe Glu
            20                  25                  30

Asn Gly His Arg Asn Leu Ala Arg Pro Cys Thr Phe Arg Arg Asn Arg
        35                  40                  45

His Leu Gly Ser Gly Ser Gly Leu Gly His His His His His His Arg
    50                  55                  60

Leu
65


<210> SEQ ID NO 41
```

```
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 41

Met Ala Tyr His Lys His Arg Val Xaa His His His Glu Asp Lys Ala
1               5                   10                  15

Thr Ser Leu Thr Ser Asn Leu Val Arg Leu Arg Leu Lys Thr Arg Ile
            20                  25                  30

Gly Asp Ile Arg Arg Ala Leu Cys Xaa Leu Ser Lys Phe Arg Tyr Leu
        35                  40                  45

Ile Asn Gly Ser Gly Ser Gly Leu Gly His His His His His His Arg
    50                  55                  60

Leu
65


<210> SEQ ID NO 42
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine

<400> SEQUENCE: 42

Met Ala Leu Leu His His Leu Arg Xaa Ile Gly Asp Ile Arg Pro Ala
1               5                   10                  15

His Cys Xaa Val Ser His Gln Arg Arg Tyr Val Pro Ile Ser Arg Lys
            20                  25                  30

Asn Val Phe Phe Lys Arg Gly Phe Asn Ser His Pro Leu Arg Lys Ile
        35                  40                  45

Leu Trp Gly Ser Gly Ser Gly Leu Gly His His His His His His Arg
    50                  55                  60

Leu
65


<210> SEQ ID NO 43
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
```

```
<223> OTHER INFORMATION: Xaa at position 41 is a glycosylated derivative
      of homopropargylglycine or homopropargylglycine

<400> SEQUENCE: 43

Met Ala Arg Phe Arg His Ser Asn Asn Tyr Tyr Leu Thr Pro Phe Leu
1               5                   10                  15

Thr Pro Leu Lys Thr Leu Ile Ser Leu Gln Leu Arg Tyr Arg Leu Ile
            20                  25                  30

Gly Asp Ile Arg Asn Ala Ser Tyr Xaa His Lys Phe Ser Asn Arg Asn
        35                  40                  45

Arg Phe Gly Ser Gly Ser Gly Leu Gly His His His His His His Arg
    50                  55                  60

Leu
65


<210> SEQ ID NO 44
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative
      of homopropargylglycine or homopropargylglycine

<400> SEQUENCE: 44

Met Ala Ile Phe Asn Gln Gly Tyr Arg Ile Lys Ala Trp Asn Asp Leu
1               5                   10                  15

Lys Asp Ile Ala Ile Gly Asp Ile Arg His Ala Leu Cys Xaa Leu Val
            20                  25                  30

Leu Ala Arg Ile Lys Leu Gln Arg Arg Xaa Val Lys Tyr Lys His Asp
        35                  40                  45

His Arg Gly Ser Gly Ser Gly Leu Gly His His His His His His Arg
    50                  55                  60

Leu
65


<210> SEQ ID NO 45
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine
<220> FEATURE:
<221> NAME/KEY: MISC_FEATURE
```

```
<222> LOCATION: (49)..(49)
<223> OTHER INFORMATION: Xaa at position 49 is a glycosylated derivative
      of homopropargylglycine or homopropargylglycine

<400> SEQUENCE: 45

Met Ala His Gln His His His Pro Asn Tyr Ala Leu Xaa Gln Arg Arg
1               5                   10                  15

Leu Ser Ile Ala Ile Gly Asp Ile Arg Leu Ala Ile Cys Xaa Phe Ala
            20                  25                  30

His Leu Tyr His Cys Tyr Arg Lys His Leu Xaa Ala Asn Thr Ile Pro
        35                  40                  45

Xaa Lys Gly Ser Gly Ser Gly Leu Gly His His His His His His Arg
    50                  55                  60

Leu
65


<210> SEQ ID NO 46
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative
      of homopropargylglycine or homopropargylglycine

<400> SEQUENCE: 46

Met Ala Phe Val Thr Tyr Gln His Xaa Ser Gln Lys Asn Phe Arg Arg
1               5                   10                  15

Tyr Gln Ile Leu Arg Asn His Phe His Pro Gln Asn Tyr Arg Phe Ile
            20                  25                  30

Gly Asp Ile Arg His Ala Leu Cys Xaa Phe Ile Phe Lys Asn Leu Xaa
        35                  40                  45

Arg His Gly Ser Gly Ser Gly Leu Gly His His His His His His Arg
    50                  55                  60

Leu
65


<210> SEQ ID NO 47
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (4)..(4)
<223> OTHER INFORMATION: Xaa at position 4 is a glycosylated derivative
      of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
```

```
<221> NAME/KEY: MISC_FEATURE
<222> LOCATION: (21)..(21)
<223> OTHER INFORMATION: Xaa at position 21 is a glycosylated derivative
      of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine

<400> SEQUENCE: 47

Met Ala Ala Xaa Lys Ile Arg Ser Lys Ile Gly Asp Ile Arg Thr Ala
1               5                   10                  15

Val Cys Xaa Phe Xaa His Arg His His His His His Ile Leu Asp Pro
            20                  25                  30

Tyr Tyr Leu Lys Xaa Ile Val Xaa Tyr Tyr Ser Leu Lys Ser Arg Ile
        35                  40                  45

Thr Leu Gly Ser Gly Ser Gly Leu Gly His His His His His His Arg
    50                  55                  60

Leu
65


<210> SEQ ID NO 48
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(9)
<223> OTHER INFORMATION: Xaa at positions 8-9 is a glycosylated
      derivative of homopropargylglycine or homopropargylglycine
<220> FEATURE:
<221> NAME/KEY: MISC_FEATURE
<222> LOCATION: (16)..(16)
<223> OTHER INFORMATION: Xaa at position 16 is a glycosylated derivative
      of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative
      of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative
      of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative
      of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative
      of homopropargylglycine or homopropargylglycine

<400> SEQUENCE: 48

Met Ala Phe Ile Lys Pro Cys Xaa Xaa Tyr Leu Leu Pro Pro Thr Xaa
1               5                   10                  15
```

Leu Asn Leu Tyr Ile Gly Asp Ile Arg Arg Ala Lys Cys Xaa Glu Ala
20 25 30

Xaa Asn Asn Phe His Xaa Asn Asn Lys Pro Leu Xaa Ala Thr Xaa Pro
35 40 45

Pro His Gly Ser Gly Ser Gly Leu Gly His His His His His His Arg
50 55 60

Leu
65

<210> SEQ ID NO 49
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 49

Met Ala Lys Asp Ile Leu Lys Leu Arg Ile Pro Phe Ala Thr Leu Ser
1 5 10 15

Gly His Arg Asn Ile Gly Asp Ile Arg His Ala Tyr Cys Xaa Ser Leu
20 25 30

Lys Arg Pro Tyr Ile Gln Val Tyr Ser Tyr Leu Asn His Leu Lys Val
35 40 45

Arg Phe Gly Ser Gly Ser Gly Leu Gly His His His His His His Arg
50 55 60

Leu
65

<210> SEQ ID NO 50
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (34)..(34)
<223> OTHER INFORMATION: Xaa at position 34 is a glycosylated derivative of homopropargylglycine or homopropargylglycine
<220> FEATURE:
<221> NAME/KEY: MISC_FEATURE
<222> LOCATION: (45)..(45)
<223> OTHER INFORMATION: Xaa at position 45 is a glycosylated derivative of homopropargylglycine or homopropargylglycine

<400> SEQUENCE: 50

Met Ala Thr Leu His Asn Ile His Asp Leu Asn His Tyr Tyr Arg Asn
1 5 10 15

Leu Asn Thr Arg Ile Gly Asp Ile Arg His Ala Thr Cys Xaa Tyr Phe
20 25 30

Phe Xaa Lys Leu Lys Leu Leu Lys His Asn Arg Phe Xaa Asp Arg Ala
35 40 45

Ile Tyr Gly Ser Gly Ser Gly Leu Gly His His His His His His Arg
50 55 60

Leu
65

<210> SEQ ID NO 51
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 51

```
Met Ala Pro Tyr Arg Ile Asn Gln Gln Xaa Asn Phe Pro Trp Ser Ser
1               5                   10                  15

Ala Leu Phe Gln Ile Gly Asp Ile Arg His Ala Arg Cys Xaa Asp Ser
            20                  25                  30

Cys Arg Arg Phe Thr Asn Ile Xaa Arg Tyr Val Tyr Leu Lys Arg Arg
        35                  40                  45

Xaa Asn Gly Ser Gly Ser Gly Leu Gly His His His His His His Arg
    50                  55                  60

Leu
65
```

<210> SEQ ID NO 52
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 52

```
Met Ala Leu Phe Lys Pro Tyr Pro Lys Ile Gly Asp Ile Arg Lys Ala
1               5                   10                  15

Arg Cys Xaa Leu Gln His Thr Leu His His Arg Thr Asn Lys Gln Pro
            20                  25                  30

Ser Tyr Arg Arg Arg Leu Lys Thr Leu Ile Pro Leu Phe Arg Arg Cys
        35                  40                  45
```

Xaa Leu Gly Ser Gly Ser Gly Leu Gly His His His His His His Arg
    50                  55                  60

Leu
65

<210> SEQ ID NO 53
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 53

Met Ala Thr Asn His Leu His Arg Thr Ile Gly Asp Ile Arg His Ala
1               5                   10                  15

Gln Cys Xaa Ile Tyr Leu Ile Tyr Leu Val Gln Asn Asp Gln Tyr Lys
            20                  25                  30

Arg Asn Asn Arg Thr Phe Arg Leu Xaa Leu Asn Pro Lys Leu Leu Lys
        35                  40                  45

Arg Phe Gly Ser Gly Ser Gly Leu Gly His His His His His His Arg
    50                  55                  60

Leu
65

<210> SEQ ID NO 54
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: Xaa at position 13 is a glycosylated derivative of homopropargylglycine or homopropargylglycine
<220> FEATURE:
<221> NAME/KEY: MISC_FEATURE
<222> LOCATION: (20)..(20)
<223> OTHER INFORMATION: Xaa at position 20 is a glycosylated derivative of homopropargylglycine or homopropargylglycine
<220> FEATURE:
<221> NAME/KEY: MISC_FEATURE
<222> LOCATION: (25)..(25)
<223> OTHER INFORMATION: Xaa at position 25 is a glycosylated derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine

<400> SEQUENCE: 54

Met Ala Thr Asn Ser Tyr Tyr His His Asn Pro Leu Xaa Arg Arg Thr
1 5 10 15

His Val Val Xaa Thr Leu Lys Pro Xaa Asn Phe Trp Ala Lys Xaa Ile
20 25 30

Gly Asp Ile Arg Arg Ala His Cys Xaa Thr Thr Ile Asn Xaa Leu Lys
35 40 45

Arg Arg Gly Ser Gly Ser Gly Leu Gly His His His His His His Arg
50 55 60

Leu
65

<210> SEQ ID NO 55
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (18)..(18)
<223> OTHER INFORMATION: Xaa at position 18 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 55

Met Ala Ile Leu Leu His Val Ser Thr Arg Ser Arg Tyr Pro His His
1 5 10 15

His Xaa Ala Ile Ile Gly Asp Ile Arg Cys Ala Ser Cys Xaa Tyr Pro
20 25 30

Val Leu Lys Trp Phe Tyr Asn Phe Asn Arg Leu Lys Thr Tyr Arg Lys
35 40 45

Gln Phe Gly Ser Gly Ser Gly Leu Gly His His His His His His Arg
50 55 60

Leu
65

<210> SEQ ID NO 56
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 56

Met Ala Tyr Arg Thr His Lys Leu Leu His His His Asn Asp Lys Trp
1 5 10 15

Lys Ser Asn Ile Phe Pro Arg Ile Phe Val Cys His Tyr Tyr Leu Ile
20 25 30

Gly Asp Ile Arg His Ala Arg Cys Xaa Ile Pro Leu Glu Ile Leu Arg
35 40 45

```
Arg Tyr Gly Ser Gly Ser Gly Leu Gly His His His His His His Arg
    50                  55                  60

Leu
65


<210> SEQ ID NO 57
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (15)..(15)
<223> OTHER INFORMATION: Xaa at position 15 is a glycosylated derivative
      of homopropargylglycine or homopropargylglycine

<400> SEQUENCE: 57

Met Ala Tyr Ser Lys His Arg Phe Ser Phe Arg His Asn Asn Xaa Leu
1               5                   10                  15

Arg Asp Arg Lys Leu Ile Arg Lys Phe Ser Tyr His Asn His Ser Ile
            20                  25                  30

Gly Asp Ile Arg Val Ala Asn Lys Phe Arg Tyr Leu His Val Phe Lys
        35                  40                  45

Phe Ile Gly Ser Gly Ser Gly Leu Gly His His His His His His Arg
    50                  55                  60

Leu
65


<210> SEQ ID NO 58
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(11)
<223> OTHER INFORMATION: Xaa at positions 10-11 is a glycosylated
      derivative of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative
      of homopropargylglycine or homopropargylglycine

<400> SEQUENCE: 58

Met Ala Ser Ile Lys Leu Ile Asn Gln Xaa Xaa Thr Thr Asn Pro His
1               5                   10                  15

Leu Arg Leu His Ile Gly Asp Ile Arg Arg Leu Ile Lys Asp Leu Tyr
            20                  25                  30

Xaa Phe Arg Val Tyr Tyr Arg Pro Thr Asn Ser Gly Arg Arg Leu Phe
        35                  40                  45

Val Asn Gly Ser Gly Ser Gly Leu Gly His His His His His His Arg
    50                  55                  60

Leu
65


<210> SEQ ID NO 59
<211> LENGTH: 65
<212> TYPE: PRT
<213> ORGANISM: Artificial Sequence
<220> FEATURE:
<223> OTHER INFORMATION: Peptide
```

```
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine

<400> SEQUENCE: 59

Met Ala His Ser His His His Ser Pro Xaa Ile Glu Phe His Ser Asn
1               5                   10                  15

Gly Arg Leu His Ile Gly Asp Ile Arg Lys Phe Tyr Ala Asp Ala Leu
            20                  25                  30

Xaa Val Leu Phe Phe Lys Xaa Ala Phe Ile Asp Arg Ile Pro Phe His
        35                  40                  45

Asp Ala Gly Ser Gly Ser Gly Leu Gly His His His His His His Arg
    50                  55                  60

Leu
65


<210> SEQ ID NO 60
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (20)..(20)
<223> OTHER INFORMATION: Xaa at position 20 is a glycosylated derivative
      of homopropargylglycine or homopropargylglycine
<220> FEATURE:
<221> NAME/KEY: MISC_FEATURE
<222> LOCATION: (34)..(34)
<223> OTHER INFORMATION: Xaa at position 34 is a glycosylated derivative
      of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative
      of homopropargylglycine or homopropargylglycine
<220> FEATURE:
<221> NAME/KEY: MISC_FEATURE
<222> LOCATION: (49)..(50)
<223> OTHER INFORMATION: Xaa at positions 49-50 is a glycosylated
      derivative of homopropargylglycine or homopropargylglycine

<400> SEQUENCE: 60

Met Ala Asn Ile Tyr Phe Cys Ser Arg Arg Thr Asn Phe His Asn Ser
1               5                   10                  15

Cys Tyr Leu Xaa Ile Gly Asp Ile Arg Gly Leu Ser Ile Tyr His His
            20                  25                  30

Ile Xaa Ile His Asn Lys Leu His Leu Leu Ile Xaa Tyr Asn Leu Leu
        35                  40                  45

Xaa Xaa Gly Ser Gly Ser Gly Leu Gly His His His His His His Arg
    50                  55                  60

Leu
65
```

<210> SEQ ID NO 61
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative of homopropargylglycine or homopropargylglycine

<400> SEQUENCE: 61

```
Met Ala Ile His Tyr His His Pro Ile Ile Gly Asp Ile Arg Leu Lys
1               5                   10                  15

His Asn Xaa Ile Asn Ala His Thr Lys His Val Pro Gln Lys Leu Tyr
            20                  25                  30

Leu Asp Ile Lys Phe Arg Arg Leu Phe Gly Leu Tyr Ile Leu Arg Xaa
        35                  40                  45

Leu Asn Gly Ser Gly Ser Gly Leu Gly His His His His His His Arg
    50                  55                  60

Leu
65
```

<210> SEQ ID NO 62
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative of homopropargylglycine or homopropargylglycine

<400> SEQUENCE: 62

```
Met Ala Ile Leu Tyr His Tyr His Asn Ile Gly Asp Ile Arg Arg Ser
1               5                   10                  15

Gln Arg His Leu Asn Xaa Gln Xaa Arg Leu Tyr Val Ser Thr Leu Leu
            20                  25                  30

His Ser Ser His Thr Leu Arg Arg Ala Ser Ile Thr His Arg Ile Arg
        35                  40                  45

Lys Phe Gly Ser Gly Ser Gly Leu Gly His His His His His His Arg
    50                  55                  60

Leu
65
```

<210> SEQ ID NO 63
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (28)..(28)

<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine

<400> SEQUENCE: 63

```
Met Ala Thr Phe Ser Arg Tyr His Thr Ile Gly Asp Ile Arg His His
1               5                   10                  15

Thr Leu Lys His His Gln Ser Lys Gly Leu Gln Xaa Arg Leu Ile Phe
            20                  25                  30

Leu Lys Arg Gln Phe Lys Ala Xaa Gly Asn Cys Leu Arg Trp Lys Ile
        35                  40                  45

Leu Phe Gly Ser Gly Ser Gly Leu Gly His His His His His His Arg
    50                  55                  60

Leu
65
```

<210> SEQ ID NO 64
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (24)..(24)
<223> OTHER INFORMATION: Xaa at position 24 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine

<400> SEQUENCE: 64

```
Met Ala Lys Tyr Thr His Ile His Ser Ile Gly Asp Ile Arg Asn Thr
1               5                   10                  15

Tyr Arg Asn Lys His Lys His Xaa Ala Leu Asn Lys Thr Asn Trp Ala
            20                  25                  30

Leu Phe Gln Gln His His Arg Xaa Leu Ile Arg Leu Phe Tyr Arg Arg
        35                  40                  45

Leu Leu Gly Ser Gly Ser Gly Leu Gly His His His His His His Arg
    50                  55                  60

Leu
65
```

<210> SEQ ID NO 65
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (44)..(44)
<223> OTHER INFORMATION: Xaa at position 44 is a glycosylated derivative of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative of homopropargylglycine or homopropargylglycine

<400> SEQUENCE: 65

Met Ala Leu Asn Lys His Lys His Leu Arg Asn His Thr Arg His His
1 5 10 15

Ser Val Pro Thr Ile Gly Asp Ile Arg Lys Arg Ile His Asn Leu Leu
20 25 30

His Tyr Leu Ala Gly Phe Arg Phe Phe Asn Gln Xaa His Ser Lys Xaa
35 40 45

Gly Val Gly Ser Gly Ser Gly Leu Gly His His His His His His Arg
50 55 60

Leu
65

<210> SEQ ID NO 66
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (36)..(36)
<223> OTHER INFORMATION: Xaa at position 36 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine

<400> SEQUENCE: 66

Met Ala Tyr Leu His Asn His His Asn Tyr Ser Ser Asn Asn Lys Leu
1 5 10 15

His His Leu Glu Ile Gly Asp Ile Arg Leu Ile Tyr Gln Lys Tyr Leu
20 25 30

Arg Asn Pro Xaa Phe Xaa Thr Phe Leu Ser Arg Lys His Xaa Asn Trp
35 40 45

Gln Arg Gly Ser Gly Ser Gly Leu Gly His His His His His His Arg
50 55 60

Leu
65

<210> SEQ ID NO 67
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (7)..(7)
<223> OTHER INFORMATION: Xaa at position 7 is a glycosylated derivative of homopropargylglycine or homopropargylglycine

<400> SEQUENCE: 67

Met Ala Asn Leu Thr Ala Xaa Ser Arg Ile Gly Asp Ile Arg Lys His
1 5 10 15

His Phe Gly Arg Pro Leu Tyr Leu Thr Lys His Gly Ala Tyr Pro Arg
20 25 30

-continued

```
Tyr His Thr Arg Tyr Lys His Leu Leu Thr Tyr Arg His His Phe Pro
        35                  40                  45

Leu Ile Gly Ser Gly Ser Gly Leu Gly His His His His His His Arg
    50                  55                  60

Leu
65


<210> SEQ ID NO 68
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 68

Met Ala Lys His Thr His Leu Arg Pro Xaa Asn Phe Thr Gln Arg Leu
1               5                   10                  15

Arg Lys Ala His Ile Gly Asp Ile Arg Leu Pro Arg Asn Ile Ser Thr
            20                  25                  30

Ser Arg Ile Arg Thr His Ile Lys Phe His Leu Ile Arg Xaa His Leu
        35                  40                  45

Arg Asn Gly Ser Gly Ser Gly Leu Gly His His His His His His Arg
    50                  55                  60

Leu
65


<210> SEQ ID NO 69
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (22)..(22)
<223> OTHER INFORMATION: Xaa at position 22 is a glycosylated derivative
      of homopropargylglycine or homopropargylglycine

<400> SEQUENCE: 69

Met Ala Phe Leu Leu Asn His Lys Arg Ile Gly Asp Ile Arg Lys Leu
1               5                   10                  15

Pro Pro Leu Asn Leu Xaa Ala Thr Lys Thr Leu Thr Lys Glu Arg Ile
            20                  25                  30

Arg Lys Ile Val Asn Gly Phe Val Gln Arg Leu Lys Gly His Ser Trp
        35                  40                  45

Trp Ile Gly Ser Gly Ser Gly Leu Gly His His His His His His Arg
    50                  55                  60

Leu
65


<210> SEQ ID NO 70
<211> LENGTH: 65
<212> TYPE: PRT
<213> ORGANISM: Artificial Sequence
```

-continued

<220> FEATURE:
<223> OTHER INFORMATION: Peptide
<220> FEATURE:
<221> NAME/KEY: MISC_FEATURE
<222> LOCATION: (32)..(32)
<223> OTHER INFORMATION: Xaa at position 32 is a glycosylated derivative
of homopropargylglycine or homopropargylglycine

<400> SEQUENCE: 70

```
Met Ala Ile His His Ser Tyr Arg Gly Phe Thr Leu Arg Ile Pro Leu
1               5                   10                  15

Thr Thr Asn Lys Ile Gly Asp Ile Arg Thr Ala Phe Pro Tyr Pro Xaa
            20                  25                  30

Leu Ser His Leu Phe Asp Arg Arg Arg Trp Lys Arg Gly Leu His Asn
        35                  40                  45

Trp Phe Gly Ser Gly Ser Gly Leu Gly His His His His His His Arg
    50                  55                  60

Leu
65
```

<210> SEQ ID NO 71
<211> LENGTH: 53
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
<223> OTHER INFORMATION: Xaa at position 41 is a glycosylated derivative
of homopropargylglycine or homopropargylglycine

<400> SEQUENCE: 71

```
Met Ala Tyr Phe Val His Lys Lys Ser Arg Leu Leu Thr Asn Lys Ala
1               5                   10                  15

Val Lys Lys Arg Leu His Gly Cys Phe Gln Asn Gln Arg Ser Thr Ile
            20                  25                  30

Gly Asp Ile Arg Tyr Ala Lys Cys Xaa Arg Val Ser Ser Asn Phe Phe
        35                  40                  45

Arg Arg Gly Ser Val
    50
```

<210> SEQ ID NO 72
<211> LENGTH: 52
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (28)..(28)
<223> OTHER INFORMATION: Xaa at position 28 is a glycosylated derivative
of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
of homopropargylglycine or homopropargylglycine

<400> SEQUENCE: 72

```
Met Ala Ser His Ile Asn Ser Asn Pro Asn Gln Leu Leu Leu Leu Tyr
1               5                   10                  15
```

Leu Lys Ser Thr Ile Gly Asp Ile Arg Cys Ala Xaa Cys Xaa Asp Phe
20 25 30

Arg His Tyr Arg Asn Thr Lys Tyr Val Phe Xaa Thr Arg His Asn Arg
35 40 45

Arg Thr Gly Tyr
50

<210> SEQ ID NO 73
<211> LENGTH: 50
<212> TYPE: PRT
<213> ORGANISM: Artificial Sequence
<220> FEATURE:
<223> OTHER INFORMATION: 91-6
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 73

Xaa Ala Ser Tyr Tyr Ile His Asp Ile Ala Val Ser Ala Tyr Ser Lys
1 5 10 15

Arg Arg Gly Tyr His Asn Ile Gln Val Glu Ser Leu Tyr Pro Lys Ile
20 25 30

Gly Asp Ile Arg Ser Ala Lys Cys Xaa Thr Trp Arg Asn His Arg His
35 40 45

Thr Xaa
50

<210> SEQ ID NO 74
<211> LENGTH: 50
<212> TYPE: PRT
<213> ORGANISM: Artificial Sequence
<220> FEATURE:
<223> OTHER INFORMATION: 91-8
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (6)..(6)
<223> OTHER INFORMATION: Xaa at position 6 is a glycosylated derivative of homopropargylglycine or homopropargylglycine
<220> FEATURE:
<221> NAME/KEY: MISC_FEATURE
<222> LOCATION: (9)..(9)
<223> OTHER INFORMATION: Xaa at position 9 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 74

Xaa Ala His Tyr Ser Xaa Asn His Xaa Arg His Pro Leu Tyr Pro Ser
1 5 10 15

Val Asn His Arg Xaa Ser Tyr Pro Arg Ile Gly Leu Leu Ser Arg Ile
20 25 30

Gly Asp Ile Arg Ser Ala Ser Cys Xaa Leu Arg Cys Phe Arg Xaa Arg
35 40 45

Ser Thr
50

<210> SEQ ID NO 75
<211> LENGTH: 50
<212> TYPE: PRT
<213> ORGANISM: Artificial Sequence
<220> FEATURE:
<223> OTHER INFORMATION: 91-9
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine
<220> FEATURE:
<221> NAME/KEY: MISC_FEATURE
<222> LOCATION: (15)..(15)
<223> OTHER INFORMATION: Xaa at position 15 is a glycosylated derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 75

Xaa Ala His Asn Leu Arg Thr Xaa Arg Asn Lys Asn Leu Ile Xaa Leu
1 5 10 15

Ala Phe Leu His Ala Pro Ile Leu Lys Ser Arg Arg Leu Val His Ile
20 25 30

Gly Asp Ile Arg Val Ala Ala Cys Thr His Xaa Val Asp Val Ala Pro
35 40 45

Xaa Tyr
50

<210> SEQ ID NO 76
<211> LENGTH: 62
<212> TYPE: PRT
<213> ORGANISM: Artificial Sequence
<220> FEATURE:
<223> OTHER INFORMATION: 91-12
<220> FEATURE:
<221> NAME/KEY: MISC_FEATURE
<222> LOCATION: (1)..(1)
<223> OTHER INFORMATION: Xaa at position 1 is a methionine, a glycosylated derivative of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 76

```
Xaa Tyr Pro Asn Thr Leu Asn Asn Val Tyr Gln Lys Cys Asn Lys Tyr
1               5                   10                  15

Asn Val Ile Gly Asp Ile Arg Xaa Ala Arg Cys Xaa His Xaa Glu His
            20                  25                  30

Phe Ser Ser Gln Asp Gln Pro Lys Ser Lys His Lys Arg Arg Tyr Lys
        35                  40                  45

Gly Phe Gly Ser Leu Gly His His His His His His Arg Leu
    50                  55                  60
```

<210> SEQ ID NO 77
<211> LENGTH: 50
<212> TYPE: PRT
<213> ORGANISM: Artificial Sequence
<220> FEATURE:
<223> OTHER INFORMATION: 92-1
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (16)..(16)
<223> OTHER INFORMATION: Xaa at position 16 is a glycosylated derivative of homopropargylglycine or homopropargylglycine

<400> SEQUENCE: 77

```
Xaa Ala Leu Ile His Ser Arg Gln Leu Val Tyr Ser Lys Asn Tyr Xaa
1               5                   10                  15

Cys Cys Leu Asp Ile Gly Asp Ile Arg His Val Leu Arg Gly Lys Tyr
            20                  25                  30

Asn Asp His Leu Phe Gly Asn Ala Ile Tyr Arg Lys Gly Val Lys Ala
        35                  40                  45

Phe Asn
    50
```

<210> SEQ ID NO 78
<211> LENGTH: 50
<212> TYPE: PRT
<213> ORGANISM: Artificial Sequence
<220> FEATURE:
<223> OTHER INFORMATION: 92-2
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (10)..(10)

<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (13)..(13)
<223> OTHER INFORMATION: Xaa at position 13 is a glycosylated derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (40)..(41)
<223> OTHER INFORMATION: Xaa at positions 40-41 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 78

```
Xaa Ala Asp Asn Glu Phe Lys Ile Leu Xaa Ile Ala Xaa Leu His Lys
1               5                   10                  15

Ser Lys His Arg Thr Tyr Leu Asp Tyr Leu Asn Leu Val Trp Xaa Ile
            20                  25                  30

Gly Asp Ile Arg Ala Phe Gln Xaa Xaa Leu Lys Thr Val Leu Xaa Glu
        35                  40                  45

Ala Lys
    50
```

<210> SEQ ID NO 79
<211> LENGTH: 50
<212> TYPE: PRT
<213> ORGANISM: Artificial Sequence
<220> FEATURE:
<223> OTHER INFORMATION: 92-3
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (6)..(6)
<223> OTHER INFORMATION: Xaa at position 6 is a glycosylated derivative of homopropargylglycine or homopropargylglycine
<220> FEATURE:
<221> NAME/KEY: MISC_FEATURE
<222> LOCATION: (11)..(11)
<223> OTHER INFORMATION: Xaa at position 11 is a glycosylated derivative of homopropargylglycine or homopropargylglycine

<400> SEQUENCE: 79

```
Xaa Ala Phe His His Xaa Pro His Phe Thr Xaa Arg Leu Pro Leu Leu
1               5                   10                  15

Arg Arg Asn Cys Ile Gly Asp Ile Arg Arg Leu Tyr Ser Pro Leu Pro
            20                  25                  30

Arg Asp Pro His Ala Asn Phe Lys Phe Ser Phe Val Glu Pro Asn Ala
        35                  40                  45

Asn Arg
    50
```

<210> SEQ ID NO 80
<211> LENGTH: 53
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (27)..(27)
<223> OTHER INFORMATION: Xaa at position 27 is a glycosylated derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 80

```
Met Ala Thr Asp His Asn His Ser His Arg Arg Pro Arg Arg Glu His
1               5                   10                  15

Leu Asp Xaa Asn Xaa His Tyr Ser Arg Pro Xaa Val Ala Asn Xaa Ile
            20                  25                  30

Gly Asp Ile Arg Thr Phe Arg Arg Arg Tyr Ile Gln Val Xaa Tyr His
        35                  40                  45

Leu Xaa Gly Ser Asp
    50
```

<210> SEQ ID NO 81
<211> LENGTH: 50
<212> TYPE: PRT
<213> ORGANISM: Artificial Sequence
<220> FEATURE:
<223> OTHER INFORMATION: 92-5
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (4)..(4)
<223> OTHER INFORMATION: Xaa at position 4 is a glycosylated derivative of homopropargylglycine or homopropargylglycine
<220> FEATURE:
<221> NAME/KEY: MISC_FEATURE
<222> LOCATION: (32)..(32)
<223> OTHER INFORMATION: Xaa at position 32 is a glycosylated derivative of homopropargylglycine or homopropargylglycine

<400> SEQUENCE: 81

```
Xaa Ala His Xaa Ser Ile Pro His His Arg Lys Ser Ile Asp Asp Ser
1               5                   10                  15

Leu Arg His Leu Ile Gly Asp Ile Arg Tyr Arg Asn Arg Tyr Leu Xaa
            20                  25                  30
```

```
Arg Ile Leu Tyr Arg Thr Ser His Tyr Lys Asn Tyr Tyr Cys Gln His
        35                  40                  45

Ser Ile
    50


<210> SEQ ID NO 82
<211> LENGTH: 50
<212> TYPE: PRT
<213> ORGANISM: Artificial Sequence
<220> FEATURE:
<223> OTHER INFORMATION: 92-6
<220> FEATURE:
<221> NAME/KEY: MISC_FEATURE
<222> LOCATION: (1)..(1)
<223> OTHER INFORMATION: Xaa at position 1 is methionine or
      homopropargylglycine
<220> FEATURE:
<221> NAME/KEY: MISC_FEATURE
<222> LOCATION: (5)..(6)
<223> OTHER INFORMATION: Xaa at positions 5-6 is a glycosylated
      derivative of homopropargylglycine or homopropargylglycine
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (45)..(47)
<223> OTHER INFORMATION: Xaa at positions 45-47 is a glycosylated
      derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative
      of homopropargylglycine or homopropargylglycine

<400> SEQUENCE: 82

Xaa Ala Asn Leu Xaa Xaa Tyr Lys Xaa Val Val Asn Xaa Thr Leu Phe
1               5                   10                  15

Gln Trp Xaa Ala Thr His Arg Tyr Ser His Phe His Asn Lys Cys Ile
            20                  25                  30

Gly Asp Ile Arg Thr Thr Xaa Ser Trp Thr Arg Ser Xaa Xaa Xaa His
        35                  40                  45

Ala Xaa
    50


<210> SEQ ID NO 83
<211> LENGTH: 53
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (28)..(28)
```

<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine

<400> SEQUENCE: 83

```
Met Ala Thr Phe Ser Arg Tyr His Thr Ile Gly Asp Ile Arg His His
1               5                   10                  15

Thr Leu Lys His His Gln Ser Lys Gly Leu Gln Xaa Arg Leu Ile Phe
            20                  25                  30

Leu Lys Arg Gln Phe Lys Ala Xaa Gly Asn Cys Leu Arg Trp Lys Ile
        35                  40                  45

Leu Phe Gly Ser Cys
    50
```

<210> SEQ ID NO 84
<211> LENGTH: 50
<212> TYPE: PRT
<213> ORGANISM: Artificial Sequence
<220> FEATURE:
<223> OTHER INFORMATION: 91-10
<220> FEATURE:
<221> NAME/KEY: MISC_FEATURE
<222> LOCATION: (1)..(1)
<223> OTHER INFORMATION: Xaa at position 1 is methionine or homopropargylglycine
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (41)..(42)
<223> OTHER INFORMATION: Xaa at positions 41-42 is a glycosylated derivative of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 84

```
Xaa Ala Leu Asn Ser Asn Ser Cys His Xaa Arg Val Ala Thr Pro Ile
1               5                   10                  15

Ser Ser Trp Lys Ile Gly Asp Ile Arg Ala Arg Phe Val Ser Tyr Leu
            20                  25                  30

His Tyr Thr Asn Phe Ser Phe Ser Xaa Xaa Lys Xaa Lys Phe Phe Thr
        35                  40                  45

Lys Xaa
    50
```

<210> SEQ ID NO 85
<211> LENGTH: 50
<212> TYPE: PRT
<213> ORGANISM: Artificial Sequence
<220> FEATURE:
<223> OTHER INFORMATION: 92-11
<220> FEATURE:
<221> NAME/KEY: MISC_FEATURE
<222> LOCATION: (1)..(1)

<223> OTHER INFORMATION: Xaa at position 1 is methionine or homopropargylglycine
<220> FEATURE:
<221> NAME/KEY: MISC_FEATURE
<222> LOCATION: (27)..(27)
<223> OTHER INFORMATION: Xaa at position 27 is a glycosylated derivative of homopropargylglycine or homopropargylglycine
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine

<400> SEQUENCE: 85

```
Xaa Ala Asn Val Phe Pro Gln Thr Asp Arg Ser Leu Glu Arg Ser Gln
1               5                   10                  15

Cys Leu Phe Glu Ala Phe His Ser Ile Val Xaa His Xaa Glu Ser Ile
            20                  25                  30

Gly Asp Ile Arg Leu Glu Cys Leu Arg Ile Thr Ile Val Ala Leu Arg
        35                  40                  45

Thr Thr
    50
```

<210> SEQ ID NO 86
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (15)..(15)
<223> OTHER INFORMATION: Xaa at position 15 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 86

```
Met Ala Ile Pro Asn Gly Tyr Arg Ala Phe Asn Arg Ala Asp Xaa Leu
1               5                   10                  15

Leu Leu Thr Arg Ile Gly Asp Ile Arg Asn Ala His Cys Xaa Ala Arg
            20                  25                  30

Cys Asn Tyr Ile Tyr Glu Leu Arg Pro Leu His His Tyr Arg Trp Ser
        35                  40                  45

Asn Arg
    50
```

<210> SEQ ID NO 87
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: Xaa at position 13 is a glycosylated derivative of homopropargylglycine or homopropargylglycine
<220> FEATURE:
<221> NAME/KEY: MISC_FEATURE
<222> LOCATION: (25)..(26)
<223> OTHER INFORMATION: Xaa at positions 25-26 is a glycosylated derivative of homopropargylglycine or homopropargylglycine
<220> FEATURE:
<221> NAME/KEY: MISC_FEATURE
<222> LOCATION: (30)..(31)

```
<223> OTHER INFORMATION: Xaa at positions 30-31 is a glycosylated
      derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative
      of homopropargylglycine or homopropargylglycine

<400> SEQUENCE: 87

Met Ala Asn Thr Phe Ser Tyr His Gln Lys Leu Lys Xaa Gly Arg His
1               5                   10                  15

Thr Asp Glu Ile Leu His Thr His Xaa Xaa His Lys Lys Xaa Xaa Ile
            20                  25                  30

Gly Asp Ile Arg Tyr Ala Thr Cys Xaa Lys Cys Val Ile Lys Ser His
        35                  40                  45

Phe Xaa
    50


<210> SEQ ID NO 88
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative
      of homopropargylglycine or homopropargylglycine

<400> SEQUENCE: 88

Met Ala Ile His Lys His Leu His Ile His Asn Lys Lys Phe Ser Thr
1               5                   10                  15

Phe Lys Ser Ile Ile Gly Asp Ile Arg Leu Ala Trp Cys Xaa Asn Glu
            20                  25                  30

Tyr Asn Ile Xaa Pro Arg Cys Asn Ser Pro Arg Arg Phe Ser Tyr Thr
        35                  40                  45

Ala Phe
    50


<210> SEQ ID NO 89
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (37)..(37)
<223> OTHER INFORMATION: Xaa at position 37 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (47)..(47)
```

```
<223> OTHER INFORMATION: Xaa at position 47 is a glycosylated derivative
      of homopropargylglycine or homopropargylglycine

<400> SEQUENCE: 89

Met Ala Phe Lys Thr Asn His Thr Arg Cys Asp His Asn Ser Gln His
1               5                   10                  15

Ile Val Ser Gln Phe Gln Lys Pro His Leu Lys Arg Ser Arg Leu Ile
            20                  25                  30

Gly Asp Ile Arg Xaa Ala Ile Cys Xaa Ile Lys Lys His Arg Xaa Cys
        35                  40                  45

His His
    50


<210> SEQ ID NO 90
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative
      of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative
      of homopropargylglycine or homopropargylglycine

<400> SEQUENCE: 90

Met Ala Lys Ile Ser Arg Arg Tyr His Thr Phe Arg Arg Val Leu Phe
1               5                   10                  15

Arg Lys Arg Gln Ile Gly Asp Ile Arg Asn Ala Ile Cys Xaa Val Leu
            20                  25                  30

His His Ala Val Xaa Tyr Xaa Gln Ser Lys Asn Asn Cys Lys Ser Xaa
        35                  40                  45

Val Xaa
    50


<210> SEQ ID NO 91
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (25)..(25)
<223> OTHER INFORMATION: Xaa at position 25 is a glycosylated derivative
      of homopropargylglycine or homopropargylglycine
<220> FEATURE:
<221> NAME/KEY: MISC_FEATURE
<222> LOCATION: (41)..(41)
```

<223> OTHER INFORMATION: Xaa at position 41 is a glycosylated derivative of homopropargylglycine or homopropargylglycine

<400> SEQUENCE: 91

Met Ala Phe Arg Leu Ser Tyr His Asn Ser Phe Asn Gly Pro Val His
1 5 10 15

Arg Pro His Val Phe Val His Asn Xaa Tyr Arg Lys Gly Leu Arg Ile
20 25 30

Gly Asp Ile Arg Phe Ala Pro Cys Xaa Thr His His Leu Asn Ser Trp
35 40 45

Ser His
50

<210> SEQ ID NO 92
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (11)..(11)
<223> OTHER INFORMATION: Xaaat position 11 is a glycosylated derivative of homopropargylglycine or homopropargylglycine
<220> FEATURE:
<221> NAME/KEY: MISC_FEATURE
<222> LOCATION: (27)..(27)
<223> OTHER INFORMATION: Xaaat position 27 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaaat position 41 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 92

Met Ala His Trp His Arg His His Gly His Xaa Ile His Tyr Pro Tyr
1 5 10 15

Arg Phe Ile Asn Leu Leu Phe Ser Pro His Xaa Leu Asp Val Val Ile
20 25 30

Gly Asp Ile Arg Lys Ala Asn Cys Xaa Trp Phe Leu Tyr Ser Val Ala
35 40 45

Xaa Ile
50

<210> SEQ ID NO 93
<211> LENGTH: 53
<212> TYPE: PRT
<213> ORGANISM: Artificial Sequence
<220> FEATURE:
<223> OTHER INFORMATION: Peptide

<400> SEQUENCE: 93

Met Ala His Phe Asp Pro Tyr Cys Arg Leu Tyr Val Pro Ala Tyr Asn
1 5 10 15

Ser His Thr Ile Tyr Tyr His Gln Lys Thr Ala Tyr Tyr Tyr Leu Phe
20 25 30

Ile Gly Asp Ile Arg Ile Asp Ala Val Ala Glu Asn Arg Ser Pro Tyr
35 40 45

Pro Leu Arg Gly Ser
50

<210> SEQ ID NO 94
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine

<400> SEQUENCE: 94

Met Ala Phe Asp His His His Xaa Leu Ile Gly Asp Ile Arg Asn Asp
1 5 10 15

His Asn Asp Phe Tyr His Val Glu Asp Gly Phe Ala Asn Val Tyr Ile
20 25 30

Ile Leu Tyr Ile Ile Tyr Ser Gln Thr Thr Ser Glu Val Leu Ile Val
35 40 45

Ser Val
50

<210> SEQ ID NO 95
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (4)..(4)
<223> OTHER INFORMATION: Xaa at position 4 is a glycosylated derivative of homopropargylglycine or homopropargylglycine

<400> SEQUENCE: 95

Met Ala Ile Xaa Phe Ala Pro Arg His Ile Gly Asp Ile Arg His Pro
1 5 10 15

Lys Gln Arg Thr Ala His Trp Lys Ile Lys Thr Ala Tyr Pro Leu Lys
20 25 30

Ser Leu Trp Lys Ile Arg Tyr Arg Leu Lys His Ile Asp Arg Ile Phe
35 40 45

Leu Ser
50

<210> SEQ ID NO 96
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (4)..(4)
<223> OTHER INFORMATION: Xaa at position 4 is a glycosylated derivative of homopropargylglycine or homopropargylglycine
<220> FEATURE:
<221> NAME/KEY: MISC_FEATURE
<222> LOCATION: (14)..(14)
<223> OTHER INFORMATION: Xaa at position 14 is a glycosylated derivative of homopropargylglycine or homopropargylglycine
<220> FEATURE:

```
<221> NAME/KEY: MISC_FEATURE
<222> LOCATION: (38)..(38)
<223> OTHER INFORMATION: Xaa at position 38 is a glycosylated derivative
      of homopropargylglycine or homopropargylglycine

<400> SEQUENCE: 96

Met Ala Asn Xaa Thr Leu Leu Gln Leu Lys Ala Leu Arg Xaa Ser Leu
1               5                   10                  15

Ser Pro Leu Phe Leu Arg Leu Pro Leu Lys Ala Ser His Ala Ser Ile
            20                  25                  30

Gly Asp Ile Arg Ile Xaa Lys Thr Arg Arg Gly Pro Ser Phe Ile Arg
        35                  40                  45

Trp Tyr
    50


<210> SEQ ID NO 97
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (29)..(29)
<223> OTHER INFORMATION: Xaa at position 29 is a glycosylated derivative
      of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 97

Met Ala Lys Phe Ala Ile Cys His Thr Ile Gly Asp Ile Arg Phe Glu
1               5                   10                  15

Phe Thr Ile Ile Tyr Thr Pro His Lys Tyr Leu Val Xaa Asp His Asp
            20                  25                  30

Arg His Val Xaa Ser Leu Ser Val Xaa Leu Xaa Ser Leu Xaa Asn His
        35                  40                  45

Ser Arg
    50


<210> SEQ ID NO 98
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (11)..(11)
<223> OTHER INFORMATION: Xaa at position 11 is a glycosylated derivative
      of homopropargylglycine or homopropargylglycine
<220> FEATURE:
```

<221> NAME/KEY: MISC_FEATURE
<222> LOCATION: (13)..(13)
<223> OTHER INFORMATION: Xaa at position 13 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 98

```
Met Ala Lys Leu Lys Asp Lys Leu Asn Asn Xaa Lys Xaa Asn Thr Thr
1               5                   10                  15

Asn Ala Ser Ala Ile Gly Asp Ile Arg Ile His Ala Asn Xaa Leu Asp
            20                  25                  30

Val Phe Leu Arg Asn Xaa His His Lys Xaa Thr Asn Tyr Gly Arg Phe
        35                  40                  45

Leu Xaa
    50
```

<210> SEQ ID NO 99
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa at position 1 is a glycosylated derivative of homopropargylglycine or homopropargylglycine
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (12)..(12)
<223> OTHER INFORMATION: Xaa at position 12 is a glycosylated derivative of homopropargylglycine or homopropargylglycine
<220> FEATURE:
<221> NAME/KEY: MISC_FEATURE
<222> LOCATION: (17)..(17)
<223> OTHER INFORMATION: Xaa at position 17 is a glycosylated derivative of homopropargylglycine or homopropargylglycine
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative of homopropargylglycine or homopropargylglycine
<220> FEATURE:
<221> NAME/KEY: MISC_FEATURE
<222> LOCATION: (41)..(41)

<223> OTHER INFORMATION: Xaa at position 41 is a glycosylated derivative
      of homopropargylglycine or homopropargylglycine

<400> SEQUENCE: 99

```
Xaa Pro His Tyr Tyr His Tyr Asn Thr Xaa His Xaa Tyr Tyr Arg His
1               5                   10                  15

Xaa His His Ser Ile Gly Asp Ile Arg Ser His Phe Xaa Pro Thr Lys
            20                  25                  30

His Ile Trp Leu Ser Gly Xaa Leu Xaa Leu Ile His Tyr Lys Ser Ser
        35                  40                  45

Asn Asn
    50
```

<210> SEQ ID NO 100
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (43)..(44)
<223> OTHER INFORMATION: Xaa at positions 43-44 is a glycosylated
      derivative of homopropargylglycine or homopropargylglycine

<400> SEQUENCE: 100

```
Met Ala His Tyr Thr Asn Asn Thr Leu Arg Pro Leu Ala Arg His His
1               5                   10                  15

His Phe Arg Leu Glu Gln Arg Phe Gly Arg His Leu Thr Ser Asn Ile
            20                  25                  30

Gly Asp Ile Arg Leu Asn His Val Phe His Xaa Xaa Leu Arg Arg Tyr
        35                  40                  45

Tyr Val
    50
```

<210> SEQ ID NO 101
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
<221> NAME/KEY: MISC_FEATURE
<222> LOCATION: (26)..(26)
<223> OTHER INFORMATION: Xaa at position 26 is a glycosylated derivative
      of homopropargylglycine or homopropargylglycine
<220> FEATURE:
<221> NAME/KEY: MISC_FEATURE
<222> LOCATION: (33)..(34)
<223> OTHER INFORMATION: Xaa at positions 33-34 is a glycosylated
      derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine

<400> SEQUENCE: 101

```
Met Ala Lys Phe His Asp Lys Asn Ser Tyr Lys Ser Lys His Lys Lys
1               5                   10                  15

Tyr Asn Xaa Leu Ile Gly Asp Ile Arg Xaa Phe Asn Ser Tyr His Arg
            20                  25                  30
```

Xaa Xaa Asn Cys Asn Lys Leu Cys His Pro Xaa Ile Ser Trp Asp Leu
35 40 45

Phe Ile
50

<210> SEQ ID NO 102
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 102

Met Ala Tyr Thr Glu Lys His Asn Gly Ile Gly Asp Ile Arg Pro Ala
1 5 10 15

Ile Cys Xaa Asn Ser Lys Asn Gln Asn His Arg Cys Asn His Tyr Gln
20 25 30

Ile Lys Leu Tyr Ile His Xaa Leu Xaa Arg Leu Pro His Asn Tyr Arg
35 40 45

Asn Ser
50

<210> SEQ ID NO 103
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine

<400> SEQUENCE: 103

Met Ala Leu Thr Leu Arg Tyr Leu Lys Ile Gly Asp Ile Arg Leu Ala
1 5 10 15

Asn Cys Xaa Thr Val Phe Pro His Phe Leu Ser Lys Lys Phe Phe Glu
20 25 30

Asn Gly His Arg Asn Leu Ala Arg Pro Cys Thr Phe Arg Arg Asn Arg
35 40 45

His Leu
50

<210> SEQ ID NO 104
<211> LENGTH: 50
<212> TYPE: PRT
<213> ORGANISM: Artificial Sequence
<220> FEATURE:
<223> OTHER INFORMATION: Peptide
<220> FEATURE:

<221> NAME/KEY: MISC_FEATURE
<222> LOCATION: (9)..(9)
<223> OTHER INFORMATION: Xaa at position 9 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 104

```
Met Ala Tyr His Lys His Arg Val Xaa His His His Glu Asp Lys Ala
1               5                   10                  15

Thr Ser Leu Thr Ser Asn Leu Val Arg Leu Arg Leu Lys Thr Arg Ile
            20                  25                  30

Gly Asp Ile Arg Arg Ala Leu Cys Xaa Leu Ser Lys Phe Arg Tyr Leu
        35                  40                  45

Ile Asn
    50
```

<210> SEQ ID NO 105
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 105

```
Met Ala Leu Leu His His Leu Arg Xaa Ile Gly Asp Ile Arg Pro Ala
1               5                   10                  15

His Cys Xaa Val Ser His Gln Arg Arg Tyr Val Pro Ile Ser Arg Lys
            20                  25                  30

Asn Val Phe Phe Lys Arg Gly Phe Asn Ser His Pro Leu Arg Lys Ile
        35                  40                  45

Leu Trp
    50
```

<210> SEQ ID NO 106
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 106

```
Met Ala Arg Phe Arg His Ser Asn Asn Tyr Tyr Leu Thr Pro Phe Leu
1               5                   10                  15

Thr Pro Leu Lys Thr Leu Ile Ser Leu Gln Leu Arg Tyr Arg Leu Ile
            20                  25                  30
```

Gly Asp Ile Arg Asn Ala Ser Tyr Xaa His Lys Phe Ser Asn Arg Asn
35 40 45

Arg Phe
50

<210> SEQ ID NO 107
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative of homopropargylglycine or homopropargylglycine

<400> SEQUENCE: 107

Met Ala Ile Phe Asn Gln Gly Tyr Arg Ile Lys Ala Trp Asn Asp Leu
1 5 10 15

Lys Asp Ile Ala Ile Gly Asp Ile Arg His Ala Leu Cys Xaa Leu Val
20 25 30

Leu Ala Arg Ile Lys Leu Gln Arg Arg Xaa Val Lys Tyr Lys His Asp
35 40 45

His Arg
50

<210> SEQ ID NO 108
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: Xaa at position 13 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 108

Met Ala His Gln His His His Pro Asn Tyr Ala Leu Xaa Gln Arg Arg
1 5 10 15

Leu Ser Ile Ala Ile Gly Asp Ile Arg Leu Ala Ile Cys Xaa Phe Ala
20 25 30

His Leu Tyr His Cys Tyr Arg Lys His Leu Xaa Ala Asn Thr Ile Pro
        35                  40                  45

Xaa Lys
    50

<210> SEQ ID NO 109
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative of homopropargylglycine or homopropargylglycine

<400> SEQUENCE: 109

Met Ala Phe Val Thr Tyr Gln His Xaa Ser Gln Lys Asn Phe Arg Arg
1               5                   10                  15

Tyr Gln Ile Leu Arg Asn His Phe His Pro Gln Asn Tyr Arg Phe Ile
            20                  25                  30

Gly Asp Ile Arg His Ala Leu Cys Xaa Phe Ile Phe Lys Asn Leu Xaa
        35                  40                  45

Arg His
    50

<210> SEQ ID NO 110
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (4)..(4)
<223> OTHER INFORMATION: Xaa at position 4 is a glycosylated derivative of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine

<400> SEQUENCE: 110

Met Ala Ala Xaa Lys Ile Arg Ser Lys Ile Gly Asp Ile Arg Thr Ala
1 5 10 15

Val Cys Xaa Phe Xaa His Arg His His His His His Ile Leu Asp Pro
20 25 30

Tyr Tyr Leu Lys Xaa Ile Val Xaa Tyr Tyr Ser Leu Lys Ser Arg Ile
35 40 45

Thr Leu
50

<210> SEQ ID NO 111
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(9)
<223> OTHER INFORMATION: Xaa at positions 8-9 is a glycosylated derivative of homopropargylglycine or homopropargylglycine
<220> FEATURE:
<221> NAME/KEY: MISC_FEATURE
<222> LOCATION: (16)..(16)
<223> OTHER INFORMATION: Xaa at position 16 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 111

Met Ala Phe Ile Lys Pro Cys Xaa Xaa Tyr Leu Leu Pro Pro Thr Xaa
1 5 10 15

Leu Asn Leu Tyr Ile Gly Asp Ile Arg Arg Ala Lys Cys Xaa Glu Ala
20 25 30

Xaa Asn Asn Phe His Xaa Asn Asn Lys Pro Leu Xaa Ala Thr Xaa Pro
35 40 45

Pro His
50

<210> SEQ ID NO 112
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 112

Met Ala Lys Asp Ile Leu Lys Leu Arg Ile Pro Phe Ala Thr Leu Ser
1 5 10 15

Gly His Arg Asn Ile Gly Asp Ile Arg His Ala Tyr Cys Xaa Ser Leu
20 25 30

Lys Arg Pro Tyr Ile Gln Val Tyr Ser Tyr Leu Asn His Leu Lys Val
35 40 45

Arg Phe
50

<210> SEQ ID NO 113
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (34)..(34)
<223> OTHER INFORMATION: Xaa at position 34 is a glycosylated derivative of homopropargylglycine or homopropargylglycine
<220> FEATURE:
<221> NAME/KEY: MISC_FEATURE
<222> LOCATION: (45)..(45)
<223> OTHER INFORMATION: Xaa at position 45 is a glycosylated derivative of homopropargylglycine or homopropargylglycine

<400> SEQUENCE: 113

Met Ala Thr Leu His Asn Ile His Asp Leu Asn His Tyr Tyr Arg Asn
1 5 10 15

Leu Asn Thr Arg Ile Gly Asp Ile Arg His Ala Thr Cys Xaa Tyr Phe
20 25 30

Phe Xaa Lys Leu Lys Leu Leu Lys His Asn Arg Phe Xaa Asp Arg Ala
35 40 45

Ile Tyr
50

<210> SEQ ID NO 114
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 114

```
Met Ala Pro Tyr Arg Ile Asn Gln Gln Xaa Asn Phe Pro Trp Ser Ser
1               5                   10                  15

Ala Leu Phe Gln Ile Gly Asp Ile Arg His Ala Arg Cys Xaa Asp Ser
            20                  25                  30

Cys Arg Arg Phe Thr Asn Ile Xaa Arg Tyr Val Tyr Leu Lys Arg Arg
        35                  40                  45

Xaa Asn
    50
```

<210> SEQ ID NO 115
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 115

```
Met Ala Leu Phe Lys Pro Tyr Pro Lys Ile Gly Asp Ile Arg Lys Ala
1               5                   10                  15

Arg Cys Xaa Leu Gln His Thr Leu His His Arg Thr Asn Lys Gln Pro
            20                  25                  30

Ser Tyr Arg Arg Arg Leu Lys Thr Leu Ile Pro Leu Phe Arg Arg Cys
        35                  40                  45

Xaa Leu
    50
```

<210> SEQ ID NO 116
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 116

```
Met Ala Thr Asn His Leu His Arg Thr Ile Gly Asp Ile Arg His Ala
1               5                   10                  15

Gln Cys Xaa Ile Tyr Leu Ile Tyr Leu Val Gln Asn Asp Gln Tyr Lys
            20                  25                  30
```

```
Arg Asn Asn Arg Thr Phe Arg Leu Xaa Leu Asn Pro Lys Leu Leu Lys
        35                  40                  45

Arg Phe
    50


<210> SEQ ID NO 117
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (20)..(20)
<223> OTHER INFORMATION: Xaa at position 20 is a glycosylated derivative
      of homopropargylglycine or homopropargylglycine
<220> FEATURE:
<221> NAME/KEY: MISC_FEATURE
<222> LOCATION: (25)..(25)
<223> OTHER INFORMATION: Xaa at position 25 is a glycosylated derivative
      of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 117

Met Ala Thr Asn Ser Tyr Tyr His His Asn Pro Leu Xaa Arg Arg Thr
1               5                   10                  15

His Val Val Xaa Thr Leu Lys Pro Xaa Asn Phe Trp Ala Lys Xaa Ile
            20                  25                  30

Gly Asp Ile Arg Arg Ala His Cys Xaa Thr Thr Ile Asn Xaa Leu Lys
        35                  40                  45

Arg Arg
    50


<210> SEQ ID NO 118
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (18)..(18)
<223> OTHER INFORMATION: Xaa at position 18 is a glycosylated derivative
      of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
```

<400> SEQUENCE: 118

Met Ala Ile Leu Leu His Val Ser Thr Arg Ser Arg Tyr Pro His His
1               5                   10                  15

His Xaa Ala Ile Ile Gly Asp Ile Arg Cys Ala Ser Cys Xaa Tyr Pro
            20                  25                  30

Val Leu Lys Trp Phe Tyr Asn Phe Asn Arg Leu Lys Thr Tyr Arg Lys
        35                  40                  45

Gln Phe
    50

<210> SEQ ID NO 119
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 119

Met Ala Tyr Arg Thr His Lys Leu Leu His His His Asn Asp Lys Trp
1               5                   10                  15

Lys Ser Asn Ile Phe Pro Arg Ile Phe Val Cys His Tyr Tyr Leu Ile
            20                  25                  30

Gly Asp Ile Arg His Ala Arg Cys Xaa Ile Pro Leu Glu Ile Leu Arg
        35                  40                  45

Arg Tyr
    50

<210> SEQ ID NO 120
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (15)..(15)
<223> OTHER INFORMATION: Xaa at position 15 is a glycosylated derivative
      of homopropargylglycine or homopropargylglycine

<400> SEQUENCE: 120

Met Ala Tyr Ser Lys His Arg Phe Ser Phe Arg His Asn Asn Xaa Leu
1               5                   10                  15

Arg Asp Arg Lys Leu Ile Arg Lys Phe Ser Tyr His Asn His Ser Ile
            20                  25                  30

Gly Asp Ile Arg Val Ala Asn Lys Phe Arg Tyr Leu His Val Phe Lys
        35                  40                  45

Phe Ile
    50

<210> SEQ ID NO 121
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(11)

<223> OTHER INFORMATION: Xaa at positions 10-11 is a glycosylated derivative of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative of homopropargylglycine or homopropargylglycine

<400> SEQUENCE: 121

```
Met Ala Ser Ile Lys Leu Ile Asn Gln Xaa Xaa Thr Thr Asn Pro His
1               5                   10                  15

Leu Arg Leu His Ile Gly Asp Ile Arg Arg Leu Ile Lys Asp Leu Tyr
            20                  25                  30

Xaa Phe Arg Val Tyr Tyr Arg Pro Thr Asn Ser Gly Arg Arg Leu Phe
        35                  40                  45

Val Asn
    50
```

<210> SEQ ID NO 122
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative of homopropargylglycine or homopropargylglycine

<400> SEQUENCE: 122

```
Met Ala His Ser His His His Ser Pro Xaa Ile Glu Phe His Ser Asn
1               5                   10                  15

Gly Arg Leu His Ile Gly Asp Ile Arg Lys Phe Tyr Ala Asp Ala Leu
            20                  25                  30

Xaa Val Leu Phe Phe Lys Xaa Ala Phe Ile Asp Arg Ile Pro Phe His
        35                  40                  45

Asp Ala
    50
```

<210> SEQ ID NO 123
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (20)..(20)
<223> OTHER INFORMATION: Xaa at position 20 is a glycosylated derivative of homopropargylglycine or homopropargylglycine
<220> FEATURE:
<221> NAME/KEY: MISC_FEATURE
<222> LOCATION: (34)..(34)
<223> OTHER INFORMATION: Xaa at position 34 is a glycosylated derivative of homopropargylglycine or homopropargylglycine
<220> FEATURE:
<221> NAME/KEY: MISC_FEATURE
<222> LOCATION: (44)..(44)

<223> OTHER INFORMATION: Xaa at position 44 is a glycosylated derivative of homopropargylglycine or homopropargylglycine
<220> FEATURE:
<221> NAME/KEY: MISC_FEATURE
<222> LOCATION: (49)..(50)
<223> OTHER INFORMATION: Xaa at positions 49-50 is a glycosylated derivative of homopropargylglycine or homopropargylglycine

<400> SEQUENCE: 123

```
Met Ala Asn Ile Tyr Phe Cys Ser Arg Arg Thr Asn Phe His Asn Ser
1               5                   10                  15

Cys Tyr Leu Xaa Ile Gly Asp Ile Arg Gly Leu Ser Ile Tyr His His
            20                  25                  30

Ile Xaa Ile His Asn Lys Leu His Leu Leu Ile Xaa Tyr Asn Leu Leu
        35                  40                  45

Xaa Xaa
    50
```

<210> SEQ ID NO 124
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative of homopropargylglycine or homopropargylglycine

<400> SEQUENCE: 124

```
Met Ala Ile His Tyr His His Pro Ile Ile Gly Asp Ile Arg Leu Lys
1               5                   10                  15

His Asn Xaa Ile Asn Ala His Thr Lys His Val Pro Gln Lys Leu Tyr
            20                  25                  30

Leu Asp Ile Lys Phe Arg Arg Leu Phe Gly Leu Tyr Ile Leu Arg Xaa
        35                  40                  45

Leu Asn
    50
```

<210> SEQ ID NO 125
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative of homopropargylglycine or homopropargylglycine

<400> SEQUENCE: 125

```
Met Ala Ile Leu Tyr His Tyr His Asn Ile Gly Asp Ile Arg Arg Ser
1               5                   10                  15

Gln Arg His Leu Asn Xaa Gln Xaa Arg Leu Tyr Val Ser Thr Leu Leu
            20                  25                  30
```

```
His Ser Ser His Thr Leu Arg Arg Ala Ser Ile Thr His Arg Ile Arg
        35                  40                  45

Lys Phe
    50


<210> SEQ ID NO 126
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa at position 1 is methionine or
      homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine

<400> SEQUENCE: 126

Xaa Ala Thr Phe Ser Arg Tyr His Thr Ile Gly Asp Ile Arg His His
1               5                   10                  15

Thr Leu Lys His His Gln Ser Lys Gly Leu Gln Xaa Arg Leu Ile Phe
            20                  25                  30

Leu Lys Arg Gln Phe Lys Ala Xaa Gly Asn Cys Leu Arg Trp Lys Ile
        35                  40                  45

Leu Phe
    50


<210> SEQ ID NO 127
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (24)..(24)
<223> OTHER INFORMATION: Xaa at position 24 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine

<400> SEQUENCE: 127

Met Ala Lys Tyr Thr His Ile His Ser Ile Gly Asp Ile Arg Asn Thr
1               5                   10                  15

Tyr Arg Asn Lys His Lys His Xaa Ala Leu Asn Lys Thr Asn Trp Ala
            20                  25                  30

Leu Phe Gln Gln His His Arg Xaa Leu Ile Arg Leu Phe Tyr Arg Arg
        35                  40                  45

Leu Leu
    50


<210> SEQ ID NO 128
<211> LENGTH: 50
```

<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (44)..(44)
<223> OTHER INFORMATION: Xaa at position 44 is a glycosylated derivative
of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative
of homopropargylglycine or homopropargylglycine

<400> SEQUENCE: 128

```
Met Ala Leu Asn Lys His Lys His Leu Arg Asn His Thr Arg His His
1               5                   10                  15

Ser Val Pro Thr Ile Gly Asp Ile Arg Lys Arg Ile His Asn Leu Leu
            20                  25                  30

His Tyr Leu Ala Gly Phe Arg Phe Phe Asn Gln Xaa His Ser Lys Xaa
        35                  40                  45

Gly Val
    50
```

<210> SEQ ID NO 129
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (36)..(36)
<223> OTHER INFORMATION: Xaa at position 36 is a glycosylated derivative
of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative
of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
of homopropargylglycine or homopropargylglycine

<400> SEQUENCE: 129

```
Met Ala Tyr Leu His Asn His His Asn Tyr Ser Ser Asn Asn Lys Leu
1               5                   10                  15

His His Leu Glu Ile Gly Asp Ile Arg Leu Ile Tyr Gln Lys Tyr Leu
            20                  25                  30

Arg Asn Pro Xaa Phe Xaa Thr Phe Leu Ser Arg Lys His Xaa Asn Trp
        35                  40                  45

Gln Arg
    50
```

<210> SEQ ID NO 130
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (7)..(7)
<223> OTHER INFORMATION: Xaa at position 7 is a glycosylated derivative
of homopropargylglycine or homopropargylglycine

<400> SEQUENCE: 130

Met Ala Asn Leu Thr Ala Xaa Ser Arg Ile Gly Asp Ile Arg Lys His
1 5 10 15

His Phe Gly Arg Pro Leu Tyr Leu Thr Lys His Gly Ala Tyr Pro Arg
20 25 30

Tyr His Thr Arg Tyr Lys His Leu Leu Thr Tyr Arg His His Phe Pro
35 40 45

Leu Ile
50

<210> SEQ ID NO 131
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine

<400> SEQUENCE: 131

Met Ala Lys His Thr His Leu Arg Pro Xaa Asn Phe Thr Gln Arg Leu
1 5 10 15

Arg Lys Ala His Ile Gly Asp Ile Arg Leu Pro Arg Asn Ile Ser Thr
20 25 30

Ser Arg Ile Arg Thr His Ile Lys Phe His Leu Ile Arg Xaa His Leu
35 40 45

Arg Asn
50

<210> SEQ ID NO 132
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine

<400> SEQUENCE: 132

Met Ala Phe Leu Leu Asn His Lys Arg Ile Gly Asp Ile Arg Lys Leu
1 5 10 15

Pro Pro Leu Asn Leu Xaa Ala Thr Lys Thr Leu Thr Lys Glu Arg Ile
20 25 30

Arg Lys Ile Val Asn Gly Phe Val Gln Arg Leu Lys Gly His Ser Trp
35 40 45

Trp Ile
50

<210> SEQ ID NO 133
<211> LENGTH: 50
<212> TYPE: PRT
<213> ORGANISM: Artificial Sequence
<220> FEATURE:

<223> OTHER INFORMATION: Peptide
<220> FEATURE:
<221> NAME/KEY: MISC_FEATURE
<222> LOCATION: (32)..(32)
<223> OTHER INFORMATION: Xaa at position 32 is a glycosylated derivative of homopropargylglycine or homopropargylglycine

<400> SEQUENCE: 133

```
Met Ala Ile His His Ser Tyr Arg Gly Phe Thr Leu Arg Ile Pro Leu
1               5                   10                  15

Thr Thr Asn Lys Ile Gly Asp Ile Arg Thr Ala Phe Pro Tyr Pro Xaa
            20                  25                  30

Leu Ser His Leu Phe Asp Arg Arg Arg Trp Lys Arg Gly Leu His Asn
        35                  40                  45

Trp Phe
    50
```

<210> SEQ ID NO 134
<211> LENGTH: 64
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (44)..(45)
<223> OTHER INFORMATION: Xaa at positions 44-45 is a glycosylated derivative of homopropargylglycine or homopropargylglycine
<220> FEATURE:
<221> NAME/KEY: MISC_FEATURE
<222> LOCATION: (49)..(50)
<223> OTHER INFORMATION: Xaa at positions 49-50 is a glycosylated derivative of homopropargylglycine or homopropargylglycine

<400> SEQUENCE: 134

```
Met Ala Tyr Phe Gln Asn Thr Ser Ile Asn Asn Ile Asn Ala Leu Asn
1               5                   10                  15

Gln Ala Thr Gln Lys Asn Phe Phe Arg Ile Arg Leu Glu Ile Xaa Thr
            20                  25                  30

Leu Asn Leu Val Ser Lys Arg Tyr Cys Asn Ala Xaa Xaa His Leu Leu
        35                  40                  45

Xaa Xaa Gly Phe Gly Ser Leu Gly His His His His His His Arg Leu
    50                  55                  60
```

<210> SEQ ID NO 135
<211> LENGTH: 64
<212> TYPE: PRT
<213> ORGANISM: Artificial Sequence
<220> FEATURE:
<223> OTHER INFORMATION: 101-11

<400> SEQUENCE: 135

```
Met Ala Arg Phe His Ser Arg Ser Pro Phe Lys Asp Ser His Leu Phe
1               5                   10                  15

Arg Asn Gly Thr Val Gly Asp Ile Arg Ser Arg Ala Val His Ala Gln
            20                  25                  30

Ala Glu Gln Arg Arg Gly Tyr Leu Leu Val Arg Leu Arg Gly His Arg
        35                  40                  45

Val Gly Gly Leu Gly Ser Leu Gly His His His His His His Arg Leu
    50                  55                  60
```

```
<210> SEQ ID NO 136
<211> LENGTH: 64
<212> TYPE: PRT
<213> ORGANISM: Artificial Sequence
<220> FEATURE:
<223> OTHER INFORMATION: 101-15
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine
<220> FEATURE:
<221> NAME/KEY: MISC_FEATURE
<222> LOCATION: (18)..(18)
<223> OTHER INFORMATION: Xaa at position 18 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 136

Met Ala Lys Leu Lys Val Cys Asn Xaa Tyr Ala Phe Ser Arg Pro Gly
1               5                   10                  15

Trp Xaa Ile Arg Lys Asp Ile Glu Phe Tyr Tyr Arg Ile Asn Leu Val
            20                  25                  30

Gly Asp Val Arg Tyr Ala Thr Cys Xaa Arg Tyr Gly Tyr Leu Ile Leu
        35                  40                  45

Thr Gln Gly Ser Gly Ser Leu Gly His His His His His His Arg Leu
    50                  55                  60


<210> SEQ ID NO 137
<211> LENGTH: 64
<212> TYPE: PRT
<213> ORGANISM: Artificial Sequence
<220> FEATURE:
<223> OTHER INFORMATION: 101-16
<220> FEATURE:
<221> NAME/KEY: MISC_FEATURE
<222> LOCATION: (6)..(6)
<223> OTHER INFORMATION: Xaa at position 6 is a glycosylated derivative
      of homopropargylglycine or homopropargylglycine
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (12)..(12)
<223> OTHER INFORMATION: Xaa at position 12 is a glycosylated derivative
      of homopropargylglycine or homopropargylglycine
<220> FEATURE:
<221> NAME/KEY: MISC_FEATURE
<222> LOCATION: (16)..(16)
<223> OTHER INFORMATION: Xaa at position 16 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine

<400> SEQUENCE: 137

Met Ala Thr Tyr His Xaa Thr Ile Asn Xaa Asn Xaa Ala Tyr Arg Xaa
1               5                   10                  15

Arg Thr Tyr Ser Ala Arg Asn Ser Ile Val Ser Thr Glu Asn His Ile
            20                  25                  30
```

```
Asp Asp Ile Arg Ala Ala Gln Cys Xaa Thr Asn Pro Lys His Leu Ser
        35                  40                  45

Phe Ile Gly Ser Gly Thr Leu Gly His His His His His His Arg Leu
    50                  55                  60


<210> SEQ ID NO 138
<211> LENGTH: 64
<212> TYPE: PRT
<213> ORGANISM: Artificial Sequence
<220> FEATURE:
<223> OTHER INFORMATION: 102-36

<400> SEQUENCE: 138

Met Ala Asn His Lys His Thr His Ile Ser Leu Lys Ser Ile Val Gln
1               5                   10                  15

Thr His Gly Gly Pro His Pro Asn Val Ala Arg Ala Ala Asn Leu Leu
            20                  25                  30

Leu Glu Gln Leu Pro Val Val Arg Arg Arg Leu Gln Arg Arg Leu Leu
        35                  40                  45

Gln Arg Gly Leu Arg Ser Leu Gly His His His His His His Arg Leu
    50                  55                  60


<210> SEQ ID NO 139
<211> LENGTH: 64
<212> TYPE: PRT
<213> ORGANISM: Artificial Sequence
<220> FEATURE:
<223> OTHER INFORMATION: 102-43
<220> FEATURE:
<221> NAME/KEY: MISC_FEATURE
<222> LOCATION: (1)..(1)
<223> OTHER INFORMATION: Xaa at position 1 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine

<400> SEQUENCE: 139

Xaa Ser Asn Tyr Val Asn Ser Tyr Leu Asn Thr His Leu Gln Leu Asp
1               5                   10                  15

Gln Ser Thr Thr Ile Gly Asp Ile His Gly Leu Arg Lys Leu Gly Arg
            20                  25                  30

Tyr Ala Thr Glu Ser Ser Phe Xaa Arg Ile His Asn Ile Ser Phe Leu
        35                  40                  45

Ser His Gly Ser Gly Ser Leu Gly His His His His His His Arg Leu
    50                  55                  60


<210> SEQ ID NO 140
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative
      of homopropargylglycine or homopropargylglycine

<400> SEQUENCE: 140

Met Ala Ile Arg Lys Asn Phe Pro Xaa Thr Phe Gly His Arg Pro His
1               5                   10                  15
```

```
Leu Arg Val Ala His Ala Gln Arg Ala Gln His Ala Leu Leu Val Leu
            20                  25                  30

Arg Arg Ala Arg Arg Leu Leu Asp Gln Glu Val Asp Ala Pro Gly Gly
        35                  40                  45

Arg Arg Gly Ser Gly Ser Gly Leu Gly His His His His His His Arg
    50                  55                  60

Leu
65


<210> SEQ ID NO 141
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative
      of homopropargylglycine or homopropargylglycine
<220> FEATURE:
<221> NAME/KEY: MISC_FEATURE
<222> LOCATION: (35)..(35)
<223> OTHER INFORMATION: Xaa at position 35 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine
<220> FEATURE:
<221> NAME/KEY: MISC_FEATURE
<222> LOCATION: (47)..(49)
<223> OTHER INFORMATION: Xaa at positions 47-49 is a glycosylated
      derivative of homopropargylglycine or homopropargylglycine

<400> SEQUENCE: 141

Met Ala His His Tyr Pro Asn Tyr His Xaa Arg Ser His Gly Asp Arg
1               5                   10                  15

Leu Thr Leu Leu Arg His Leu Xaa Ser Phe Leu Val Asp His Lys Gln
            20                  25                  30

Ile Leu Xaa Phe Leu Leu Arg Xaa Arg Lys Asn His Val Ser Xaa Xaa
        35                  40                  45

Xaa Thr Gly Ser Gly Ser Gly Leu Gly His His His His His His Arg
    50                  55                  60

Leu
65


<210> SEQ ID NO 142
<211> LENGTH: 52
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (31)..(31)
<223> OTHER INFORMATION: Xaa at position 31 is a glycosylated derivative
      of homopropargylglycine or homopropargylglycine
```

-continued

<220> FEATURE:
<221> NAME/KEY: MISC_FEATURE
<222> LOCATION: (44)..(45)
<223> OTHER INFORMATION: Xaa at position 44-45 is a glycosylated derivative of homopropargylglycine or homopropargylglycine
<220> FEATURE:
<221> NAME/KEY: MISC_FEATURE
<222> LOCATION: (49)..(50)
<223> OTHER INFORMATION: Xaa at position 49-50 is a glycosylated derivative of homopropargylglycine or homopropargylglycine

<400> SEQUENCE: 142

```
Met Ala Tyr Phe Gln Asn Thr Ser Ile Asn Asn Ile Asn Ala Leu Asn
1               5                   10                  15

Gln Ala Thr Gln Lys Asn Phe Phe Arg Ile Arg Leu Glu Ile Xaa Thr
            20                  25                  30

Leu Asn Leu Val Ser Lys Arg Tyr Cys Asn Ala Xaa Xaa His Leu Leu
        35                  40                  45

Xaa Xaa Gly Phe
    50
```

<210> SEQ ID NO 143
<211> LENGTH: 52
<212> TYPE: PRT
<213> ORGANISM: Artificial Sequence
<220> FEATURE:
<223> OTHER INFORMATION: Peptide

<400> SEQUENCE: 143

```
Met Ala Arg Phe His Ser Arg Ser Pro Phe Lys Asp Ser His Leu Phe
1               5                   10                  15

Arg Asn Gly Thr Val Gly Asp Ile Arg Ser Arg Ala Val His Ala Gln
            20                  25                  30

Ala Glu Gln Arg Arg Gly Tyr Leu Leu Val Arg Leu Arg Gly His Arg
        35                  40                  45

Val Gly Gly Leu
    50
```

<210> SEQ ID NO 144
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative of homopropargylglycine or homopropargylglycine
<220> FEATURE:
<221> NAME/KEY: MISC_FEATURE
<222> LOCATION: (18)..(18)
<223> OTHER INFORMATION: Xaa at position 18 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 144

```
Met Ala Lys Leu Lys Val Cys Asn Xaa Tyr Ala Phe Ser Arg Pro Gly
1               5                   10                  15

Trp Xaa Ile Arg Lys Asp Ile Glu Phe Tyr Tyr Arg Ile Asn Leu Val
            20                  25                  30
```

Gly Asp Val Arg Tyr Ala Thr Cys Xaa Arg Tyr Gly Tyr Leu Ile Leu
35 40 45

Thr Gln
50

<210> SEQ ID NO 145
<211> LENGTH: 54
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (6)..(6)
<223> OTHER INFORMATION: Xaa at position 6 is a glycosylated derivative of homopropargylglycine or homopropargylglycine
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (12)..(12)
<223> OTHER INFORMATION: Xaa at position 12 is a glycosylated derivative of homopropargylglycine or homopropargylglycine
<220> FEATURE:
<221> NAME/KEY: MISC_FEATURE
<222> LOCATION: (16)..(16)
<223> OTHER INFORMATION: Xaa at position 16 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 145

Met Ala Thr Tyr His Xaa Thr Ile Asn Xaa Asn Xaa Ala Tyr Arg Xaa
1 5 10 15

Arg Thr Tyr Ser Ala Arg Asn Ser Ile Val Ser Thr Glu Asn His Ile
20 25 30

Asp Asp Ile Arg Ala Ala Gln Cys Xaa Thr Asn Pro Lys His Leu Ser
35 40 45

Phe Ile Gly Ser Gly Thr
50

<210> SEQ ID NO 146
<211> LENGTH: 53
<212> TYPE: PRT
<213> ORGANISM: Artificial Sequence
<220> FEATURE:
<223> OTHER INFORMATION: Peptide

<400> SEQUENCE: 146

Met Ala Asn His Lys His Thr His Ile Ser Leu Lys Ser Ile Val Gln
1 5 10 15

Thr His Gly Gly Pro His Pro Asn Val Ala Arg Ala Ala Asn Leu Leu
20 25 30

Leu Glu Gln Leu Pro Val Val Arg Arg Arg Leu Gln Arg Arg Leu Leu
35 40 45

Gln Arg Gly Leu Arg
50

<210> SEQ ID NO 147
<211> LENGTH: 50

<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa at position 1 is a glycosylated derivative
of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
of homopropargylglycine or homopropargylglycine

<400> SEQUENCE: 147

```
Xaa Ser Asn Tyr Val Asn Ser Tyr Leu Asn Thr His Leu Gln Leu Asp
1               5                   10                  15

Gln Ser Thr Thr Ile Gly Asp Ile His Gly Leu Arg Lys Leu Gly Arg
            20                  25                  30

Tyr Ala Thr Glu Ser Ser Phe Xaa Arg Ile His Asn Ile Ser Phe Leu
        35                  40                  45

Ser His
    50
```

<210> SEQ ID NO 148
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (9)..(9)
<223> OTHER INFORMATION: Xaa at position 9 is a glycosylated derivative
of homopropargylglycine or homopropargylglycine

<400> SEQUENCE: 148

```
Met Ala Ile Arg Lys Asn Phe Pro Xaa Thr Phe Gly His Arg Pro His
1               5                   10                  15

Leu Arg Val Ala His Ala Gln Arg Ala Gln His Ala Leu Leu Val Leu
            20                  25                  30

Arg Arg Ala Arg Arg Leu Leu Asp Gln Glu Val Asp Ala Pro Gly Gly
        35                  40                  45

Arg Arg
    50
```

<210> SEQ ID NO 149
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative
of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative
of homopropargylglycine or homopropargylglycine
<220> FEATURE:
<221> NAME/KEY: MISC_FEATURE
<222> LOCATION: (35)..(35)
<223> OTHER INFORMATION: Xaa at position 35 is a glycosylated derivative
of homopropargylglycine or homopropargylglycine
<220> FEATURE:

<221> NAME/KEY: MISC_FEATURE
<222> LOCATION: (40)..(40)
<223> OTHER INFORMATION: Xaa at position 40 is a glycosylated derivative of homopropargylglycine or homopropargylglycine
<220> FEATURE:
<221> NAME/KEY: MISC_FEATURE
<222> LOCATION: (47)..(49)
<223> OTHER INFORMATION: Xaa at positions 47-49 is a glycosylated derivative of homopropargylglycine or homopropargylglycine

<400> SEQUENCE: 149

```
Met Ala His His Tyr Pro Asn Tyr His Xaa Arg Ser His Gly Asp Arg
1               5                   10                  15

Leu Thr Leu Leu Arg His Leu Xaa Ser Phe Leu Val Asp His Lys Gln
            20                  25                  30

Ile Leu Xaa Phe Leu Leu Arg Xaa Arg Lys Asn His Val Ser Xaa Xaa
        35                  40                  45

Xaa Thr
    50
```

<210> SEQ ID NO 150
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine

<400> SEQUENCE: 150

```
Met Ala Asn His Ser His Gly His Asn Ile Gly Asp Ile Arg Asp Ala
1               5                   10                  15

Thr Cys Xaa Leu Ser Asn Cys Tyr His Tyr Asn Asn Arg Arg Lys Asn
            20                  25                  30

Arg Phe Thr Leu Phe Thr Leu Leu Arg Ile Leu Val Gln Lys Ser Leu
        35                  40                  45

Phe Arg Gly Ser Gly Ser Gly Leu Gly His His His His His His Arg
    50                  55                  60

Leu
65
```

<210> SEQ ID NO 151
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative of homopropargylglycine or homopropargylglycine

<400> SEQUENCE: 151

```
Met Ala Ile Phe Asn Gln Gly Tyr Arg Ile Lys Ala Trp Asn Asp Leu
1               5                   10                  15

Lys Asp Ile Ala Ile Gly Asp Ile Arg His Ala Leu Cys Xaa Leu Val
            20                  25                  30
```

```
Leu Ala Arg Ile Lys Leu Gln Arg Arg Xaa Val Lys Tyr Lys His Asp
        35                  40                  45

His Arg Gly Ser Gly Ser Gly Leu Gly His His His His His His Arg
    50                  55                  60

Leu
65


<210> SEQ ID NO 152
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (27)..(27)
<223> OTHER INFORMATION: Xaa at position 27 is a glycosylated derivative
      of homopropargylglycine or homopropargylglycine

<400> SEQUENCE: 152

Met Ala Ile His His Thr His Leu Asn Ile Gly Asp Ile Arg Phe Arg
1               5                   10                  15

His Phe Pro Arg Arg Tyr Arg Asn Asn Trp Xaa Asn Phe Leu Phe Leu
            20                  25                  30

Val Leu Arg Ala Leu Thr Trp Lys Asn Arg Leu Ala Phe Phe Ser Asn
        35                  40                  45

Asp His Gly Ser Gly Ser Gly Leu Gly His His His His His His Arg
    50                  55                  60

Leu
65


<210> SEQ ID NO 153
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (5)..(5)
<223> OTHER INFORMATION: Xaa at position 5 is a glycosylated derivative
      of homopropargylglycine or homopropargylglycine

<400> SEQUENCE: 153

Met Ala Ile Asn Xaa Ser Ile Arg Leu Ile Gly Asp Ile Arg Pro Ala
1               5                   10                  15

Gln Ala Gln Arg Gly His Leu Ala Pro His Ala Arg Arg Val Arg His
            20                  25                  30

Glu Val Leu Gly Leu Val Leu Glu Arg Leu Leu Val Leu Arg Arg Leu
        35                  40                  45

Val Arg Gly Ser Gly Ser Gly Leu Gly His His His His His His Arg
    50                  55                  60

Leu
65


<210> SEQ ID NO 154
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
```

<222> LOCATION: (22)..(22)
<223> OTHER INFORMATION: Xaa at position 22 is a glycosylated derivative
      of homopropargylglycine or homopropargylglycine

<400> SEQUENCE: 154

```
Met Ala Phe Leu Leu Asn His Lys Arg Ile Gly Asp Ile Arg Lys Leu
1               5                   10                  15

Pro Pro Leu Asn Leu Xaa Ala Thr Lys Thr Leu Thr Lys Glu Arg Ile
            20                  25                  30

Arg Lys Ile Val Asn Gly Phe Val Gln Arg Leu Lys Gly His Ser Trp
        35                  40                  45

Trp Ile Gly Ser Gly Ser Gly Leu Gly His His His His His His Arg
    50                  55                  60

Leu
65
```

<210> SEQ ID NO 155
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine

<400> SEQUENCE: 155

```
Met Ala Asn His Ser His Gly His Asn Ile Gly Asp Ile Arg Asp Ala
1               5                   10                  15

Thr Cys Xaa Leu Ser Asn Cys Tyr His Tyr Asn Asn Arg Arg Lys Asn
            20                  25                  30

Arg Phe Thr Leu Phe Thr Leu Leu Arg Ile Leu Val Gln Lys Ser Leu
        35                  40                  45

Phe Arg
    50
```

<210> SEQ ID NO 156
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative
      of homopropargylglycine or homopropargylglycine

<400> SEQUENCE: 156

```
Met Ala Ile Phe Asn Gln Gly Tyr Arg Ile Lys Ala Trp Asn Asp Leu
1               5                   10                  15

Lys Asp Ile Ala Ile Gly Asp Ile Arg His Ala Leu Cys Xaa Leu Val
            20                  25                  30

Leu Ala Arg Ile Lys Leu Gln Arg Arg Xaa Val Lys Tyr Lys His Asp
        35                  40                  45

His Arg
    50
```

<210> SEQ ID NO 157
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (27)..(27)
<223> OTHER INFORMATION: Xaa at position 27 is a glycosylated derivative of homopropargylglycine or homopropargylglycine

<400> SEQUENCE: 157

```
Met Ala Ile His His Thr His Leu Asn Ile Gly Asp Ile Arg Phe Arg
1               5                   10                  15

His Phe Pro Arg Arg Tyr Arg Asn Asn Trp Xaa Asn Phe Leu Phe Leu
            20                  25                  30

Val Leu Arg Ala Leu Thr Trp Lys Asn Arg Leu Ala Phe Phe Ser Asn
        35                  40                  45

Asp His
    50
```

<210> SEQ ID NO 158
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (5)..(5)
<223> OTHER INFORMATION: Xaa at position 5 is a glycosylated derivative of homopropargylglycine or homopropargylglycine

<400> SEQUENCE: 158

```
Met Ala Ile Asn Xaa Ser Ile Arg Leu Ile Gly Asp Ile Arg Pro Ala
1               5                   10                  15

Gln Ala Gln Arg Gly His Leu Ala Pro His Ala Arg Arg Val Arg His
            20                  25                  30

Glu Val Leu Gly Leu Val Leu Glu Arg Leu Leu Val Leu Arg Arg Leu
        35                  40                  45

Val Arg
    50
```

<210> SEQ ID NO 159
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine

<400> SEQUENCE: 159

```
Met Ala Phe Leu Leu Asn His Lys Arg Ile Gly Asp Ile Arg Lys Leu
1               5                   10                  15

Pro Pro Leu Asn Leu Xaa Ala Thr Lys Thr Leu Thr Lys Glu Arg Ile
            20                  25                  30

Arg Lys Ile Val Asn Gly Phe Val Gln Arg Leu Lys Gly His Ser Trp
        35                  40                  45
```

Trp Ile
50

<210> SEQ ID NO 160
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine

<400> SEQUENCE: 160

Met Ala Tyr Lys Lys Thr Phe Xaa Asp Ile Gly Asp Ser Tyr Gly Glu
1 5 10 15

Leu His Ala Gln Ala Arg Arg Arg Glu Ala Val Arg Arg Leu Leu Arg
20 25 30

Leu Val Arg His Arg Val Leu Leu His Leu Leu Arg Ala Val Leu His
35 40 45

Ala Arg Gly Ser Gly Ser Gly Leu Gly His His His His His His Arg
50 55 60

Leu
65

<210> SEQ ID NO 161
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (15)..(15)
<223> OTHER INFORMATION: Xaa at position 15 is a glycosylated derivative of homopropargylglycine or homopropargylglycine

<400> SEQUENCE: 161

Met Ala Ser Ser Phe Arg Leu His Asn Xaa Gly Pro Ser Arg Xaa Arg
1 5 10 15

His Trp Asp Arg Leu Leu Thr Ile Tyr Ser Ile Gly Val Ser Thr Leu
20 25 30

Ala Asn Ser Leu Arg Val Leu His Gly Val Ala His Arg Gly Arg His
35 40 45

Leu Gly Gly Ser Gly Ser Gly Leu Gly His His His His His His Arg
50 55 60

Leu
65

<210> SEQ ID NO 162
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (16)..(16)
<223> OTHER INFORMATION: Xaa at position 16 is a glycosylated derivative of homopropargylglycine or homopropargylglycine

<400> SEQUENCE: 162

Met Ala Tyr Tyr Asn His Pro Lys Leu Arg Gln Tyr Leu Val Lys Xaa
1 5 10 15

Leu Thr Arg Leu Arg Arg Tyr Ser Tyr Arg Glu Leu His Asp Gly Asp
20 25 30

Asp His Ala Arg Gln Ala His Arg Gly Arg Leu Leu Gln Asp Leu Val
35 40 45

Asp Arg Gly Ser Gly Ser Gly Leu Gly His His His His His His Arg
50 55 60

Leu
65

<210> SEQ ID NO 163
<211> LENGTH: 65
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine

<400> SEQUENCE: 163

Met Ala Tyr Asp Pro Leu His Lys Ala Ser His Ser Asn His Pro Gln
1 5 10 15

Pro Tyr Arg Tyr Ile Gly Val Ile Arg His Pro Leu Xaa Arg Gln Ser
20 25 30

Ile Ser Gln Ile Phe Lys Ile Leu Leu Ile Arg Tyr Leu Arg Lys His
35 40 45

Arg Arg Gly Ser Gly Ser Gly Leu Gly His His His His His His Arg
50 55 60

Leu
65

<210> SEQ ID NO 164
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine

<400> SEQUENCE: 164

Met Ala Tyr Lys Lys Thr Phe Xaa Asp Ile Gly Asp Ser Tyr Gly Glu
1 5 10 15

Leu His Ala Gln Ala Arg Arg Arg Glu Ala Val Arg Arg Leu Leu Arg
20 25 30

Leu Val Arg His Arg Val Leu Leu His Leu Leu Arg Ala Val Leu His
35 40 45

Ala Arg
50

<210> SEQ ID NO 165
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (15)..(15)
<223> OTHER INFORMATION: Xaa at position 15 is a glycosylated derivative of homopropargylglycine or homopropargylglycine

<400> SEQUENCE: 165

```
Met Ala Ser Ser Phe Arg Leu His Asn Xaa Gly Pro Ser Arg Xaa Arg
1               5                   10                  15

His Trp Asp Arg Leu Leu Thr Ile Tyr Ser Ile Gly Val Ser Thr Leu
            20                  25                  30

Ala Asn Ser Leu Arg Val Leu His Gly Val Ala His Arg Gly Arg His
        35                  40                  45

Leu Gly
    50
```

<210> SEQ ID NO 166
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (16)..(16)
<223> OTHER INFORMATION: Xaa at position 16 is a glycosylated derivative of homopropargylglycine or homopropargylglycine

<400> SEQUENCE: 166

```
Met Ala Tyr Tyr Asn His Pro Lys Leu Arg Gln Tyr Leu Val Lys Xaa
1               5                   10                  15

Leu Thr Arg Leu Arg Arg Tyr Ser Tyr Arg Glu Leu His Asp Gly Asp
            20                  25                  30

Asp His Ala Arg Gln Ala His Arg Gly Arg Leu Leu Gln Asp Leu Val
        35                  40                  45

Asp Arg
    50
```

<210> SEQ ID NO 167
<211> LENGTH: 50
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine

<400> SEQUENCE: 167

```
Met Ala Tyr Asp Pro Leu His Lys Ala Ser His Ser Asn His Pro Gln
1               5                   10                  15

Pro Tyr Arg Tyr Ile Gly Val Ile Arg His Pro Leu Xaa Arg Gln Ser
            20                  25                  30
```

```
Ile Ser Gln Ile Phe Lys Ile Leu Leu Ile Arg Tyr Leu Arg Lys His
        35                  40                  45

Arg Arg
    50


<210> SEQ ID NO 168
<211> LENGTH: 47
<212> TYPE: PRT
<213> ORGANISM: Artificial Sequence
<220> FEATURE:
<223> OTHER INFORMATION: Preselection sequence 12A

<400> SEQUENCE: 168

Met Ser Thr Thr Leu Ser Thr Cys Ser Ser Thr Leu Pro Gln Phe Pro
1               5                   10                  15

Thr Ala Pro Cys Gly Ala Ile Asn Asn Asn Thr Thr Arg Gly Thr Arg
            20                  25                  30

Pro Gly Ser Gly Ser Leu Gly His His His His His His Arg Leu
        35                  40                  45


<210> SEQ ID NO 169
<211> LENGTH: 38
<212> TYPE: DNA
<213> ORGANISM: Artificial Sequence
<220> FEATURE:
<223> OTHER INFORMATION: Primer

<400> SEQUENCE: 169

taatacgact cactataggg ttaactttag taaggagg                             38


<210> SEQ ID NO 170
<211> LENGTH: 43
<212> TYPE: DNA
<213> ORGANISM: Artificial Sequence
<220> FEATURE:
<223> OTHER INFORMATION: Primer

<400> SEQUENCE: 170

ctagctacct atagccggtg gtgatggtga tggtggccta agc                        43


<210> SEQ ID NO 171
<211> LENGTH: 8
<212> TYPE: PRT
<213> ORGANISM: Artificial Sequence
<220> FEATURE:
<223> OTHER INFORMATION: FLAG-tag

<400> SEQUENCE: 171

Asp Tyr Lys Asp Asp Asp Asp Lys
1               5


<210> SEQ ID NO 172
<211> LENGTH: 30
<212> TYPE: DNA
<213> ORGANISM: Artificial Sequence
<220> FEATURE:
<223> OTHER INFORMATION: Cut-Fr1-FP

<400> SEQUENCE: 172

ctcggatcct aatacgactc actatagggt                                      30


<210> SEQ ID NO 173
<211> LENGTH: 44
<212> TYPE: DNA
<213> ORGANISM: Artificial Sequence
```

<220> FEATURE:
<223> OTHER INFORMATION: Cut-Fr1-RP-0

<400> SEQUENCE: 173
tttgtcatcg tcgtctttat aatccattta gctgtcctcc ttac 44

<210> SEQ ID NO 174
<211> LENGTH: 53
<212> TYPE: DNA
<213> ORGANISM: Artificial Sequence
<220> FEATURE:
<223> OTHER INFORMATION: Cut-Fr2-FP-10F2

<400> SEQUENCE: 174
gattataaag acgacgatga caaaggctcc ggtcatccgt acaacacgtc gcg 53

<210> SEQ ID NO 175
<211> LENGTH: 53
<212> TYPE: DNA
<213> ORGANISM: Artificial Sequence
<220> FEATURE:
<223> OTHER INFORMATION: Cut-Fr2-FP-10F3

<400> SEQUENCE: 175
gattataaag acgacgatga caaaggctcc ggtgatacac tacaccttaa gca 53

<210> SEQ ID NO 176
<211> LENGTH: 53
<212> TYPE: DNA
<213> ORGANISM: Artificial Sequence
<220> FEATURE:
<223> OTHER INFORMATION: Cut-Fr2-FP-10F5

<400> SEQUENCE: 176
gattataaag acgacgatga caaaggctcc ggtagtccac atctccccgt act 53

<210> SEQ ID NO 177
<211> LENGTH: 53
<212> TYPE: DNA
<213> ORGANISM: Artificial Sequence
<220> FEATURE:
<223> OTHER INFORMATION: Cut-Fr2-FP-10F6

<400> SEQUENCE: 177
gattataaag acgacgatga caaaggctcc ggtttgatgt ttatccgcat tta 53

<210> SEQ ID NO 178
<211> LENGTH: 53
<212> TYPE: DNA
<213> ORGANISM: Artificial Sequence
<220> FEATURE:
<223> OTHER INFORMATION: Cut-Fr2-FP-10F8

<400> SEQUENCE: 178
gattataaag acgacgatga caaaggctcc ggtttactga aaatggtgga tca 53

<210> SEQ ID NO 179
<211> LENGTH: 53
<212> TYPE: DNA
<213> ORGANISM: Artificial Sequence
<220> FEATURE:
<223> OTHER INFORMATION: Cut-Fr2-FP-10F9

<400> SEQUENCE: 179
gattataaag acgacgatga caaaggctcc ggtcgatcaa cacttaattc act 53

<210> SEQ ID NO 180
<211> LENGTH: 53
<212> TYPE: DNA
<213> ORGANISM: Artificial Sequence
<220> FEATURE:
<223> OTHER INFORMATION: Cut-Fr2-FP-10F12

<400> SEQUENCE: 180
gattataaag acgacgatga caaaggctcc ggttgctatg tgactgttat tcc 53

<210> SEQ ID NO 181
<211> LENGTH: 53
<212> TYPE: DNA
<213> ORGANISM: Artificial Sequence
<220> FEATURE:
<223> OTHER INFORMATION: Cut-Fr2-FP-10V1

<400> SEQUENCE: 181
gattataaag acgacgatga caaaggctcc ggtgccacca agaccaactg caa 53

<210> SEQ ID NO 182
<211> LENGTH: 53
<212> TYPE: DNA
<213> ORGANISM: Artificial Sequence
<220> FEATURE:
<223> OTHER INFORMATION: Cut-Fr2-FP-10V8

<400> SEQUENCE: 182
gattataaag acgacgatga caaaggctcc ggtgtgttgc ccaccatcat ctc 53

<210> SEQ ID NO 183
<211> LENGTH: 53
<212> TYPE: DNA
<213> ORGANISM: Artificial Sequence
<220> FEATURE:
<223> OTHER INFORMATION: Cut-Fr2-FP-10V9

<400> SEQUENCE: 183
gattataaag acgacgatga caaaggctcc ggtaccagca tcccctacac cta 53

<210> SEQ ID NO 184
<211> LENGTH: 30
<212> TYPE: DNA
<213> ORGANISM: Artificial Sequence
<220> FEATURE:
<223> OTHER INFORMATION: Cut-Fr2-RP

<400> SEQUENCE: 184
catgctcgag ctagctacct atagccggtg 30

<210> SEQ ID NO 185
<211> LENGTH: 82
<212> TYPE: DNA
<213> ORGANISM: Artificial Sequence
<220> FEATURE:
<223> OTHER INFORMATION: Fragment 1

<400> SEQUENCE: 185
ctcggatcct aatacgactc actatagggt taactttagt aaggaggaca gctaaatgga 60
ttataaagac gacgatgaca aa 82

<210> SEQ ID NO 186
<211> LENGTH: 212
<212> TYPE: DNA
<213> ORGANISM: Artificial Sequence
<220> FEATURE:
<223> OTHER INFORMATION: Fragment 2 - 10F2

<400> SEQUENCE: 186
gattataaag acgacgatga caaaggctcc ggtcatccgt acaacacgtc gcgtacttca 60
gctatgatgg ccgctctgaa gatgcaagtt actgatatgt atgccttggc cttgttccat 120
aggatactgg gctccggttc tctgggtcat caccaccatc accaccggct ataggtagct 180
agctcgagca tgcatctaga gggcccaatt cg 212

<210> SEQ ID NO 187
<211> LENGTH: 57
<212> TYPE: PRT
<213> ORGANISM: Artificial Sequence
<220> FEATURE:
<223> OTHER INFORMATION: MFLAG-10F2

<400> SEQUENCE: 187

Met Asp Tyr Lys Asp Asp Asp Asp Lys Gly Ser Gly His Pro Tyr Asn
1 5 10 15

Thr Ser Arg Thr Ser Ala Met Met Ala Ala Leu Lys Met Gln Val Thr
20 25 30

Asp Met Tyr Ala Leu Ala Leu Phe His Arg Ile Leu Gly Ser Gly Leu
35 40 45

Gly His His His His His His Arg Leu
50 55

<210> SEQ ID NO 188
<211> LENGTH: 297
<212> TYPE: DNA
<213> ORGANISM: Artificial Sequence
<220> FEATURE:
<223> OTHER INFORMATION: MFLAG-10F2

<400> SEQUENCE: 188
catgattacg ccaagcttgg taccgagctc ggatcctaat acgactcact atagggttaa 60
ctttagtaag gaggacagct aaatggatta taaagacgac gatgacaaag gctccggtca 120
tccgtacaac acgtcgcgta cttcagctat gatggccgct ctgaagatgc aagttactga 180
tatgtatgcc ttggccttgt tccataggat actgggctcc ggttctctgg gtcatcacca 240
ccatcaccac cggctatagg tagctagctc gagcatgcat ctagagggcc caattcg 297

<210> SEQ ID NO 189
<211> LENGTH: 57
<212> TYPE: PRT
<213> ORGANISM: Artificial Sequence
<220> FEATURE:
<223> OTHER INFORMATION: MFLAG-10F3

<400> SEQUENCE: 189

Met Asp Tyr Lys Asp Asp Asp Asp Lys Gly Ser Gly Asp Thr Leu His
1 5 10 15

Leu Lys Gln Ile Gly Gly Met Pro Asn Cys Ile Thr Gln Gln Asp Val
20 25 30

Arg Met Thr Ser Ile Pro Tyr Thr Tyr Thr Trp Pro Gly Ser Gly Leu
35 40 45

Gly His His His His His His Arg Leu
50 55

<210> SEQ ID NO 190

-continued

<211> LENGTH: 297
<212> TYPE: DNA
<213> ORGANISM: Artificial Sequence
<220> FEATURE:
<223> OTHER INFORMATION: MFLAG-10F3

<400> SEQUENCE: 190
catgattacg ccaagcttgg taccgagctc ggatcctaat acgactcact atagggttaa 60
ctttagtaag gaggacagct aaatggatta taaagacgac gatgacaaag gctccggtga 120
tacactacac cttaagcaga tcggaggaat gccaaattgc atcactcaac aggacgtacg 180
aatgacatcc attccatata cctatacatg gcctggctcc ggttctctgg gtcatcacca 240
ccatcaccac cggctatagg tagctagctc gagcatgcat ctagagggcc caattcg 297

<210> SEQ ID NO 191
<211> LENGTH: 57
<212> TYPE: PRT
<213> ORGANISM: Artificial Sequence
<220> FEATURE:
<223> OTHER INFORMATION: MFLAG-10F5

<400> SEQUENCE: 191

Met Asp Tyr Lys Asp Asp Asp Asp Lys Gly Ser Gly Ser Pro His Leu
1 5 10 15

Pro Val Leu Leu Cys Lys Met Val Leu Asn Asp Gly Arg Arg Ile Val
20 25 30

Gln Met Ser Cys Glu Leu Pro Met Val Arg Arg Ser Gly Ser Gly Leu
35 40 45

Gly His His His His His His Arg Leu
50 55

<210> SEQ ID NO 192
<211> LENGTH: 297
<212> TYPE: DNA
<213> ORGANISM: Artificial Sequence
<220> FEATURE:
<223> OTHER INFORMATION: MFLAG-10F5

<400> SEQUENCE: 192
catgattacg ccaagcttgg taccgagctc ggatcctaat acgactcact atagggttaa 60
ctttagtaag gaggacagct aaatggatta taaagacgac gatgacaaag gctccggtag 120
tccacatctc cccgtactgt tatgtaagat ggtcctaaac gatggtagac ggattgttca 180
aatgtcttgt gaactgccaa tggttcgacg atcaggctcc ggttctctgg gtcatcacca 240
ccatcaccac cggctatagg tagctagctc gagcatgcat ctagagggcc caattcg 297

<210> SEQ ID NO 193
<211> LENGTH: 57
<212> TYPE: PRT
<213> ORGANISM: Artificial Sequence
<220> FEATURE:
<223> OTHER INFORMATION: MFLAG-10F6

<400> SEQUENCE: 193

Met Asp Tyr Lys Asp Asp Asp Asp Lys Gly Ser Gly Leu Met Phe Ile
1 5 10 15

Arg Ile Tyr Pro Thr Arg Met Gln Tyr Val Tyr His Ala Pro Leu Leu
20 25 30

Thr Met Val Arg Met Ser Pro Thr Gly Pro Leu Ile Gly Ser Gly Leu
35 40 45

```
Gly His His His His His His Arg Leu
    50                  55


<210> SEQ ID NO 194
<211> LENGTH: 297
<212> TYPE: DNA
<213> ORGANISM: Artificial Sequence
<220> FEATURE:
<223> OTHER INFORMATION: MFLAG-10F6

<400> SEQUENCE: 194

catgattacg ccaagcttgg taccgagctc ggatcctaat acgactcact atagggttaa     60

ctttagtaag gaggacagct aaatggatta taaagacgac gatgacaaag gctccggttt    120

gatgtttatc cgcatttatc ctacccgcat gcagtatgtc tatcacgctc ctctgcttac    180

gatggttcgt atgtccccga ctggtcccct aatcggctcc ggttctctgg gtcatcacca    240

ccatcaccac cggctatagg tagctagctc gagcatgcat ctagagggcc caattcg       297


<210> SEQ ID NO 195
<211> LENGTH: 57
<212> TYPE: PRT
<213> ORGANISM: Artificial Sequence
<220> FEATURE:
<223> OTHER INFORMATION: MFLAG-10F8

<400> SEQUENCE: 195

Met Asp Tyr Lys Asp Asp Asp Asp Lys Gly Ser Gly Leu Leu Lys Met
1               5                   10                  15

Val Asp Gln Ser Arg Leu Met Pro Val Pro Gly Ile Gly Val Thr Leu
            20                  25                  30

His Met Arg Ser Ile Pro Tyr Ser Tyr Leu Pro Ile Gly Ser Gly Leu
        35                  40                  45

Gly His His His His His His Arg Leu
    50                  55


<210> SEQ ID NO 196
<211> LENGTH: 297
<212> TYPE: DNA
<213> ORGANISM: Artificial Sequence
<220> FEATURE:
<223> OTHER INFORMATION: MFLAG-10F8

<400> SEQUENCE: 196

catgattacg ccaagcttgg taccgagctc ggatcctaat acgactcact atagggttaa     60

ctttagtaag gaggacagct aaatggatta taaagacgac gatgacaaag gctccggttt    120

actgaaaatg gtggatcaat cgagactcat gcccgttccc ggaattgggg tgactttgca    180

tatgagatct attccttata gttacttacc aataggctcc ggttctctgg gtcatcacca    240

ccatcaccac cggctatagg tagctagctc gagcatgcat ctagagggcc caattcg       297


<210> SEQ ID NO 197
<211> LENGTH: 57
<212> TYPE: PRT
<213> ORGANISM: Artificial Sequence
<220> FEATURE:
<223> OTHER INFORMATION: MFLAG-10F9

<400> SEQUENCE: 197

Met Asp Tyr Lys Asp Asp Asp Asp Lys Gly Ser Gly Arg Ser Thr Leu
1               5                   10                  15
```

```
Asn Ser Leu Glu Tyr Arg Met Gln Tyr Ala Thr Glu Asp Pro Arg Ile
            20                  25                  30

Arg Met Ala Ser Ile Pro Tyr Thr Tyr Trp Trp Pro Gly Ser Gly Leu
        35                  40                  45

Gly His His His His His His Arg Leu
    50                  55


<210> SEQ ID NO 198
<211> LENGTH: 297
<212> TYPE: DNA
<213> ORGANISM: Artificial Sequence
<220> FEATURE:
<223> OTHER INFORMATION: MFLAG-10F8

<400> SEQUENCE: 198

catgattacg ccaagcttgg taccgagctc ggatcctaat acgactcact atagggttaa     60

ctttagtaag gaggacagct aaatggatta taaagacgac gatgacaaag gctccggtcg    120

atcaacactt aattcactag aataccgaat gcaatatgca actgaggacc caaggatacg    180

catggctagt ataccctaca catattggtg gcccggctcc ggttctctgg gtcatcacca    240

ccatcaccac cggctatagg tagctagctc gagcatgcat ctagagggcc caattcg       297


<210> SEQ ID NO 199
<211> LENGTH: 57
<212> TYPE: PRT
<213> ORGANISM: Artificial Sequence
<220> FEATURE:
<223> OTHER INFORMATION: MFLAG-10F12

<400> SEQUENCE: 199

Met Asp Tyr Lys Asp Asp Asp Asp Lys Gly Ser Gly Cys Tyr Val Thr
1               5                   10                  15

Val Ile Pro Ala Met Asn Met Pro Glu Ala Arg Leu Gly Ile Val Cys
            20                  25                  30

His Met Pro Gly Ile Arg Arg Gly Lys Ala Leu Tyr Gly Ser Gly Leu
        35                  40                  45

Gly His His His His His His Arg Leu
    50                  55


<210> SEQ ID NO 200
<211> LENGTH: 297
<212> TYPE: DNA
<213> ORGANISM: Artificial Sequence
<220> FEATURE:
<223> OTHER INFORMATION: MFLAG-10F12

<400> SEQUENCE: 200

catgattacg ccaagcttgg taccgagctc ggatcctaat acgactcact atagggttaa     60

ctttagtaag gaggacagct aaatggatta taaagacgac gatgacaaag gctccggttg    120

ctatgtgact gttattccgg ctatgaatat gccggaagct agactcggca ttgtctgcca    180

catgcctggg atcaggcgtg ggaaggcctt gtacggctcc ggttctctgg gtcatcacca    240

ccatcaccac cggctatagg tagctagctc gagcatgcat ctagagggcc caattcg       297


<210> SEQ ID NO 201
<211> LENGTH: 57
<212> TYPE: PRT
<213> ORGANISM: Artificial Sequence
<220> FEATURE:
<223> OTHER INFORMATION: MFLAG-10V1
```

<400> SEQUENCE: 201

Met Asp Tyr Lys Asp Asp Asp Asp Lys Gly Ser Gly Ala Thr Lys Thr
1 5 10 15

Asn Cys Lys Arg Glu Lys Thr Met Asp Asn His Val Thr Ile Met Arg
20 25 30

Ser Ile Pro Trp Tyr Thr Tyr Arg Trp Leu Pro Asn Gly Ser Gly Leu
35 40 45

Gly His His His His His His Arg Leu
50 55

<210> SEQ ID NO 202
<211> LENGTH: 297
<212> TYPE: DNA
<213> ORGANISM: Artificial Sequence
<220> FEATURE:
<223> OTHER INFORMATION: MFLAG-10V1

<400> SEQUENCE: 202
catgattacg ccaagcttgg taccgagctc ggatcctaat acgactcact atagggttaa 60
ctttagtaag gaggacagct aaatggatta taaagacgac gatgacaaag gctccggtgc 120
caccaagacc aactgcaagc gggagaagac catggacaac cacgtgacga tcatgaggag 180
catcccgtgg tacacgtacc gctggttgcc caacggctcc ggtagcttag gccaccatca 240
ccatcaccac cggctatagg tagctagctc gagcatgcat ctagagggcc caattcg 297

<210> SEQ ID NO 203
<211> LENGTH: 57
<212> TYPE: PRT
<213> ORGANISM: Artificial Sequence
<220> FEATURE:
<223> OTHER INFORMATION: MFLAG-10V8

<400> SEQUENCE: 203

Met Asp Tyr Lys Asp Asp Asp Asp Lys Gly Ser Gly Val Leu Pro Thr
1 5 10 15

Ile Ile Ser Thr Asn Val Asn Pro Phe Arg Met Leu Ser Ile Pro Thr
20 25 30

Tyr Thr Tyr Leu Met Pro Ile Thr Trp Gly Glu Ile Gly Ser Gly Leu
35 40 45

Gly His His His His His His Arg Leu
50 55

<210> SEQ ID NO 204
<211> LENGTH: 297
<212> TYPE: DNA
<213> ORGANISM: Artificial Sequence
<220> FEATURE:
<223> OTHER INFORMATION: MFLAG-10V8

<400> SEQUENCE: 204
catgattacg ccaagcttgg taccgagctc ggatcctaat acgactcact atagggttaa 60
ctttagtaag gaggacagct aaatggatta taaagacgac gatgacaaag gctccggtgt 120
gttgcccacc atcatctcga ccaacgtgaa cccgttccgg atgctctcga tcccgaccta 180
cacgtacctg atgcccatca cgtggggcga gatcggctcc ggtagcttag gccaccatca 240
ccatcaccac cggctatagg tagctagctc gagcatgcat ctagagggcc caattcg 297

<210> SEQ ID NO 205

<211> LENGTH: 57
<212> TYPE: PRT
<213> ORGANISM: Artificial Sequence
<220> FEATURE:
<223> OTHER INFORMATION: MFLAG-10V9

<400> SEQUENCE: 205

```
Met Asp Tyr Lys Asp Asp Asp Asp Lys Gly Ser Gly Thr Ser Ile Pro
1               5                   10                  15

Tyr Thr Tyr Leu Asn Arg Ser Leu Trp Thr Asn Tyr Arg Val Asn Ser
            20                  25                  30

Trp Ser Met Ser Lys Asn Val Asn Val Met Pro Leu Gly Ser Gly Leu
        35                  40                  45

Gly His His His His His His Arg Leu
    50                  55
```

<210> SEQ ID NO 206
<211> LENGTH: 298
<212> TYPE: DNA
<213> ORGANISM: Artificial Sequence
<220> FEATURE:
<223> OTHER INFORMATION: MFLAG-10V9

<400> SEQUENCE: 206

```
catgattacg ccaagcttgg taccgagctc ggatcctaat acgactcact atagggttaa     60

ctttagtaag gaggacagct aaatggatta taaagacgac gatgacaaag gctccggtac    120

cagcatcccc tacacctacc tcaaccgctc gctgtggacg aactaccgcg tcaacagctg    180

gagcatgtcc aagaacgtga acgtgatgcc gttgggctcc ggtagcttag gccaccatca    240

ccattcacca ccggctatag gtagctagct cgagcatgca tctagagggc ccaattcg      298
```

<210> SEQ ID NO 207
<211> LENGTH: 42
<212> TYPE: DNA
<213> ORGANISM: Artificial Sequence
<220> FEATURE:
<223> OTHER INFORMATION: FixL-RP-CHRL

<400> SEQUENCE: 207

```
ctagctacct atagccggtg gcagtggtga tggtggtgat ga                        42
```

<210> SEQ ID NO 208
<211> LENGTH: 42
<212> TYPE: DNA
<213> ORGANISM: Artificial Sequence
<220> FEATURE:
<223> OTHER INFORMATION: VarL-RP-CHRL

<400> SEQUENCE: 208

```
ctagctacct atagccggtg gcagtggtga tggtgatggt gg                        42
```

<210> SEQ ID NO 209
<211> LENGTH: 29
<212> TYPE: DNA
<213> ORGANISM: Artificial Sequence
<220> FEATURE:
<223> OTHER INFORMATION: MAP-FP

<400> SEQUENCE: 209

```
cgtcatatgg ctatctcaat caagacccc                                       29
```

<210> SEQ ID NO 210
<211> LENGTH: 30

<212> TYPE: DNA
<213> ORGANISM: Artificial Sequence
<220> FEATURE:
<223> OTHER INFORMATION: MAP-RP

<400> SEQUENCE: 210
agccggatcc ttattcgtcg tgcgagatta 30

<210> SEQ ID NO 211
<211> LENGTH: 39
<212> TYPE: DNA
<213> ORGANISM: Artificial Sequence
<220> FEATURE:
<223> OTHER INFORMATION: PDF-FP

<400> SEQUENCE: 211
gcatacatat gtcagttttg caagtgttac atattccgg 39

<210> SEQ ID NO 212
<211> LENGTH: 30
<212> TYPE: DNA
<213> ORGANISM: Artificial Sequence
<220> FEATURE:
<223> OTHER INFORMATION: PDF-RP

<400> SEQUENCE: 212
ggtgctcgag agcccgggct ttcagacgat 30

<210> SEQ ID NO 213
<211> LENGTH: 73
<212> TYPE: DNA
<213> ORGANISM: Artificial Sequence
<220> FEATURE:
<223> OTHER INFORMATION: MH6C-1

<400> SEQUENCE: 213
taatacgact cactataggg ttaactttag taaggaggac agctaaatgc accaccatca 60
ccatcactgc aaa 73

<210> SEQ ID NO 214
<211> LENGTH: 76
<212> TYPE: DNA
<213> ORGANISM: Artificial Sequence
<220> FEATURE:
<223> OTHER INFORMATION: MAH6C-1

<400> SEQUENCE: 214
taatacgact cactataggg ttaactttag taaggaggac agctaaatgg cgcaccacca 60
tcaccatcac tgcaaa 76

<210> SEQ ID NO 215
<211> LENGTH: 77
<212> TYPE: DNA
<213> ORGANISM: Artificial Sequence
<220> FEATURE:
<223> OTHER INFORMATION: MH6C-2AAdeltaM

<400> SEQUENCE: 215
ctagctacct atagccggtg gcatttatgg gtcagacgcg ccgggtcgat gtaggctttg 60
cagtgatggt gatggtg 77

<210> SEQ ID NO 216
<211> LENGTH: 24
<212> TYPE: PRT

<213> ORGANISM: Artificial Sequence
<220> FEATURE:
<223> OTHER INFORMATION: MH6C-2AAdeltaM

<400> SEQUENCE: 216

Met His His His His His His Cys Lys Ala Tyr Ile Asp Pro Ala Arg
1               5                   10                  15

Leu Thr His Lys Cys His Arg Leu
            20

<210> SEQ ID NO 217
<211> LENGTH: 25
<212> TYPE: PRT
<213> ORGANISM: Artificial Sequence
<220> FEATURE:
<223> OTHER INFORMATION: MAH6C-2AAdeltaM

<400> SEQUENCE: 217

Met Ala His His His His His His Cys Lys Ala Tyr Ile Asp Pro Ala
1               5                   10                  15

Arg Leu Thr His Lys Cys His Arg Leu
            20                  25

<210> SEQ ID NO 218
<211> LENGTH: 49
<212> TYPE: PRT
<213> ORGANISM: Artificial Sequence
<220> FEATURE:
<223> OTHER INFORMATION: H-E-2
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: MISC_FEATURE
<222> LOCATION: (18)..(18)
<223> OTHER INFORMATION: Xaa at position 18 is a glycosylated derivative
of homopropargylglycine or homopropargylglycine
<220> FEATURE:
<221> NAME/KEY: misc_feature
<222> LOCATION: (19)..(49)
<223> OTHER INFORMATION: Xaa can be any naturally occurring amino acid

<400> SEQUENCE: 218

Ala Xaa Xaa Xaa Xaa Xaa Xaa Xaa Ile Gly Asp Ile Arg Xaa Ala Xaa
1               5                   10                  15

Cys Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 219
<211> LENGTH: 197
<212> TYPE: DNA
<213> ORGANISM: Artificial Sequence
<220> FEATURE:
<223> OTHER INFORMATION: H-E-2
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:

<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 219
gtggtgatga cccagagaac cggagccsnn snnsnnsnns nnsnnsnnsn nsnnsnnsnn 60
snnsnnsnns nnsnnsnnsn nsnnsnnsnn snnsnnsnns nnsnnsnnsn nsnnsnnsnn 120
catgcasnnc gcsnnacgaa tatcgccaat snnsnnsnns nnsnnsnnsn ncgccattta 180
gctgtcctcc ttactaa 197

<210> SEQ ID NO 220
<211> LENGTH: 49
<212> TYPE: PRT
<213> ORGANISM: Artificial Sequence
<220> FEATURE:
<223> OTHER INFORMATION: H-M-2
<220> FEATURE:
<221> NAME/KEY: misc_feature
<222> LOCATION: (2)..(19)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine
<220> FEATURE:
<221> NAME/KEY: misc_feature
<222> LOCATION: (30)..(49)
<223> OTHER INFORMATION: Xaa can be any naturally occurring amino acid

<400> SEQUENCE: 220

Ala Xaa Xaa Xaa Xaa Xaa Xaa Xaa Xaa Xaa Xaa Xaa Xaa Xaa Xaa Xaa
1 5 10 15

Xaa Xaa Xaa Ile Gly Asp Ile Arg Xaa Ala Xaa Cys Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa

<210> SEQ ID NO 221
<211> LENGTH: 197
<212> TYPE: DNA
<213> ORGANISM: Artificial Sequence
<220> FEATURE:
<223> OTHER INFORMATION: H-M-2
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)

<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 221
gtggtgatga cccagagaac cggagccsnn snnsnnsnns nnsnnsnnsn nsnnsnnsnn 60
snnsnnsnns nnsnnsnnsn nsnnsnncat gcasnncgcs nnacgaatat cgccaatsnn 120
snnsnnsnns nnsnnsnnsn nsnnsnnsnn snnsnnsnns nnsnnsnnsn ncgccattta 180
gctgtcctcc ttactaa 197

<210> SEQ ID NO 222
<211> LENGTH: 49
<212> TYPE: PRT
<213> ORGANISM: Artificial Sequence
<220> FEATURE:

<223> OTHER INFORMATION: H-L-2
<220> FEATURE:
<221> NAME/KEY: misc_feature
<222> LOCATION: (2)..(30)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: MISC_FEATURE
<222> LOCATION: (40)..(40)
<223> OTHER INFORMATION: Xaa at position 40 is a glycosylated derivative
of homopropargylglycine or homopropargylglycine
<220> FEATURE:
<221> NAME/KEY: misc_feature
<222> LOCATION: (41)..(49)
<223> OTHER INFORMATION: Xaa can be any naturally occurring amino acid

<400> SEQUENCE: 222

Ala Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Ile Gly
20 25 30

Asp Ile Arg Xaa Ala Xaa Cys Xaa Xaa Xaa Xaa Xaa Xaa Xaa Xaa Xaa
35 40 45

Xaa

<210> SEQ ID NO 223
<211> LENGTH: 197
<212> TYPE: DNA
<213> ORGANISM: Artificial Sequence
<220> FEATURE:
<223> OTHER INFORMATION: H-L-2
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)

<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 223

```
gtggtgatga cccagagaac cggagccsnn snnsnnsnns nnsnnsnnsn nsnncatgca     60

snncgcsnna cgaatatcgc caatsnnsnn snnsnnsnns nnsnnsnnsn nsnnsnnsnn    120

snnsnnsnns nnsnnsnnsn nsnnsnnsnn snnsnnsnns nnsnnsnnsn ncgccattta    180

gctgtcctcc ttactaa                                                   197
```

<210> SEQ ID NO 224
<211> LENGTH: 49
<212> TYPE: PRT
<213> ORGANISM: Artificial Sequence
<220> FEATURE:
<223> OTHER INFORMATION: L-E-3
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: misc_feature
<222> LOCATION: (14)..(49)
<223> OTHER INFORMATION: Xaa can be any naturally occurring amino acid

<400> SEQUENCE: 224

```
Ala Xaa Xaa Xaa Xaa Xaa Xaa Xaa Ile Gly Asp Ile Arg Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30
```

Xaa Xaa Xaa Xaa Xaa Xaa Xaa Xaa Xaa Xaa Xaa Xaa Xaa Xaa Xaa Xaa
35 40 45

Xaa

<210> SEQ ID NO 225
<211> LENGTH: 197
<212> TYPE: DNA
<213> ORGANISM: Artificial Sequence
<220> FEATURE:
<223> OTHER INFORMATION: L-E-3
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:

<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 225
gtgatggtgg cctaagctac cggagccsnn snnsnnsnns nnsnnsnnsn nsnnsnnsnn 60
snnsnnsnns nnsnnsnnsn nsnnsnnsnn snnsnnsnns nnsnnsnnsn nsnnsnnsnn 120
snnsnnsnns nnsnnacgaa tatcgccaat snnsnnsnns nnsnnsnnsn ncgccattta 180
gctgtcctcc ttactaa 197

<210> SEQ ID NO 226
<211> LENGTH: 49
<212> TYPE: PRT
<213> ORGANISM: Artificial Sequence
<220> FEATURE:
<223> OTHER INFORMATION: L-M-3
<220> FEATURE:
<221> NAME/KEY: misc_feature
<222> LOCATION: (2)..(19)
<223> OTHER INFORMATION: Xaa can be any naturally occurring amino acid
<220> FEATURE:
<221> NAME/KEY: misc_feature
<222> LOCATION: (25)..(49)
<223> OTHER INFORMATION: Xaa can be any naturally occurring amino acid

<400> SEQUENCE: 226

Ala Xaa Xaa Xaa Xaa Xaa Xaa Xaa Xaa Xaa Xaa Xaa Xaa Xaa Xaa Xaa
1 5 10 15

Xaa Xaa Xaa Ile Gly Asp Ile Arg Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa

<210> SEQ ID NO 227
<211> LENGTH: 197
<212> TYPE: DNA
<213> ORGANISM: Artificial Sequence
<220> FEATURE:
<223> OTHER INFORMATION: L-M-3
<220> FEATURE:
<221> NAME/KEY: misc_feature
<222> LOCATION: (29)..(30)
<223> OTHER INFORMATION: n is a, c, g, or t
<220> FEATURE:

<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)

<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 227
gtgatggtgg cctaagctac cggagccsnn snnsnnsnns nnsnnsnnsn nsnnsnnsnn 60
snnsnnsnns nnsnnsnnsn nsnnsnnsnn snnsnnsnns nnacgaatat cgccaatsnn 120
snnsnnsnns nnsnnsnnsn nsnnsnnsnn snnsnnsnns nnsnnsnnsn ncgccattta 180
gctgtcctcc ttactaa 197

<210> SEQ ID NO 228
<211> LENGTH: 49
<212> TYPE: PRT
<213> ORGANISM: Artificial Sequence
<220> FEATURE:
<223> OTHER INFORMATION: L-L-3
<220> FEATURE:
<221> NAME/KEY: misc_feature
<222> LOCATION: (2)..(30)
<223> OTHER INFORMATION: Xaa can be any naturally occurring amino acid
<220> FEATURE:
<221> NAME/KEY: misc_feature
<222> LOCATION: (36)..(49)
<223> OTHER INFORMATION: Xaa can be any naturally occurring amino acid

<400> SEQUENCE: 228

Ala Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Ile Gly
20 25 30

Asp Ile Arg Xaa Xaa Xaa Xaa Xaa Xaa Xaa Xaa Xaa Xaa Xaa Xaa Xaa
35 40 45

Xaa

<210> SEQ ID NO 229
<211> LENGTH: 197
<212> TYPE: DNA
<213> ORGANISM: Artificial Sequence
<220> FEATURE:
<223> OTHER INFORMATION: L-L-3
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)

<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 229
gtgatggtgg cctaagctac cggagccsnn snnsnnsnns nnsnnsnnsn nsnnsnnsnn 60
snnsnnsnna cgaatatcgc caatsnnsnn snnsnnsnns nnsnnsnnsn nsnnsnnsnn 120

```
snnsnnsnns nnsnnsnnsn nsnnsnnsnn snnsnnsnns nnsnnsnnsn ncgccattta    180

gctgtcctcc ttactaa                                                    197


<210> SEQ ID NO 230
<211> LENGTH: 49
<212> TYPE: PRT
<213> ORGANISM: Artificial Sequence
<220> FEATURE:
<223> OTHER INFORMATION: L-O-3
<220> FEATURE:
<221> NAME/KEY: misc_feature
<222> LOCATION: (2)..(49)
<223> OTHER INFORMATION: Xaa can be any naturally occurring amino acid

<400> SEQUENCE: 230

Ala Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa


<210> SEQ ID NO 231
<211> LENGTH: 197
<212> TYPE: DNA
<213> ORGANISM: Artificial Sequence
<220> FEATURE:
<223> OTHER INFORMATION: L-O-3
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
```

<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:

<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t

<400> SEQUENCE: 231
gtgatggtgg cctaagctac cggagccsnn snnsnnsnns nnsnnsnnsn nsnnsnnsnn 60
snnsnnsnns nnsnnsnnsn nsnnsnnsnn snnsnnsnns nnsnnsnnsn nsnnsnnsnn 120
snnsnnsnns nnsnnsnnsn nsnnsnnsnn snnsnnsnns nnsnnsnnsn ncgccattta 180
gctgtcctcc ttactaa 197

<210> SEQ ID NO 232
<211> LENGTH: 46
<212> TYPE: DNA
<213> ORGANISM: Artificial Sequence
<220> FEATURE:
<223> OTHER INFORMATION: Forward extending primer

<400> SEQUENCE: 232
taatacgact cactataggg ttaactttag taaggaggac agctaa 46

<210> SEQ ID NO 233
<211> LENGTH: 46
<212> TYPE: DNA
<213> ORGANISM: Artificial Sequence
<220> FEATURE:
<223> OTHER INFORMATION: Heavily biased reverse extending primer

<400> SEQUENCE: 233
ctagctacct atagccggtg gtgatggtgg tgatgaccca gagaac 46

<210> SEQ ID NO 234
<211> LENGTH: 46
<212> TYPE: DNA
<213> ORGANISM: Artificial Sequence
<220> FEATURE:
<223> OTHER INFORMATION: Less biased reverse extending primer

<400> SEQUENCE: 234
ctagctacct atagccggtg gtgatggtga tggtggccta agctac 46

<210> SEQ ID NO 235
<211> LENGTH: 249
<212> TYPE: DNA
<213> ORGANISM: Artificial Sequence
<220> FEATURE:
<223> OTHER INFORMATION: H-E-2 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (89)..(90)

<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 235
taatacgact cactataggg ttaactttag taaggaggac agctaaatgg cgnnsnnsnn 60
snnsnnsnns nnsattggcg atattcgtnn sgcgnnstgc atgnnsnnsn nsnnsnnsnn 120
snnsnnsnns nnsnnsnnsn nsnnsnnsnn snnsnnsnns nnsnnsnnsn nsnnsnnsnn 180
snnsnnsnns nnsnnsggct ccggttctct gggtcatcac caccatcacc accggctata 240
ggtagctag 249

<210> SEQ ID NO 236
<211> LENGTH: 249
<212> TYPE: DNA
<213> ORGANISM: Artificial Sequence
<220> FEATURE:
<223> OTHER INFORMATION: H-M-2 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:

<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 236
taatacgact cactataggg ttaactttag taaggaggac agctaaatgg cgnnsnnsnn 60
snnsnnsnns nnsnnsnnsn nsnnsnnsnn snnsnnsnns nnsnnsattg gcgatattcg 120

-continued

```
tnnsgcgnns tgcatgnnsn nsnnsnnsnn snnsnnsnns nnsnnsnnsn nsnnsnnsnn    180

snnsnnsnns nnsnnsggct ccggttctct gggtcatcac caccatcacc accggctata    240

ggtagctag                                                            249


<210> SEQ ID NO 237
<211> LENGTH: 249
<212> TYPE: DNA
<213> ORGANISM: Artificial Sequence
<220> FEATURE:
<223> OTHER INFORMATION: H-L-2 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
```

<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:

<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 237
taatacgact cactataggg ttaactttag taaggaggac agctaaatgg cgnnsnnsnn 60
snnsnnsnns nnsnnsnnsn nsnnsnnsnn snnsnnsnns nnsnnsnnsn nsnnsnnsnn 120
snnsnnsnns nnsnnsnnsa ttggcgatat tcgtnnsgcg nnstgcatgn nsnnsnnsnn 180
snnsnnsnns nnsnnsggct ccggttctct gggtcatcac caccatcacc accggctata 240
ggtagctag 249

<210> SEQ ID NO 238
<211> LENGTH: 249
<212> TYPE: DNA
<213> ORGANISM: Artificial Sequence
<220> FEATURE:
<223> OTHER INFORMATION: L-E-3 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)

<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 238
taatacgact cactataggg ttaactttag taaggaggac agctaaatgg cgnnsnnsnn 60
snnsnnsnns nnsattggcg atattcgtnn snnsnnsnns nnsnnsnnsn nsnnsnnsnn 120
snnsnnsnns nnsnnsnnsn nsnnsnnsnn snnsnnsnns nnsnnsnnsn nsnnsnnsnn 180
snnsnnsnns nnsnnsggct ccggtagctt aggccaccat caccatcacc accggctata 240
ggtagctag 249

<210> SEQ ID NO 239
<211> LENGTH: 249
<212> TYPE: DNA
<213> ORGANISM: Artificial Sequence
<220> FEATURE:
<223> OTHER INFORMATION: L-M-3 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:

<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 239
taatacgact cactataggg ttaactttag taaggaggac agctaaatgg cgnnsnnsnn 60
snnsnnsnns nnsnnsnnsn nsnnsnnsnn snnsnnsnns nnsnnsattg gcgatattcg 120
tnnsnnsnns nnsnnsnnsn nsnnsnnsnn snnsnnsnns nnsnnsnnsn nsnnsnnsnn 180
snnsnnsnns nnsnnsggct ccggtagctt aggccaccat caccatcacc accggctata 240
ggtagctag 249

<210> SEQ ID NO 240
<211> LENGTH: 249
<212> TYPE: DNA
<213> ORGANISM: Artificial Sequence
<220> FEATURE:
<223> OTHER INFORMATION: L-L-3 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)

<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (185)..(186)
<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 240
taatacgact cactataggg ttaactttag taaggaggac agctaaatgg cgnnsnnsnn 60
snnsnnsnns nnsnnsnnsn nsnnsnnsnn snnsnnsnns nnsnnsnnsn nsnnsnnsnn 120
snnsnnsnns nnsnnsnnsa ttggcgatat tcgtnnsnns nnsnnsnnsn nsnnsnnsnn 180
snnsnnsnns nnsnnsggct ccggtagctt aggccaccat caccatcacc accggctata 240
ggtagctag 249

<210> SEQ ID NO 241
<211> LENGTH: 249
<212> TYPE: DNA
<213> ORGANISM: Artificial Sequence
<220> FEATURE:
<223> OTHER INFORMATION: L-0-3 full
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:

<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (113)..(114)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature
<222> LOCATION: (119)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (125)..(126)
<223> OTHER INFORMATION: n is a, c, g, or t
<220> FEATURE:
<221> NAME/KEY: misc_feature
<222> LOCATION: (128)..(129)
<223> OTHER INFORMATION: n is a, c, g, or t
<220> FEATURE:
<221> NAME/KEY: misc_feature
<222> LOCATION: (131)..(132)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (137)..(138)
<223> OTHER INFORMATION: n is a, c, g, or t
<220> FEATURE:
<221> NAME/KEY: misc_feature
<222> LOCATION: (140)..(141)
<223> OTHER INFORMATION: n is a, c, g, or t
<220> FEATURE:
<221> NAME/KEY: misc_feature
<222> LOCATION: (143)..(144)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t
<220> FEATURE:
<221> NAME/KEY: misc_feature
<222> LOCATION: (161)..(162)
<223> OTHER INFORMATION: n is a, c, g, or t
<220> FEATURE:
<221> NAME/KEY: misc_feature
<222> LOCATION: (164)..(165)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t
<220> FEATURE:
<221> NAME/KEY: misc_feature
<222> LOCATION: (182)..(183)
<223> OTHER INFORMATION: n is a, c, g, or t
<220> FEATURE:
<221> NAME/KEY: misc_feature
<222> LOCATION: (185)..(186)

<223> OTHER INFORMATION: n is a, c, g, or t
<220> FEATURE:
<221> NAME/KEY: misc_feature
<222> LOCATION: (188)..(189)
<223> OTHER INFORMATION: n is a, c, g, or t
<220> FEATURE:
<221> NAME/KEY: misc_feature
<222> LOCATION: (191)..(192)
<223> OTHER INFORMATION: n is a, c, g, or t
<220> FEATURE:
<221> NAME/KEY: misc_feature
<222> LOCATION: (194)..(195)
<223> OTHER INFORMATION: n is a, c, g, or t

<400> SEQUENCE: 241
taatacgact cactataggg ttaactttag taaggaggac agctaaatgg cgnnsnnsnn 60
snnsnnsnns nnsnnsnnsn nsnnsnnsnn snnsnnsnns nnsnnsnnsn nsnnsnnsnn 120
snnsnnsnns nnsnnsnnsn nsnnsnnsnn snnsnnsnns nnsnnsnnsn nsnnsnnsnn 180
snnsnnsnns nnsnnsggct ccggtagctt aggccaccat caccatcacc accggctata 240
ggtagctag 249

<210> SEQ ID NO 242
<211> LENGTH: 38
<212> TYPE: DNA
<213> ORGANISM: Artificial Sequence
<220> FEATURE:
<223> OTHER INFORMATION: H-RT-RP

<400> SEQUENCE: 242
tttttttttt tttttgtgat ggtggtgatg acccagag 38

<210> SEQ ID NO 243
<211> LENGTH: 38
<212> TYPE: DNA
<213> ORGANISM: Artificial Sequence
<220> FEATURE:
<223> OTHER INFORMATION: L-RT-RP

<400> SEQUENCE: 243
tttttttttt tttttgtgat ggtgatggtg gcctaagc 38

<210> SEQ ID NO 244
<211> LENGTH: 43
<212> TYPE: DNA
<213> ORGANISM: Artificial Sequence
<220> FEATURE:
<223> OTHER INFORMATION: Heavily biased reverse primer

<400> SEQUENCE: 244
ctagctacct atagccggtg gtgatggtgg tgatgaccca gag 43

<210> SEQ ID NO 245
<211> LENGTH: 64
<212> TYPE: PRT
<213> ORGANISM: Artificial Sequence
<220> FEATURE:
<223> OTHER INFORMATION: H-pre-2
<220> FEATURE:
<221> NAME/KEY: MISC_FEATURE
<222> LOCATION: (18)..(18)
<223> OTHER INFORMATION: Xaa at position 18 is a glycosylated derivative
of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative
of homopropargylglycine or homopropargylglycine

<400> SEQUENCE: 245

Met Ala Pro Leu Lys Pro Lys Gly Ser Leu Ala Thr Arg Ala Ala Thr
1 5 10 15

Phe Xaa Ser Arg Ile Gly Asp Ile Arg Ala Ala Phe Cys Xaa Phe Asn
20 25 30

Gly Arg Ala Ser Leu Leu Val Leu Leu Phe Ile Leu Arg Ala Leu His
35 40 45

Val Asp Gly Ser Gly Ser Leu Gly His His His His His His Arg Leu
50 55 60

<210> SEQ ID NO 246
<211> LENGTH: 64
<212> TYPE: PRT
<213> ORGANISM: Artificial Sequence
<220> FEATURE:
<223> OTHER INFORMATION: H-pre-6
<220> FEATURE:
<221> NAME/KEY: MISC_FEATURE
<222> LOCATION: (6)..(6)
<223> OTHER INFORMATION: Xaa at position 6 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 246

Met Ala Asn Arg Thr Xaa Tyr Asn His Ile Arg Val Asn Asp Trp Thr
1 5 10 15

His Leu Ala Ile Xaa Leu Leu Asp Glu Val Arg Lys Gln Ser Cys Ile
20 25 30

Gly Asp Ile Arg Arg Ala Asn Cys Xaa Pro Trp Lys Ser Ser Asp Gln
35 40 45

Asn Glu Gly Ser Gly Ser Leu Gly His His His His His His Arg Leu
50 55 60

<210> SEQ ID NO 247
<211> LENGTH: 64
<212> TYPE: PRT
<213> ORGANISM: Artificial Sequence
<220> FEATURE:
<223> OTHER INFORMATION: H-pre-8
<220> FEATURE:
<221> NAME/KEY: MISC_FEATURE
<222> LOCATION: (6)..(6)
<223> OTHER INFORMATION: Xaa at position 6 is a glycosylated derivative of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine

<400> SEQUENCE: 247

Met Ala Pro Pro Thr Xaa Ala Cys Pro Ile Gly Asp Ile Arg Cys Ala
1 5 10 15

```
Ile Cys Xaa Leu Pro Thr Lys Pro Pro Trp Phe Asn Pro Xaa Ala Arg
            20                  25                  30

Leu Asp Ile Ala Asn Gln His Leu Ser His Thr Pro Asn Ser His Phe
        35                  40                  45

Thr Arg Gly Ser Gly Ser Leu Gly His His His His His His Arg Leu
    50                  55                  60


<210> SEQ ID NO 248
<211> LENGTH: 64
<212> TYPE: PRT
<213> ORGANISM: Artificial Sequence
<220> FEATURE:
<223> OTHER INFORMATION: H-pre-10
<220> FEATURE:
<221> NAME/KEY: MISC_FEATURE
<222> LOCATION: (5)..(5)
<223> OTHER INFORMATION: Xaa at position 5 is a glycosylated derivative
      of homopropargylglycine or homopropargylglycine
<220> FEATURE:
<221> NAME/KEY: MISC_FEATURE
<222> LOCATION: (16)..(17)
<223> OTHER INFORMATION: Xaa at positions 16-17 is a glycosylated
      derivative of homopropargylglycine or homopropargylglycine
<220> FEATURE:
<221> NAME/KEY: MISC_FEATURE
<222> LOCATION: (20)..(20)
<223> OTHER INFORMATION: Xaa at position 20 is a glycosylated derivative
      of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 248

Met Ala His Phe Xaa Ser Leu Arg Ala Ala Ser Ala Ala Tyr Asn Xaa
1               5                   10                  15

Xaa Thr Asn Xaa Ile Thr Val Thr Pro Ser Gln Val Lys His Gly Ile
            20                  25                  30

Gly Asp Ile Arg Pro Ala His Cys Xaa Tyr Pro Pro Thr Xaa Lys Val
        35                  40                  45

Leu Asp Gly Ser Gly Ser Leu Gly His His His His His His Arg Leu
    50                  55                  60


<210> SEQ ID NO 249
<211> LENGTH: 62
<212> TYPE: PRT
<213> ORGANISM: Artificial Sequence
<220> FEATURE:
<223> OTHER INFORMATION: H-pre-11
<220> FEATURE:
<221> NAME/KEY: MISC_FEATURE
<222> LOCATION: (17)..(17)
<223> OTHER INFORMATION: Xaa at position 17 is a glycosylated derivative
      of homopropargylglycine or homopropargylglycine

<400> SEQUENCE: 249

Met Ala Arg Arg Ala Leu Cys Ile Gly Asp Ile Arg Glu Ala Thr Cys
1               5                   10                  15

Xaa Leu Leu Phe Cys Gln Pro Phe Phe Ile Asp His Leu His Asn Phe
            20                  25                  30
```

```
Ala Lys Phe His Arg Gln Ile His Gly His Ala Ile Thr Thr Thr Ser
        35                  40                  45

Gly Ser Gly Ser Leu Gly His His His His His His Arg Leu
    50                  55                  60


<210> SEQ ID NO 250
<211> LENGTH: 65
<212> TYPE: PRT
<213> ORGANISM: Artificial Sequence
<220> FEATURE:
<223> OTHER INFORMATION: H-pre-12
<220> FEATURE:
<221> NAME/KEY: MISC_FEATURE
<222> LOCATION: (27)..(27)
<223> OTHER INFORMATION: Xaa at position 27 is a glycosylated derivative
      of homopropargylglycine or homopropargylglycine

<400> SEQUENCE: 250

Met Ala Val Pro Thr Lys Glu Ala Trp Ser Ala Pro Ser Pro Leu Lys
1               5                   10                  15

Trp Lys Ile Thr Tyr Pro His His Ser Pro Xaa Tyr Pro Phe Thr Ile
            20                  25                  30

Gly Asp Ile Arg His Arg Arg Ala Cys Pro Ala Ser Pro Ala Ser Ser
        35                  40                  45

Thr Ser Ala Pro Val Leu Trp Val Ile Thr Thr Ile Thr Thr Gly Tyr
    50                  55                  60

Arg
65


<210> SEQ ID NO 251
<211> LENGTH: 64
<212> TYPE: PRT
<213> ORGANISM: Artificial Sequence
<220> FEATURE:
<223> OTHER INFORMATION: L-pre-3
<220> FEATURE:
<221> NAME/KEY: MISC_FEATURE
<222> LOCATION: (26)..(26)
<223> OTHER INFORMATION: Xaa at position 26 is a glycosylated derivative
      of homopropargylglycine or homopropargylglycine

<400> SEQUENCE: 251

Met Ala Thr Tyr Phe Pro Thr Thr Ser Ile Gly Asp Ile Arg Pro Tyr
1               5                   10                  15

Thr Gly Leu Pro Leu Val Thr Gln Thr Xaa Asn Thr Pro Ile Asn Arg
            20                  25                  30

Leu Arg Asn Ser Tyr Ser Leu Gln Asn Tyr Arg Phe His Arg Lys Ser
        35                  40                  45

Pro Asn Gly Ser Gly Ser Leu Gly His His His His His His Arg Leu
    50                  55                  60


<210> SEQ ID NO 252
<211> LENGTH: 64
<212> TYPE: PRT
<213> ORGANISM: Artificial Sequence
<220> FEATURE:
<223> OTHER INFORMATION: L-pre-5
<220> FEATURE:
<221> NAME/KEY: MISC_FEATURE
<222> LOCATION: (21)..(21)
<223> OTHER INFORMATION: Xaa at position 21 is a glycosylated derivative
      of homopropargylglycine or homopropargylglycine
<220> FEATURE:
<221> NAME/KEY: MISC_FEATURE
<222> LOCATION: (46)..(46)
```

<223> OTHER INFORMATION: Xaa at position 46 is a glycosylated derivative of homopropargylglycine or homopropargylglycine

<400> SEQUENCE: 252

```
Met Ala His Pro Ala Arg Phe Ile Tyr Ile Gly Asp Ile Arg Gly Val
1               5                   10                  15

Pro Leu Asp His Xaa Lys His Gly Phe Asn Asn Ser Thr Arg Leu Glu
            20                  25                  30

Pro Gly Gly Leu Ser Val Cys Leu His Asn His Glu Cys Xaa Asn Tyr
        35                  40                  45

Trp Thr Gly Ser Gly Ser Leu Gly His His His His His His Arg Leu
    50                  55                  60
```

<210> SEQ ID NO 253
<211> LENGTH: 64
<212> TYPE: PRT
<213> ORGANISM: Artificial Sequence
<220> FEATURE:
<223> OTHER INFORMATION: L-pre-6
<220> FEATURE:
<221> NAME/KEY: MISC_FEATURE
<222> LOCATION: (7)..(7)
<223> OTHER INFORMATION: Xaa at position 7 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 253

```
Met Ala Pro Leu His Ile Xaa Val Tyr Ile Gly Asp Ile Arg Pro Tyr
1               5                   10                  15

Thr Ile Gly Asp Xaa Arg Arg Ser Ile Gln Ser Ile Xaa Asp His Ser
            20                  25                  30

Tyr Leu Lys Cys Gln Asn Val Xaa His Cys Ile Asp Asp His Xaa Leu
        35                  40                  45

His Val Gly Ser Gly Ser Leu Gly His His His His His His Arg Leu
    50                  55                  60
```

<210> SEQ ID NO 254
<211> LENGTH: 64
<212> TYPE: PRT
<213> ORGANISM: Artificial Sequence
<220> FEATURE:
<223> OTHER INFORMATION: L-pre-7
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine
<220> FEATURE:
<221> NAME/KEY: MISC_FEATURE
<222> LOCATION: (49)..(49)

<223> OTHER INFORMATION: Xaa at position 49 is a glycosylated derivative of homopropargylglycine or homopropargylglycine

<400> SEQUENCE: 254

Met Ala Arg Tyr Pro Thr Tyr Glu Ala Ile Gly Asp Ile Arg Arg Tyr
1               5                   10                  15

Leu Ala Ser Leu Gln Ile Arg Thr Gln Val Leu Leu Lys Thr Leu Arg
            20                  25                  30

Gln Thr Thr Glu His Xaa Gln Leu Ile Asp Gln Ile Thr Leu Val Asn
        35                  40                  45

Xaa Tyr Gly Ser Gly Ser Leu Gly His His His His His His Arg Leu
    50                  55                  60

<210> SEQ ID NO 255
<211> LENGTH: 64
<212> TYPE: PRT
<213> ORGANISM: Artificial Sequence
<220> FEATURE:
<223> OTHER INFORMATION: L-pre-8
<220> FEATURE:
<221> NAME/KEY: MISC_FEATURE
<222> LOCATION: (14)..(14)
<223> OTHER INFORMATION: Xaa at position 14 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (45)..(45)
<223> OTHER INFORMATION: Xaa at position 45 is a glycosylated derivative of homopropargylglycine or homopropargylglycine

<400> SEQUENCE: 255

Met Ala Tyr Ser Ala Arg Arg Asn Phe Asp Val Arg Ser Xaa Tyr Asp
1               5                   10                  15

Ser Phe Ser Glu Asn Arg Asn Thr Ile Gln Thr Arg Tyr Tyr Phe Ile
            20                  25                  30

Gly Asp Ile Arg His Gln Lys Lys Xaa Thr Arg Ser Xaa Thr Gln Leu
        35                  40                  45

Phe Leu Gly Ser Gly Ser Leu Gly His His His His His His Arg Leu
    50                  55                  60

<210> SEQ ID NO 256
<211> LENGTH: 64
<212> TYPE: PRT
<213> ORGANISM: Artificial Sequence
<220> FEATURE:
<223> OTHER INFORMATION: L-pre-12
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 256

Met Ala Phe Leu Thr Thr Cys Arg Leu Ile Gly Asp Ile Arg Arg Ile
1               5                   10                  15

Tyr Asn Tyr Ser Ile Thr Lys Gly Arg Leu Thr Ser Leu Ile Arg Gln
            20                  25                  30

Arg Arg His Arg Leu Lys Gly Gln Leu Asn Thr Leu Asn Leu Tyr Lys
        35                  40                  45

Leu Xaa Gly Ser Gly Ser Leu Gly His His His His His His Arg Leu
50 55 60

<210> SEQ ID NO 257
<211> LENGTH: 65
<212> TYPE: PRT
<213> ORGANISM: Artificial Sequence
<220> FEATURE:
<223> OTHER INFORMATION: 102-21
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine
<220> FEATURE:
<221> NAME/KEY: MISC_FEATURE
<222> LOCATION: (20)..(20)
<223> OTHER INFORMATION: Xaa at position 20 is a glycosylated derivative of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative of homopropargylglycine or homopropargylglycine
<220> FEATURE:
<221> NAME/KEY: MISC_FEATURE
<222> LOCATION: (48)..(48)
<223> OTHER INFORMATION: Xaa at position 48 is a glycosylated derivative of homopropargylglycine or homopropargylglycine

<400> SEQUENCE: 257

Met Ala Ile His Asn Asn Ser Arg Ile Xaa Asp Leu Leu Ile Ile Arg
1 5 10 15

His Arg Trp Xaa Ile Gly Asp Ile Arg Thr Thr His Ile Leu Asn Asn
20 25 30

Arg Lys Thr Xaa Ser Ser Leu Ile Lys Arg Asn Ser Lys Asn Gly Xaa
35 40 45

Ser Ile Ala Pro Gly Ser Leu Gly His His His His His Ala Ile Gly
50 55 60

Ser
65

<210> SEQ ID NO 258
<211> LENGTH: 64
<212> TYPE: PRT
<213> ORGANISM: Artificial Sequence
<220> FEATURE:
<223> OTHER INFORMATION: 102-28

<400> SEQUENCE: 258

Met Ala Lys Phe Ala Ile Cys His Thr Ile Gly Asp Ile Arg Phe Glu
1 5 10 15

Phe Thr Ile Ile Tyr Thr Pro His Lys Tyr Leu Val Met Asp His Asp
20 25 30

Arg His Val Met Ser Leu Ser Val Met Leu Met Ser Leu Met Asn His
35 40 45

Ser Arg Gly Ser Gly Ser Leu Gly His His His His His His Arg Leu
50 55 60

<210> SEQ ID NO 259
<211> LENGTH: 64
<212> TYPE: PRT
<213> ORGANISM: Artificial Sequence
<220> FEATURE:
<223> OTHER INFORMATION: 102-37
<220> FEATURE:

<221> NAME/KEY: MISC_FEATURE
<222> LOCATION: (37)..(38)
<223> OTHER INFORMATION: Xaa at positions 37-38 is a glycosylated
      derivative of homopropargylglycine or homopropargylglycine

<400> SEQUENCE: 259

```
Met Ala Lys Tyr Leu Thr Thr Asn Arg Leu His Val Leu Thr Arg Lys
1               5                   10                  15

Thr Glu Gly Leu Tyr Asp His Asn Val Leu Thr Arg Pro Thr Arg Ile
            20                  25                  30

Gly Asp Ile Arg Xaa Xaa Leu Leu Asn Tyr Arg Lys Thr Leu Gln His
        35                  40                  45

Phe Tyr Gly Ser Gly Ser Leu Gly His His His His His His Arg Leu
    50                  55                  60
```

<210> SEQ ID NO 260
<211> LENGTH: 66
<212> TYPE: PRT
<213> ORGANISM: Artificial Sequence
<220> FEATURE:
<223> OTHER INFORMATION: 102-39
<220> FEATURE:
<221> NAME/KEY: MISC_FEATURE
<222> LOCATION: (3)..(3)
<223> OTHER INFORMATION: Xaa at position 3 is a glycosylated derivative
      of homopropargylglycine or homopropargylglycine

<400> SEQUENCE: 260

```
Met Ala Xaa Phe Val Tyr His Ser Thr His Pro Asn Arg Tyr His Asn
1               5                   10                  15

Leu Thr Leu His Ile Gly Asp Ile Arg Gln Arg Thr Ile Gln Gln Glu
            20                  25                  30

Arg Ile Arg Val Phe Leu Leu Phe Asn Leu Asn Leu Leu Gly Lys Asn
        35                  40                  45

Lys Tyr Gly Ser Gly Ser Leu Gly Pro Ser Pro Ser Pro Pro Ala Ile
    50                  55                  60

Gly Ser
65
```

<210> SEQ ID NO 261
<211> LENGTH: 64
<212> TYPE: PRT
<213> ORGANISM: Artificial Sequence
<220> FEATURE:
<223> OTHER INFORMATION: 7H130-2
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine

<400> SEQUENCE: 261

```
Met Ala Ile Lys Leu Leu Pro Thr Arg Ala Phe Asn Gln Asn Lys His
1               5                   10                  15

Gln Arg Pro Arg Ile Gly Asp Ile Arg Pro Ala Gly Cys Xaa Thr Tyr
            20                  25                  30

Leu Ile Thr His His Lys Leu Lys Gly Ile Phe Lys Arg Lys Leu Thr
        35                  40                  45

Thr Leu Gly Ser Gly Ser Leu Gly His His His His His His Arg Leu
    50                  55                  60
```

<210> SEQ ID NO 262
<211> LENGTH: 64

```
<212> TYPE: PRT
<213> ORGANISM: Artificial Sequence
<220> FEATURE:
<223> OTHER INFORMATION: 7H130-3
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine

<400> SEQUENCE: 262

Met Ala Phe Ile Lys Arg Asn Lys His Leu Asp Asp Thr Ser Arg Ser
1               5                   10                  15

Arg Arg His Gly Ile Gly Asp Ile Arg Arg Ala Phe Cys Xaa Ile Arg
            20                  25                  30

Lys Ile Val His Pro Tyr Leu Lys Trp Pro Arg Phe Lys Cys Ile Gln
        35                  40                  45

Arg Asn Gly Ser Gly Ser Leu Gly His His His His His His Arg Leu
    50                  55                  60


<210> SEQ ID NO 263
<211> LENGTH: 64
<212> TYPE: PRT
<213> ORGANISM: Artificial Sequence
<220> FEATURE:
<223> OTHER INFORMATION: 7H130-4
<220> FEATURE:
<221> NAME/KEY: MISC_FEATURE
<222> LOCATION: (5)..(7)
<223> OTHER INFORMATION: Xaa at positions 5-7 is a glycosylated
      derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative
      of homopropargylglycine or homopropargylglycine

<400> SEQUENCE: 263

Met Ala Leu Thr Xaa Xaa Xaa Ser Phe Pro Arg Thr Thr Ile Ser Ser
1               5                   10                  15

Ser Ile Val Pro Ser Phe Thr His His Ala Gln Trp Phe Cys Thr Ile
            20                  25                  30

Gly Asp Ile Arg Ser Ala Glu Cys Xaa Ser Xaa Val His Ser Leu Glu
        35                  40                  45

Ser Thr Gly Ser Gly Ser Leu Gly His His His His His His Arg Leu
    50                  55                  60


<210> SEQ ID NO 264
<211> LENGTH: 64
<212> TYPE: PRT
<213> ORGANISM: Artificial Sequence
<220> FEATURE:
<223> OTHER INFORMATION: 7H130-5
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine

<400> SEQUENCE: 264

Met Ala Thr Ser Asp Tyr Gln Arg His Ile Gly Asp Ile Arg Leu Ala
1               5                   10                  15
```

```
Cys Cys Xaa Thr Ser Lys Cys Thr Trp Leu Ile Cys Leu Arg His Pro
            20                  25                  30

Cys Leu Leu Ser Ala Ala Arg Val Pro Glu Cys Leu His Ile Ser Arg
        35                  40                  45

Arg Phe Gly Ser Gly Ser Leu Gly His His His His His His Arg Leu
    50                  55                  60


<210> SEQ ID NO 265
<211> LENGTH: 64
<212> TYPE: PRT
<213> ORGANISM: Artificial Sequence
<220> FEATURE:
<223> OTHER INFORMATION: 7H130-6
<220> FEATURE:
<221> NAME/KEY: MISC_FEATURE
<222> LOCATION: (10)..(10)
<223> OTHER INFORMATION: Xaa at position 10 is a glycosylated derivative
      of homopropargylglycine or homopropargylglycine
<220> FEATURE:
<221> NAME/KEY: MISC_FEATURE
<222> LOCATION: (41)..(42)
<223> OTHER INFORMATION: Xaa at positions 41-42 is a glycosylated
      derivative of homopropargylglycine or homopropargylglycine

<400> SEQUENCE: 265

Met Ala Asn Asn Thr Leu Phe Lys Thr Xaa Arg Gln Gly Tyr Leu Asn
1               5                   10                  15

Pro Leu Lys Lys Phe Leu Gln Gln Arg Asn Leu Tyr Pro Lys Phe Ile
            20                  25                  30

Gly Asp Val Arg Thr Ala Pro Cys Xaa Xaa Asn Tyr Ile Asn Ser Phe
        35                  40                  45

Tyr Thr Gly Ser Gly Ser Leu Gly His His His His His His Arg Leu
    50                  55                  60


<210> SEQ ID NO 266
<211> LENGTH: 64
<212> TYPE: PRT
<213> ORGANISM: Artificial Sequence
<220> FEATURE:
<223> OTHER INFORMATION: 7H130-7
<220> FEATURE:
<221> NAME/KEY: MISC_FEATURE
<222> LOCATION: (21)..(22)
<223> OTHER INFORMATION: Xaa at positions 21-22 is a glycosylated
      derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative
      of homopropargylglycine or homopropargylglycine
<220> FEATURE:
<221> NAME/KEY: MISC_FEATURE
<222> LOCATION: (49)..(49)
<223> OTHER INFORMATION: Xaa at position 49 is a glycosylated derivative
      of homopropargylglycine or homopropargylglycine

<400> SEQUENCE: 266

Met Ala Ser His Asn Ser Arg Arg Lys Leu Leu Arg Asn Leu Ala Tyr
1               5                   10                  15

Leu Thr Ile Trp Xaa Xaa Thr Leu Leu Leu Lys Ala Arg Ile Val Ile
            20                  25                  30

Gly Asp Ile Arg His Ala His Cys Xaa Glu His Asn Ala Asn Asn Ala
        35                  40                  45

Xaa Ile Gly Ser Gly Ser Leu Gly His His His His His His Arg Leu
    50                  55                  60
```

<210> SEQ ID NO 267
<211> LENGTH: 64
<212> TYPE: PRT
<213> ORGANISM: Artificial Sequence
<220> FEATURE:
<223> OTHER INFORMATION: 7H130-8
<220> FEATURE:
<221> NAME/KEY: MISC_FEATURE
<222> LOCATION: (15)..(15)
<223> OTHER INFORMATION: Xaa at position 15 is a glycosylated derivative of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 267

```
Met Ala Val Asn Leu Leu Gln Arg Gln Ile Gly Asp Ile Arg Xaa Ala
1               5                   10                  15

Ser Cys Xaa Leu Thr Leu Asn Thr Tyr Lys His Tyr Cys Thr His Ser
            20                  25                  30

Thr Asp Val Xaa Ser Leu His Thr Xaa Arg His Leu Phe Cys Ser Pro
        35                  40                  45

Gln Gly Gly Tyr Gly Ser Leu Gly His His His His His His Arg Leu
    50                  55                  60
```

<210> SEQ ID NO 268
<211> LENGTH: 64
<212> TYPE: PRT
<213> ORGANISM: Artificial Sequence
<220> FEATURE:
<223> OTHER INFORMATION: 7H130-9
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (32)..(32)
<223> OTHER INFORMATION: Xaa at position 32 is a glycosylated derivative of homopropargylglycine or homopropargylglycine

<400> SEQUENCE: 268

```
Met Ala Ile Asn Phe Ser Ser Ile Phe Lys Arg Cys Tyr His Thr Lys
1               5                   10                  15

Thr Pro Arg Pro Ile Gly Asp Ile Arg Asn Ala His Cys Xaa Thr Xaa
            20                  25                  30

Ile Lys Arg Leu Leu Gln Ile Asp Val Leu Pro Trp Lys Leu His Tyr
        35                  40                  45

Ala Ile Gly Ser Gly Ser Leu Gly His His His His His His Arg Leu
    50                  55                  60
```

<210> SEQ ID NO 269
<211> LENGTH: 62
<212> TYPE: PRT
<213> ORGANISM: Artificial Sequence
<220> FEATURE:

<223> OTHER INFORMATION: 7H130-10
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine

<400> SEQUENCE: 269

```
Met Ala His Gln Ile Ile Asp Pro Ile Pro Thr Arg Thr Arg Ala Gly
1               5                   10                  15

Arg Arg Thr Ala Leu Ala Ile Phe Val Trp Cys Xaa Leu Lys Asn Phe
            20                  25                  30

Leu Ala Ala Arg Leu Leu Pro Asn Arg His Thr Tyr Ala Ile His Asn
        35                  40                  45

Gly Ser Gly Ser Leu Gly His His His His His His Arg Leu
    50                  55                  60
```

<210> SEQ ID NO 270
<211> LENGTH: 64
<212> TYPE: PRT
<213> ORGANISM: Artificial Sequence
<220> FEATURE:
<223> OTHER INFORMATION: 7H130-12
<220> FEATURE:
<221> NAME/KEY: MISC_FEATURE
<222> LOCATION: (11)..(11)
<223> OTHER INFORMATION: Xaa at position 11 is a glycosylated derivative of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 270

```
Met Ala Tyr His Pro Tyr Phe Ile Cys Ser Xaa Tyr His Ser Phe Asp
1               5                   10                  15

Lys Lys Xaa Thr Lys His Arg Leu Ser Ser Leu His Lys Pro Thr Ile
            20                  25                  30

Gly Asp Ile Arg His Ala Tyr Tyr Xaa Arg Ala Leu Leu Leu Pro Lys
        35                  40                  45

Tyr Phe Asp Ser Gly Ser Leu Gly His His His His His His Arg Leu
    50                  55                  60
```

<210> SEQ ID NO 271
<211> LENGTH: 63
<212> TYPE: PRT
<213> ORGANISM: Artificial Sequence
<220> FEATURE:
<223> OTHER INFORMATION: 7L130-2

<400> SEQUENCE: 271

```
Met Ala Ile Asn Pro Asn Ser Lys Arg Arg Thr Arg Ser Arg His Tyr
1               5                   10                  15

Asn Gly Asp His Ile Gly Asp Ile Arg Ala Lys His Leu Ser His Arg
            20                  25                  30

Lys Ile Thr Leu Leu Gly Ile Tyr Arg Ile Arg Leu Lys Val Ala Leu
        35                  40                  45

Asn Leu Leu Arg Ser Leu Gly His His His His His His Arg Leu
    50                  55                  60
```

<210> SEQ ID NO 272
<211> LENGTH: 65
<212> TYPE: PRT
<213> ORGANISM: Artificial Sequence
<220> FEATURE:
<223> OTHER INFORMATION: 7L130-2

<400> SEQUENCE: 272

Met Ala Ser His Ala Asp His Leu His His Ile Asn Ala His His Met
1 5 10 15

Asp Val Trp Ile Ile Gly Asp Ile Arg Leu Ile Gly His Ile Leu Arg
20 25 30

Cys Lys Arg Val Cys Leu Asn Asn Leu Arg Gln Ser Phe Arg His Ser
35 40 45

Leu Ser Gly Ser Gly Ser Leu Gly His His His His His His Arg Leu
50 55 60

Arg
65

<210> SEQ ID NO 273
<211> LENGTH: 64
<212> TYPE: PRT
<213> ORGANISM: Artificial Sequence
<220> FEATURE:
<223> OTHER INFORMATION: 7L130-3
<220> FEATURE:
<221> NAME/KEY: MISC_FEATURE
<222> LOCATION: (49)..(49)
<223> OTHER INFORMATION: Xaa at position 49 is a glycosylated derivative of homopropargylglycine or homopropargylglycine

<400> SEQUENCE: 273

Met Ala Phe Asn His His Phe Pro Pro Tyr Lys Phe Phe Glu Lys Ile
1 5 10 15

His Thr Phe Arg Ile Gly Asp Ile Arg Ser Ile Leu Phe Leu Arg Ser
20 25 30

Leu Gln Arg Ala Asn His Ile Lys Lys His Ser Pro Tyr Phe Ile Lys
35 40 45

Xaa Phe Gly Ser Gly Ser Leu Gly His His His His His His Arg Leu
50 55 60

<210> SEQ ID NO 274
<211> LENGTH: 64
<212> TYPE: PRT
<213> ORGANISM: Artificial Sequence
<220> FEATURE:
<223> OTHER INFORMATION: 7L130-4
<220> FEATURE:
<221> NAME/KEY: MISC_FEATURE
<222> LOCATION: (11)..(11)
<223> OTHER INFORMATION: Xaa at position 11 is a glycosylated derivative of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine

<400> SEQUENCE: 274

Met Ala Asn Phe Lys Leu His Arg Thr Val Xaa Thr Ala Ile Gln Asn
1 5 10 15

His Val Xaa His Asn Lys Arg Lys Phe Ile Leu Asn Ile Ser Phe Ile
20 25 30

Gly Asp Ile Arg Gly Arg Arg Lys His Pro Leu Gln Tyr Arg Thr Asn
        35                  40                  45

Val Val Gly Ser Gly Ser Leu Gly His His His His His His Arg Leu
    50                  55                  60

<210> SEQ ID NO 275
<211> LENGTH: 64
<212> TYPE: PRT
<213> ORGANISM: Artificial Sequence
<220> FEATURE:
<223> OTHER INFORMATION: 7L130-6
<220> FEATURE:
<221> NAME/KEY: MISC_FEATURE
<222> LOCATION: (11)..(11)
<223> OTHER INFORMATION: Xaa at position 11 is a glycosylated derivative of homopropargylglycine or homopropargylglycine
<220> FEATURE:
<221> NAME/KEY: MISC_FEATURE
<222> LOCATION: (15)..(16)
<223> OTHER INFORMATION: Xaa at positions 15-16 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (45)..(45)
<223> OTHER INFORMATION: Xaa at position 45 is a glycosylated derivative of homopropargylglycine or homopropargylglycine

<400> SEQUENCE: 275

Met Ala Thr Asn Asn Gln Arg His Thr Tyr Xaa Asn Ile Pro Xaa Xaa
1               5                   10                  15

Ser Cys Leu Arg Ile Gly Asp Ile Arg Ser Val Xaa Ser Leu Cys Thr
            20                  25                  30

Asn Arg Arg Cys Leu Asp Ile Ser Val Asn Pro Leu Xaa Leu Asn Glu
        35                  40                  45

His Gly Gly Ser Gly Ser Leu Gly His His His His His His Arg Leu
    50                  55                  60

<210> SEQ ID NO 276
<211> LENGTH: 64
<212> TYPE: PRT
<213> ORGANISM: Artificial Sequence
<220> FEATURE:
<223> OTHER INFORMATION: 7L130-7
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine

<400> SEQUENCE: 276

Met Ala Cys His His His Asn His Ile Tyr Lys Pro Arg Glu Ala Thr
1               5                   10                  15

Tyr Ile Ser Pro Ile Gly Asp Ile Arg Lys Phe Leu Thr Leu Thr Leu
            20                  25                  30

Leu Lys Tyr Gln Leu Phe Ile Asn Arg Ile Tyr Ser Lys Xaa His Leu
        35                  40                  45

Ser Lys Gly Ser Gly Ser Leu Gly His His His His His His Arg Leu
    50                  55                  60

<210> SEQ ID NO 277
<211> LENGTH: 64
<212> TYPE: PRT

<213> ORGANISM: Artificial Sequence
<220> FEATURE:
<223> OTHER INFORMATION: 7L130-8
<220> FEATURE:
<221> NAME/KEY: MISC_FEATURE
<222> LOCATION: (9)..(9)
<223> OTHER INFORMATION: Xaa at position 9 is a glycosylated derivative
of homopropargylglycine or homopropargylglycine
<220> FEATURE:
<221> NAME/KEY: MISC_FEATURE
<222> LOCATION: (35)..(35)
<223> OTHER INFORMATION: Xaa at position 35 is a glycosylated derivative
of homopropargylglycine or homopropargylglycine

<400> SEQUENCE: 277

Met Ala Phe Ile Ile Pro Pro Arg Xaa Lys Val Pro Arg Tyr Ser Pro
1 5 10 15

His Ser Lys Leu Ile Gly Asp Ile Arg Arg His Ser Phe Leu Asn Leu
20 25 30

Ile His Xaa Lys His Val Ser Tyr Ile Pro Phe Ser Lys Trp Lys Lys
35 40 45

Tyr Cys Gly Ser Gly Cys Leu Gly His His His His His His Arg Leu
50 55 60

<210> SEQ ID NO 278
<211> LENGTH: 64
<212> TYPE: PRT
<213> ORGANISM: Artificial Sequence
<220> FEATURE:
<223> OTHER INFORMATION: 7L130-9

<400> SEQUENCE: 278

Met Ala Ser Asn Arg Asn Arg Arg Ser Lys His Asn Thr His Asn Glu
1 5 10 15

Lys Leu Lys Leu Phe Tyr Asp Gln Asn Gln Tyr Asn Phe His Leu Ile
20 25 30

Gly Asp Ile Arg Ile Thr His Ser Ser Asn Lys Ser Ser Tyr Leu Pro
35 40 45

Thr His Gly Ser Gly Ser Leu Gly His His His His His His Arg Leu
50 55 60

<210> SEQ ID NO 279
<211> LENGTH: 64
<212> TYPE: PRT
<213> ORGANISM: Artificial Sequence
<220> FEATURE:
<223> OTHER INFORMATION: 7L130-10
<220> FEATURE:
<221> NAME/KEY: MISC_FEATURE
<222> LOCATION: (35)..(35)
<223> OTHER INFORMATION: Xaa at position 35 is a glycosylated derivative
of homopropargylglycine or homopropargylglycine

<400> SEQUENCE: 279

Met Ala Asn Glu Tyr Ile His Ser Asn Ile Gly Asp Ile Arg Gly Arg
1 5 10 15

His Asn Arg His Arg Lys Asn Lys Leu Ile Gln Phe Ala Tyr Thr Cys
20 25 30

Tyr Asn Xaa Leu Val Arg Asn Thr Thr Arg Arg Ala Ile Arg Asn Leu
35 40 45

Val Ala Gly Phe Gly Ser Leu Gly His His His His His His Arg Leu
50 55 60

<210> SEQ ID NO 280

-continued

<211> LENGTH: 10
<212> TYPE: PRT
<213> ORGANISM: Artificial Sequence
<220> FEATURE:
<223> OTHER INFORMATION: Conserved element
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa at position 10 is a glycosylated derivative of homopropargylglycine or homopropargylglycine

<400> SEQUENCE: 280

```
Ile Gly Asp Ile Arg Xaa Ala Xaa Cys Xaa
1               5                   10
```

<210> SEQ ID NO 281
<211> LENGTH: 50
<212> TYPE: PRT
<213> ORGANISM: Artificial Sequence
<220> FEATURE:
<223> OTHER INFORMATION: 91-1
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine

<400> SEQUENCE: 281

```
Xaa Ala Tyr Phe Val His Lys Lys Ser Arg Leu Leu Thr Asn Lys Ala
1               5                   10                  15

Val Lys Lys Arg Leu His Gly Cys Phe Gln Asn Gln Arg Ser Thr Ile
            20                  25                  30

Gly Asp Ile Arg Tyr Ala Lys Cys Xaa Arg Val Ser Ser Asn Phe Phe
        35                  40                  45

Arg Arg
    50
```

<210> SEQ ID NO 282
<211> LENGTH: 50
<212> TYPE: PRT
<213> ORGANISM: Artificial Sequence
<220> FEATURE:
<223> OTHER INFORMATION: 91-2
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (34)..(34)
<223> OTHER INFORMATION: Xaa at position 34 is a glycosylated derivative of homopropargylglycine or homopropargylglycine
<220> FEATURE:
<221> NAME/KEY: MISC_FEATURE
<222> LOCATION: (38)..(38)

<223> OTHER INFORMATION: Xaa at position 38 is a glycosylated derivative of homopropargylglycine or homopropargylglycine

<400> SEQUENCE: 282

```
Xaa Ala Pro His Gln His Arg His Leu Ile Gly Asp Ile Arg Arg Ala
1               5                   10                  15

Trp Cys Xaa Ala Arg Val Pro Asn Val Asn Ala His His Ser Phe Lys
            20                  25                  30

Thr Xaa Thr Arg Leu Xaa Val Phe Thr Pro Trp Ile Trp Ala Arg Asn
        35                  40                  45

Lys Val
    50
```

<210> SEQ ID NO 283
<211> LENGTH: 50
<212> TYPE: PRT
<213> ORGANISM: Artificial Sequence
<220> FEATURE:
<223> OTHER INFORMATION: 91-3
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (9)..(9)
<223> OTHER INFORMATION: Xaa at position 9 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (32)..(32)
<223> OTHER INFORMATION: Xaa at position 32 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine

<400> SEQUENCE: 283

```
Xaa Ala Lys Phe Ile His Thr Arg Xaa Pro His Lys Ala Leu Arg Arg
1               5                   10                  15

Ile His Pro Ile Ile Gly Asp Ile Arg Arg Asp Xaa His His Asn Xaa
            20                  25                  30

Arg Arg Arg Leu Arg Xaa Asn Ile Arg Asn Thr Tyr Leu Arg Phe Arg
        35                  40                  45

Arg Arg
    50
```

<210> SEQ ID NO 284
<211> LENGTH: 50
<212> TYPE: PRT
<213> ORGANISM: Artificial Sequence
<220> FEATURE:
<223> OTHER INFORMATION: 91-5
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (30)..(30)
<223> OTHER INFORMATION: Xaa at position 30 is a glycosylated derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative of homopropargylglycine or homopropargylglycine

<400> SEQUENCE: 284

```
Xaa Ala Ser His Ile Asn Ser Asn Pro Asn Gln Leu Leu Leu Leu Tyr
1               5                   10                  15

Leu Lys Ser Thr Ile Gly Asp Ile Arg Cys Ala Xaa Cys Xaa Asp Phe
            20                  25                  30

Arg His Tyr Arg Asn Thr Lys Tyr Val Phe Xaa Thr Arg His Asn Arg
        35                  40                  45

Arg Thr
    50
```

<210> SEQ ID NO 285
<211> LENGTH: 50
<212> TYPE: PRT
<213> ORGANISM: Artificial Sequence
<220> FEATURE:
<223> OTHER INFORMATION: 91-7
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine

<400> SEQUENCE: 285

```
Xaa Ala Tyr Tyr Ser Gly Pro Lys Thr Ile Gly Asp Ile Arg Gln Thr
1               5                   10                  15

Ser His Xaa Arg Phe Xaa Ser Tyr Arg Tyr Asn Xaa Arg Arg Leu Pro
            20                  25                  30

Asn Ala Val Arg Gly Asp Tyr His Trp Ile Arg Ile Leu Ile Asn Arg
        35                  40                  45

Leu Arg
    50
```

<210> SEQ ID NO 286
<211> LENGTH: 50
<212> TYPE: PRT
<213> ORGANISM: Artificial Sequence
<220> FEATURE:
<223> OTHER INFORMATION: 92-4
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (21)..(21)
<223> OTHER INFORMATION: Xaa at position 21 is a glycosylated derivative of homopropargylglycine or homopropargylglycine
<220> FEATURE:
<221> NAME/KEY: MISC_FEATURE
<222> LOCATION: (27)..(27)
<223> OTHER INFORMATION: Xaa at position 27 is a glycosylated derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine
<220> FEATURE:
<221> NAME/KEY: MISC_FEATURE
<222> LOCATION: (50)..(50)
<223> OTHER INFORMATION: Xaa at position 50 is a glycosylated derivative of homopropargylglycine or homopropargylglycine

<400> SEQUENCE: 286

```
Xaa Ala Thr Asp His Asn His Ser His Arg Arg Pro Arg Arg Glu His
1               5                   10                  15

Leu Asp Xaa Asn Xaa His Tyr Ser Arg Pro Xaa Val Ala Asn Xaa Ile
            20                  25                  30

Gly Asp Ile Arg Thr Phe Arg Arg Arg Tyr Ile Gln Val Xaa Tyr His
        35                  40                  45

Leu Xaa
    50
```

<210> SEQ ID NO 287
<211> LENGTH: 50
<212> TYPE: PRT
<213> ORGANISM: Artificial Sequence
<220> FEATURE:
<223> OTHER INFORMATION: 92-9
<220> FEATURE:
<221> NAME/KEY: MISC_FEATURE
<222> LOCATION: (1)..(1)
<223> OTHER INFORMATION: Xaa at position 1 is homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (44)..(45)
<223> OTHER INFORMATION: Xaa at positions 44-45 is a glycosylated derivative of homopropargylglycine or homopropargylglycine
<220> FEATURE:
<221> NAME/KEY: MISC_FEATURE
<222> LOCATION: (49)..(50)
<223> OTHER INFORMATION: Xaa at positions 49-50 is a glycosylated derivative of homopropargylglycine or homopropargylglycine

<400> SEQUENCE: 287

```
Xaa Ala Tyr Phe Gln Asn Thr Ser Ile Asn Asn Ile Asn Ala Leu Asn
1               5                   10                  15

Gln Ala Thr Gln Lys Asn Phe Phe Arg Ile Arg Leu Glu Ile Xaa Thr
            20                  25                  30
```

Leu Asn Leu Val Ser Lys Arg Tyr Cys Asn Ala Xaa Xaa His Leu Leu
        35                  40                  45

Xaa Xaa
    50

<210> SEQ ID NO 288
<211> LENGTH: 41
<212> TYPE: PRT
<213> ORGANISM: Artificial Sequence
<220> FEATURE:
<223> OTHER INFORMATION: 10F2
<220> FEATURE:
<221> NAME/KEY: MISC_FEATURE
<222> LOCATION: (12)..(13)
<223> OTHER INFORMATION: Xaa at positions 12-13 is a glycosylated derivative of homopropargylglycine or homopropargylglycine
<220> FEATURE:
<221> NAME/KEY: MISC_FEATURE
<222> LOCATION: (19)..(19)
<223> OTHER INFORMATION: Xaa at position 19 is a glycosylated derivative of homopropargylglycine or homopropargylglycine
<220> FEATURE:
<221> NAME/KEY: MISC_FEATURE
<222> LOCATION: (24)..(24)
<223> OTHER INFORMATION: Xaa at position 24 is a glycosylated derivative of homopropargylglycine or homopropargylglycine

<400> SEQUENCE: 288

Met His Pro Tyr Asn Thr Ser Arg Thr Ser Ala Xaa Xaa Ala Ala Leu
1               5                   10                  15

Lys Met Xaa Gln Val Thr Asp Xaa Tyr Ala Leu Ala Leu Phe His Arg
            20                  25                  30

Ile Leu Gly Ser Gly Ser Gly Cys Gly
        35                  40

<210> SEQ ID NO 289
<211> LENGTH: 10
<212> TYPE: PRT
<213> ORGANISM: Artificial Sequence
<220> FEATURE:
<223> OTHER INFORMATION: Conserved sequence motif
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 289

Ile Gly Asp Ile Arg Xaa Ala Xaa Cys Met
1               5                   10

<210> SEQ ID NO 290
<211> LENGTH: 48
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (17)..(17)
<223> OTHER INFORMATION: Xaa at position 17 is a glycosylated derivative of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
of homopropargylglycine or homopropargylglycine

<400> SEQUENCE: 290

Tyr Thr Glu Lys His Asn Gly Ile Gly Asp Ile Arg Pro Ala Ile Cys
1 5 10 15

Xaa Asn Ser Lys Asn Gln Asn Tyr Arg Cys Asn His Tyr Gln Ile Lys
20 25 30

Leu Tyr Ile His Xaa Leu Xaa Arg Leu Ser His Asn Tyr Arg Asn Ser
35 40 45

<210> SEQ ID NO 291
<211> LENGTH: 48
<212> TYPE: PRT
<213> ORGANISM: Artificial Sequence
<220> FEATURE:
<223> OTHER INFORMATION: H-1
<220> FEATURE:
<221> NAME/KEY: MISC_FEATURE
<222> LOCATION: (17)..(17)
<223> OTHER INFORMATION: Xaa at position 17 is a glycosylated derivative
of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative
of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
of homopropargylglycine or homopropargylglycine

<400> SEQUENCE: 291

Tyr Thr Glu Lys His Asn Gly Ile Gly Asp Ile Arg Pro Ala Ile Cys
1 5 10 15

Xaa Asn Ser Lys Asn Gln Asn His Arg Cys Asn His Tyr Gln Ile Lys
20 25 30

Leu Tyr Ile His Xaa Leu Xaa Arg Leu Pro His Asn Tyr Arg Asn Ser
35 40 45

<210> SEQ ID NO 292
<211> LENGTH: 48
<212> TYPE: PRT
<213> ORGANISM: Artificial Sequence
<220> FEATURE:
<223> OTHER INFORMATION: H-11
<220> FEATURE:
<221> NAME/KEY: MISC_FEATURE
<222> LOCATION: (17)..(17)
<223> OTHER INFORMATION: Xaa at position 17 is a glycosylated derivative
of homopropargylglycine or homopropargylglycine

<400> SEQUENCE: 292

Leu Thr Leu Arg Tyr Leu Lys Ile Gly Asp Ile Arg Leu Ala Asn Cys
1 5 10 15

Xaa Thr Val Phe Pro His Phe Leu Ser Lys Lys Phe Phe Glu Asn Gly
20 25 30

His Arg Asn Leu Ala Arg Pro Cys Thr Phe Arg Arg Asn Arg His Leu
35 40 45

<210> SEQ ID NO 293
<211> LENGTH: 48
<212> TYPE: PRT

<213> ORGANISM: Artificial Sequence
<220> FEATURE:
<223> OTHER INFORMATION: H-52
<220> FEATURE:
<221> NAME/KEY: MISC_FEATURE
<222> LOCATION: (7)..(7)
<223> OTHER INFORMATION: Xaa at position 7 is a glycosylated derivative
of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
of homopropargylglycine or homopropargylglycine

<400> SEQUENCE: 293

```
Tyr His Lys His Arg Val Xaa His His His Glu Asp Lys Ala Thr Ser
1               5                   10                  15

Leu Thr Ser Asn Leu Val Arg Leu Arg Leu Lys Thr Arg Ile Gly Asp
            20                  25                  30

Ile Arg Arg Ala Leu Cys Xaa Leu Ser Lys Phe Arg Tyr Leu Ile Asn
        35                  40                  45
```

<210> SEQ ID NO 294
<211> LENGTH: 48
<212> TYPE: PRT
<213> ORGANISM: Artificial Sequence
<220> FEATURE:
<223> OTHER INFORMATION: H-14
<220> FEATURE:
<221> NAME/KEY: MISC_FEATURE
<222> LOCATION: (7)..(7)
<223> OTHER INFORMATION: Xaa at position 7 is a glycosylated derivative
of homopropargylglycine or homopropargylglycine
<220> FEATURE:
<221> NAME/KEY: MISC_FEATURE
<222> LOCATION: (17)..(17)
<223> OTHER INFORMATION: Xaa at position 17 is a glycosylated derivative
of homopropargylglycine or homopropargylglycine

<400> SEQUENCE: 294

```
Leu Leu His His Leu Arg Xaa Ile Gly Asp Ile Arg Pro Ala His Cys
1               5                   10                  15

Xaa Val Ser His Gln Arg Arg Tyr Val Pro Ile Ser Arg Lys Asn Val
            20                  25                  30

Phe Phe Lys Arg Gly Phe Asn Ser His Pro Leu Arg Lys Ile Leu Trp
        35                  40                  45
```

<210> SEQ ID NO 295
<211> LENGTH: 48
<212> TYPE: PRT
<213> ORGANISM: Artificial Sequence
<220> FEATURE:
<223> OTHER INFORMATION: H-25
<220> FEATURE:
<221> NAME/KEY: MISC_FEATURE
<222> LOCATION: (39)..(39)
<223> OTHER INFORMATION: Xaa at position 39 is a glycosylated derivative
of homopropargylglycine or homopropargylglycine

<400> SEQUENCE: 295

```
Arg Phe Arg His Ser Asn Asn Tyr Tyr Leu Thr Pro Phe Leu Thr Pro
1               5                   10                  15

Leu Lys Thr Leu Ile Ser Leu Gln Leu Arg Tyr Arg Leu Ile Gly Asp
            20                  25                  30

Ile Arg Asn Ala Ser Tyr Xaa His Lys Phe Ser Asn Arg Asn Arg Phe
        35                  40                  45
```

<210> SEQ ID NO 296
<211> LENGTH: 48
<212> TYPE: PRT
<213> ORGANISM: Artificial Sequence
<220> FEATURE:
<223> OTHER INFORMATION: H-5

<400> SEQUENCE: 296

His Gln Thr His Ser Tyr Arg Ile Gly Asp Ile Arg Ile Ala His Leu
1 5 10 15

His Gly Gln Pro His Ala Pro Val Gln Gly Leu Pro Pro Val Leu Arg
20 25 30

Arg Arg Arg Glu Leu Gln Val Pro Leu Arg Ala Arg Ala Leu Leu Val
35 40 45

<210> SEQ ID NO 297
<211> LENGTH: 48
<212> TYPE: PRT
<213> ORGANISM: Artificial Sequence
<220> FEATURE:
<223> OTHER INFORMATION: H-53
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative of homopropargylglycine or homopropargylglycine

<400> SEQUENCE: 297

Ile Phe Asn Gln Gly Tyr Arg Ile Lys Ala Trp Asn Asp Leu Lys Asp
1 5 10 15

Ile Ala Ile Gly Asp Ile Arg His Ala Leu Cys Xaa Leu Val Leu Ala
20 25 30

Arg Ile Lys Leu Gln Arg Arg Xaa Val Lys Tyr Lys His Asp His Arg
35 40 45

<210> SEQ ID NO 298
<211> LENGTH: 48
<212> TYPE: PRT
<213> ORGANISM: Artificial Sequence
<220> FEATURE:
<223> OTHER INFORMATION: H-9
<220> FEATURE:
<221> NAME/KEY: MISC_FEATURE
<222> LOCATION: (11)..(11)
<223> OTHER INFORMATION: Xaa at position 11 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (41)..(41)
<223> OTHER INFORMATION: Xaa at position 41 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 298

His Gln His His His Pro Asn Tyr Ala Leu Xaa Gln Arg Arg Leu Ser
1 5 10 15

```
Ile Ala Ile Gly Asp Ile Arg Leu Ala Ile Cys Xaa Phe Ala His Leu
            20                  25                  30

Tyr His Cys Tyr Arg Lys His Leu Xaa Ala Asn Thr Ile Pro Xaa Lys
        35                  40                  45


<210> SEQ ID NO 299
<211> LENGTH: 48
<212> TYPE: PRT
<213> ORGANISM: Artificial Sequence
<220> FEATURE:
<223> OTHER INFORMATION: H-36
<220> FEATURE:
<221> NAME/KEY: MISC_FEATURE
<222> LOCATION: (7)..(7)
<223> OTHER INFORMATION: Xaa at position 7 is a glycosylated derivative
      of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 299

Phe Val Thr Tyr Gln His Xaa Ser Gln Lys Asn Phe Arg Arg Tyr Gln
1               5                   10                  15

Ile Leu Arg Asn His Phe His Pro Gln Asn Tyr Arg Phe Ile Gly Asp
            20                  25                  30

Ile Arg His Ala Leu Cys Xaa Phe Ile Phe Lys Asn Leu Xaa Arg His
        35                  40                  45


<210> SEQ ID NO 300
<211> LENGTH: 48
<212> TYPE: PRT
<213> ORGANISM: Artificial Sequence
<220> FEATURE:
<223> OTHER INFORMATION: H-103

<400> SEQUENCE: 300

Arg Leu His His Asn Ile His Ser His Pro Gln Lys Tyr Leu Glu His
1               5                   10                  15

Pro Leu Ala His Leu Ala Gly His Val Leu Gly Arg His His Trp Arg
            20                  25                  30

Tyr Ser Ser Gly Val Val His Gly His Arg Val Arg His Leu Asp Gln
        35                  40                  45


<210> SEQ ID NO 301
<211> LENGTH: 48
<212> TYPE: PRT
<213> ORGANISM: Artificial Sequence
<220> FEATURE:
<223> OTHER INFORMATION: H-375
<220> FEATURE:
<221> NAME/KEY: MISC_FEATURE
<222> LOCATION: (2)..(2)
<223> OTHER INFORMATION: Xaa at position 2 is a glycosylated derivative
      of homopropargylglycine or homopropargylglycine
<220> FEATURE:
<221> NAME/KEY: MISC_FEATURE
<222> LOCATION: (17)..(17)
<223> OTHER INFORMATION: Xaa at position 17 is a glycosylated derivative
      of homopropargylglycine or homopropargylglycine
<220> FEATURE:
<221> NAME/KEY: MISC_FEATURE
```

<222> LOCATION: (19)..(19)
<223> OTHER INFORMATION: Xaa at position 19 is a glycosylated derivative
of homopropargylglycine or homopropargylglycine
<220> FEATURE:
<221> NAME/KEY: MISC_FEATURE
<222> LOCATION: (35)..(35)
<223> OTHER INFORMATION: Xaa at position 35 is a glycosylated derivative
of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative
of homopropargylglycine or homopropargylglycine

<400> SEQUENCE: 301

Ala Xaa Lys Ile Arg Ser Lys Ile Gly Asp Ile Arg Thr Ala Val Cys
1 5 10 15

Xaa Phe Xaa His Arg His His His His His Ile Leu Asp Pro Tyr Tyr
20 25 30

Leu Lys Xaa Ile Val Xaa Tyr Tyr Ser Leu Lys Ser Arg Ile Thr Leu
35 40 45

<210> SEQ ID NO 302
<211> LENGTH: 48
<212> TYPE: PRT
<213> ORGANISM: Artificial Sequence
<220> FEATURE:
<223> OTHER INFORMATION: H-42
<220> FEATURE:
<221> NAME/KEY: MISC_FEATURE
<222> LOCATION: (6)..(7)
<223> OTHER INFORMATION: Xaa at positions 6-7 is a glycosylated
derivative of homopropargylglycine or homopropargylglycine
<220> FEATURE:
<221> NAME/KEY: MISC_FEATURE
<222> LOCATION: (14)..(14)
<223> OTHER INFORMATION: Xaa at position 14 is a glycosylated derivative
of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative
of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative
of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative
of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative
of homopropargylglycine or homopropargylglycine
<220> FEATURE:
<221> NAME/KEY: MISC_FEATURE
<222> LOCATION: (45)..(45)
<223> OTHER INFORMATION: Xaa at position 45 is a glycosylated derivative
of homopropargylglycine or homopropargylglycine

<400> SEQUENCE: 302

Phe Ile Lys Pro Cys Xaa Xaa Tyr Leu Leu Pro Pro Thr Xaa Leu Asn
1 5 10 15

Leu Tyr Ile Gly Asp Ile Arg Arg Ala Lys Cys Xaa Glu Ala Xaa Asn
20 25 30

Asn Phe His Xaa Asn Asn Lys Pro Leu Xaa Ala Thr Xaa Pro Pro His
35 40 45

<210> SEQ ID NO 303
<211> LENGTH: 48
<212> TYPE: PRT
<213> ORGANISM: Artificial Sequence
<220> FEATURE:
<223> OTHER INFORMATION: H-443
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine

<400> SEQUENCE: 303

```
Lys Asp Ile Leu Lys Leu Arg Ile Pro Phe Ala Thr Leu Ser Gly His
1               5                   10                  15

Arg Asn Ile Gly Asp Ile Arg His Ala Tyr Cys Xaa Ser Leu Lys Arg
            20                  25                  30

Pro Tyr Ile Gln Val Tyr Ser Tyr Leu Asn His Leu Lys Val Arg Phe
        35                  40                  45
```

<210> SEQ ID NO 304
<211> LENGTH: 48
<212> TYPE: PRT
<213> ORGANISM: Artificial Sequence
<220> FEATURE:
<223> OTHER INFORMATION: H-158
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (32)..(32)
<223> OTHER INFORMATION: Xaa at position 32 is a glycosylated derivative of homopropargylglycine or homopropargylglycine
<220> FEATURE:
<221> NAME/KEY: MISC_FEATURE
<222> LOCATION: (43)..(43)
<223> OTHER INFORMATION: Xaa at position 43 is a glycosylated derivative of homopropargylglycine or homopropargylglycine

<400> SEQUENCE: 304

```
Thr Leu His Asn Ile His Asp Leu Asn His Tyr Tyr Arg Asn Leu Asn
1               5                   10                  15

Thr Arg Ile Gly Asp Ile Arg His Ala Thr Cys Xaa Tyr Phe Phe Xaa
            20                  25                  30

Lys Leu Lys Leu Leu Lys His Asn Arg Phe Xaa Asp Arg Ala Ile Tyr
        35                  40                  45
```

<210> SEQ ID NO 305
<211> LENGTH: 48
<212> TYPE: PRT
<213> ORGANISM: Artificial Sequence
<220> FEATURE:
<223> OTHER INFORMATION: H-221
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 305

Pro Tyr Arg Ile Asn Gln Gln Xaa Asn Phe Pro Trp Ser Ser Ala Leu
1               5                   10                  15

Phe Gln Ile Gly Asp Ile Arg His Ala Arg Cys Xaa Asp Ser Cys Arg
            20                  25                  30

Arg Phe Thr Asn Ile Xaa Arg Tyr Val Tyr Leu Lys Arg Arg Xaa Asn
        35                  40                  45

<210> SEQ ID NO 306
<211> LENGTH: 48
<212> TYPE: PRT
<213> ORGANISM: Artificial Sequence
<220> FEATURE:
<223> OTHER INFORMATION: H-22
<220> FEATURE:
<221> NAME/KEY: MISC_FEATURE
<222> LOCATION: (17)..(17)
<223> OTHER INFORMATION: Xaa at position 17 is a glycosylated derivative of homopropargylglycine or homopropargylglycine
<220> FEATURE:
<221> NAME/KEY: MISC_FEATURE
<222> LOCATION: (47)..(47)
<223> OTHER INFORMATION: Xaa at position 47 is a glycosylated derivative of homopropargylglycine or homopropargylglycine

<400> SEQUENCE: 306

Leu Phe Lys Pro Tyr Pro Lys Ile Gly Asp Ile Arg Lys Ala Arg Cys
1               5                   10                  15

Xaa Leu Gln His Thr Leu His His Arg Thr Asn Lys Gln Pro Ser Tyr
            20                  25                  30

Arg Arg Arg Leu Lys Thr Leu Ile Pro Leu Phe Arg Arg Cys Xaa Leu
        35                  40                  45

<210> SEQ ID NO 307
<211> LENGTH: 48
<212> TYPE: PRT
<213> ORGANISM: Artificial Sequence
<220> FEATURE:
<223> OTHER INFORMATION: H-247
<220> FEATURE:
<221> NAME/KEY: MISC_FEATURE
<222> LOCATION: (17)..(17)
<223> OTHER INFORMATION: Xaa at position 17 is a glycosylated derivative of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative of homopropargylglycine or homopropargylglycine

<400> SEQUENCE: 307

Thr Asn His Leu His Arg Thr Ile Gly Asp Ile Arg His Ala Gln Cys
1               5                   10                  15

Xaa Ile Tyr Leu Ile Tyr Leu Val Gln Asn Asp Gln Tyr Lys Arg Asn
            20                  25                  30

Asn Arg Thr Phe Arg Leu Xaa Leu Asn Pro Lys Leu Leu Lys Arg Phe
        35                  40                  45

<210> SEQ ID NO 308
<211> LENGTH: 48
<212> TYPE: PRT
<213> ORGANISM: Artificial Sequence
<220> FEATURE:
<223> OTHER INFORMATION: H-61
<220> FEATURE:
<221> NAME/KEY: MISC_FEATURE
<222> LOCATION: (11)..(11)
<223> OTHER INFORMATION: Xaa at position 11 is a glycosylated derivative of homopropargylglycine or homopropargylglycine
<220> FEATURE:
<221> NAME/KEY: MISC_FEATURE
<222> LOCATION: (18)..(18)
<223> OTHER INFORMATION: Xaa at position 18 is a glycosylated derivative of homopropargylglycine or homopropargylglycine
<220> FEATURE:
<221> NAME/KEY: MISC_FEATURE
<222> LOCATION: (23)..(23)
<223> OTHER INFORMATION: Xaa at position 23 is a glycosylated derivative of homopropargylglycine or homopropargylglycine
<220> FEATURE:
<221> NAME/KEY: MISC_FEATURE
<222> LOCATION: (29)..(29)
<223> OTHER INFORMATION: Xaa at position 29 is a glycosylated derivative of homopropargylglycine or homopropargylglycine
<220> FEATURE:
<221> NAME/KEY: MISC_FEATURE
<222> LOCATION: (39)..(39)
<223> OTHER INFORMATION: Xaa at position 39 is a glycosylated derivative of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative of homopropargylglycine or homopropargylglycine

<400> SEQUENCE: 308

```
Thr Asn Ser Tyr Tyr His His Asn Pro Leu Xaa Arg Arg Thr His Val
1               5                   10                  15

Val Xaa Thr Leu Lys Pro Xaa Asn Phe Trp Ala Lys Xaa Ile Gly Asp
            20                  25                  30

Ile Arg Arg Ala His Cys Xaa Thr Thr Ile Asn Xaa Leu Lys Arg Arg
        35                  40                  45
```

<210> SEQ ID NO 309
<211> LENGTH: 48
<212> TYPE: PRT
<213> ORGANISM: Artificial Sequence
<220> FEATURE:
<223> OTHER INFORMATION: H-13
<220> FEATURE:
<221> NAME/KEY: MISC_FEATURE
<222> LOCATION: (16)..(16)
<223> OTHER INFORMATION: Xaa at position 16 is a glycosylated derivative of homopropargylglycine or homopropargylglycine
<220> FEATURE:
<221> NAME/KEY: MISC_FEATURE
<222> LOCATION: (28)..(28)
<223> OTHER INFORMATION: Xaa at position 28 is a glycosylated derivative of homopropargylglycine or homopropargylglycine

<400> SEQUENCE: 309

```
Ile Leu Leu His Val Ser Thr Arg Ser Arg Tyr Pro His His His Xaa
1               5                   10                  15

Ala Ile Ile Gly Asp Ile Arg Cys Ala Ser Cys Xaa Tyr Pro Val Leu
            20                  25                  30

Lys Trp Phe Tyr Asn Phe Asn Arg Leu Lys Thr Tyr Arg Lys Gln Phe
        35                  40                  45
```

<210> SEQ ID NO 310

```
<211> LENGTH: 48
<212> TYPE: PRT
<213> ORGANISM: Artificial Sequence
<220> FEATURE:
<223> OTHER INFORMATION: H-74
<220> FEATURE:
<221> NAME/KEY: MISC_FEATURE
<222> LOCATION: (39)..(39)
<223> OTHER INFORMATION: Xaa at position 39 is a glycosylated derivative
      of homopropargylglycine or homopropargylglycine

<400> SEQUENCE: 310

Tyr Arg Thr His Lys Leu Leu His His His Asn Asp Lys Trp Lys Ser
1               5                   10                  15

Asn Ile Phe Pro Arg Ile Phe Val Cys His Tyr Tyr Leu Ile Gly Asp
            20                  25                  30

Ile Arg His Ala Arg Cys Xaa Ile Pro Leu Glu Ile Leu Arg Arg Tyr
        35                  40                  45


<210> SEQ ID NO 311
<211> LENGTH: 48
<212> TYPE: PRT
<213> ORGANISM: Artificial Sequence
<220> FEATURE:
<223> OTHER INFORMATION: L-8
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine

<400> SEQUENCE: 311

Tyr Ser Lys His Arg Phe Ser Phe Arg His Asn Asn Xaa Leu Arg Asp
1               5                   10                  15

Arg Lys Leu Ile Arg Lys Phe Ser Tyr His Asn His Ser Ile Gly Asp
            20                  25                  30

Ile Arg Val Ala Asn Lys Phe Arg Tyr Leu His Val Phe Lys Phe Ile
        35                  40                  45


<210> SEQ ID NO 312
<211> LENGTH: 48
<212> TYPE: PRT
<213> ORGANISM: Artificial Sequence
<220> FEATURE:
<223> OTHER INFORMATION: L-1
<220> FEATURE:
<221> NAME/KEY: MISC_FEATURE
<222> LOCATION: (8)..(9)
<223> OTHER INFORMATION: Xaa at positions 8-9 is a glycosylated
      derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative
      of homopropargylglycine or homopropargylglycine

<400> SEQUENCE: 312

Ser Ile Lys Leu Ile Asn Gln Xaa Xaa Thr Thr Asn Pro His Leu Arg
1               5                   10                  15

Leu His Ile Gly Asp Ile Arg Arg Leu Ile Lys Asp Leu Tyr Xaa Phe
            20                  25                  30

Arg Val Tyr Tyr Arg Pro Thr Asn Ser Gly Arg Arg Leu Phe Val Asn
        35                  40                  45


<210> SEQ ID NO 313
<211> LENGTH: 48
<212> TYPE: PRT
```

<213> ORGANISM: Artificial Sequence
<220> FEATURE:
<223> OTHER INFORMATION: L-52
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine
<220> FEATURE:
<221> NAME/KEY: MISC_FEATURE
<222> LOCATION: (31)..(31)
<223> OTHER INFORMATION: Xaa at position 31 is a glycosylated derivative of homopropargylglycine or homopropargylglycine
<220> FEATURE:
<221> NAME/KEY: MISC_FEATURE
<222> LOCATION: (37)..(37)
<223> OTHER INFORMATION: Xaa at position 37 is a glycosylated derivative of homopropargylglycine or homopropargylglycine

<400> SEQUENCE: 313

```
His Ser His His His Ser Pro Xaa Ile Glu Phe His Ser Asn Gly Arg
1               5                   10                  15

Leu His Ile Gly Asp Ile Arg Lys Phe Tyr Ala Asp Ala Leu Xaa Val
            20                  25                  30

Leu Phe Phe Lys Xaa Ala Phe Ile Asp Arg Ile Pro Phe His Asp Ala
        35                  40                  45
```

<210> SEQ ID NO 314
<211> LENGTH: 48
<212> TYPE: PRT
<213> ORGANISM: Artificial Sequence
<220> FEATURE:
<223> OTHER INFORMATION: L-67
<220> FEATURE:
<221> NAME/KEY: MISC_FEATURE
<222> LOCATION: (18)..(18)
<223> OTHER INFORMATION: Xaa at position 18 is a glycosylated derivative of homopropargylglycine or homopropargylglycine
<220> FEATURE:
<221> NAME/KEY: MISC_FEATURE
<222> LOCATION: (32)..(32)
<223> OTHER INFORMATION: Xaa at position 32 is a glycosylated derivative of homopropargylglycine or homopropargylglycine
<220> FEATURE:
<221> NAME/KEY: MISC_FEATURE
<222> LOCATION: (42)..(42)
<223> OTHER INFORMATION: Xaa at position 42 is a glycosylated derivative of homopropargylglycine or homopropargylglycine
<220> FEATURE:
<221> NAME/KEY: MISC_FEATURE
<222> LOCATION: (47)..(48)
<223> OTHER INFORMATION: Xaa at positions 47-48 is a glycosylated derivative of homopropargylglycine or homopropargylglycine

<400> SEQUENCE: 314

```
Asn Ile Tyr Phe Cys Ser Arg Arg Thr Asn Phe His Asn Ser Cys Tyr
1               5                   10                  15

Leu Xaa Ile Gly Asp Ile Arg Gly Leu Ser Ile Tyr His His Ile Xaa
            20                  25                  30

Ile His Asn Lys Leu His Leu Leu Ile Xaa Tyr Asn Leu Leu Xaa Xaa
        35                  40                  45
```

<210> SEQ ID NO 315
<211> LENGTH: 48
<212> TYPE: PRT
<213> ORGANISM: Artificial Sequence
<220> FEATURE:
<223> OTHER INFORMATION: L-11

<400> SEQUENCE: 315

Ile His Leu Leu Pro Leu Arg His Asn Arg Arg Ser His Asn Arg Pro
1 5 10 15

Ser Arg Leu Ser Trp Gln Lys Asn Asp Tyr Phe Lys Ser Ile Gly Asp
20 25 30

Ile Arg Ala Thr Tyr Trp Leu Arg His Asn Phe Leu Tyr Arg Leu Ser
35 40 45

<210> SEQ ID NO 316
<211> LENGTH: 48
<212> TYPE: PRT
<213> ORGANISM: Artificial Sequence
<220> FEATURE:
<223> OTHER INFORMATION: L-61

<400> SEQUENCE: 316

His Val Val Val Leu His His Ser Gly Phe His Gly Asn Arg Phe Ser
1 5 10 15

Arg Leu Pro Lys Leu Leu Arg Asn Gln His Tyr Gln Asn Ile Gly Asp
20 25 30

Ile Arg Arg Leu Tyr Asn Trp Ile Pro Tyr Thr Lys Arg Tyr Phe Gln
35 40 45

<210> SEQ ID NO 317
<211> LENGTH: 48
<212> TYPE: PRT
<213> ORGANISM: Artificial Sequence
<220> FEATURE:
<223> OTHER INFORMATION: L-2
<220> FEATURE:
<221> NAME/KEY: MISC_FEATURE
<222> LOCATION: (17)..(17)
<223> OTHER INFORMATION: Xaa at position 17 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine

<400> SEQUENCE: 317

Ile His Tyr His His Pro Ile Ile Gly Asp Ile Arg Leu Lys His Asn
1 5 10 15

Xaa Ile Asn Ala His Thr Lys His Val Pro Gln Lys Leu Tyr Leu Asp
20 25 30

Ile Lys Phe Arg Arg Leu Phe Gly Leu Tyr Ile Leu Arg Xaa Leu Asn
35 40 45

<210> SEQ ID NO 318
<211> LENGTH: 48
<212> TYPE: PRT
<213> ORGANISM: Artificial Sequence
<220> FEATURE:
<223> OTHER INFORMATION: L-120
<220> FEATURE:
<221> NAME/KEY: MISC_FEATURE
<222> LOCATION: (7)..(7)
<223> OTHER INFORMATION: Xaa at position 7 is a glycosylated derivative of homopropargylglycine or homopropargylglycine

<400> SEQUENCE: 318

Ile Arg Lys Asn Phe Pro Xaa Thr Phe Gly His Arg Pro His Leu Arg
1 5 10 15

Val Ala His Ala Gln Arg Ala Gln His Ala Leu Leu Val Leu Arg Arg
20 25 30

Ala Arg Arg Leu Leu Asp Gln Glu Val Asp Ala Pro Gly Gly Arg Arg
35 40 45

<210> SEQ ID NO 319
<211> LENGTH: 48
<212> TYPE: PRT
<213> ORGANISM: Artificial Sequence
<220> FEATURE:
<223> OTHER INFORMATION: l-65
<220> FEATURE:
<221> NAME/KEY: MISC_FEATURE
<222> LOCATION: (20)..(20)
<223> OTHER INFORMATION: Xaa at position 20 is a glycosylated derivative of homopropargylglycine or homopropargylglycine
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine

<400> SEQUENCE: 319

Ile Leu Tyr His Tyr His Asn Ile Gly Asp Ile Arg Arg Ser Gln Arg
1 5 10 15

His Leu Asn Xaa Gln Xaa Arg Leu Tyr Val Ser Thr Leu Leu His Ser
20 25 30

Ser His Thr Leu Arg Arg Ala Ser Ile Thr His Arg Ile Arg Lys Phe
35 40 45

<210> SEQ ID NO 320
<211> LENGTH: 48
<212> TYPE: PRT
<213> ORGANISM: Artificial Sequence
<220> FEATURE:
<223> OTHER INFORMATION: L-44
<220> FEATURE:
<221> NAME/KEY: MISC_FEATURE
<222> LOCATION: (26)..(26)
<223> OTHER INFORMATION: Xaa at position 26 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine

<400> SEQUENCE: 320

Thr Phe Ser Arg Tyr His Thr Ile Gly Asp Ile Arg His His Thr Leu
1 5 10 15

Lys His His Gln Ser Lys Gly Leu Gln Xaa Arg Leu Ile Phe Leu Lys
20 25 30

Arg Gln Phe Lys Ala Xaa Gly Asn Cys Leu Arg Trp Lys Ile Leu Phe
35 40 45

<210> SEQ ID NO 321
<211> LENGTH: 48
<212> TYPE: PRT
<213> ORGANISM: Artificial Sequence
<220> FEATURE:
<223> OTHER INFORMATION: L-272

<400> SEQUENCE: 321

Thr Lys Asp Tyr Arg Gln Lys Val Arg Lys Ile Phe Ser His His Ile
1 5 10 15

Thr Lys Ile Gly Asp Ile Arg Leu Ala Glu His Gln His Phe Ala Lys
20 25 30

Ser Arg Leu Leu Lys Gly Phe Val Arg Ala Arg Asn Arg Val Arg Tyr
35 40 45

<210> SEQ ID NO 322
<211> LENGTH: 48
<212> TYPE: PRT
<213> ORGANISM: Artificial Sequence
<220> FEATURE:
<223> OTHER INFORMATION: L-128
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine
<220> FEATURE:
<221> NAME/KEY: MISC_FEATURE
<222> LOCATION: (33)..(33)
<223> OTHER INFORMATION: Xaa at position 33 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine
<220> FEATURE:
<221> NAME/KEY: MISC_FEATURE
<222> LOCATION: (45)..(47)
<223> OTHER INFORMATION: Xaa at positions 45-47 is a glycosylated derivative of homopropargylglycine or homopropargylglycine

<400> SEQUENCE: 322

His His Tyr Pro Asn Tyr His Xaa Arg Ser His Gly Asp Arg Leu Thr
1 5 10 15

Leu Leu Arg His Leu Xaa Ser Phe Leu Val Asp His Lys Gln Ile Leu
20 25 30

Xaa Phe Leu Leu Arg Xaa Arg Lys Asn His Val Ser Xaa Xaa Xaa Thr
35 40 45

<210> SEQ ID NO 323
<211> LENGTH: 48
<212> TYPE: PRT
<213> ORGANISM: Artificial Sequence
<220> FEATURE:
<223> OTHER INFORMATION: L-4
<220> FEATURE:
<221> NAME/KEY: MISC_FEATURE
<222> LOCATION: (22)..(22)
<223> OTHER INFORMATION: Xaa at position 22 is a glycosylated derivative of homopropargylglycine or homopropargylglycine
<220> FEATURE:
<221> NAME/KEY: MISC_FEATURE
<222> LOCATION: (38)..(38)
<223> OTHER INFORMATION: Xaa at position 38 is a glycosylated derivative of homopropargylglycine or homopropargylglycine

<400> SEQUENCE: 323

Lys Tyr Thr His Ile His Ser Ile Gly Asp Ile Arg Asn Thr Tyr Arg
1 5 10 15

Asn Lys His Lys His Xaa Ala Leu Asn Lys Thr Asn Trp Ala Leu Phe
20 25 30

Gln Gln His His Arg Xaa Leu Ile Arg Leu Phe Tyr Arg Arg Leu Leu
35 40 45

<210> SEQ ID NO 324
<211> LENGTH: 48
<212> TYPE: PRT
<213> ORGANISM: Artificial Sequence
<220> FEATURE:
<223> OTHER INFORMATION: L-15
<220> FEATURE:
<221> NAME/KEY: MISC_FEATURE
<222> LOCATION: (42)..(42)
<223> OTHER INFORMATION: Xaa at position 42 is a glycosylated derivative of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative of homopropargylglycine or homopropargylglycine

<400> SEQUENCE: 324

Leu Asn Lys His Lys His Leu Arg Asn His Thr Arg His His Ser Val
1               5                   10                  15

Pro Thr Ile Gly Asp Ile Arg Lys Arg Ile His Asn Leu Leu His Tyr
            20                  25                  30

Leu Ala Gly Phe Arg Phe Phe Asn Gln Xaa His Ser Lys Xaa Gly Val
        35                  40                  45

<210> SEQ ID NO 325
<211> LENGTH: 48
<212> TYPE: PRT
<213> ORGANISM: Artificial Sequence
<220> FEATURE:
<223> OTHER INFORMATION: L-182

<400> SEQUENCE: 325

Ile Arg Asn Gln Thr Lys Lys Ile Gly Asp Ile Arg Gly His His Arg
1               5                   10                  15

Thr Lys Pro Gln Tyr Phe Glu His Pro Phe Val Asp Leu Tyr Lys His
            20                  25                  30

Tyr Gln Tyr Arg Val Phe His Arg Gly Tyr Leu Lys Leu Phe Arg Glu
        35                  40                  45

<210> SEQ ID NO 326
<211> LENGTH: 48
<212> TYPE: PRT
<213> ORGANISM: Artificial Sequence
<220> FEATURE:
<223> OTHER INFORMATION: L-310
<220> FEATURE:
<221> NAME/KEY: MISC_FEATURE
<222> LOCATION: (34)..(34)
<223> OTHER INFORMATION: Xaa at position 34 is a glycosylated derivative of homopropargylglycine or homopropargylglycine
<220> FEATURE:
<221> NAME/KEY: MISC_FEATURE
<222> LOCATION: (36)..(36)
<223> OTHER INFORMATION: Xaa at position 36 is a glycosylated derivative of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative of homopropargylglycine or homopropargylglycine

<400> SEQUENCE: 326

Tyr Leu His Asn His His Asn Tyr Ser Ser Asn Asn Lys Leu His His
1               5                   10                  15

Leu Glu Ile Gly Asp Ile Arg Leu Ile Tyr Gln Lys Tyr Leu Arg Asn
            20                  25                  30

Pro Xaa Phe Xaa Thr Phe Leu Ser Arg Lys His Xaa Asn Trp Gln Arg
35 40 45

<210> SEQ ID NO 327
<211> LENGTH: 48
<212> TYPE: PRT
<213> ORGANISM: Artificial Sequence
<220> FEATURE:
<223> OTHER INFORMATION: L-1079
<220> FEATURE:
<221> NAME/KEY: MISC_FEATURE
<222> LOCATION: (5)..(5)
<223> OTHER INFORMATION: Xaa at position 5 is a glycosylated derivative of homopropargylglycine or homopropargylglycine

<400> SEQUENCE: 327

Asn Leu Thr Ala Xaa Ser Arg Ile Gly Asp Ile Arg Lys His His Phe
1 5 10 15

Gly Arg Pro Leu Tyr Leu Thr Lys His Gly Ala Tyr Pro Arg Tyr His
20 25 30

Thr Arg Tyr Lys His Leu Leu Thr Tyr Arg His His Phe Pro Leu Ile
35 40 45

<210> SEQ ID NO 328
<211> LENGTH: 48
<212> TYPE: PRT
<213> ORGANISM: Artificial Sequence
<220> FEATURE:
<223> OTHER INFORMATION: L-98
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine
<220> FEATURE:
<221> NAME/KEY: MISC_FEATURE
<222> LOCATION: (44)..(44)
<223> OTHER INFORMATION: Xaa at position 44 is a glycosylated derivative of homopropargylglycine or homopropargylglycine

<400> SEQUENCE: 328

Lys His Thr His Leu Arg Pro Xaa Asn Phe Thr Gln Arg Leu Arg Lys
1 5 10 15

Ala His Ile Gly Asp Ile Arg Leu Pro Arg Asn Ile Ser Thr Ser Arg
20 25 30

Ile Arg Thr His Ile Lys Phe His Leu Ile Arg Xaa His Leu Arg Asn
35 40 45

<210> SEQ ID NO 329
<211> LENGTH: 48
<212> TYPE: PRT
<213> ORGANISM: Artificial Sequence
<220> FEATURE:
<223> OTHER INFORMATION: L-103
<220> FEATURE:
<221> NAME/KEY: MISC_FEATURE
<222> LOCATION: (20)..(20)
<223> OTHER INFORMATION: Xaa at position 20 is a glycosylated derivative of homopropargylglycine or homopropargylglycine

<400> SEQUENCE: 329

Phe Leu Leu Asn His Lys Arg Ile Gly Asp Ile Arg Lys Leu Pro Pro
1 5 10 15

Leu Asn Leu Xaa Ala Thr Lys Thr Leu Thr Lys Glu Arg Ile Arg Lys
20 25 30

```
Ile Val Asn Gly Phe Val Gln Arg Leu Lys Gly His Ser Trp Trp Ile
        35                  40                  45


<210> SEQ ID NO 330
<211> LENGTH: 64
<212> TYPE: PRT
<213> ORGANISM: Artificial Sequence
<220> FEATURE:
<223> OTHER INFORMATION: Heavily biased library peptide
<220> FEATURE:
<221> NAME/KEY: MISC_FEATURE
<222> LOCATION: (1)..(1)
<223> OTHER INFORMATION: Xaa at position 1 is a glycosylated derivative
      of homopropargylglycine or homopropargylglycine
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: Xaa at position 19 is a glycosylated derivative
      of homopropargylglycine or homopropargylglycine
<220> FEATURE:
<221> NAME/KEY: misc_feature
<222> LOCATION: (20)..(50)
<223> OTHER INFORMATION: Xaa can be any naturally occurring amino acid

<400> SEQUENCE: 330

Xaa Ala Xaa Xaa Xaa Xaa Xaa Xaa Xaa Ile Gly Asp Ile Arg Xaa Ala
1               5                   10                  15

Xaa Cys Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Gly Ser Gly Ser Leu Gly His His His His His His Arg Leu
    50                  55                  60


<210> SEQ ID NO 331
<211> LENGTH: 64
<212> TYPE: PRT
<213> ORGANISM: Artificial Sequence
<220> FEATURE:
<223> OTHER INFORMATION: Heavily biased library peptide
<220> FEATURE:
<221> NAME/KEY: MISC_FEATURE
<222> LOCATION: (1)..(1)
<223> OTHER INFORMATION: Xaa at position 1 is a glycosylated derivative
      of homopropargylglycine or homopropargylglycine
<220> FEATURE:
<221> NAME/KEY: misc_feature
<222> LOCATION: (3)..(20)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: MISC_FEATURE
<222> LOCATION: (30)..(30)
```

<223> OTHER INFORMATION: Xaa at position 30 is a glycosylated derivative
of homopropargylglycine or homopropargylglycine
<220> FEATURE:
<221> NAME/KEY: misc_feature
<222> LOCATION: (31)..(50)
<223> OTHER INFORMATION: Xaa can be any naturally occurring amino acid

<400> SEQUENCE: 331

Xaa Ala Xaa Xaa Xaa Xaa Xaa Xaa Xaa Xaa Xaa Xaa Xaa Xaa Xaa Xaa
1 5 10 15

Xaa Xaa Xaa Xaa Ile Gly Asp Ile Arg Xaa Ala Xaa Cys Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Gly Ser Gly Ser Leu Gly His His His His His His Arg Leu
50 55 60

<210> SEQ ID NO 332
<211> LENGTH: 64
<212> TYPE: PRT
<213> ORGANISM: Artificial Sequence
<220> FEATURE:
<223> OTHER INFORMATION: Heavily biased library peptide
<220> FEATURE:
<221> NAME/KEY: MISC_FEATURE
<222> LOCATION: (1)..(1)
<223> OTHER INFORMATION: Xaa at position 1 is a glycosylated derivative
of homopropargylglycine or homopropargylglycine
<220> FEATURE:
<221> NAME/KEY: misc_feature
<222> LOCATION: (3)..(31)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: MISC_FEATURE
<222> LOCATION: (41)..(41)
<223> OTHER INFORMATION: Xaa at position 41 is a glycosylated derivative
of homopropargylglycine or homopropargylglycine
<220> FEATURE:
<221> NAME/KEY: misc_feature
<222> LOCATION: (42)..(50)
<223> OTHER INFORMATION: Xaa can be any naturally occurring amino acid

<400> SEQUENCE: 332

Xaa Ala Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Ile
20 25 30

Gly Asp Ile Arg Xaa Ala Xaa Cys Xaa Xaa Xaa Xaa Xaa Xaa Xaa Xaa
35 40 45

Xaa Xaa Gly Ser Gly Ser Leu Gly His His His His His His Arg Leu
50 55 60

<210> SEQ ID NO 333
<211> LENGTH: 64
<212> TYPE: PRT
<213> ORGANISM: Artificial Sequence
<220> FEATURE:
<223> OTHER INFORMATION: Less biased library peptide
<220> FEATURE:
<221> NAME/KEY: MISC_FEATURE
<222> LOCATION: (1)..(1)

-continued

```
<223> OTHER INFORMATION: Xaa  at position 1 is a glycosylated derivative
      of homopropargylglycine or homopropargylglycine
<220> FEATURE:
<221> NAME/KEY: misc_feature
<222> LOCATION: (3)..(9)
<223> OTHER INFORMATION: Xaa can be any naturally occurring amino acid
<220> FEATURE:
<221> NAME/KEY: misc_feature
<222> LOCATION: (15)..(50)
<223> OTHER INFORMATION: Xaa can be any naturally occurring amino acid

<400> SEQUENCE: 333

Xaa Ala Xaa Xaa Xaa Xaa Xaa Xaa Xaa Ile Gly Asp Ile Arg Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Gly Ser Gly Ser Leu Gly His His His His His His Arg Leu
    50                  55                  60


<210> SEQ ID NO 334
<211> LENGTH: 74
<212> TYPE: PRT
<213> ORGANISM: Artificial Sequence
<220> FEATURE:
<223> OTHER INFORMATION: Less biased library peptide
<220> FEATURE:
<221> NAME/KEY: MISC_FEATURE
<222> LOCATION: (1)..(1)
<223> OTHER INFORMATION: Xaa at position 1 is a glycosylated derivative
      of homopropargylglycine or homopropargylglycine
<220> FEATURE:
<221> NAME/KEY: misc_feature
<222> LOCATION: (3)..(30)
<223> OTHER INFORMATION: Xaa can be any naturally occurring amino acid
<220> FEATURE:
<221> NAME/KEY: misc_feature
<222> LOCATION: (36)..(60)
<223> OTHER INFORMATION: Xaa can be any naturally occurring amino acid

<400> SEQUENCE: 334

Xaa Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Ile Gly
            20                  25                  30

Asp Ile Arg Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Gly Ser Gly Ser
    50                  55                  60

Leu Gly His His His His His His Arg Leu
65                  70


<210> SEQ ID NO 335
<211> LENGTH: 64
<212> TYPE: PRT
<213> ORGANISM: Artificial Sequence
<220> FEATURE:
<223> OTHER INFORMATION: Less biased library peptide
<220> FEATURE:
<221> NAME/KEY: MISC_FEATURE
<222> LOCATION: (1)..(1)
<223> OTHER INFORMATION: Xaa at position 1 is a glycosylated derivative
      of homopropargylglycine or homopropargylglycine
<220> FEATURE:
<221> NAME/KEY: misc_feature
```

<222> LOCATION: (3)..(31)
<223> OTHER INFORMATION: Xaa can be any naturally occurring amino acid
<220> FEATURE:
<221> NAME/KEY: misc_feature
<222> LOCATION: (37)..(50)
<223> OTHER INFORMATION: Xaa can be any naturally occurring amino acid

<400> SEQUENCE: 335

```
Xaa Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Ile
            20                  25                  30

Gly Asp Ile Arg Xaa Xaa Xaa Xaa Xaa Xaa Xaa Xaa Xaa Xaa Xaa Xaa
        35                  40                  45

Xaa Xaa Gly Ser Gly Ser Leu Gly His His His His His His Arg Leu
    50                  55                  60
```

<210> SEQ ID NO 336
<211> LENGTH: 64
<212> TYPE: PRT
<213> ORGANISM: Artificial Sequence
<220> FEATURE:
<223> OTHER INFORMATION: Less biased library peptide
<220> FEATURE:
<221> NAME/KEY: MISC_FEATURE
<222> LOCATION: (1)..(1)
<223> OTHER INFORMATION: Xaa at position 1 is a glycosylated derivative of homopropargylglycine or homopropargylglycine
<220> FEATURE:
<221> NAME/KEY: misc_feature
<222> LOCATION: (3)..(50)
<223> OTHER INFORMATION: Xaa can be any naturally occurring amino acid

<400> SEQUENCE: 336

```
Xaa Ala Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Gly Ser Gly Ser Leu Gly His His His His His His Arg Leu
    50                  55                  60
```

<210> SEQ ID NO 337
<211> LENGTH: 12
<212> TYPE: RNA
<213> ORGANISM: Artificial Sequence
<220> FEATURE:
<223> OTHER INFORMATION: mRNA sequence

<400> SEQUENCE: 337
caccggcuau ag 12

<210> SEQ ID NO 338
<211> LENGTH: 63
<212> TYPE: PRT
<213> ORGANISM: Artificial Sequence
<220> FEATURE:
<223> OTHER INFORMATION: 91-8cy
<220> FEATURE:
<221> NAME/KEY: MISC_FEATURE
<222> LOCATION: (5)..(5)
<223> OTHER INFORMATION: Xaa at position 5 is a glycosylated derivative of homopropargylglycine or homopropargylglycine
<220> FEATURE:
<221> NAME/KEY: MISC_FEATURE
<222> LOCATION: (8)..(8)

<223> OTHER INFORMATION: Xaa at position 8 is a glycosylated derivative
      of homopropargylglycine or homopropargylglycine
<220> FEATURE:
<221> NAME/KEY: MISC_FEATURE
<222> LOCATION: (20)..(20)
<223> OTHER INFORMATION: Xaa at position 20 is a glycosylated derivative
      of homopropargylglycine or homopropargylglycine
<220> FEATURE:
<221> NAME/KEY: MISC_FEATURE
<222> LOCATION: (40)..(40)
<223> OTHER INFORMATION: Xaa at position 40 is a glycosylated derivative
      of homopropargylglycine or homopropargylglycine
<220> FEATURE:
<221> NAME/KEY: MISC_FEATURE
<222> LOCATION: (46)..(46)
<223> OTHER INFORMATION: Xaa at position 46 is a glycosylated derivative
      of homopropargylglycine or homopropargylglycine

<400> SEQUENCE: 338

```
Ala His Tyr Ser Xaa Asn His Xaa Arg His Pro Leu Tyr Pro Ser Val
1               5                   10                  15

Asn His Arg Xaa Ser Tyr Pro Arg Ile Gly Leu Leu Ser Arg Ile Gly
            20                  25                  30

Asp Ile Arg Ser Ala Ser Cys Xaa Leu Arg Cys Phe Arg Xaa Arg Ser
        35                  40                  45

Thr Gly Ser Gly Ser Leu Gly His His His His His His Arg Leu
    50                  55                  60
```

<210> SEQ ID NO 339
<211> LENGTH: 40
<212> TYPE: PRT
<213> ORGANISM: Artificial Sequence
<220> FEATURE:
<223> OTHER INFORMATION: 10V1
<220> FEATURE:
<221> NAME/KEY: MISC_FEATURE
<222> LOCATION: (13)..(13)
<223> OTHER INFORMATION: Xaa at position 13 is a glycosylated derivative
      of homopropargylglycine or homopropargylglycine
<220> FEATURE:
<221> NAME/KEY: MISC_FEATURE
<222> LOCATION: (20)..(20)
<223> OTHER INFORMATION: Xaa at position 20 is a glycosylated derivative
      of homopropargylglycine or homopropargylglycine

<400> SEQUENCE: 339

```
Met Ala Thr Lys Thr Asn Cys Lys Arg Glu Lys Thr Xaa Asp Asn His
1               5                   10                  15

Val Thr Ile Xaa Arg Ser Ile Pro Trp Tyr Thr Tyr Arg Trp Leu Pro
            20                  25                  30

Asn Gly Ser Gly Ser Gly Cys Gly
        35                  40
```

<210> SEQ ID NO 340
<211> LENGTH: 48
<212> TYPE: PRT
<213> ORGANISM: Artificial Sequence
<220> FEATURE:
<223> OTHER INFORMATION: L-160
<220> FEATURE:
<221> NAME/KEY: MISC_FEATURE
<222> LOCATION: (30)..(30)
<223> OTHER INFORMATION: Xaa at position 30 is a glycosylated derivative
      of homopropargylglycine or homopropargylglycine

<400> SEQUENCE: 340

```
Ile His His Ser Tyr Arg Gly Phe Thr Leu Arg Ile Pro Leu Thr Thr
1               5                   10                  15
```

```
Asn Lys Ile Gly Asp Ile Arg Thr Ala Phe Pro Tyr Pro Xaa Leu Ser
            20                  25                  30

His Leu Phe Asp Arg Arg Arg Trp Lys Arg Gly Leu His Asn Trp Phe
        35                  40                  45


<210> SEQ ID NO 341
<211> LENGTH: 48
<212> TYPE: PRT
<213> ORGANISM: Artificial Sequence
<220> FEATURE:
<223> OTHER INFORMATION: H-3

<400> SEQUENCE: 341

Phe Arg Ser Asn Asp Pro Lys Ile Gly Asp Ile Arg His Glu Leu His
1               5                   10                  15

Val Ala His Pro Val Asp Val Val Leu Leu Arg Leu Leu Arg Arg Val
            20                  25                  30

Leu Ala Val His Leu Ala Gln His Val Val Val Ala Leu Arg His Arg
        35                  40                  45


<210> SEQ ID NO 342
<211> LENGTH: 48
<212> TYPE: PRT
<213> ORGANISM: Artificial Sequence
<220> FEATURE:
<223> OTHER INFORMATION: H-37
<220> FEATURE:
<221> NAME/KEY: MISC_FEATURE
<222> LOCATION: (17)..(17)
<223> OTHER INFORMATION: Xaa at position 17 is a glycosylated derivative
      of homopropargylglycine or homopropargylglycine

<400> SEQUENCE: 342

Asn His Ser His Gly His Asn Ile Gly Asp Ile Arg Asp Ala Thr Cys
1               5                   10                  15

Xaa Leu Ser Asn Cys Tyr His Tyr Asn Asn Arg Arg Lys Asn Arg Phe
            20                  25                  30

Thr Leu Phe Thr Leu Leu Arg Ile Leu Val Gln Lys Ser Leu Phe Arg
        35                  40                  45


<210> SEQ ID NO 343
<211> LENGTH: 48
<212> TYPE: PRT
<213> ORGANISM: Artificial Sequence
<220> FEATURE:
<223> OTHER INFORMATION: H-67

<400> SEQUENCE: 343

Gln Leu Tyr Asn Leu Lys Val Ile Gly Asp Ile Arg Arg Arg Gly Leu
1               5                   10                  15

His Val Arg Arg Leu Val Ala Leu Ala His His Val Arg Asp Arg Leu
            20                  25                  30

His Leu Ala Arg Arg Leu Leu His Leu His His Gly Val Arg Leu Gly
        35                  40                  45


<210> SEQ ID NO 344
<211> LENGTH: 48
<212> TYPE: PRT
<213> ORGANISM: Artificial Sequence
<220> FEATURE:
<223> OTHER INFORMATION: H-36
<220> FEATURE:
<221> NAME/KEY: MISC_FEATURE
<222> LOCATION: (6)..(6)
```

<223> OTHER INFORMATION: Xaa at position 6 is a glycosylated derivative of homopropargylglycine or homopropargylglycine

<400> SEQUENCE: 344

Tyr Lys Lys Thr Phe Xaa Asp Ile Gly Asp Ser Tyr Gly Glu Leu His
1 5 10 15

Ala Gln Ala Arg Arg Arg Glu Ala Val Arg Arg Leu Leu Arg Leu Val
20 25 30

Arg His Arg Val Leu Leu His Leu Leu Arg Ala Val Leu His Ala Arg
35 40 45

<210> SEQ ID NO 345
<211> LENGTH: 48
<212> TYPE: PRT
<213> ORGANISM: Artificial Sequence
<220> FEATURE:
<223> OTHER INFORMATION: H-50

<400> SEQUENCE: 345

Arg Ser Ile His Ser Gln Lys Ile Gly Asp Ile Arg Lys Gly Ala Leu
1 5 10 15

His Ala Arg Val Val Arg Pro Val Glu Gln Arg Gln Pro Leu Arg Val
20 25 30

Leu Leu Ala Arg Val His Arg Leu Ala Asp Val Leu Ala Leu Leu His
35 40 45

<210> SEQ ID NO 346
<211> LENGTH: 48
<212> TYPE: PRT
<213> ORGANISM: Artificial Sequence
<220> FEATURE:
<223> OTHER INFORMATION: H-74
<220> FEATURE:
<221> NAME/KEY: MISC_FEATURE
<222> LOCATION: (8)..(8)
<223> OTHER INFORMATION: Xaa at position 8 is a glycosylated derivative of homopropargylglycine or homopropargylglycine
<220> FEATURE:
<221> NAME/KEY: MISC_FEATURE
<222> LOCATION: (13)..(13)
<223> OTHER INFORMATION: Xaa at position 13 is a glycosylated derivative of homopropargylglycine or homopropargylglycine

<400> SEQUENCE: 346

Ser Ser Phe Arg Leu His Asn Xaa Gly Pro Ser Arg Xaa Arg His Trp
1 5 10 15

Asp Arg Leu Leu Thr Ile Tyr Ser Ile Gly Val Ser Thr Leu Ala Asn
20 25 30

Ser Leu Arg Val Leu His Gly Val Ala His Arg Gly Arg His Leu Gly
35 40 45

<210> SEQ ID NO 347
<211> LENGTH: 48
<212> TYPE: PRT
<213> ORGANISM: Artificial Sequence
<220> FEATURE:
<223> OTHER INFORMATION: H-47

<400> SEQUENCE: 347

Leu Lys Asn Leu Val Gln Leu Ile Gly Asp Ile Arg Arg Gly Leu His
1 5 10 15

Glu His Leu His Leu Ala Leu Ala Gly Gln Arg Asp Asp Gln Leu Leu
20 25 30

Leu Val Leu Leu Val His Arg Val His Arg Gly Ala His Arg His Arg
        35                  40                  45

<210> SEQ ID NO 348
<211> LENGTH: 48
<212> TYPE: PRT
<213> ORGANISM: Artificial Sequence
<220> FEATURE:
<223> OTHER INFORMATION: H-7
<220> FEATURE:
<221> NAME/KEY: MISC_FEATURE
<222> LOCATION: (14)..(14)
<223> OTHER INFORMATION: Xaa at position 14 is a glycosylated derivative
      of homopropargylglycine or homopropargylglycine

<400> SEQUENCE: 348

Tyr Tyr Asn His Pro Lys Leu Arg Gln Tyr Leu Val Lys Xaa Leu Thr
1               5                   10                  15

Arg Leu Arg Arg Tyr Ser Tyr Arg Glu Leu His Asp Gly Asp Asp His
            20                  25                  30

Ala Arg Gln Ala His Arg Gly Arg Leu Leu Gln Asp Leu Val Asp Arg
        35                  40                  45

<210> SEQ ID NO 349
<211> LENGTH: 48
<212> TYPE: PRT
<213> ORGANISM: Artificial Sequence
<220> FEATURE:
<223> OTHER INFORMATION: H-84

<400> SEQUENCE: 349

Leu Thr Val Arg Thr Gln Leu His His His His Ala Gln Arg Pro Gly
1               5                   10                  15

Asp Leu Leu Ala Leu Val Leu Leu Leu Arg Pro Arg His Trp Arg Tyr
            20                  25                  30

Ser Tyr Arg Val Val His Ala Arg Pro Gln Gly Arg His Asp His Arg
        35                  40                  45

<210> SEQ ID NO 350
<211> LENGTH: 48
<212> TYPE: PRT
<213> ORGANISM: Artificial Sequence
<220> FEATURE:
<223> OTHER INFORMATION: L-4

<400> SEQUENCE: 350

Ile Gln His His Asn Phe Phe Pro Arg Thr Ser Arg Tyr Ile Tyr Pro
1               5                   10                  15

Arg Arg Ile Gly Asp Ile Arg Pro Ile Leu Arg Gln Asn Ile Phe His
            20                  25                  30

His Leu Lys Lys Phe Leu His Val Val Lys Thr Arg Tyr Phe Ser Phe
        35                  40                  45

<210> SEQ ID NO 351
<211> LENGTH: 48
<212> TYPE: PRT
<213> ORGANISM: Artificial Sequence
<220> FEATURE:
<223> OTHER INFORMATION: L-35
<220> FEATURE:
<221> NAME/KEY: MISC_FEATURE
<222> LOCATION: (25)..(25)
<223> OTHER INFORMATION: Xaa at position 25 is a glycosylated derivative
      of homopropargylglycine or homopropargylglycine

<400> SEQUENCE: 351

Ile His His Thr His Leu Asn Ile Gly Asp Ile Arg Phe Arg His Phe
1 5 10 15

Pro Arg Arg Tyr Arg Asn Asn Trp Xaa Asn Phe Leu Phe Leu Val Leu
20 25 30

Arg Ala Leu Thr Trp Lys Asn Arg Leu Ala Phe Phe Ser Asn Asp His
35 40 45

<210> SEQ ID NO 352
<211> LENGTH: 48
<212> TYPE: PRT
<213> ORGANISM: Artificial Sequence
<220> FEATURE:
<223> OTHER INFORMATION: L-73

<400> SEQUENCE: 352

Ile Asn Pro Asn Ser Lys Arg Arg Thr Arg Ser Arg His Tyr Asn Gly
1 5 10 15

Asp His Ile Gly Asp Ile Arg Ala Lys His Leu Ser His Arg Lys Ile
20 25 30

Thr Leu Leu Gly Ile Tyr Arg Ile Arg Leu Lys Val Ala Leu Asn Leu
35 40 45

<210> SEQ ID NO 353
<211> LENGTH: 48
<212> TYPE: PRT
<213> ORGANISM: Artificial Sequence
<220> FEATURE:
<223> OTHER INFORMATION: L-124

<400> SEQUENCE: 353

Tyr Ile Thr His Ser Pro His Ile Gly Asp Ile Arg His Ser Lys Ser
1 5 10 15

Leu Leu Leu Phe Arg Asn His Gly Leu Leu Glu Leu Leu Arg Leu Leu
20 25 30

Val Arg Val Gly Arg Gln Glu Val Arg Val His Asp Val Gln His Arg
35 40 45

<210> SEQ ID NO 354
<211> LENGTH: 48
<212> TYPE: PRT
<213> ORGANISM: Artificial Sequence
<220> FEATURE:
<223> OTHER INFORMATION: L-140
<220> FEATURE:
<221> NAME/KEY: MISC_FEATURE
<222> LOCATION: (3)..(3)
<223> OTHER INFORMATION: Xaa at position 3 is a glycosylated derivative of homopropargylglycine or homopropargylglycine

<400> SEQUENCE: 354

Ile Asn Xaa Ser Ile Arg Leu Ile Gly Asp Ile Arg Pro Ala Gln Ala
1 5 10 15

Gln Arg Gly His Leu Ala Pro His Ala Arg Arg Val Arg His Glu Val
20 25 30

Leu Gly Leu Val Leu Glu Arg Leu Leu Val Leu Arg Arg Leu Val Arg
35 40 45

<210> SEQ ID NO 355
<211> LENGTH: 48
<212> TYPE: PRT
<213> ORGANISM: Artificial Sequence
<220> FEATURE:

<223> OTHER INFORMATION: L-37

<400> SEQUENCE: 355

Asn His Ile His Leu Ser Asp Ile Gly Asp Ile Arg His Leu Lys Asn
1 5 10 15

Phe His Asn Thr Tyr Tyr Asn Lys Lys Arg Leu Ile Ser Val Leu Phe
20 25 30

Phe Leu Ser Leu Trp Gln Leu Arg Phe Leu Ala Lys Asn Phe Tyr Leu
35 40 45

<210> SEQ ID NO 356
<211> LENGTH: 48
<212> TYPE: PRT
<213> ORGANISM: Artificial Sequence
<220> FEATURE:
<223> OTHER INFORMATION: L-47

<400> SEQUENCE: 356

Asp Ser His Pro Tyr Asn Ile Ile Arg Tyr Ser Phe Gln Pro Pro His
1 5 10 15

Leu His Glu Glu Leu Leu Pro Gln Arg Arg Leu Leu Arg Gly Val His
20 25 30

Val Gln Gly Val His Pro Val Val Arg Leu Leu His Arg Val Gln Arg
35 40 45

<210> SEQ ID NO 357
<211> LENGTH: 48
<212> TYPE: PRT
<213> ORGANISM: Artificial Sequence
<220> FEATURE:
<223> OTHER INFORMATION: L-64

<400> SEQUENCE: 357

Ile Arg Thr Arg Val Ser Gln Ile Gly Asp Ile Arg His Asp Leu Lys
1 5 10 15

Arg Asn Thr Thr Ile Phe Lys Asn Ala Leu Phe Leu Ile Tyr Leu Ile
20 25 30

Lys Thr Tyr Asn Arg Lys Asn Tyr His Leu Lys Asn Leu Lys Asp Leu
35 40 45

<210> SEQ ID NO 358
<211> LENGTH: 48
<212> TYPE: PRT
<213> ORGANISM: Artificial Sequence
<220> FEATURE:
<223> OTHER INFORMATION: L-187
<220> FEATURE:
<221> NAME/KEY: MISC_FEATURE
<222> LOCATION: (27)..(27)
<223> OTHER INFORMATION: Xaa at position 27 is a glycosylated derivative of homopropargylglycine or homopropargylglycine

<400> SEQUENCE: 358

Tyr Asp Pro Leu His Lys Ala Ser His Ser Asn His Pro Gln Pro Tyr
1 5 10 15

Arg Tyr Ile Gly Val Ile Arg His Pro Leu Xaa Arg Gln Ser Ile Ser
20 25 30

Gln Ile Phe Lys Ile Leu Leu Ile Arg Tyr Leu Arg Lys His Arg Arg
35 40 45